(12) United States Patent
Bradbury et al.

(10) Patent No.: US 8,399,667 B2
(45) Date of Patent: Mar. 19, 2013

(54) 4-ANILINO QUINAZOLINE DERIVATIVES AS ANTIPROLIFERATIVE AGENTS

(75) Inventors: Robert Hugh Bradbury, Cheshire (GB); Laurent Francois Andre Hennequin, Cheshire (GB); Jason Grant Kettle, Cheshire (GB)

(73) Assignee: Astrazeneca AB, Alderley Park, Macclesfield, Cheshire (GB)

( * ) Notice: Subject to any disclaimer, the term of this patent is extended or adjusted under 35 U.S.C. 154(b) by 0 days.

(21) Appl. No.: 12/706,675

(22) Filed: Feb. 16, 2010

(65) Prior Publication Data
US 2010/0152442 A1 Jun. 17, 2010

Related U.S. Application Data

(63) Continuation of application No. 12/147,250, filed on Jun. 26, 2008, now abandoned, which is a continuation of application No. 10/508,675, filed as application No. PCT/GB03/01306 on Mar. 26, 2003, now abandoned.

(30) Foreign Application Priority Data

Mar. 28, 2002 (GB) .................................. 0207323.7
Dec. 24, 2002 (GB) .................................. 0230086.1
Jan. 28, 2003 (GB) .................................. 0301916.3

(51) Int. Cl.
C07D 239/72 (2006.01)
(52) U.S. Cl. ......................................................... 544/293
(58) Field of Classification Search .................... 544/293
See application file for complete search history.

(56) References Cited

U.S. PATENT DOCUMENTS

| | | | |
|---|---|---|---|
| 3,985,749 A | 10/1976 | Foster | |
| 4,322,420 A | 3/1982 | Kobayashi et al. | |
| 4,335,127 A | 6/1982 | Vandenberk et al. | |
| 4,640,920 A | 2/1987 | Boyle et al. | |
| 4,921,863 A | 5/1990 | Sugimoto et al. | |
| 5,252,586 A | 10/1993 | Cain et al. | |
| 5,405,843 A | 4/1995 | Fukazawa et al. | |
| 5,457,105 A | 10/1995 | Barker | |
| 5,616,582 A | 4/1997 | Barker | |
| 5,721,237 A | 2/1998 | Myers et al. | |
| 5,747,498 A | 5/1998 | Schnur et al. | |
| 5,770,599 A | 6/1998 | Gibson | |
| 5,770,603 A | 6/1998 | Gibson | |
| 5,821,246 A | 10/1998 | Brown et al. | |
| 5,866,572 A | 2/1999 | Barker et al. | |
| 5,929,080 A | 7/1999 | Frost et al. | |
| 5,962,458 A | 10/1999 | Lohmann et al. | |
| 6,004,967 A | 12/1999 | McMahon et al. | |
| 6,046,206 A | 4/2000 | Pamukcu et al. | |
| 6,117,433 A | 9/2000 | Edens et al. | |
| 6,126,917 A | 10/2000 | Mishani et al. | |
| 6,177,433 B1 | 1/2001 | Uckun et al. | |
| 6,225,318 B1 | 5/2001 | Sobolov-Jaynes et al. | |
| 6,262,054 B1 | 7/2001 | Fennelly et al. | |
| 6,297,258 B1 | 10/2001 | Wissner et al. | |
| 6,313,130 B1 | 11/2001 | Uckun et al. | |
| 6,326,373 B1 | 12/2001 | Uckun et al. | |
| 6,384,223 B1 | 5/2002 | Gletsos | |
| 6,562,319 B2 | 5/2003 | Mishani et al. | |
| 6,617,329 B2 | 9/2003 | Himmelsbach et al. | |
| 6,627,651 B1 | 9/2003 | Shiraishi et al. | |
| 6,653,305 B2 | 11/2003 | Himmelsbach et al. | |
| 6,656,946 B2 | 12/2003 | Himmelsbach et al. | |
| 6,673,803 B2 | 1/2004 | Thomas et al. | |
| 6,740,651 B2 | 5/2004 | Himmelsbach et al. | |
| 6,924,285 B2 | 8/2005 | Himmelsbach et al. | |
| 6,972,288 B1 | 12/2005 | Himmelsbach et al. | |
| 7,019,012 B2 | 3/2006 | Himmelsbach et al. | |
| 7,119,084 B2 | 10/2006 | Himmelsbach et al. | |
| 7,160,981 B2 | 1/2007 | La Thangue et al. | |
| 7,220,750 B2 | 5/2007 | Himmelsbach et al. | |
| 7,294,629 B2 | 11/2007 | Kitano et al. | |
| 2002/0049197 A1 | 4/2002 | Himmelsbach et al. | |
| 2002/0082270 A1 | 6/2002 | Himmelsbach et al. | |
| 2002/0082271 A1 | 6/2002 | Himmelsbach et al. | |
| 2002/0128553 A1 | 9/2002 | Mishani et al. | |

(Continued)

FOREIGN PATENT DOCUMENTS

CA 2086968 7/1993
CA 2375259 12/2000

(Continued)

OTHER PUBLICATIONS

Alferez et al., "Inhibiting Signaling by erbB Receptor Tyrosine Kinases with AZD8931, a Potent Reversible small Molecule Inhibitor, Reduces Intestinal Adenoma Formation in the ApcMin/+ Mouse Model". EORTC-NCI-AACR (2010), Abstract 471.

(Continued)

Primary Examiner — Douglas M Willis
(74) Attorney, Agent, or Firm — Astrazeneca AB

(57) ABSTRACT

The invention concerns quinazoline derivatives of Formula (I) wherein each of $Q^1$, Z, $R^1$ and $Q^2$ have any of the meanings defined in the description; processes for their preparation, pharmaceutical compositions containing them and their use in the manufacture of a medicament for use as an antiproliferative agent in the prevention or treatment of tumours which are sensitive to inhibition of erbB receptor tyrosine kinases.

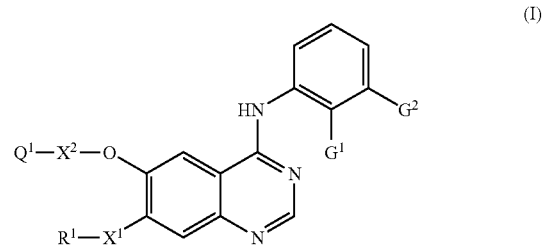

(I)

11 Claims, No Drawings

U.S. PATENT DOCUMENTS

| | | |
|---|---|---|
| 2002/0169180 A1 | 11/2002 | Himmelsbach et al. |
| 2002/0173509 A1 | 11/2002 | Himmelsbach et al. |
| 2002/0173646 A1 | 11/2002 | Thomas et al. |
| 2002/0177601 A1 | 11/2002 | Himmelsbach et al. |
| 2003/0149062 A1 | 8/2003 | Jung et al. |
| 2003/0158196 A1 | 8/2003 | Jung et al. |
| 2004/0006846 A1 | 1/2004 | Rupprechter |
| 2004/0013091 A1 | 1/2004 | Liu |
| 2004/0044014 A1 | 3/2004 | Himmelsbach et al. |
| 2004/0048880 A1 | 3/2004 | Himmelsbach et al. |
| 2004/0053972 A1 | 3/2004 | Nara et al. |
| 2004/0176361 A1 | 9/2004 | Fujio et al. |
| 2004/0192664 A1 | 9/2004 | Kunz et al. |
| 2004/0198997 A1 | 10/2004 | Scholz et al. |
| 2005/0043395 A1 | 2/2005 | Wedge |
| 2005/0130995 A1 | 6/2005 | Nishino et al. |
| 2005/0148607 A1 | 7/2005 | Suzuki et al. |
| 2005/0165035 A1 | 7/2005 | Bradbury et al. |
| 2005/0182043 A1 | 8/2005 | Himmelsbach et al. |
| 2005/0215574 A1 | 9/2005 | Bradbury et al. |
| 2006/0167026 A1 | 7/2006 | Nawa et al. |
| 2006/0188501 A1 | 8/2006 | Homma et al. |
| 2006/0270672 A1 | 11/2006 | Himmelsbach et al. |
| 2007/0037837 A1 | 2/2007 | Hennequin et al. |
| 2007/0043010 A1 | 2/2007 | Bradbury et al. |
| 2007/0099943 A1 | 5/2007 | Bradbury et al. |
| 2008/0076415 A1 | 3/2008 | Kang et al. |
| 2008/0096881 A1 | 4/2008 | Hennequin et al. |
| 2008/0269487 A1 | 10/2008 | Bradbury et al. |
| 2009/0312313 A1 | 12/2009 | Shimizu et al. |

FOREIGN PATENT DOCUMENTS

| | | |
|---|---|---|
| CA | 2417050 | 3/2002 |
| CA | 2417652 | 1/2003 |
| CA | 2417897 | 1/2003 |
| CA | 2417907 | 1/2003 |
| CA | 2417042 | 3/2003 |
| EP | 0288563 | 11/1988 |
| EP | 566226 | 10/1993 |
| EP | 0607439 | 7/1994 |
| EP | 0602851 | 10/1996 |
| EP | 0520722 | 12/1996 |
| EP | 078772 | 8/1997 |
| EP | 0837063 | 4/1998 |
| EP | 0326330 | 8/1999 |
| EP | 0635507 | 9/1999 |
| EP | 1230919 | 8/2002 |
| EP | 1283039 | 2/2003 |
| EP | 1369418 | 12/2003 |
| GB | 2033894 | 5/1980 |
| GB | 2160201 | 12/1985 |
| GB | 2295387 | 5/1996 |
| JP | 11189586 | 7/1999 |
| JP | 2003246780 | 9/2003 |
| WO | WO 88/02365 | 4/1988 |
| WO | WO 92/14746 | 9/1992 |
| WO | WO 92/20642 | 11/1992 |
| WO | WO 93/08170 | 4/1993 |
| WO | WO 93/17682 | 9/1993 |
| WO | WO 94/27965 | 12/1994 |
| WO | WO 95/00146 | 1/1995 |
| WO | WO 95/03283 | 2/1995 |
| WO | WO 95/15758 | 6/1995 |
| WO | WO 95/24190 | 9/1995 |
| WO | WO 96/09294 | 3/1996 |
| WO | WO 96/15118 | 5/1996 |
| WO | WO 96/16960 | 6/1996 |
| WO | WO 96/30347 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | WO 96/39145 | 12/1996 |
| WO | WO 97/03069 | 1/1997 |
| WO | WO 97/11692 | 4/1997 |
| WO | WO 97/18813 | 5/1997 |
| WO | WO 97/22596 | 6/1997 |
| WO | WO 97/30034 | 8/1997 |
| WO | WO 97/30035 | 8/1997 |
| WO | WO 97/30044 | 8/1997 |
| WO | WO 97/32856 | 9/1997 |
| WO | WO 97/38983 | 10/1997 |
| WO | WO 97/38994 | 10/1997 |
| WO | WO 97/42187 | 11/1997 |
| WO | WO 98/02434 | 1/1998 |
| WO | WO 98/13354 | 4/1998 |
| WO | WO 98/38984 | 9/1998 |
| WO | WO 9850038 | 11/1998 |
| WO | WO 9850370 | 11/1998 |
| WO | WO 99/06378 | 2/1999 |
| WO | WO 99/09016 | 2/1999 |
| WO | WO 9906378 | 2/1999 |
| WO | WO 99/10349 | 3/1999 |
| WO | WO 99/24037 | 5/1999 |
| WO | WO 9924037 | 5/1999 |
| WO | WO 9935132 | 7/1999 |
| WO | WO 9961428 | 12/1999 |
| WO | WO 0000202 | 1/2000 |
| WO | WO 00/09481 | 2/2000 |
| WO | WO 0006555 | 2/2000 |
| WO | WO 00/10981 | 3/2000 |
| WO | WO 00/12497 | 3/2000 |
| WO | WO 00/18740 | 4/2000 |
| WO | WO 00/20402 | 4/2000 |
| WO | WO 0009481 | 4/2000 |
| WO | WO 0019788 | 4/2000 |
| WO | WO 00/24718 | 5/2000 |
| WO | WO 00/44728 | 8/2000 |
| WO | WO 00/47212 | 8/2000 |
| WO | WO 00/51587 | 9/2000 |
| WO | WO 00/51991 | 9/2000 |
| WO | WO 00/55141 | 9/2000 |
| WO | WO 00/55162 | 9/2000 |
| WO | WO 00/56338 | 9/2000 |
| WO | WO 00/56720 | 9/2000 |
| WO | WO 00/68203 | 11/2000 |
| WO | WO 00/73260 | 12/2000 |
| WO | WO 00/78735 | 12/2000 |
| WO | WO 0072849 | 12/2000 |
| WO | WO 0073260 | 12/2000 |
| WO | WO 01/04102 | 1/2001 |
| WO | WO 01/07432 | 2/2001 |
| WO | WO 01/12227 | 2/2001 |
| WO | WO 01/21594 | 3/2001 |
| WO | WO 01/21595 | 3/2001 |
| WO | WO 01/21596 | 3/2001 |
| WO | WO 01/21597 | 3/2001 |
| WO | WO 0121160 | 3/2001 |
| WO | WO 01/32632 | 5/2001 |
| WO | WO 01/32651 | 5/2001 |
| WO | WO 0132155 | 5/2001 |
| WO | WO 01/45641 | 6/2001 |
| WO | WO 01/66099 | 9/2001 |
| WO | WO 0164642 | 9/2001 |
| WO | WO 01/76586 | 10/2001 |
| WO | WO 01/77085 | 10/2001 |
| WO | WO 01/94341 | 12/2001 |
| WO | WO 01/98277 | 12/2001 |
| WO | WO 02/02579 | 1/2002 |
| WO | WO 0205791 | 1/2002 |
| WO | WO 02/16352 | 2/2002 |
| WO | WO 02/18351 | 3/2002 |
| WO | WO 02/18370 | 3/2002 |
| WO | WO 02/18372 | 3/2002 |
| WO | WO 02/18373 | 3/2002 |
| WO | WO 02/18376 | 3/2002 |
| WO | WO 02/24684 | 3/2002 |
| WO | WO 0217712 | 3/2002 |
| WO | WO 0220020 | 3/2002 |
| WO | WO 02/30924 | 4/2002 |
| WO | WO 0230358 | 4/2002 |
| WO | WO 0234711 | 5/2002 |
| WO | WO 0234744 | 5/2002 |
| WO | WO 0241882 | 5/2002 |
| WO | WO 0244166 | 6/2002 |

| | | |
|---|---|---|
| WO | WO 0248117 | 6/2002 |
| WO | WO 0250043 | 6/2002 |
| WO | WO 02056882 | 7/2002 |
| WO | WO 02062767 | 8/2002 |
| WO | WO 02066445 | 8/2002 |
| WO | WO 02/073235 | 9/2002 |
| WO | WO 02068409 | 9/2002 |
| WO | WO 02073235 | 9/2002 |
| WO | WO 02076976 | 10/2002 |
| WO | WO 02092577 | 11/2002 |
| WO | WO 02092578 | 11/2002 |
| WO | WO 02092579 | 11/2002 |
| WO | WO 02094760 | 11/2002 |
| WO | WO 03000188 | 1/2003 |
| WO | WO 03031406 | 4/2003 |
| WO | WO 03039551 | 5/2003 |
| WO | WO 03040108 | 5/2003 |
| WO | WO 03040109 | 5/2003 |
| WO | WO 03045364 | 6/2003 |
| WO | WO 03045395 | 6/2003 |
| WO | WO 03049740 | 6/2003 |
| WO | WO 03064413 | 8/2003 |
| WO | WO 03082290 | 10/2003 |
| WO | WO 03082831 | 10/2003 |
| WO | WO 03096615 | 11/2003 |
| WO | WO 03097086 | 11/2003 |
| WO | WO 03099276 | 12/2003 |
| WO | WO 2004010929 | 2/2004 |
| WO | WO 2004064718 | 8/2004 |
| WO | WO 2004072038 | 8/2004 |
| WO | WO 2004085385 | 10/2004 |
| WO | WO 2004093880 | 11/2004 |
| WO | WO 2004096224 | 11/2004 |
| WO | WO 2004096226 | 11/2004 |
| WO | WO 2005001053 | 1/2005 |
| WO | WO 2005003325 | 1/2005 |
| WO | WO 2005012290 | 2/2005 |
| WO | WO 2005016347 | 2/2005 |
| WO | WO 2005026150 | 3/2005 |
| WO | WO 2005026151 | 3/2005 |
| WO | WO 2005026152 | 3/2005 |
| WO | WO 2005026156 | 3/2005 |
| WO | WO 2005026157 | 3/2005 |
| WO | WO 2005028469 | 3/2005 |
| WO | WO 2005028470 | 3/2005 |
| WO | WO 2005030140 | 4/2005 |
| WO | WO 2005030757 | 4/2005 |
| WO | WO 2005030765 | 5/2005 |
| WO | WO 2005041973 | 5/2005 |
| WO | WO 2005051923 | 6/2005 |
| WO | WO 2005075439 | 8/2005 |
| WO | WO 2005118572 | 12/2005 |
| WO | WO 2006064196 | 6/2006 |
| WO | WO 2006090163 | 8/2006 |
| WO | WO 2006092573 | 9/2006 |
| WO | WO 2006092574 | 9/2006 |
| WO | WO 2006117521 | 11/2006 |
| WO | WO 2006117523 | 11/2006 |
| WO | WO 2007034143 | 3/2007 |
| WO | WO 2007034144 | 3/2007 |
| WO | WO 2007054551 | 5/2007 |
| WO | WO 2007063291 | 6/2007 |
| WO | WO 2007063293 | 6/2007 |
| WO | WO 2009138779 | 11/2009 |
| WO | WO 2009138780 | 11/2009 |
| WO | WO 2009138781 | 11/2009 |
| WO | WO 2010061208 | 6/2010 |
| WO | WO 2010122340 | 10/2010 |

OTHER PUBLICATIONS

Alferez et al., "Inhibiting Signaling by erbB Receptor Tyrosine Kinases with AZD8931, a Potent Reversible small Molecule Inhibitor, Reduces Intestinal Adenoma Formation in the ApcMin/+ Mouse Model". EORTC-NCI-AACR (2010), Poster.

Ballard et al., "5-Substituted 4-anilinoquinazolines as potent, selective and orally active inhibitors of erbB2 receptor tyrosine kinase", Bioorganic & Medicinal Chemistry Letters 15(19):4226-4229 (2005).

Ballard et al., "Inhibitors of epidermal growth factor receptor tyrosine kinase: Novel C-5 substituted anilinoquinazolines designed to target the ribose pocket", Bioorganic & Medicinal Chemistry Letters 16(6):1633-1637 (2006).

Ballard et al., "Inhibitors of epidermal growth factor receptor tyrosine kinase: Optimization of potency and in vivo pharmacokinets", Bioorganic & Medicinal Chemistry Letters 16(18):4908-4912 (2006).

Barker et al., "Studies Leading to the Identification of ZD1839 (Iressa™): An Orally Active, Selective Epidermal Growth Factor Receptor Tyrosine Kinase Inhibitor Targeted to the Treatment of Cancer", Bioorg. Med. Chem. Lett. 11(14):1911-1914 (2001).

Blowers "AZD8931". IASLC Annual Targeted Therapies of the Treatment of Lung Cancer Meeting (2011), Santa Monica, CA, PowerPoint Presentation.

Bridges et al., "Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor", J. Med. Chem. 39:267-276 (1996).

Chen et al., "Eludicating inhibitory models of the inhibitors of epidermal growth factor receptor by docking and 3D-QSAR", Bioorganic and Medicinal Chemistry 12:2409-2417 (2004).

Ciardiello et al., "Phase II study of gefitinib in combination with docetaxel as first-line therapy in metastic breast cancer", British Journal of Cancer 94(11):1604-1609 (2006).

Communication from European Patent Office dated Mar. 9, 2006, in EP App. No. 03710015.3, the European counterpart of the U.S. Appl. No. 10/508,675.

Communication from European Patent Office in EP App. No. 03710015.3, the European counterpart of the present application, U.S. Appl. No. 10/508,675, dated Sep. 22, 2006.

Communication from European Patent Office dated May 27, 2005, in EP App. No. 03710015.3, the European counterpart of U.S. Appl. No. 10/508,675.

Corrected version of Examination report in Singapore App. No. 200601647-1, the Singapore counterpart to the present application dated Sep. 5, 2008.

Cristofanilli et al., "Exploratory Subset Analysis According to Prior Endocrine Treatment of Two Randomized Phase II Trials Comparing Gefitinib (G) with Placebo (P) in Combination with Tamoxifen (T) or Anastrozole (A) in Hormone Receptor-Positive (HR+) Metastatic Breast Cancer (MBC)". J Clin. Oncol. (2009), vol. 27, 15s, Abstract 1014.

*Daiichi Sankyo Company, Ltd. et al.* v. *Matrix Laboratories, Ltd., et al.*, Appeal from the US District Court for the District of NJ in Case No. 06-CV-03462, 2009-1511, Decided Sep. 9, 2010.

Decision in Patent Interferences 105,595 McK and 105,596 McK dated Jun. 17, 2008.

Dennison et al., "A phase II clinical trial of ZD1839 (Iressa (TM)) in combination with docetaxel as first-line treatment in patients with advanced breast cancer", Investigational New Drugs; The Journal of New Anticancer Agents, Kluwer Academic Publishers 25(6):545-551 (2007).

Gazit et al., "Tyrophostins IV-Highly Potent Inhibitors . . . Relationship Study of 4-Anilidoquinazolines", Bioorganic & Medicinal Chemistry 4(8):1203-1207 (1996).

Ghosh et al., "Structure-based design of potent inhibitors of EGF-receptor tyrosine kinase as anti-cancer gents", Anti-Cancer Drug Design 14:403-410 (1999).

Grunwald et al., "Developing Inhibitors of the Epidermal Growth Factor Receptor for Cancer Treatment", J. National Cancer Institute 95(12):851-887 (2003).

Harris et al., "Selective alkylation of a 6,7-dihydroxyquinazoline", Tetrahedron Letters 46(45):7715-7719 (2005).

Harris et al., Poster presented at the XXII Colloquium on Heterocyclic Chemistry (XXII ECHC-2006) in Bari, Italy, on Sep. 2-6, 2006.

Harris et al., "Facile synthesis of 7-amino anilinoquinazolines via direct amination of the quinazoline core", Tetrahedron Letters 46(43):7381-7384 (2005).

Hennequin et al., "Novel 4-anilinoquinazolines with C-6 carbon-linked side chains: Synthesis and structure-activity relationship of a series of potent, orally active, EGF receptor tyrosine kinase inhibitors", Bioorganic & Medicinal Chemistry Letters 16(10):2672-2676 (2006).

Hennequin et al., "Design and structure-activity relationship of a new class of potent VEGF receptor tyrosine kinase inhibitors", J. Med. Chem. 42:5369-5389 (1999).

Hennequin et al., "Novel 4-anilinoquinazolines with C-7 basis side chains. Design and structure activity relationship of a series of potent, orally active, VEGF receptor tyrosine kinase inhibitors", J. Med. Chem. 45(6):1300-1312 (2002).

Hickinson et al., "AZD8931, an Equipotent, Reversible Inhibitor of Signaling by Epidermal Growht Factor Receptor, ERBB2 (HER2), and ERBB3: A Unique Agent for Simultaneous ERBB Receptor Blockage in Cancer", Clinical Cancer Research 16:1159-1169 (2010).

Keilholz et al. "Phase I Dose-Finding Study of Monotherapy with AZD8931, an Inhibitor of erbB 1, 2 and 3 Signaling, in Patients with Advanced Solid Tumors". ASCO (2011), Poster.

Keilholz et al. "Phase I Dose-Finding Study of Monotherapy with AZD8931, an Inhibitor of erbB 1, 2 and 3 Signaling, in Patients with Advanced Solid Tumors". J Clin Oncol. (2011), vol. 29, Abstract 3097.

Klinowska et al. "AZD8931, an Equipotent, Reversible Inhibitor of erbB 1, erbB2 and erbB3 Receptor Signaling: Characterisation of Pharmacological Profile". European Journal of Cancer Supplements (2009), vol. 7, No. 2, 127.

Kurebayashi et al., "Inhibition of HER1 signaling pathway enhances antitumor effect of endocrine therapy in breast cancer", 11(1):38-41 (2004).

Liu et al., "Blockage of epidermal growth factor receptor by quinazoline tyrosine kinase inhibitors suppresses growth of human hepatocellular carcinoma", Cancer Letters 248:32-40 (2007).

Lopez-Martin et al. "Phase I Dose-Finding Study of AZD8931, an Inhibitor of erbBl, 2 and 3 Receptor Signaling, in Combination with Paclitaxel". J Clin. Oncol. (2011), vol. 29, Abstract 3105.

Lopez Martin et al. "Phase I Dose-Finding Study of AZD8931, an Inhibitor of erbBl, 2 and 3 Receptor Signaling, in Combination with Paclitaxel". ASCO (2011), Poster.

March, J. Advanced Organic Chemistry—Reactions, Mechanisms, and Structure, $4^{th}$ Ed., John Wiley & Sons, NY, NY 357-362 (1992).

Marshall et al. "Evaluation of AZD8931, an Equipotent Inhibitor of erbB 1, erbB2 and erbB3 Receptor Signaling, on Ligand Stimulated Breast Cancer Cell Lines with Differing Levels of erbB2 Expression". SABCS (2009), Abstract 5059.

Mendelsohn "Targeting the Epidermal Growth Factor Receptor for Cancer Therapy", Journal of Clinical Oncology 29(18s):2s-13s (2002).

Mendelsohn et al., "Status of Epidermal Growth Factor Receptor Antagonists in the Biology and Treatment of Cancer", Journal of Clinical Oncology 21(14):2787-2799 (2003).

Myers et al., "The preparation and SAR of 4-(aniline),4-(phenoxy), and 4-(thiophenoxy)-quinazolines: inhibitors of p561ck and EGF-R tyrosine kinase activity", Bioorg. Med. Chem. Lett. 7(4):417-420 (1997).

Normanno et al. "Target-based therapies in breast cancer: current status and future perspectives". Endocr Relat Cancer (2009), vol. 16(3): 675-702.

Notices of Allowability and Allowance dated Jul. 26, 2006, in copending U.S. Appl. No. 10/857,342.

Office Action in copending U.S. Appl. No. 10/571,991 mailed Aug. 19, 2008.

Office Action in copending U.S. Appl. No. 10/572,048 mailed Oct. 31, 2008.

Office Action in copending U.S. Appl. No. 10/571,991 mailed Jan. 6, 2009.

Office Action in copending U.S. Appl. No. 12/147,250 mailed Aug. 17, 2009.

Office Action in copending U.S. Appl. No. 11/636,549 mailed Sep. 29, 2009.

Office Action in copending U.S. Appl. No. 10/572,048 mailed Jan. 5, 2010.

Office Action in copending U.S. Appl. No. 10/572,048 mailed Jun. 9, 2009.

Office Action in copending U.S. Appl. No. 10/573,352 mailed Oct. 28, 2009.

Office Action in copending U.S. Appl. No. 10/573,352 mailed Mar. 5, 2009.

Office Action in Singapore App. No. 200601647-1, the Singapore counterpart to the present application dated Sep. 7, 2007.

Okubo et al., "Additive antitumour effect of the epidermal growth factor receptor tyrosine kinase inhibitor gefitinib (Iressa, ZD 1839) and the antioestrogen fulvestrant (Faslodex, ICI 18, 780) in breast cancer cells", British Journal of Cancer 90(1):236-244 (2004).

Pao et al., "Epidermal Growth Factor Receptor Mutations, Small-Molecule Kinase Inhibitors, and Non-Small-Cell Lung Cancer: Current Knowledge and Future Directions", Journal of Clinical Oncology 23(11):1-13 (2005).

Patani et al., "Bioisosterism: A Rational Approach in Drug Design", Chem. Rev. 96:3147-3176 (1996).

Polychronis et al., "Preoperative gefitinib versus gefitinib and anastrozole in postmenopausal patents with oestrogen-receptor positive and epiderman-growth-factor-receptor-positive primary breast cancer: a double-blind placebo-controlled phase II randomized trial", 6(6):383-391 (2005).

Rewcastle et al., "Tyrosine Kinase Inhibitors. 5 . . . 4-(Phenylamino)quinazolines as Potent . . . Inhibitors of the Tyrosine Kinase Domain of the Epidermal Growth Factor Receptor", J. Med. Chem. 38:3482-3487 (1995).

Rewcastle et al., "Tyrosine Kinase Inhibitors. 12. Synthesis and Strukcture-Activity Relationships for 6-Substituted 4-(Phenylamino)pyrimido[5,4-d]pyrimidines Designed as Inhibitors of the Epidermal Growth Factor Receptor", J. Med. Chem. 40:1820-1826 (1997).

Singh et al., "Inhibitors of the epidermal growth factor receptor protein tyrosine kinase: A quantitative structure-activity relationship analysis", J. Enzyme Inhibition 13:125-134 (1998).

Smaill et al., "Tyrosine kinase inhibitors. 17. Irreversible inhibitors of the epidermal growth factor receptor: 4-(Phenylamino)quinazoline- and4-(Phe-nylamino)pyrido", J. Med. Chem. 43(16):3199 (2000).

Speake et al. "Characterization of AZD8931, a Potent Reversible Small Molecule Inhibitor Against Epidermal Growth Factor Receptor (EGFR), Erythroblastic Leukemia Viral Oncogene Homolog 2 (HER2) and 3 (HER3) with a Unique and Balanced Pharmacological Profile". J Clin. Oncol. (2009), vol. 27, 15s, Abstract 11072.

Stamos et al., "Structure of the Epidermal Growth Factor Receptor Kinase Domain Alone and in Complex with a 4-Anilinoquinazoline Inhibitor", J. Bio. Chem. 277(48):46265-46272 (2002).

Takabatake et al., "Tumor inhibitory effect of gefitinib (ZD1839, Iressa) and taxane combination therapy in EGFR-overexpressing breast cancer cell lines (MCMADR, MDA-MB-231)", International Journal of Cancer 120(1):181-188 (2007).

Thompson et al., "Tyrosine Kinase Inhibitors. 13. Structure-Activity Relationships for Soluble 7-Substituted 4-[(3-Bromophenyl)amino]pyrido[4,4-d]pyrimidines Designed as Inhibitors of the Tyrosine Kinase Activity of the Epidermal Growth Factor Receptor", J. Med. Chem. 40:3915-3925 (1997).

Traxler et al., "4-(Phenylamino)pyrrolopyrimidines: Potent and Selective, ATP Site Directed Inhibitors of the EFT-Receptor Protein Tyrosine Kinase", J. Med. Chem. 39:2285-2292 (1996).

Traxler "Oncologic, Endocrine & Metabolic: Protein tyrosine kinase inhibitors in cancer treatment", Expert Opinion on Therapeutic Patents 7:571-588 (1997).

Traxler "Monthly Focus: Oncologic, Endocrine & Metabolic: Tyrosine kinase inhibitors in cancer treatment (Part II)", Expert Opinion on Therapeutic Patents 8:1599-1625 (1998).

Tsou et al., "6-Substituted-4-(3-bromophenylamino)quinazolines as Putative Irreversible Inhibitors of the Epidermal Growth Factor Receptor (Egfr) and Human Epidermal Growth Factor Receptor (Her-2) Tyrosine Kinases with Enhanced Antitumor Activity", J. Med. Chem. 44:2719-2734 (2001).

Vema et al., "Design of EGFR Kinase Inhibitors: A Ligand-Based Approach and Its Confirmation with Structure-Based Studies," Bioorg. Med. Chem. 11:4643-4653 (2003).

Wright et al., "Allosteric inhibition of fructose-1,6-bisphosphatase by anilinoquinazolines", Bioorg Med. Chem. Lett. 11(1):17-21 (2001).

Xue et al., "ErbB3-dependent motility and intravasation in breast cancer metastasis", Cancer Research 66(3):1418-1426 (2006).

Chevalier et al. 'Induction of DNA Replication by Peroxisome Proliferators is Independent of Both Tumour Necrosis Factor alpha Priming and EGF-receptor Tyrosine Kinase Activity' Journal of Cell Science (1999); vol. 112; No. 24; pp. 4785-4791.

English translation of the opposition writ filed under Chilean Patent Application No. 2355/2044; Aug. 1, 2006.

European file history for European Patent No. 1667992; Jan. 24, 2007.

International Preliminary Report on Patentability in PCT/GB2004/003937; Mar. 30, 2006.

English Translation of Response to Office Action in Japanese Patent Appl. No. 2003-580299, the Japanese counterpart of U.S. Appl. No. 10/508,675, dated Oct. 26, 2006.

Response to Office Action in Chinese Patent Appl. No. 03811739.8, the Chinese counterpart of U.S. Appl. No. 10/508,675, dated Dec. 5, 2006.

English Translation of Response to Office Action in Chinese Patent Appl. No. 03811739.8, the Chinese counterpart of U.S. Appl. No. 10/508,675, dated Dec. 5, 2006.

Denny et al., "Structure-Activity Relationships for 4-Anilinoquinazolines as Potent Inhibitors at the ATP Binding Site for the Epidermal Growth Factor Receptor in vitro", Clinical and Experimental Pharmacology and Physiology 23: 424-427 (1996).

English Translation of Office Action in Japanese Patent Appl. No. 2003-580299, the Japanese counterpart of U.S. Appl. No. 10/508,675, dated May 11, 2006.

Response to Office Action in Japanese Patent Appl. No. 2003-580299, the Japanese counterpart of the present application, dated Jul. 28, 2006.

English Translation of Response to Office Action in Japanese Patent Appl. No. 2003-580299, the Japanese counterpart of U.S. Appl. No. 10/508,675, dated Jul. 28, 2006.

Office Action in Indian Patent Appl. No. 2630/DELNP/2004, the Indian counterpart of the present application, dated Apr. 20, 2006.

Response to Office Action in Indian Patent Appl. No. 2630/DELNP/2004, the Indian counterpart of the present application, dated Jul. 24, 2006.

English Translation of Office Action in Chinese Patent Appl. No. 03811739.8, the Chinese counterpart of the present application, dated Jul. 21, 2006.

Pending U.S. Appl. No. 11/487,727, filed Aug. 2, 2006.

Reply to May 27, 2005 communication for EPO dated Sep. 20, 2005, in EP Appl. No. 03710015.3.

Bradbury et al., "5-Substituted 4-anilionoquinazolines as Potent, Selective and Orally Active Inhibitors of erbB2 Receptor Tyrosine Kinase", Bioorganic & Medicinal Chemistry Letters 15(19): 4226-4229 (2005).

Kettle et al., "Inhibitors of Epidermal Growth Factor Receptor Tyrosine Kinase: Novel C-5 Substituted Anilinoquinazolines Designed to Target the Ribose Pocket", Bioorganic & Medicinal Chemistry Letters 16(6): 1633-1637 (2006).

Kettle et al., "Inhibitors of Epidermal Growth Factor Receptor Tyrosine Kinase: Optimization of Potency and in vivo Pharmacokinetics", Bioorganic & Medicinal Chemistry Letters 16(18): 4908-4912 (2006).

Hennequin et al., "Novel 4-anilinoquinazolines with C-6 Carbon-linked Side Chains: Synthesis and Structure Activity Relationship of a series of Potent, Orally Active, EGF Receptor Tyrosine Kinase Inhibitors", Bioorganic & Medicinal Chemistry Letters 16(10): 2672-2676 (2006).

4-ANILINO QUINAZOLINE DERIVATIVES AS ANTIPROLIFERATIVE AGENTS

This is a continuation of application Ser. No. 12/147,250, filed Jun. 26, 2008, now abandoned which is a continuation of application Ser. No. 10/508,675, filed Sep. 22, 2004, now abandoned which is a National Stage of PCT/GB03/01306 filed Mar. 26, 2003, and claims the benefit of GB 0207323.7, filed Mar. 28, 2002, GB 0230086.1, filed Dec. 24, 2002, and GB 0301916.3, filed Jan. 28, 2003, all of which are incorporated herein by reference.

The invention concerns certain novel quinazoline derivatives, or pharmaceutically-acceptable salts thereof, which possess anti-tumour activity and are accordingly useful in methods of treatment of the human or animal body. The invention also concerns processes for the manufacture of said quinazoline derivatives, to pharmaceutical compositions containing them and to their use in therapeutic methods, for example in the manufacture of medicaments for use in the prevention or treatment of solid tumour disease in a warm-blooded animal such as man.

Many of the current treatment regimes for diseases resulting from the abnormal regulation of cellular proliferation such as psoriasis and cancer, utilise compounds that inhibit DNA synthesis and cellular proliferation. To date, compounds used in such treatments are generally toxic to cells however their enhanced effects on rapidly dividing cells such as tumour cells can be beneficial. Alternative approaches to these cytotoxic anti-tumour agents are currently being developed, for example selective inhibitors of cell signalling pathways. These types of inhibitors are likely to have the potential to display an enhanced selectivity of action against tumour cells and so are likely to reduce the probability of the therapy possessing unwanted side effects.

Eukaryotic cells are continually responding to many diverse extracellular signals that enable communication between cells within an organism. These signals regulate a wide variety of physical responses in the cell including proliferation, differentiation, apoptosis and motility. The extracellular signals take the form of a diverse variety of soluble factors including growth factors as well as paracrine and endocrine factors. By binding to specific transmembrane receptors, these ligands integrate the extracellular signal to the intracellular signalling pathways, therefore transducing the signal across the plasma membrane and allowing the individual cell to respond to its extracellular signals. Many of these signal transduction processes utilise the reversible process of the phosphorylation of proteins that are involved in the promotion of these diverse cellular responses. The phosphorylation status of target proteins is regulated by specific kinases and phosphatases that are responsible for the regulation of about one third of all proteins encoded by the mammalian genome. As phosphorylation is such an important regulatory mechanism in the signal transduction process, it is therefore not surprising that aberrations in these intracellular pathways result in abnormal cell growth and differentiation and so promote cellular transformation (reviewed in Cohen et al, *Curr Opin Chem Biol*, 1999, 3, 459-465).

It has been widely shown that a number of these tyrosine kinases are mutated to constitutively active forms and/or when over-expressed result in the transformation of a variety of human cells. These mutated and over-expressed forms of the kinase are present in a large proportion of human tumours (reviewed in Kolibaba et al, Biochimica et Biophysica Acta, 1997, 133, F217-F248). As tyrosine kinases play fundamental roles in the proliferation and differentiation of a variety of tissues, much focus has centred on these enzymes in the development of novel anti-cancer therapies. This family of enzymes is divided into two groups—receptor and non-receptor tyrosine kinases e.g. EGF Receptors and the SRC family respectively. From the results of a large number of studies including the Human Genome Project, about 90 tyrosine kinase have been identified in the human genome, of this 58 are of the receptor type and 32 are of the non-receptor type. These can be compartmentalised in to 20 receptor tyrosine kinase and 10 non-receptor tyrosine kinase sub-families (Robinson et al, *Oncogene*, 2000, 19, 5548-5557).

The receptor tyrosine kinases are of particular importance in the transmission of mitogenic signals that initiate cellular replication. These large glycoproteins, which span the plasma membrane of the cell possess an extracellular binding domain for their specific ligands (such as Epidermal Growth Factor (EGF) for the EGF Receptor). Binding of ligand results in the activation of the receptor's kinase enzymatic activity that is encoded by the intracellular portion of the receptor. This activity phosphorylates key tyrosine amino acids in target proteins, resulting in the transduction of proliferative signals across the plasma membrane of the cell.

It is known that the erbB family of receptor tyrosine kinases, which include EGFR, erbB2, erbB3 and erbB4, are frequently involved in driving the proliferation and survival of tumour cells (reviewed in Olayioye et al., *EMBO J.*, 2000, 19, 3159). One mechanism in which this can be accomplished is by overexpression of the receptor at the protein level, generally as a result of gene amplification. This has been observed in many common human cancers (reviewed in Klapper et al., *Adv. Cancer Res.*, 2000, 77, 25) such as breast cancer (Sainsbury et al., *Brit. J. Cancer*, 1988, 58, 458; Guerin et al., *Oncogene Res.*, 1988, 3, 21; Slamon et al, *Science*, 1989, 244, 707; Klijn et al., *Breast Cancer Res. Treat.*, 1994, 29, 73 and reviewed in Salomon et al., *Crit. Rev. Oncol. Hematol.*, 1995, 19, 183), non-small cell lung cancers (NSCLCs) including adenocarcinomas (Cerny et al., *Brit. J. Cancer*, 1986, 54, 265; Reubi et al, *Int. J. Cancer*, 1990, 45, 269; Rusch et al, *Cancer Research*, 1993, 53, 2379; Brabender et al, *Clin. Cancer Res.*, 2001, 7, 1850) as well as other cancers of the lung (Hendler et al., *Cancer Cells*, 1989, 7, 347; Ohsaki et al., *Oncol. Rep.*, 2000, 7, 603), bladder cancer (Neal et al., *Lancet*, 1985, 366; Chow et al., *Clin. Cancer Res.*, 2001, 7, 1957, Zhau et al., *Mol. Carcinog.*, 3, 254), oesophageal cancer (Mukaida et al., *Cancer*, 1991, 68, 142), gastrointestinal cancer such as colon, rectal or stomach cancer (Bolen et al., *Oncogene Res.*, 1987, 1, 149; Kapitanovic et al., *Gastroenterology*, 2000, 112, 1103; Ross et al., *Cancer Invest.*, 2001, 19, 554), cancer of the prostate (Visakorpi et al., *Histochem J.*, 1992, 24, 481; Kumar et al., 2000, 32, 73; Scher et al., *J. Natl. Cancer Inst.*, 2000, 92, 1866), leukaemia (Konaka et al., *Cell*, 1984, 37, 1035, Martin-Subero et al., *Cancer Genet Cytogenet.*, 2001, 127, 174), ovarian (Hellstrom et al., *Cancer Res.*, 2001, 61, 2420), head and neck (Shiga et al., *Head Neck*, 2000, 22, 599) or pancreatic cancer (Ovotny et al., *Neoplasma*, 2001, 48, 188). As more human tumour tissues are tested for expression of the erbB family of receptor tyrosine kinases it is expected that their widespread prevalence and importance will be further enhanced in the future.

As a consequence of the mis-regulation of one or more of these receptors, it is widely believed that many tumours become clinically more aggressive and so correlate with a poorer prognosis for the patient (Brabender et al, *Clin. Cancer Res.*, 2001, 7, 1850; Ross et al, *Cancer Investigation*, 2001, 19, 554, Yu et al., *Bioessays*, 2000, 22.7, 673). In addition to these clinical findings, a wealth of pre-clinical information suggests that the erbB family of receptor tyrosine kinases are involved in cellular transformation. This includes the observations that many tumour cell lines overexpress one or more of the erbB receptors and that EGFR or erbB2 when transfected into non-tumour cells have the ability to transform these cells. This tumourigenic potential has been further verified as transgenic mice that overexpress erbB2 spontaneously develop tumours in the mammary gland. In addition to this, a number of pre-clinical studies have demonstrated that anti-proliferative effects can be induced by knocking out one or more erbB activities by small molecule inhibitors, dominant negatives or inhibitory antibodies (reviewed in Mendelsohn et al., *Oncogene*, 2000, 19, 6550). Thus it has been recognised that inhibitors of these receptor tyrosine kinases should be of value as a selective inhibitor of the proliferation of mammalian cancer cells (Yaish et al. *Science*, 1988, 242, 933, Kolibaba et al, Biochimica et Biophysica Acta, 1997, 133, F217-F248; Al-Obeidi et al, 2000, *Oncogene*, 19, 5690-5701; Mendelsohn et al, 2000, *Oncogene*, 19, 6550-6565). In addition to this pre-clinical data, findings using inhibitory antibodies against EGFR and erbB2 (c-225 and trastuzumab respectively) have proven to be beneficial in the clinic for the treatment of selected solid tumours (reviewed in Mendelsohn et al, 2000, *Oncogene*, 19, 6550-6565).

Amplification and/or activity of members of the erbB type receptor tyrosine kinases have been detected and so have been implicated to play a role in a number of non-malignant proliferative disorders such as psoriasis (Ben-Bassat, *Curr. Pharm. Des.*, 2000, 6, 933; Elder et al., *Science*, 1989, 243, 811), benign prostatic hyperplasia (BPH) (Kumar et al., *Int. Urol. Nephrol.*, 2000, 32, 73), atherosclerosis and restenosis (Bokemeyer et al., *Kidney Int.*, 2000, 58, 549). It is therefore expected that inhibitors of erbB type receptor tyrosine kinases will be useful in the treatment of these and other non-malignant disorders of excessive cellular proliferation.

European patent application EP 566 226 discloses certain 4-anilinoquinazolines that are receptor tyrosine kinase inhibitors.

International patent applications WO 96/33977, WO 96/33978, WO 96/33979, WO 96/33980, WO 96/33981, WO 97/30034, WO 97/38994 disclose that certain quinazoline derivatives which bear an anilino substituent at the 4-position and a substituent at the 6- and/or 7-position possess receptor tyrosine kinase inhibitory activity.

European patent application EP 837 063 discloses aryl substituted 4-aminoquinazoline derivatives carrying moiety containing an aryl or heteroaryl group at the 6- or 7-position on the quinazoline ring. The compounds are stated to be useful for treating hyperproliferative disorders.

International patent applications WO 97/30035 and WO 98/13354 disclose certain 4-anilinoquinazolines substituted at the 7-position are vascular endothelial growth factor receptor tyrosine kinase inhibitors.

WO 00/55141 discloses 6,7-substituted 4-anilinoquinazoline compounds characterised in that the substituents at the 6- and/or 7-position carry an ester linked moiety (RO—CO).

WO 00/56720 discloses 6,7-dialkoxy-4-anilinoquinazoline compounds for the treatment of cancer or allergic reactions.

WO 02/41882 discloses 4-anilinoquinazoline compounds substituted at the 6- and/or 7-position by a substituted pyrrolidinyl-alkoxy or piperidinyl-alkoxy group.

None of the prior art discloses 4-(2,3-dihalogenoanilino) quinazoline compounds.

We have now surprisingly found that certain 4-(2,3-dihalogenoanilino)quinazoline derivatives possess potent anti-tumour activity. Without wishing to imply that the compounds disclosed in the present invention possess pharmacological activity only by virtue of an effect on a single biological process, it is believed that the compounds provide an anti-tumour effect by way of inhibition of one or more of the erbB family of receptor tyrosine kinases that are involved in the signal transduction steps which lead to the proliferation of tumour cells. In particular, it is believed that the compounds of the present invention provide an anti-tumour effect by way of inhibition of EGFR and/or erbB2 receptor tyrosine kinases.

Generally the compounds of the present invention possess potent inhibitory activity against the erbB receptor tyrosine kinase family, for example by inhibition of EGFR and/or erbB2 and/or erbB4 receptor tyrosine kinases, whilst possessing less potent inhibitory activity against other kinases. Furthermore, certain compounds of the present invention possess substantially better potency against the EGFR over that of the erbB2 tyrosine kinase. The invention also includes compounds that are active against all or a combination of EGFR, erbB2 and erbB4 receptor tyrosine kinases, thus potentially providing treatments for conditions mediated by one or more of these receptor tyrosine kinases.

Generally the compounds of the present invention exhibit favourable physical properties such as a high solubility whilst retaining high antiproliferative activity. Furthermore, many of the compounds according to the present invention are inactive or only weakly active in a hERG assay.

According to a first aspect of the invention there is provided a quinazoline derivative of the Formula I:

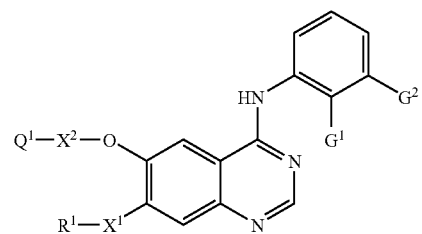

I wherein:
$G^1$ and $G^2$ each independently is halogeno;
$X^1$ is a direct bond or O;
$R^1$ is selected from hydrogen and (1-6C)alkyl, wherein the (1-6C)alkyl group is optionally substituted by one or more substituents, which may be the same or different, selected from hydroxy and halogeno, and/or a substituent selected from amino, nitro, carboxy, cyano, halogeno, (1-6C) alkoxy, hydroxy(1-6C)alkoxy, (2-8C)alkenyl, (2-8C)alkynyl, (1-6C)alkylthio, (1-6C)alkylsulfinyl, (1-6C)alkylsulfonyl, (1-6C)alkylamino, di-[(1-6C)alkyl]amino, carbamoyl, N-(1-6C)alkylcarbamoyl, N, Ndi-[(1-6C)alkyl]carbamoyl, (2-6C)alkanoyl, (2-6C)alkanoyloxy, (2-6C)alkanoylamino, N-(1-6C)alkyl-(2-6C)alkanoylamino, (1-6C)alkoxycarbonyl, sulfamoyl, N-(1-6C)alkylsulfamoyl, N, N-di-[(1-6C)alkyl]sulfamoyl, (1-6C)alkanesulfonylamino and N-(1-6C)alkyl-(1-6C)alkanesulfonylamino;
$X^2$ is a direct bond or $[CR^2R^3]_m$, wherein m is an integer from 1 to 6,
and each of $R^2$ and $R^3$ independently is selected from hydrogen, hydroxy, (1-4C)alkyl and hydroxy(1-4C)alkyl;
$Q^1$ is (3-7C)cycloalkyl or heterocyclyl, wherein $Q^1$ optionally bears 1, 2 or 3 substituents, which may be the same or different, selected from halogeno, trifluoromethyl, trifluoromethoxy, cyano, nitro, hydroxy, amino, carboxy, carbamoyl, acryloyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (2-6C)alkenylthio, (2-6C)alkynylthio, (1-6C)alkylsulfinyl, (2-6C)alkenylsulfinyl, (2-6C)alkynylsulfinyl, (1-6C)alkylsulfonyl, (2-6C)alkenylsulfonyl, (2-6C)alkynylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, sulfamoyl, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, carbamoyl(1-6C)alkyl, N-(1-6C)alkylcarbamoyl(1-6C)alkyl, N,N-di-[(1-6C)alkyl]carbamoyl (1-6C)alkyl, sulfamoyl(1-6C)alkyl, N-(1-6C)alkylsulfamoyl(1-6C)alkyl, N,N-di-[(1-6C)alkyl]sulfarnoyl(1-6C)alkyl, (2-6C)alkanoyl (1-6C)alkyl, (2-6C)alkanoyloxy(1-6C)alkyl, (2-6C)alkanoylamino(1-6C)alkyl, N-(1-6C)alkyl-(2-6C)alkanoylamino(1-6C)alkyl and (1-6C)alkoxycarbonyl(1-6C)alkyl, or from a group of the formula:

$Q^2$-$X^3$— wherein $X^3$ is CO and $Q^2$ is heterocyclyl, and wherein $Q^2$ optionally bears 1 or 2 substituents, which may be the same or different, selected from halogeno, hydroxy, (1-4C)alkyl, (2-4C)alkanoyl and (1-4C)alkylsulfonyl, and wherein any (1-6C)alkyl, (2-8C)alkenyl, (2-8C)alkynyl and (2-6C)alkanoyl group within $Q^1$ optionally bears one or more substituents (for example 1, 2 or 3) which may be the same or different selected from halogen, hydroxy and (1-6C)alkyl and/or optionally a substituent selected from cyano, nitro, carboxy, (2-8C)alkenyl, (2-4C)alkynyl, (1-6C)alkoxy, hydroxy(1-6C)alkoxy, (1-4C)alkoxy(1-6C)alkoxy, (2-6C)alkanoyl, (2-6C)alkanoyloxy and $NR^aR^b$, wherein $R^a$ is hydrogen or (1-4C)alkyl and $R^b$ is hydrogen or (1-4C)alkyl, and wherein any (1-4C)alkyl in $R^a$ or $R^b$ optionally bears one or more substituents (for example 1, 2 or 3) which may be the same or different selected from halogeno and hydroxy and/or optionally a substituent selected from cyano, nitro, (2-4C)alkenyl, (2-4C)alkynyl, (1-4C)alkoxy, hydroxy(1-4C)alkoxy and (1-2C)alkoxy(1-4C)alkoxy, or $R^a$ and $R^b$ together with the nitrogen atom to which they are attached form a 4, 5 or 6 membered ring, which optionally bears 1 or 2 substituents, which may be the same or different, on an available ring carbon atom selected from halogeno, hydroxy, (1-4C)alkyl and (1-3C)alkylenedioxy, and may optionally bear on any available ring nitrogen a substituent (provided the ring is not thereby quaternised) selected from (1-4C)alkyl, (2-4C)alkanoyl and (1-4C)alkylsulfonyl, and wherein any (1-4C)alkyl or (2-4C)alkanoyl group present as a substituent on the ring formed by $R^a$ and $R^b$ together with the nitrogen atom to which they are attached, optionally bears one or more substituents (for example 1, 2 or 3) which may be the same or different selected from halogeno and hydroxy and/or optionally a substituent selected from (1-4C)alkyl and (1-4C)alkoxy;

and wherein any heterocyclyl group within the $Q^1$-$X^2$— group optionally bears 1 or 2 oxo (=O) or thioxo (=S) substituents;

or a pharmaceutically acceptable salt thereof.

According to a further aspect of the present invention there is provided a quinazoline derivative of the Formula I wherein each of $R^1$, $G^1$, $G^2$, $X^1$ and $X^2$ has any of the meanings defined hereinbefore; and $Q^1$ is (3-7C)cycloalkyl or heterocyclyl, wherein $Q^1$ optionally bears 1, 2 or 3 substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (2-6C)alkenylsulfonyl, (1-6C)alkylamino, di-[(1-6C)alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, sulfamoyl, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, carbamoyl(1-6C)alkyl, N-(1-6C)alkylcarbamoyl(1-6C)alkyl, N,N-di-[(1-6C)alkyl]carbamoyl(1-6C)alkyl, (2-6C)alkanoyl (1-6C)alkyl, (2-6C)alkanoyloxy(1-6C)alkyl, (2-6C)alkanoylamino(1-6C)alkyl, N-(1-6C)alkyl-(2-6C)alkanoylamino(1-6C)alkyl and (1-6C)alkoxycarbonyl(1-6C)alkyl, or from a group of the formula:

$Q^2$-$X^3$— wherein $X^3$ is CO and $Q^2$ is heterocyclyl, and wherein $Q^2$ optionally bears 1 or 2 substituents, which may be the same or different, selected from (1-4C)alkyl, (2-4C)alkanoyl and (1-4C)alkylsulfonyl, and wherein any (1-6C)alkyl, (2-8C)alkenyl, (2-8C)alkynyl and (2-6C)alkanoyl group within $Q^1$ optionally bears one or more substituents (for example 1, 2 or 3) which may be the same or different selected from halogeno, hydroxy and (1-6C)alkyl and/or optionally a substituent selected from cyano, nitro, carboxy, (2-8C)alkenyl, (2-8C)alkynyl, (1-6C)alkoxy, hydroxy(1-6C)alkoxy, (2-6C)alkanoyl, (2-6C)alkanoyloxy and $NR^aR^b$, wherein $R^a$ is hydrogen or (1-4C)alkyl and $R^b$ is hydrogen or (1-4C)alkyl, or $R^a$ and $R^b$ together with the nitrogen atom to which they are attached faun a 4, 5 or 6 membered ring, which optionally bears 1 or 2 substituents, which may be the same or different, on an available ring carbon atom selected from (1-4C)alkyl, and may optionally bear on any available ring nitrogen a substituent (provided the ring is not thereby quaternised) selected from (1-4C)alkyl, (2-4C)alkanoyl and (1-4C)alkylsulfonyl;

and wherein any heterocyclyl group within the $Q^1$-$X^2$— group optionally bears 1 or 2 oxo (=O) or thioxo (=S) substituents;

or a pharmaceutically acceptable salt thereof.

According to a further aspect of the present invention there is provided a quinazoline derivative of the Formula I wherein each of $R^1$, $G^1$, $G^2$, $X^1$ and $X^2$ has any of the meanings defined hereinbefore; and $Q^1$ is (3-7C)cycloalkyl or heterocyclyl, wherein $Q^1$ optionally bears 1, 2 or 3 substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C) alkyl]amino, (1-6C)alkoxycarbonyl, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, sulfamoyl, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, carbamoyl(1-6C)alkyl, N-(1-6C)alkylcarbamoyl(1-6C)alkyl, N,N-di-[(1-6C)alkyl]carbamoyl(1-6C)alkyl, (2-6C)alkanoyl(1-6C)alkyl, (2-6C)alkanoyloxy(1-6C)alkyl, (2-6C)alkanoylamino(1-6C)alkyl, N-(1-6C)alkyl-(2-6C)alkanoylamino(1-6C)alkyl and (1-6C)alkoxycarbonyl(1-6C)alkyl, wherein any (1-6C)alkyl, (2-8C)alkenyl, (2-8C)alkynyl and (2-6C)alkanoyl group within $Q^1$ optionally bears one or more substituents (for example 1, 2 or 3) which may be the same or different selected from halogeno, hydroxy and (1-6C)alkyl and/or optionally a substituent selected from cyano, nitro, carboxy, (2-8C)alkenyl, (2-8C)alkynyl, (1-6C)alkoxy, hydroxy(1-6C)alkoxy and $NR^aR^b$, wherein $R^a$ is hydrogen or (1-4C)alkyl and $R^b$ is hydrogen or (1-4C)alkyl, or $R^a$ and $R^b$ together with the nitrogen atom to which they are attached form a 4, 5 or 6 membered ring;

and wherein any heterocyclyl group within the $Q^1$-$X^2$— group optionally bears 1 or 2 oxo (=O) or thioxo (=S) substituents;

or a pharmaceutically acceptable salt thereof.

According to a further aspect of the present invention there is provided a quinazoline derivative of the Formula I wherein each of $R^1$, $G^1$, $G^2$, $X^1$ and $X^2$ has any of the meanings defined hereinbefore; and $Q^1$ is a non-aromatic saturated or partially saturated 3 to 7 (for example 4, 5 or 6) membered monocyclic heterocyclyl ring with 1 ring nitrogen heteroatom and optionally 1 or 2 heteroatoms selected from nitrogen and sulfur, which ring is linked to the group $X^2$—O— by a ring carbon atom, and wherein $Q^1$ optionally bears 1, 2 or 3 substituents, which may be the same or different, selected from halogeno, trifluoromethyl, trifluoromethoxy, cyano, nitro, hydroxy, amino, carbamoyl, acryloyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (2-6C)alkenylthio, (2-6C)alkynylthio, (1-6C)alkylsulfinyl, (2-6C)alkenylsulfinyl, (2-6C)alkynylsulfinyl, (1-6C)alkylsulfonyl, (2-6C)alkenylsulfonyl, (2-6C)alkynylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoylamino, N-(1-6C)alkyl-(2-6C)alkanoylamino, sulfamoyl, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, carbamoyl(1-6C)alkyl, N-(1-6C)alkylcarbamoyl(1-6C)alkyl, N,N-di-[(1-6C)alkyl]carbamoyl(1-6C)alkyl, sulfamoyl(1-6C)alkyl, N-(1-6C)alkylsulfamoyl(1-6C)alkyl, N,N-di-[(1-6C)alkyl]sulfamoyl(1-6C)alkyl, (2-6C)alkanoyl(1-6C)alkyl, (2-6C)alkanoyloxy(1-6C)alkyl, (2-6C)alkanoylamino(1-6C)alkyl and N-(1-6C)alkyl-(2-6C)alkanoylamino(1-6C)alkyl, or from a group of the formula:

$$Q^2\text{-}X^3\text{—}$$

wherein $X^3$ is CO and $Q^2$ is a heterocyclyl group selected from morpholino and a 4, 5 or 6-membered monocycle heterocyclyl group containing 1 nitrogen heteroatom and optionally 1 or 2 heteroatoms selected from sulfur and nitrogen, and wherein $Q^2$ optionally bears 1 or 2 substituents, which may be the same or different, selected from halogeno, hydroxy, (1-4C)alkyl, (2-4C)alkanoyl and (1-4C)alkylsulfonyl, and wherein any (1-6C)alkyl, (2-8C)alkenyl, (2-8C)alkynyl and (2-6C)alkanoyl group within $Q^1$ optionally bears one or more substituents (for example 1, 2 or 3) which may be the same or different selected from halogeno, hydroxy and (1-6C)alkyl and/or optionally a substituent selected from cyano, nitro, (2-8C)alkenyl, (2-8C)alkynyl, (1-6C)alkoxy, hydroxy(1-6C)alkoxy, (1-4C)alkoxy(1-6C)alkoxy, (2-6C)alkanoyl, (2-6C)alkanoyloxy and $NR^aR^b$, wherein $R^b$ is hydrogen or (1-4C)alkyl and $R^b$ is hydrogen or (1-4C)alkyl, and wherein any (1-4C)alkyl in $R^a$ or $R^b$ optionally bears one or more substituents (for example 1, 2 or 3) which may be the same or different selected from halogeno and hydroxy and/or optionally a substituent selected from cyano, nitro, (2-4C)alkenyl, (2-4C)alkynyl, (1-4C)alkoxy, hydroxy(1-4C)alkoxy and (1-2C)alkoxy(1-4C)alkoxy, or $R^a$ and $R^b$ together with the nitrogen atom to which they are attached form a 4, 5 or 6 membered ring, which optionally bears 1 or 2 substituents, which may be the same or different, on an available ring carbon atom selected from halogen, hydroxy, (1-4C)alkyl and (1-3C)alkylenedioxy, and may optionally bear on any available ring nitrogen a substituent (provided the ring is not thereby quaternised) selected from (1-4C)alkyl, (2-4C)alkanoyl and (1-4C)alkylsulfonyl, and wherein any (1-4C)alkyl or (2-4C)alkanoyl group present as a substituent on the ring formed by $R^a$ and $R^b$ together with the nitrogen atom to which they are attached optionally bears one or more substituents (for example 1, 2 or 3), which may be the same or different, selected from halogeno and hydroxy and/or optionally a substituent selected from (1-4C)alkyl and (1-4C)alkoxy;

and wherein any heterocyclyl group within the $Q^1$-$X^2$— group optionally bears 1 or 2 oxo (=C) or thioxo (=S) substituents;

provided that when $X^2$ is $[CH_2]_m$, is an integer from 1 to 6, and $Q^1$ is a pyrrolidinyl or piperidinyl group substituted at the 1-position by a (2-4C)alkyl car (2-5C)alkanoyl group, then the (2-4C)alkyl or (2-5C)alkanoyl group at the 1-position on $Q^1$ is not substituted by a 2-oxo-morpholino group;

or a pharmaceutically acceptable salt thereof.

In this specification the generic term "alkyl" includes both straight-chain and branched-chain alkyl groups such as propyl, isopropyl and tert-butyl, and (3-7C)cycloalkyl groups such as cyclopropyl, cyclobutyl, cyclopentyl, cyclohexyl and cycloheptyl. However references to individual alkyl groups such as "propyl" are specific for the straight-chain version only, references to individual branched-chain alkyl groups such as "isopropyl" are specific for the branched-chain version only and references to individual cycloalkyl groups such as "cyclopentyl" are specific for that 5-membered ring only. An analogous convention applies to other generic terms, for example (1-6C)alkoxy includes methoxy, ethoxy, cyclopropyloxy and cyclopentyloxy, (1-6C)alkylamino includes methylamino, ethylamino, cyclobutylamino and cyclohexylamino, and di-[(1-6Calkyl]amino includes dimethylamino, diethylamine, N-cyclobutyl-N-methylamino and N-cyclohexyl-N-ethylamino.

It is to be understood that, insofar as certain of the compounds of Formula I defined above may exist in optically active or racemic forms by virtue of one or more asymmetrically substituted carbon and/or sulfur atoms, and accordingly may exist in, and be isolated as enantiomerically pure, a mixture of diastereoisomers or as a racemate. The present invention includes in its definition any racemic, optically-active, enantiomerically pure, mixture of diastereoisomers, stereoisomeric form of the compound of Formula (I), or mixtures thereof, which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

The invention relates to all tautomeric forms of the compounds of the Formula I that possess antiproliferative activity.

It is also to be understood that certain compounds of the Formula I may exist in solvated as well as unsolvated forms such as, for example, hydrated forms. It is to be understood that the invention encompasses all such solvated forms which possess antiproliferative activity.

It is also to be understood that certain compounds of the Formula I may exhibit polymorphism, and that the invention encompasses all such forms which possess antiproliferative activity.

Suitable values for the generic radicals referred to above include those set out below.

A suitable value for $Q^1$ when it is (3-7C)cycloalkyl is, for example, cyclopropyl, cyclobutyl, cyclopentyl, cyclohexyl, cycloheptyl or bicyclo[2.2.1]heptyl.

When $Q^1$ or $Q^2$ is heterocyclyl it is a non-aromatic saturated (i.e. with the maximum degree of saturation) or partially saturated (i.e. ring systems retaining some, but not the full, degree of unsaturation) 3 to 10 membered monocyclic ring with up to five heteroatoms selected from oxygen, nitrogen and sulfur (but not containing any O—O, O—S or S—S bonds), and linked via a ring carbon atom, or a ring nitrogen atom (provided the ring is not thereby quaternised). Suitable values for $Q^1$ or $Q^2$ include for example, oxiranyl, oxetanyl, azetidinyl, tetrahydrofuranyl, tetrahydropyranyl, oxepanyl, oxazepanyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothienyl, tetrahydrothiopyranyl, thiomorpholinyl, more specifically including for example, tetrahydrofuran-3-yl, tetrahydrofuran-2-yl, tetrahydropyran-4-yl, tetrahydrothien-3-yl, tetrahydrothiopyran-4-yl, pyrrolidin-3-yl, pyrrolidin-2-yl, 3-pyrrolin-3-yl, morpholino, 1,1-dioxotetrahydro-4H-1,4-thiazin-4-yl, piperidino, piperidin-4-yl, piperidin-3-yl, piperidin-2-yl, homopiperidin-3-yl, homopiperidin-4-yl, piperazin-1-yl, 1,4-oxazepanyl, or 1,2,3,6-tetrahydropyridin-4-yl. A nitrogen or sulfur atom within a heterocyclyl group may be oxidized to give the corresponding N or S oxide(s), for example 1,1-dioxotetrahydrothienyl, 1-oxotetrahydrothienyl, 1,1-dioxotetrahydrothiopyranyl or 1-oxotetrahydrothiopyranyl. A suitable value for such a group which bears 1 or 2 oxo or thioxo substituents is, for example, 2-oxopyrrolidinyl, 2-oxopiperazinyl, 2-thioxopyrrolidinyl, 2-oxopiperidinyl, 2,5-dioxopyrrolidinyl or 2,6-dioxopiperidinyl.

Particular values for $Q^1$ and $Q^2$ include, for example, non-aromatic saturated or partially saturated 3 to 7 membered monocyclic heterocyclyl rings with 1 ring nitrogen or sulfur heteroatom and optionally 1 or 2 heteroatoms selected from nitrogen, oxygen and sulfur. Examples of such rings include azetidinyl, oxazepanyl, pyrrolinyl, pyrrolidinyl, morpholinyl, tetrahydro-1,4-thiazinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothienyl, tetrahydrothiopyranyl or thiomorpholinyl.

Further particular values for $Q^1$ include, for example, non-aromatic saturated or partially saturated 3 to 7 membered monocyclic heterocyclyl rings with 1 ring nitrogen heteroatom and optionally 1 or 2 heteroatoms selected from nitrogen and sulfur, which rings are linked to $X^2$—O by a ring carbon atom, such as, for example, azetidinyl, pyrrolinyl, pyrrolidinyl, tetrahydro-1,4-thiazinyl, piperidinyl, homopiperidinyl, piperazinyl, homopiperazinyl, dihydropyridinyl, tetrahydropyridinyl, dihydropyrimidinyl, tetrahydropyrimidinyl, tetrahydrothiopyranyl car thiomorpholinyl. More particularly $Q^1$ is a non-aromatic saturated or partially saturated 4, 5 or 6 membered monocyclic heterocyclyl ring with 1 or 2 ring nitrogen heteroatom(s), which ring is linked to the group $X^2$—O— by a ring carbon atom, more particularly pyrrolidin-3-yl, pyrrolidin-2-yl, 3-pyrrolin-3-yl-, piperidin-4-yl, piperidin-3-yl, piperidin-2-yl, homopiperidin-3-yl, homopiperidin-4-yl, piperazin-2-yl, piperazin-3-yl, or 1,2,3,6-tetrahydropyridin-4-yl. A nitrogen atom within a heterocyclyl group may be oxidized to give the corresponding N oxide.

Particular values for $Q^2$ include, for example, morpholine, or 4, 5 or 6 membered heterocyclyl rings containing 1 nitrogen atom and optionally 1 or 2 heteroatoms selected from nitrogen and sulfur such as piperazinyl, pyrrolidinyl, piperidinyl, particularly pyrrolidin-1-yl, pyrrolidin-2-yl, piperazin-1-yl or piperidino.

When $R^a$ and $R^b$ together with the nitrogen atom to which they are attached form a 4, 5 or 6 membered ring, the ring is a saturated or partially saturated non-aromatic heterocyclyl ring containing 1 nitrogen and optionally 1 or 2 heteroatoms selected from oxygen, sulfur and nitrogen (but not containing any O—O, O—S or S—S bonds), and wherein the zing so formed is linked via a ring nitrogen atom to the group to which the ring is attached. The ring may optionally bear 1 or 2 substituents on an available ring carbon atom as hereinbefore defined (for example selected from (1-4C)alkyl), and may optionally bear on any available ring nitrogen a substituent (provided the ring is not thereby quaternised) as hereinbefore defined (for example selected from (1-4C)alkyl, (2-4C)alkanoyl and (1-4C)alkylsulfonyl). Suitable values for $R^a$ and $R^b$ together with the nitrogen atom to which they are attached form a 4, 5 or 6 membered ring include, for example, 2-pyrrolin-1-yl, 3-pyrrolin-1-yl, pyrrolidin-1-yl, piperidino, piperazin-1-yl and morpholino.

Suitable values for any of the $R^1$, $R^2$, $R^3$, $R^4$, $R^4$, $R^a$, $R^b$, $G^1$, $G^2$ or for various groups within $Q^1$ as defined hereinbefore or hereafter in this specification include: —

| | |
|---|---|
| for halogeno | fluoro, chloro, bromo and iodo; |
| for (1-6C)alkyl: | methyl, ethyl, propyl, isopropyl, tert-butyl, pentyl and hexyl; |
| for (1-4C)alkyl: | methyl, ethyl, propyl, isopropyl and tert-butyl; |
| for (1-6C)alkoxy: | methoxy, ethoxy, propoxy, isopropoxy and butoxy; |
| for (2-8C)alkenyl: | vinyl, isopropenyl, allyl and but-2-enyl; |
| for (2-8C)alkynyl: | ethynyl, 2-propynyl and but-2-ynyl; |
| for (2-6C)alkenyloxy: | vinyloxy and allyloxy; |
| for (2-6C)alkynyloxy: | ethynyloxy and 2-propynyloxy; |
| for (1-6C)alkylthio: | methylthio, ethylthio and propylthio; |
| for (2-6C)alkenylthio: | vinylthio and allylthio; |
| for (2-6C)alkynylthio: | ethynylthio and 2-propynylthio |
| for (1-6C)alkylsulfinyl: | methylsulfinyl and ethylsulfinyl; |

-continued

| | |
|---|---|
| for (2-6C)alkenylsulfinyl: | vinylsulfinyl and allylsulfinyl; |
| for (2-6C)alkynylsulfinyl: | ethynylsulfinyl and 2-propynylsulfinyl |
| for (1-6C)alkylsulfonyl: | methylsulfonyl and ethylsulfonyl; |
| for (2-6C)alkenylsulfonyl: | vinylsulfonyl and allylsulfonyl; |
| for (2-6C)alkynylsulfonyl: | ethynylsulfonyl and 2-propynylsulfonyl; |
| for (1-6C)alkylamino: | methylamino, ethylamino, propylamino, isopropylamino and butylamino; |
| for di-[(1-6C)alkyl]amino: | dimethylamino, diethylamino, N-ethyl-N-methylamino and diisopropylamino; |
| for (1-6C)alkoxycarbonyl: | methoxycarbanyl, ethoxycarbonyl, propoxycarbonyl and tert-butoxycarbonyl; |
| for N-(1-6C)alkylcarbamoyl: | N-methylcarbamoyl, N-ethylcarbamoyl, N-propylcarbamoyl and N-isopropylcarbamoyl; |
| for N,N-d-[(1-6C)alkyl]carbamoyl: | N,N-dimethylcarbamoyl, N-ethyl-N-methylcarbamoyl and N,N-diethylcarbamoyl; |
| for (2-6C)alkanoyl: | acetyl, propionyl and isobutyryl; |
| for (2-6C)alkanoyloxy: | acetoxy and propionyloxy; |
| for (2-6C)alkanoylamino: | acetamido and propionamido; |
| for N-(1-6C)alkyl-(2-6C)alkanoylamino: | N-methylacetamido and N-methylpropionamido; |
| for N-(1-6C)alkylsulfamoyl: | N-methylsulfamoyl, N-ethylsulfamoyl and N-isopropylsulfamoyl; |
| for N,N-di-[(1-6C)alkyl]sulfamoyl: | N,N-dimethylsulfamoyl and N-methyl-N-ethylsulfamoyl; |
| for (1-6C)alkanesulfonylamino: | methanesulfonylamino and ethanesulfonylamino; |
| for N-(1-6C)alkyl-(1-6C)alkanesulfonylamino: | N-methylmethanesulfonylamino and N-methylethanesulfonylamino; |
| for amino-(1-6C)alkyl; | aminomethyl, 2-aminoethyl, 1-aminoethyl and 3-aminopropyl; |
| for (1-6C)alkylamino-(1-6C)alkyl: | methylaminomethyl, ethylaminomethyl, 1-methylaminoethyl, 2-methylaminoethyl, 2-ethylaminoethyl and 3-methylaminopropyl; |
| for di-[(1-6C)alkyflamino-(1-6C)alkyl: | dimethylaminomethyl, diethylaminomethyl, 1-dimethylaminoethyl, 2-dimethylaminoethyl and 3-dimethylaminopropyl; |
| for halogeno-(1-6C)alkyl: | chloromethyl, 2-chloroethyl, 1-chloroethyl and 3-chloropropyl; |
| for hydroxy-(1-6C)alkyl: | hydroxymethyl, 2-hydroxyethyl, 1-hydroxyethyl and 3-hydroxypropyl; |
| for hydroxy-(1-6C)alkoxy: | hydroxymethoxy, 2-hydroxyethoxy, 1-hydroxyethoxy and 3-hydroxypropoxy; |
| for (1-6C)alkoxy-(1-6C)alkyl: | methoxymethyl, ethoxymethyl, 1-methoxyethyl, 2-methoxyethyl, 2-ethoxyethyl and 3-methoxypropyl; |
| for cyano-(1-6C)alkyl: | cyanomethyl, 2-cyanoethyl, 1-cyanoethyl and 3-cyanopropyl; |
| for amino(2-6C)alkanoyl: | aminoacetyl and 2-aminopropionyl; |
| for (1-6C)alkylamino-(2-6C)alkanoyl: | methylaminoacetyl and 3-(methylamino)propionyl; |
| for N,N-di-[(1-6C)alkyl]amino-(2-6C)alkanoyl: | di-methylaminoacetyl and 3-(di-methylamino)propionyl; |
| for (2-6C)alkanoylamino-(1-6C)alkyl: | acetamidomethyl, propionamidomethyl and 2-acetamidoethyl; |
| for N-(1-6C)alkyl-(2-6C)alkanoylamino(1-6C)alkyl: | N-methylacetamidomethyl, N-methylpropionamidomethyl, 2-(N-methylacetamido)ethyl and 2-(N-methylpropionamido)ethyl; |
| for (1-6C)alkoxycarbonylamino-(1-6C)alkyl: | methoxycarbonylaminomethyl, ethoxycarbonylaminomethyl, tert-butoxycarbonylaminomethyl and 2-methoxycarbonylaminoethyl; |
| for carbamoyl(1-6C)alkyl: | carbamoylmethyl, 1-carbamoylethyl, 2-carbamoylethyl and 3-carbamoylpropyl; |
| for N-(1-6C)alkylcarbamoyl(1-6C)alkyl: | N-methylcarbamoylmethyl, N-ethylcarbamoylmethyl, N-propylcarbamoylmethyl, 1-(N-methylcarbamoyl)ethyl, 2-(N-methylcarbamoyl)ethyl and 3-(N-methylcarbamoyl)propyl; |
| for N,N di-(1-6C)alkylcarbamoyl(1-6C)alkyl: | N,N-dimethylcarbamoylmethyl, N,N-diethylcarbamoylmethyl, N methyl,N-ethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl; |
| for sulfamoyl(1-6C)alkyl: | sulfamoylmethyl, 1-sulfamoylethyl, 2-sulfamoylethyl and 3-sulfamoylpropyl; |

| | |
|---|---|
| for N-(1-6C)alkylsulfamoyl(1-6C)alkyl: | N-methylsulfamoylmethyl, N-ethylsulfamoylmethyl, N-propylsulfamoylmethyl, 1-(N-methylsulfamoyl)ethyl, 2-(N-methylsulfamoyl)ethyl and 3-(N-methylsulfamoyl)propyl; |
| for N,N di-(1-6C)alkylsulfamoyl(1-6C)alkyl: | N,N-dimethylsulfamoylmethyl, N,N-diethylsulfamoylmethyl, N methyl,N-ethylsulfamoylmethyl, 1-(N,N-dimethylsulfamoypethyl, 1-(N,N-diethylsulfamoyl)ethyl, 2-(N,N-dimethylsulfamoyl)ethyl, 2-(N,N-diethylsulfamoyl)ethyl and 3-(N,N-dimethylsulfamoyl)propyl; |
| for (2-6C)alkanoyl(1-6C)alkyl: | acetylinethyl, propionylmethyl, 2-acetylethyl and 2-propionylethyl; |
| for (2-6C)alkanoyloxy(1-6C)alkyl: | acetoxymethyl, propionyloxymethyl, 2-acetoxyethyl and 3-acetoxypropyl; |
| for (1-6C)alkoxy(1-6C)alkylS(O)$_q$: | 2-methoxyethylsulfonyl, 2-methoxyethylsulpinyl and 2-methoxyethylthio; |
| for amino(1-6C)alkylS(O)$_q$: | 2-aminoethylsulfonyl, 2-aminoethylsulfinyl and 2-aminoethylthio; |
| for N-(1-6C)alkylamino(1-6C)alkylS(O)$_q$: | 2-(methylamino)ethylsulfonyl, 2-(ethylamino)ethylsulfinyl and 2-(methylamino)ethylthio; and |
| for N,N-di[(1-6C)alkyl]amino(1-6C)alkylS(O)$_q$: | 2-(dimethylamino)ethylsulfonyl, 3-(dimethlyamino)propylsulfonyl, 2-(di-ethylamino)ethylsulfinyl and 2-(N-methyl-N-ethylamino)ethylthio. |

A suitable value for a (1-3C)alkylenedioxy group which may be present as a substituent on the ring formed by $R^a$ and $R^b$ together with the nitrogen atom to which they are attached is, for example, methylenedioxy, ethylidenedioxy, isopropylidenedioxy or ethylenedioxy and the oxygen atoms thereof occupy adjacent ring positions. For example when $R^a$ and $R^b$ together with the nitrogen atom to which they are attached faun a pyrrolidin-1-yl ring the ring may substituted with a methylenedioxy group to give a 3,4-methylenedioxypyrrolidin-1-yl group.

As defined hereinbefore, a (1-6C)alkyl, (2-8C)alkenyl, (2-8C)alkynyl or (2-6C)alkanoyl group within $Q^1$ may be substituted by, for example, a group such as hydroxy, (2-8C) alkenyl, (2-6C)alkanoyl, (2-6C)alkanoyloxy or $NR^aR^b$, wherein $R^a$ and $R^b$ are as hereinbefore defined. For example when $Q^1$ is substituted by an acetyl group, the acetyl group may itself be substituted with a di-[(1-6C)alkyl]amino group to form for example a di-methylaminoacetyl or N-methyl-N-ethylamino-acetyl group on $Q^1$, or an acetyl group may be substituted with a (2-8C)alkenyl group to give an alkenoyl group, for example an acetyl group substituted by an allyl group to give but-3-enoyl. Similarly when, for example $Q^1$ is substituted by a (1-6C)alkyl sulfonyl group such as propylsulfonyl, the (1-6C)alkyl group may be substituted with, for example, a dimethylamino group to give a dimethylamino-(1-6C)alkyl sulfonyl group such as 3-(dimethylamino)propylsulfonyl. By way of a further example, when $Q^1$ is substituted by a N-methylcarbamoyl group, the methyl group may, for example be substituted by a (2-6C)alkenyl or (2-6C)alkynyl group to give, for example a N-allylcarbamoyl or N-(2-propynyl)carbamoyl group.

It is to be understood that when, $R^1$ is a group (1-6C)alkyl substituted by, for example amino to give for example a 2-aminoethyl group, it is the (1-6C)alkyl group that is attached to the group $X^1$ (or the quinazoline ring when $X^1$ is a direct bond). An analogous convention applies to the other groups defined herein. For example, when $Q^1$ is carries a (1-6C)alkyl group substituted by (1-6C)alkoxy to give a (1-6C)alkoxy(1-6C)alkyl substituent, it is the (1-6C)alkyl that is linked to $Q^1$.

It is to be understood that when $X^3$ is CO, it is a carbonyl group.

When it is stated herein that "any heterocyclyl group within the $Q^1$-$X^2$— group optionally bears 1 or 2 oxo (=O) or thioxo (=S) substituents", the oxo and/or thioxo groups may be present on any heterocyclyl group within $Q^1$ including heterocyclyl groups represented by $Q^1$ itself, by $Q^2$ and when $R^a$ and $R^b$ together with the nitrogen atom to which they are attached form a 4, 5 or 6 membered heterocyclyl ring.

When in this specification reference is made to a (1-4C) alkyl group it is to be understood that such groups refer to alkyl groups containing up to 4 carbon atoms. A skilled person will realise that representative examples of such groups are those listed above under (1-6C)alkyl that contain up to 4 carbon atoms, such as methyl, ethyl, propyl, isopropyl, butyl and tert-butyl. Similarly, reference to a (1-3C)alkyl group refers to alkyl groups containing up to 3 carbon atoms such as methyl, ethyl, propyl and isopropyl. A similar convention is adopted for the other groups listed above such as (1-4C) alkoxy, (2-4C)alkenyl, (2-4C)alkynyl and (2-4C)alkanoyl.

In the compound of Formula I hydrogen atoms are present at the 2, 5 and 8 positions on the quinazoline ring.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulfuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

Particular novel compounds of the invention include, for example, quinazoline derivatives of the Formula I, or pharmaceutically-acceptable salts thereof, wherein, unless otherwise stated, each of m, $R^1$, $R^2$, $R^3$, $Q^1$, $Q^2$, $X^1$, $X^2$, m, $G^1$ and $G^2$ has any of the meanings defined hereinbefore or in paragraphs (a) to (qqq) hereinafter:—

(a) $Q^1$ is a non-aromatic saturated or partially saturated 3 to 7 membered monocyclic heterocyclyl ring with 1, 2 or 3 heteroatoms selected from oxygen, nitrogen and sulfur, linked to the group $X^2$—O by a ring carbon or a ring nitrogen (provided that the ring is not thereby quaternized), and wherein any available nitrogen in $Q^1$ optionally bears a substituent (where such substitution does not result in quaternization) selected from trifluoromethyl, cyano, carbamoyl, trifluoromethyl, (1-6C)alkyl, (2-8C)alkenyl, (2-8C)alkynyl, (1-6C)alkylthio, (1-6C)alkylsulfinyl, (1-6C)alkylsulfonyl, (1-6C)alkoxycarbonyl, N-(1-6C)alkylcarbamoyl, N,N-di-[(1-6C)alkyl]carbamoyl, (2-6C)alkanoyl, sulfamoyl, N-(1-6C)alkylsulfamoyl, N,N-di-[(1-6C)alkyl]sulfamoyl, carbamoyl(1-6C)alkyl, N-(1-6C)alkylcarbamoyl(1-6C)alkyl, N,N-di-[(1-6C)alkyl]carbamoyl(1-6C)alkyl, (2-6C)alkanoyl(1-6C)alkyl, (2-6C)alkanoyloxy(1-6C)alkyl, (2-6C)alkanoylamino(1-6C)alkyl, N-(1-6C)alkyl-(2-6C)alkanoylamino(1-6C)alkyl and (1-6C)alkoxycarbonyl(1-6C)alkyl, wherein any (1-6C)alkyl, (2-8C)alkenyl, (2-8C)alkynyl and (2-6C)alkanoyl group within an optional substituent on an available nitrogen is optionally substituted by one or more substituents, which maybe the same or different, selected from fluoro, chloro, hydroxy and (1-4C)alkyl, and/or optionally a substituent selected from cyano, nitro, carboxy, (1-4C)alkoxy, hydroxy(1-4C)alkoxy and $NR^aR^b$, wherein $R^a$ is hydrogen or (1-4C)alkyl and $R^b$ is hydrogen or (1-4C)alkyl, and $Q^1$ optionally bears on any available carbon atom in the ring 1 or 2 (suitably 1) substituents selected from halogeno, trifluoromethyl, cyano, nitro, hydroxy, amino, carboxy, carbamoyl, (1-4C)alkyl, (2-6C)alkenyl, (2-6C)alkynyl, (1-4C)alkoxy, (1-6C)alkylamino, di-[(1-6C)alkyl]amino, (2-6C)alkanoylamino, N-(1-6C)alkyl-(2-6C)alkanoylamino, hydroxy(1-6C)alkyl, cyano(1-6C)alkyl, amino(1-6C)alkyl, (1-6C)alkylamino(1-6C)alkyl, di-[(1-6C)alkyl]amino(1-6C)alkyl and (1-6C)alkoxy(1-6C)alkyl, and wherein $Q^1$ optionally bears 1 or 2 oxo or thioxo substituents;

(b) $Q^1$ is a non-aromatic saturated or partially saturated 3 to 7 membered monocyclic heterocyclyl ring with 1, 2 or 3 heteroatoms selected from oxygen, nitrogen and sulfur, linked to the group $X^2$— O by a ring carbon, and wherein any available nitrogen in $Q^1$ optionally bears a substituent (where such substitution does not result in quaternization) selected from trifluoromethyl, cyano, carbamoyl, (1-6C)alkyl, (2-8C)alkenyl, (2-8C)alkynyl, (1-6C)alkylthio, (1-6C)alkylsulfinyl, (1-6C)alkylsulfonyl, (1-6C)alkoxycarbonyl, N-(1-6C)alkylcarbamoyl, N,N-di-[(1-6C)alkyl]carbamoyl, (2-6C)alkanoyl, sulfamoyl, N-(1-6C)alkylsulfamoyl, N,N-di-[(1-6C)alkyl]sulfamoyl, carbamoyl(1-6C)alkyl, N-(1-6C)alkylcarbamoyl(1-6C)alkyl, N,N-di-[(1-6C)alkyl]carbamoyl(1-6C)alkyl, (2-6C)alkanoyl(1-6C)alkyl, (2-6C)alkanoyloxy(1-6C)alkyl, (2-6C)alkanoylamino(1-6C)alkyl, N-(1-6C)alkyl-(2-6C)alkanoylamino(1-6C)alkyl and (1-6C)alkoxycarbonyl(1-6C)alkyl, wherein any (1-6C)alkyl, (2-8C)alkenyl, (2-8C)alkynyl and (2-6C)alkanoyl group within an optional substituent on an available nitrogen is optionally substituted by one or more substituents, which maybe the same or different, selected from fluoro, chloro, hydroxy and (1-4C)alkyl, and/or optionally a substituent selected from cyano, nitro, carboxy, (1-4C)alkoxy, hydroxy(1-4C)alkoxy and $NR^aR^b$, wherein $R^a$ is hydrogen or (1-4C)alkyl and $R^b$ is hydrogen or (1-4C)alkyl, and $Q^1$ optionally bears on any available carbon atom in the ring 1 or 2 (suitably 1) substituents selected from halogeno, trifluoromethyl, cyano, nitro, hydroxy, amino, carboxy, carbamoyl, (1-4C)alkyl, (2-6C)alkenyl, (2-6C)alkynyl, (1-4C)alkoxy, (1-6C)alkylamino, di-[(1-6C)alkyl]amino, (2-6C)alkanoylamino, N-(1-6C)alkyl-(2-6C)alkanoylamino, hydroxy(1-6C)alkyl, cyano(1-6C)alkyl, amino(1-6C)alkyl, (1-6C)alkylamino(1-6C)alkyl, di-[(1-6C)alkyl]amino(1-6C)alkyl and (1-6C)alkoxy(1-6C)alkyl, and wherein $Q^1$ optionally bears 1 or 2 oxo or thioxo substituents;

(c) $Q^1$ is a non-aromatic saturated or partially saturated 3 to 7 membered monocyclic heterocyclyl ring with 1 nitrogen heteroatom and optionally 1 or 2 heteroatoms selected from oxygen, nitrogen and sulfur, which ring is linked to the group $X^2$—O— by a carbon atom in the ring, and wherein the nitrogen atom of any NH group in $Q^1$ optionally bears a substituent selected from cyano, carbamoyl, trifluoromethyl, (1-6C)alkyl, (2-8C)alkenyl, (2-8C)alkynyl, (1-6C)alkylthio, (1-6C)alkylsulfinyl, (1-6C)alkylsulfonyl, (1-6C)alkoxycarbonyl, N-(1-6C)alkylcarbamoyl, N,N-di-[(1-6C)alkyl]carbamoyl, (2-6C)alkanoyl, sulfamoyl, N-(1-6C)alkylsulfamoyl, N,N-di-[(1-6C)alkyl]sulfamoyl, hydroxy(1-6C)alkyl, to cyano(1-6C)alkyl, amino(1-6C)alkyl, (1-6C)alkylamino(1-6C)alkyl, di-[(1-6C)alkyl]amino(1-6C)alkyl, amino(2-6C)alkanoyl, (1-6C)alkylamino-(2-6C)alkanoyl, N,N-di-[(1-6C)alkyl]amino-(2-6C)alkanoyl, (1-6C)alkoxy(1-6C)alkyl, hydroxy(1-6C)alkoxy(1-6C)alkyl, carbamoyl(1-6C)alkyl, N-(1-6C)alkylcarbamoyl(1-6C)alkyl, N,N-di-[(1-6C)alkyl]carbamoyl(1-6C)alkyl, (2-6C)alkanoyl(1-6C)alkyl, (2-6C)alkanoyloxy(1-6C)alkyl, (2-6C)alkanoylamino(1-6C)alkyl, N-(1-6C)alkyl-(2-6C)alkanoylamino(1-6C)alkyl, (1-6C)alkoxycarbonyl(1-6C)alkyl, (1-6C)alkoxy(1-6C)alkylS(O)$_q$ (wherein q is 0, 1 or 2), amino(1-6C)alkylS(O)$_q$ (wherein q is 0, 1 or 2), N-(1-6C)alkylamino(1-6C)alkylS(O)$_q$ (wherein q is 0, 1 or 2) and N,N-di[(1-6C)alkyl]amino(1-6C)alkylS(O)$_q$ (wherein q is 0, 1 or 2), and $Q^1$ optionally bears on any available carbon atom in the ring 1 or 2 substituents selected from cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (1-6C)alkylamino, di-[(1-6C)alkyl]amino, hydroxy(1-6C)alkyl, cyano(1-6C)alkyl, amino(1-6C)alkyl, (1-6C)alkylamino(1-6C)alkyl, di-[(1-6C)alkyl]amino(1-6C)alkyl and (1-6C)alkoxy(1-6C)alkyl, and wherein any (1-6C)alkyl, (2-8C)alkenyl, (2-8C)alkynyl or (2-6C)alkanoyl group in $Q^1$ optionally bears 1 or 2 substituents which may be the same or different selected from fluoro and chloro, and wherein $Q^1$ optionally bears 1 or 2 oxo substituents;

(d) $Q^1$ is a non-aromatic saturated 3 to 7 membered monocyclic heterocyclyl ring with 1 nitrogen heteroatom and optionally 1 or 2 heteroatoms selected from oxygen, nitrogen and sulfur, which ring is linked to the group $X^2$—O— by a carbon atom in the ring, and wherein the nitrogen atom of any NH group in $Q^1$ optionally bears a substituent as hereinbefore defined in (c) and any ring carbon in $Q^1$ is optionally substituted as hereinbefore defined in (c) and wherein $Q^1$ optionally bears 1 or 2 oxo substituents;

(e) $Q^1$ is a non-aromatic partially saturated 3 to 7 membered monocyclic heterocyclyl ring with a single carbon-carbon double bond, 1 nitrogen heteroatom and optionally 1 or 2 heteroatoms selected from oxygen, nitrogen and sulfur, which ring is linked to the group $X^2$—O— by one of the ring carbon atoms carrying said carbon-carbon double bond (for example 3-pyrrolin-3-yl or 1,2,3,6-tetrahydropyridin-4-yl), and wherein the nitrogen atom of any NH group in $Q^1$ optionally bears a substituent as hereinbefore defined in (c) and any ring carbon in $Q^1$ is optionally substituted as hereinbefore defined in (c), and wherein $Q^1$ optionally bears 1 or 2 oxo substituents;

(f) $Q^1$ is selected from cyclobutyl, cyclopentyl and cyclohexyl optionally substituted by 1 or 2 substituents selected from (1-6C)alkyl, (2-8C)alkenyl, (2-8C)alkynyl and (1-6C)alkoxy;

(g) $Q^1$ is selected from $Q^1$ is a non-aromatic saturated 5 or 6 membered monocyclic heterocyclyl ring with 1 nitrogen heteroatom and optionally 1 or 2 (suitably 1) heteroatoms selected from oxygen and nitrogen, which ring is linked to the group $X^2$—O— by a carbon atom in the ring, and wherein the nitrogen atom of any NH group in $Q^1$ optionally bears a substituent selected from cyano, carbamoyl, (1-4C)alkyl, (2-6C)alkenyl, (2-6C)alkynyl, (1-4C)alkylsulfonyl, N-(1-4C)alkylcarbamoyl, N,N-di-[(1-4C)alkyl]carbamoyl, (2-4C)alkanoyl, sulfamoyl, N-(1-4C)alkylsulfamoyl, N,N-di-[(1-4C)alkyl]sulfamoyl, cyano(1-4C)alkyl, (1-4C)alkoxy(1-4C)alkyl, amino(2-4C)alkanoyl, (1-4C)alkylamino-(2-4C)alkanoyl, N,N-di-[(1-4C)alkyl]amino-(2-4C)alkanoyl, carbamoyl(1-3C)alkyl, N-(1-4C)alkylcarbamoyl(1-3C)alkyl, N,N-di-[(1-4C)alkyl]carbamoyl(1-3C)alkyl, (1-4C)alkoxy(1-3C)alkylS(O)$_q$ (wherein q is 0, 1 or particularly 2), amino(1-3C)alkylS(O)$_q$ (wherein q is 0, 1 or particularly 2), N-(1-4C)alkylamino(1-3C)alkylS(O)$_q$ (wherein q is 0, 1 or particularly 2) and N,N-di[(1-4)alkyl]amino(1-3C)alkylS(O)$_q$ (wherein q is 0, 1 or particularly 2), and $Q^1$ optionally bears on any available carbon atom in the ring 1 or 2 substituents selected from cyano, oxo, amino, carboxy, carbamoyl, (1-4C)alkyl, (2-6C)alkenyl and (2-6C)alkynyl, and wherein any (1-4C)alkyl, (2-6C)alkenyl, (2-6C)alkynyl or (2-4C)alkanoyl group in $Q^1$ optionally bears 1 or 2 substituents which may be the same or different selected from fluoro and chloro;

(h) $Q^1$ is selected from cyclopropyl, cyclopentyl, cyclohexyl, oxetan-3-yl, tetrahydrofuran-3-yl, tetrahydrofuran-2-yl, 1,3-dioxolan-(2, 4 or 5-yl), 3- or 4-tetrahydropyranyl, 3- or 4-oxepanyl, 1-, 2- or 3-pyrrolidinyl, 2-pyrrolin-2-yl, 2-pyrrolin-3-yl, 3-pyrrolin-3-yl, morpholino, morpholin-2-yl, morpholin-3-yl, thiomorpholino, thiomorpholin-2-yl, thiomorpholin-3-yl, piperidine, piperidin-2-yl, piperidin-3-yl, piperidin-4-yl, 1-, 2-3- or 4-homopiperidinyl, piperazin-1-yl, piperazin-2-yl, 1,2,3,6-tetrahydropyridin-4-yl, 1,2,3,6-tetrahydropyridin-5-yl, 1,2,3,4-tetrahydropyridin-5-yl, 1,2,3,6-tetrahydropyridin-6-yl, homopiperazinyl, azetidin-3-yl, tetrahydrothien-3-yl, 1,1-dioxotetrahydrothien-3-yl, 1-oxotetrahydrothien-3-yl, tetrahydrothiopyran-3-yl, tetrahydrothiopyran-4-yl, 1-oxotetrahydrothiopyran-3-yl, 1,1-dioxotetrahydrothiopyran-3-yl, 1-oxotetrahydrothiopyran-4-yl and 1,1-dioxotetrahydrothiopyran-4-yl, and wherein the nitrogen atom of any NH group in $Q^1$ optionally bears a substituent selected from cyano, (1-4C)alkyl, cyano(1-4C)alkyl, (1-4C)alkoxy(1-4C)alkyl, (1-4C)alkylsulfonyl, trifluoromethyl, carbamoyl, N-(1-4C)alkylcarbamoyl, N,N-di-[(1-4C)alkyl]carbamoyl, (2-4C)alkanoyl, sulfamoyl, N-(1-4C)alkylsulfamoyl, N,N-di-[(1-4C)alkyl]sulfamoyl, amino(2-4C)alkanoyl, (1-4C)alkylamino-(2-4C)alkanoyl, N,N-di-[(1-4C)alkyl]amino-(2-4C)alkanoyl, carbamoyl(1-3C)alkyl, N-(1-4C)alkylcarbamoyl(1-3C)alkyl, N,N-di-[(1-4C)alkyl]carbamoyl(1-3C)alkyl, (1-4C)alkoxy(1-3C)alkylsulfonyl, amino(1-3C)alkylsulfonyl, N-(1-4C)alkylamino(1-3C)alkylsulfonyl and N,N-di[(1-4)alkyl]amino(1-3C)alkylsulfonyl, and $Q^1$ optionally bears on any available carbon atom in the ring 1 or 2 substituents selected from oxo and (1-4C)alkyl, and wherein any (1-4C)alkyl group in $Q^1$ optionally bears 1 or 2 fluoro substituents;

(i) $Q^1$ is selected from pyrrolidin-2-yl, 2-pyrrolin-2-yl, 2-pyrrolin-3-yl, 3-pyrrolin-3-yl, morpholin-2-yl, morpholin-3-yl, thiomorpholin-2-yl, thiomorpholin-3-yl, piperidin-2-yl, piperidin-4-yl, 2-, 3- or 4-homopiperidinyl, piperazin-1-yl, 2-oxopiperazin-1-yl, 3-oxopiperazin-1-yl, piperazin-2-yl, 1,2,3,6-tetrahydropyridin-4-yl, 1,2,3,6-tetrahydropyridin-5-yl, 1,2,3,4-tetrahydropyridin-5-yl, 1,2,3,6-tetrahydropyridin-6-yl, 2,3,4,6 or 7-homopiperazinyl, azetidin-3-yl, and wherein the nitrogen atom of any NH group in $Q^1$ optionally bears a substituent selected from cyano, (1-4C)alkyl, cyano(1-4C)alkyl, (1-4C)alkoxy(1-4C)alkyl, (1-4C)alkylsulfonyl, trifluoromethyl, carbamoyl, N-(1-4C)alkylcarbamoyl, N,N-di-[(1-4C)alkyl]carbamoyl, (2-4C)alkanoyl, sulfamoyl, N-(1-4C)alkylsulfamoyl, N,N-di-[(1-4C)alkyl]sulfamoyl, amino(2-4C)alkanoyl, (1-4C)alkylamino-(2-4C)alkanoyl, N,N-di-[(1-4C)alkyl]amino-(2-4C)alkanoyl, carbamoyl(1-3C)alkyl, N-(1-4C)alkylcarbamoyl(1-3C)alkyl, N,N-di-[(1-4C)alkyl]carbamoyl(1-3C)alkyl, (1-4C)alkoxy(1-3C)alkylsulfonyl, amino(1-3C)alkylsulfonyl, N-(1-4C)alkylamino(1-3C)alkylsulfonyl and N,N-di[(1-4)alkyl]amino(1-3C)alkylsulfonyl, and $Q^1$ optionally bears on any available carbon atom in the ring 1 or 2 substituents selected from (1-4C)alkyl and oxo, and wherein any (1-4C)alkyl group in $Q^1$ optionally bears 1 or 2 fluoro substituents;

(j) $Q^1$ is selected from pyrrolidin-2-yl, pyrrolidines-3-yl, piperidin-2-yl, piperidin-3-yl and piperidin-4-yl, and wherein the nitrogen atom of any NH group in $Q^1$ optionally bears a substituent selected from cyano, cyanomethyl, methyl, ethyl, carbamoyl, carbamoylmethyl, 2-methoxyethyl, methylsulfonyl and ethylsulfonyl (particularly methylsulfonyl and carbamoylmethyl), and $Q^1$ optionally bears on any available carbon atom in the ring 1 or 2 substituents selected from methyl, ethyl and oxo;

(k) $X^2$ is a direct bond;

(l) $X^2$ is $[CR^2R^3]_m$, wherein in is 1 or 2 and $R^2$ and $R^3$ are hydrogen;

(m) $X^2$ is a direct bond or $CH_2$;

(n) $Q^1$-$X^2$ is selected from pyrrolidin-2-yl, pyrrolidine-2-ylmethyl, 2-pyrrolidin-2-ylethyl, 3-pyrrolidin-2-ylpropyl, pyrrolidin-3-yl, pyrrolidin-3-ylmethyl, 2-pyrrolidin-3-ylethyl, 3-pyrrolidin-3-ylpropyl, 2-pyrrolin-2-yl, 2-pyrrolin-2-ylmethyl, 2-pyrrolin-3-yl, pyrrolin-3-ylmethyl, 3-pyrrolin-3-yl, morpholin-2-yl, morpholin-2-ylmethyl, 2-morpholin-2-ylethyl, morpholin-3-yl, morpholin-3-ylmethyl, 2-morpholin-3-ylethyl, thiomorpholinomethyl, thiomorpholin-2-yl, thiomorpholin-2-ylmethyl, 2-thiomorpholin-2-ylethyl, thiomorpholin-3-yl thiomorpholin-3-ylmethyl, 2-thiomorpholin-3-ylethyl, piperidinomethyl, 2-piperidinoethyl, piperidin-2-yl, piperidin-2-ylmethyl, 2-piperidin-2-ylethyl, 3-piperidin-2-ylpropyl, piperidin-3-yl, piperidin-3-ylmethyl, 3-piperidin-3-ylpropyl, piperidin-4-yl, piperidin-4-ylmethyl, 2-piperidin-4-ylethyl, 3-piperidin-4-ylpropyl, piperazin-1-ylmethyl, 2-piperazin-1-ylethyl, 3-piperazin-1-ylpropyl, 2-oxopiperazin-1-ylmethyl, 2-(2-oxopiperazin-1-yl)ethyl, 3-(2-oxopiperazin-1-yl)propyl, 3-oxopiperazin-1-ylmethyl, 2-(3-oxopiperazin-1-yl)ethyl, 3-(3-oxopiperazin-1-yl)propyl, piperazin-2-yl, piperazin-2-ylmethyl, 2-piperazin-2-ylethyl and 3-piperazin-2-ylpropyl, and wherein the nitrogen atom of any NH group in $Q^1$ optionally bears a substituent selected from cyano, cyanomethyl, 2-cyanoethyl, methyl, ethyl, 2-methoxyethyl, 2-ethoxyethyl, methylsulfonyl, trifluoromethyl, carbamoyl, N-methylcarbamoyl, N-ethylcarbamoyl, N,N-di-methylcarbamoyl, N,N-di-ethylcarbamoyl, acetyl, propionyl, sulfamoyl, N-methylsulfamoyl, N-ethylsulfamoyl, N,N-di-methylsulfamoyl, N,N-di-ethylcarbamoyl, 3-aminopropionyl, 3-(methylamino)propionyl, 3-(di-methylamino)propionyl, carbamoylmethyl, 2-carbamoylethyl, N-methylcarbamoylmethyl, 2-(N-methylcarbamoyl)ethyl, N,N-di-methylcarbamoylmethyl, 2-(N,N-di-methylcarbamoyl)ethyl, methoxymethylsulfonyl, 2-methoxyethylsulfonyl, 2-aminoethylsulfonyl, 2-(Nmethylamino)ethylsulfonyl and 2-(N,N-di-methylamino)ethylsulfonyl;

(o) $Q^1$-$X^2$ is selected from piperidin-4-yl and piperidin-4-ylmethyl, wherein the nitrogen atom in the piperidinyl ring optionally bears a substituent selected from cyano, cyanomethyl, methyl, ethyl, carbamoyl, carbamoylmethyl, 2-methoxyethyl, methylsulfonyl and ethylsulfonyl;

(p) $Q^1$-$X^2$ is selected from 1-carbamoylmethylpiperidin-4-yl and 1-methylsulfonylpiperidin-4-yl;

(q) $R^1$—$X^1$ is selected from hydrogen, (1-4C)alkoxy and (1-4C)alkoxy(1-4C)alkoxy;

(r) $R^1$—$X^1$ is selected from hydrogen, methoxy, ethoxy and 2-methoxyethoxy;

(s) $R^1$—$X^1$ is methoxy;

(t) $G^1$ and $G^2$ each independently is selected from fluoro and chloro;

(u) $G^1$ is fluoro and $G^2$ is chloro;

(v) $Q^1$ is a non-aromatic saturated 5 or 6 membered monocyclic heterocyclyl ring with 1 nitrogen heteroatom and optionally 1 or 2 additional heteroatoms selected from oxygen, nitrogen and sulfur, which ring is linked to the group $X^2$—O— by a carbon atom in the ring, and wherein $Q^1$ bears 1 or 2 substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (2-6C)alkenylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, sulfamoyl, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, carbamoyl(1-6C)alkyl, N-(1-6C)alkylcarbamoyl(1-6C)alkyl, N,N-di-[(1-6C)alkyl]carbamoyl(1-6C)alkyl, (2-6C)alkanoyl(1-6C)alkyl, (2-6C)alkanoyloxy(1-6C)alkyl, (2-6C)alkanoylamino(1-6C)alkyl and N-(1-6C)alkyl-(2-6C)alkanoylamino(1-6C)alkyl, or from a group of the formula:

$$Q^2\text{-}X^3\text{—}$$

wherein $X^3$ is CO and $Q^2$ is a saturated 5 or 6 membered monocyclic heterocyclyl ring with 1 nitrogen heteroatom and optionally 1 or 2 additional heteroatoms selected from oxygen, nitrogen and sulfur, which ring is linked to the group $X^3$ by a nitrogen atom in the ring; and wherein $Q^2$ optionally bears 1 or 2 substituents, selected from (1-4C)alkyl, (2-4C)alkanoyl and (1-4C)alkylsulfonyl, and wherein any (1-6C)alkyl, (2-8C)alkenyl, (2-8C)alkynyl and (2-6C)alkanoyl group within $Q^1$ optionally bears one or more substituents (for example 1, 2 or 3) which may be the same or different selected from halogeno and hydroxy and/or optionally a substituent selected from cyano, nitro, carboxy, (2-8C)alkenyl, (2-6C)alkanoyl, (2-6C)alkanoyloxy and $NR^aR^b$, wherein $R^a$ is hydrogen or (1-4C)alkyl and $R^b$ is hydrogen or (1-4C)alkyl, or $R^a$ and $R^b$ together with the nitrogen atom to which they are attached form a 4, 5 or 6 membered ring, which optionally bears 1 or 2 substituents, which may be the same or different, on an available ring carbon atom selected from (1-4C)alkyl, and may optionally bear on any available ring nitrogen a substituent (provided the ring is not thereby quaternised) selected from (1-4C)alkyl, (2-4C)alkanoyl and (1-4C)alkylsulfonyl;

and wherein any heterocyclyl group within the $Q^1$-$X^2$— group optionally bears 1 or 2 oxo (=O) or thioxo (=S) substituents;

(w) $Q^1$ is a non-aromatic saturated 5 or 6 membered monocyclic heterocyclyl ring with 1 nitrogen heteroatom and optionally 1 or 2 additional heteroatoms selected from oxygen, nitrogen and sulfur, which ring is linked to the group $X^2$—O— by a carbon atom in the ring, and wherein $Q^1$ bears 1 or 2 substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio, (1-6C)alkylsulfinyl, (1-6C)alkylsulfonyl, (2-6C)alkenylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, sulfamoyl, N-(1-6C)alkylsulfamoyl, N,N-di-[(1-6C)alkyl]sulfamoyl, (1-6C)alkanesulfonylamino, N-(1-6C)alkyl-(1-6C)alkanesulfonylamino, carbamoyl(1-6C)alkyl, N-(1-6C)alkylcarbamoyl(1-6C)alkyl, N,N-di-[(1-6C)alkyl]carbamoyl(1-6C)alkyl, (2-6C)alkanoyl(1-6C)alkyl, (2-6C)alkanoyloxy(1-6C)alkyl, (2-6C)alkanoylamino(1-6C)alkyl and N-(1-6C)alkyl-(2-6C)alkanoylamino(1-6C)alkyl, or from a group of the formula:

$$Q^2\text{-}X^3\text{—}$$

wherein $X^3$ is CO and $Q^2$ is selected from pyrrolidin-1-yl, piperidino, piperazin-1-yl and morpholino, and wherein $Q^2$ optionally bears 1 or 2 substituents, selected from (1-4C)alkyl, (2-4C)alkanoyl and (1-4C)alkylsulfonyl, and wherein any (1-6C)alkyl, (2-8C)alkenyl, (2-8C)alkynyl and (2-6C)alkanoyl group within $Q^1$ optionally bears one or more substituents (for example 1, 2 or 3) which may be the same or different selected from halogeno and hydroxy and/or optionally a substituent selected from cyano, nitro, carboxy, (2-8C)alkenyl, (2-6C)alkanoyl, (2-6C)alkanoyloxy and $NR^aR^b$, wherein $R^a$ is hydrogen or (1-4C)alkyl and $R^b$ is hydrogen or (1-4C)alkyl, or $R^a$ and $R^b$ together with the nitrogen atom to which they are attached faun a 4, 5 or 6 membered ring, which optionally bears 1 or 2 substituents, which may be the same or different, on an available ring carbon atom selected from (1-4C)alkyl, and may optionally bear on any available ring nitrogen a substituent (provided the ring is not thereby quaternised) selected from (1-4C)alkyl, (2-4C)alkanoyl and (1-4C)alkylsulfonyl;

and wherein any heterocyclyl group within the $Q^1$-$X^2$— group optionally bears 1 or 2 oxo (=O) or thioxo (=S) substituents;

(x) $Q^1$ is a non-aromatic saturated 5 or 6 membered monocyclic heterocyclyl ring with 1 nitrogen heteroatom and optionally 1 or 2 heteroatoms selected from oxygen, nitrogen and sulfur, which ring is linked to the group $X^2$—O— by a carbon atom in the ring, and wherein $Q^1$ bears 1 or 2 substituents, which may be the same or different, selected from halogeno, trifluoromethyl, trifluoromethoxy, cyano, nitro, hydroxy, amino, carboxy, carbamoyl, (1-6C)alkyl, (2-8C)alkenyl, (2-8C)alkynyl, (1-6C)alkoxy, (2-6C)alkenyloxy, (2-6C)alkynyloxy, (1-6C)alkylthio (1-6C)alkylsulfinyl, (1-6C) alkylsulfonyl, (2-6C)alkenylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, (2-6C)alkanoyloxy, (2-6C)alkanoylamino, N-(1-6C)alkyl-(2-6C)alkanoylamino, sulfamoyl, N-(1-6C)alkylsulfamoyl, N,N-di-[(1-6C)alkyl]sulfamoyl, (1-6C)alkanesulfonylamino, carbamoyl(1-6C)alkyl, N-(1-6C)alkylcarbamoyl(1-6C)alkyl, N,N-di-[(1-6C)alkyl]carbamoyl(1-6C)alkyl, (2-6C)alkanoyl(1-6C)alkyl, (2-6C)alkanoyloxy(1-6C)alkyl, (2-6C)alkanoylamino(1-6C)alkyl and N-(1-6C)alkyl-(2-6C)alkanoylamino(1-6C)alkyl, or a group of the formula:

$Q^2$-$X^3$— wherein $X^3$ is CO and $Q^2$ is selected from pyrrolidin-1-yl, morpholino and piperidino, and wherein any (1-6C)alkyl, (2-8C)alkenyl, (2-8C)alkynyl and (2-6C)alkanoyl group within $Q^1$ optionally bears one or more substituents (for example 1, 2 or 3) which may be the same or different selected from halogeno and hydroxy and/or optionally a substituent selected from cyano, nitro, carboxy, (2-8C)alkenyl, (2-6C)alkanoyl, (2-6C)alkanoyloxy and $NR^aR^b$, wherein $R^a$ is hydrogen or (1-4C)alkyl and $R^b$ is hydrogen or (1-4C)alkyl, or $R^a$ and $R^b$ together with the nitrogen atom to which they are attached form a 4, 5 or 6 membered ring, which optionally bears 1 or 2 substituents, which may be the same or different, on an available ring carbon atom selected from (1-4C)alkyl, and may optionally bear on any available ring nitrogen a substituent (provided the ring is not thereby quaternised) selected from (1-4C)alkyl, (2-4C)alkanoyl and (1-4C)alkylsulfonyl;

and wherein any heterocyclyl group within the $Q^1$-$X^2$— group optionally bears 1 or 2 oxo (=O) or thioxo (=S) substituents;

(y) $Q^1$ is a fully saturated 5 or 6 membered monocyclic heterocyclyl ring with 1 nitrogen heteroatom and optionally 1 or 2 heteroatoms selected from oxygen, nitrogen and sulfur, which ring is linked to the group $X^2$—O— by a carbon atom in the ring, and wherein $Q^1$ bears 1 or 2 substituents, which may be the same or different, selected from carbamoyl, (1-6C)alkyl, (1-6C)alkoxy, (1-6C)alkylsulfonyl, (1-6C)alkylamino, di-[(1-6C)alkyl]amino, N-(1-6C)alkylcarbamoyl, N,N-di-[(1-6C)alkyl]carbamoyl, (2-6C)alkanoyl, sulfamoyl, N-(1-6C)alkylsulfamoyl, N,N-di-[(1-6C)alkyl]sulfamoyl, carbamoyl(1-6C)alkyl, N-(1-6C)alkylcarbamoyl(1-6C)alkyl, N,N-di-[(1-6C)alkyl]carbamoyl(1-6C)alkyl and (2-6C)alkanoyl(1-6C)alkyl, or a group of the formula:

$Q^2$-$X^3$— wherein $X^3$ is CO and $Q^2$ is selected from pyrrolidin-1-yl, morpholino and piperidino, and wherein any (1-6C)alkyl or (2-6C)alkanoyl group within $Q^1$ optionally bears a substituent selected from hydroxy, (2-6C)alkanoyl, (2-6C)alkanoyloxy and $NR^aR^b$, wherein $R^a$ is hydrogen or (1-4C)alkyl and $R^b$ is (1-4C)alkyl, or $R^a$ and $R^b$ together with the nitrogen atom to which they are attached form a pyrrolidin-1-yl, piperidino, piperazin-1-yl or morpholino ring, which ring optionally bears 1 or 2 substituents, which may be the same or different, selected from (1-4C)alkyl;

and wherein any heterocyclyl group within the $Q^1$-$X^2$— group optionally bears 1 or 2 oxo (=O) substituents; and $X^2$ is a direct bond or $CH_2$;

(z) $Q^1$ is a fully saturated 5 or 6 membered monocyclic heterocyclyl ring with 1 nitrogen heteroatom and optionally 1 additional heteroatom selected from oxygen, nitrogen and sulfur, which ring is linked to the group $X^2$—O— by a carbon atom in the ring, and wherein the nitrogen atom of any NH group in $Q^1$ bears a substituent selected from carbamoyl, (1-4C)alkyl, (1-4C)alkylsulfonyl, (1-4C)alkylamino, di-[(1-4C)alkyl]amino, N-(1-4C)alkylcarbamoyl, N,N-di-[(1-4C)alkyl]carbamoyl, (2-4C)alkanoyl, sulfamoyl, N-(1-4C)alkylsulfamoyl, N,N-di-[(1-4C)alkyl]sulfamoyl, carbamoyl(1-3C)alkyl, N-(1-4C)alkylcarbamoyl(1-3C)alkyl, N,N-di-[(1-4C)alkyl]carbamoyl(1-3C)alkyl, (2-4C)alkanoyl(1-3C)alkyl, hydroxy(2-4C)alkanoyl, amino(2-4C)alkanoyl, (1-4C)alkylamino-(2-4C)alkanoyl, N,N-di-[(1-4C)alkyl]amino-(2-4C)alkanoyl, (2-4C)alkanoyloxy-(2-4C)alkanoyl, amino(1-3C)alkylsulfonyl, N-(1-4C)alkylamino-(1-3C)alkylsulfonyl, N,N-di[(1-4)alkyl]amino(1-3C)alkylsulfonyl, pyrrolidin-1-yl-(2-4C)alkanoyl, piperidino-(2-4C)alkanoyl, piperazin-1-yl-(2-4C)alkanoyl and morpholino-(2-4C)alkanoyl;

and wherein any heterocyclyl group within the $Q^1$-$X^2$— group optionally bears an oxo (=O) substituent; and $X^2$ is a direct bond or $CH_2$;

(aa) $Q^1$ is a fully saturated 5 or 6 membered monocyclic heterocyclyl ring with 1 nitrogen heteroatom and optionally 1 additional heteroatom selected from oxygen, nitrogen and sulfur, which ring is linked to the group $X^2$—O— by a carbon atom in the ring, and wherein $Q^1$ bears one substituent on a ring carbon atom selected from carbamoyl, N-(1-4C)alkylcarbamoyl, N,N-di-[(1-4C)alkyl]carbamoyl, carbamoyl(1-3C)alkyl, N-(1-4C)alkylcarbamoyl(1-3C)alkyl, N,N-di-[(1-4C)alkyl]carbamoyl(1-3C)alkyl, (2-4C)alkanoyl, amino(2-4C)alkanoyl, (1-4C)alkylamino-(2-4C)alkanoyl, N,N-di-[(1-4C)alkyl]amino-(2-4C)alkanoyl, pyrrolidin-1-yl-(2-4C)alkanoyl, piperidino-(2-4C)alkanoyl, piperazin-1-yl-(2-4C)alkanoyl and morpholino-(2-4C)alkanoyl, or a group of the formula:

$Q^2$-$X^3$— wherein $X^3$ is CO and $Q^2$ is selected from pyrrolidin-1-yl, morpholino and piperidino, and wherein the nitrogen atom of any NH group in $Q^1$ optionally bears a substituent selected from (1-4C)alkyl, and wherein any heterocyclyl group within the $Q^1$-$X^2$— group optionally bears an oxo (=O) substituent; and $X^2$ is a direct bond or $CH_2$;

(bb) $Q^1$ is selected from pyrrolidinyl and piperidinyl linked to the group $X^2$—O— by a ring carbon atom and wherein the pyrrolidinyl or piperidinyl group is substituted by 1 or 2 groups selected from carbamoyl, (1-4C)alkyl, (1-4C)alkylsulfonyl, (1-4C)alkylamino, di-[(1-4C)alkyl]amino, N-(1-4C)alkylcarbamoyl, N,N-di-[(1-4C)alkyl]carbamoyl, (2-4C)alkanoyl, sulfamoyl, N-(1-4C)alkylsulfamoyl, N,N-di-[(1-4C)alkyl]sulfamoyl, carbamoyl(1-3C)alkyl, N-(1-4C)alkylcarbamoyl(1-3C)alkyl, N,N-di-[(1-4C)alkyl]carbamoyl(1-3C)alkyl, (2-4C)alkanoyl(1-3C)alkyl, hydroxy(2-4C)alkanoyl, amino(2-4C)alkanoyl, (1-4C)alkylamino-(2-4C)alkanoyl, N,N-di-[(1-4C)alkyl]amino-(2-4C)alkanoyl, (2-4C)alkanoyloxy-(2-4C)alkanoyl, amino(1-3C)alkylsulfonyl, N-(1-4C)alkylamino-(1-3C)alkylsulfonyl, N,N-di[(1-4alkyl]amino(1-3C)alkylsulfonyl, pyrrolidin-1-yl-(2-4C)alkanoyl, piperidino-(2-4C)alkanoyl, piperazin-1-yl-(2-4C)alkanoyl, morpholino-(2-4C)alkanoyl and a group of the formula:

$Q^2$-$X^3$— wherein $X^3$ is CO and $Q^2$ is selected from pyrrolidin-1-yl, morpholino and piperidino;

and wherein any heterocyclyl group within the $Q^1$-$X^2$— group optionally bears an oxo (=O) substituent; and $X^2$ is a direct bond or $CH_2$;

(cc) $Q^1$-$X^2$ is selected from pyrrolidin-3-yl, piperidin-3-yl, piperidin-4-yl, pyrrolidin-2-ylmethyl, pyrrolidin-3-ylmethyl, piperidin-2-ylmethyl, piperidin-3-ylmethyl and piperidin-4-ylmethyl, and wherein a pyrrolidinyl or piperidinyl group in $Q^1$-$X^2$ carries one or two substituents selected from (1-4C)alkyl, (1-4C)alkylsulfonyl, N-(1-4C)alkylcarbamoyl, N,N-di-[(1-4C)alkyl]carbamoyl, (2-4C)alkanoyl, N,N-di-[(1-4C)alkyl]sulfamoyl, N-(1-4C)alkylcarbamoyl(1-3C)alkyl, N,N-di-[(1-4C)alkyl]carbamoyl(1-3C)alkyl, hydroxy(2-4C)alkanoyl, N-(1-4C)alkylamino-(2-4C)alkanoyl, N,N-di-[(1-4C)alkyl]amino-(2-4C)alkanoyl, (2-4C)alkanoyloxy-(2-4C)alkanoyl, N-(1-4)alkylamino-(1-3C)alkylsulfonyl, N,N-di[(1-4)alkyl]amino(1-3C)alkylsulfonyl, pyrrolidin-1-yl-(2-4C)alkanoyl, piperidino-(2-4C)alkanoyl, morpholino-(2-4C)alkanoyl and a group of the formula:

$Q^2$-$X^3$— wherein $X^3$ is CO and $Q^2$ is selected from pyrrolidin-1-yl, morpholino and piperidino;

(dd) $Q^1$-$X^2$ is selected from pyrrolidin-3-yl, piperidin-3-yl, piperidin-4-yl, pyrrolidin-2-ylmethyl, pyrrolidin-3-ylmethyl, piperidin-2-ylmethyl, piperidin-3-ylmethyl and piperidin-4-ylmethyl, and wherein a pyrrolidinyl or piperidinyl group in $Q^1$-$X^2$ carries one or two substituents selected from (1-4C)alkyl, (1-4C)alkylsulfonyl, N,N-di-[(1-4C)alkyl]carbamoyl, (2-4C)alkanoyl, N,N-di-[(1-4C)alkyl]sulfamoyl, N,N-di-[(1-4C)alkyl]carbamoyl(1-3C)alkyl, hydroxy(2-4C)alkanoyl, N-(1-4C)alkylamino-(2-4C)alkanoyl, N,N-di-[(1-4C)alkyl]amino-(2-4C)alkanoyl, (2-4C)alkanoyloxy-(2-4C)alkanoyl, N,N-di[(1-4)alkyl]amino(1-3C)alkylsulfonyl, pyrrolidin-1-yl-(2-4C)alkanoyl, piperidino-(2-4C)alkanoyl and morpholino-(2-4C)alkanoyl or a group of the formula:

$Q^2$-$X^3$— wherein $X^3$ is CO and $Q^2$ is morpholino;

(ee) $Q^1$-$X^2$ is selected from pyrrolidin-3-yl, piperidin-3-yl, piperidin-4-yl, pyrrolidin-2-ylmethyl, pyrrolidin-3-ylmethyl, piperidin-2-ylmethyl, piperidin-3-ylmethyl and piperidin-4-ylmethyl, and wherein a pyrrolidinyl or piperidinyl group in $Q^1$-$X^2$ is substituted on a ring nitrogen by a substituent selected from methyl, ethyl, methylsulfonyl, ethylsulfonyl, N,N-dimethylcarbamoyl, N,N-diethylcarbamoyl, N-methyl-N-ethylcarbamoyl, acetyl, propionyl, N,N-dimethylsulfamoyl, N,N-diethylsulfamoyl, N-methyl-N-ethylsulfamoyl, N,N-dimethylcarbamoylmethyl, 2-(N,N-dimethylcarbamoyl)ethyl, N,N-diethylcarbamoylmethyl, 2-(N,N-diethylcarbamoyl)ethyl, hydroxyacetyl, 2-hydroxypropionyl, N-methylaminoacetyl, N-ethylaminoacetyl, 2-(N-methylamino)propionyl, 2-(N-ethylamino)propionyl, N,N-dimethylaminoacetyl, 2-(N,N-di-methylamino)propionyl, N,N-diethylaminoacetyl, 2-(N,N-diethylamino)propionyl, N-methyl-N-ethylaminoacetyl, 2-(N-methyl-N-ethylamino)propionyl, acetoxyacetyl, 2-(acetoxy)propionyl, 2-methylamino)ethylsulfonyl, 2-(N-ethylamino)ethylsulfonyl, 2-(N,N-di-methylamino)ethylsulfonyl, 2-(N,N-di-ethylamino)ethylsulfonyl, 3-(N-methylamino)propylsulfonyl, 3-(N-ethylamino)propylsulfonyl, 3-(N,N-di-methylamino)propylsulfonyl, 3-(N,N-di-ethylamino)propylsulfonyl, pyrrolidin-1-ylacetyl, 2-(pyrrolidin-1-yl)priopionyl, piperidinoacetyl, 2-piperidinopropionyl, morpholinoacetyl, 2-morpholinopropionyl and a group of the formula:

$Q^2$-$X^3$— wherein $X^3$ is CO and $Q^2$ is morpholino;

(ff) $Q^1$-$X^2$ is selected from pyrrolidin-3-yl, piperidin-3-yl, pyrrolidin-2-ylmethyl, pyrrolidin-3-ylmethyl, piperidin-2-ylmethyl, piperidin-3-ylmethyl and piperidin-4-ylmethyl, and wherein a pyrrolidinyl or piperidinyl group in $Q^1$-$X^2$ is substituted on a ring nitrogen by a substituent selected from methyl, ethyl, methylsulfonyl, N,N-dimethylcarbamoyl, acetyl, hydroxyacetyl, N-methylaminoacetyl, N,N-dimethylaminoacetyl, 3-(N,N-di-methylamino)propylsulfonyl, pyrrolidin-1-ylacetyl, piperidinoacetyl, 2-piperidinopropionyl and morpholinoacetyl;

(gg) $Q^1$-$X^2$ is selected from pyrrolidin-3-yl, piperidin-3-yl, piperidin-4-yl, pyrrolidin-2-ylmethyl, pyrrolidin-3-ylmethyl, piperidin-2-ylmethyl, piperidin-3-ylmethyl and piperidin-4-ylmethyl, and wherein the pyrrolidinyl or piperidinyl group in $Q^1$-$X^2$ is carries one substituent in an ortho position to the ring nitrogen in the pyrrolidinyl or piperidinyl group selected from carbamoyl, N-(1-4C)alkylcarbamoyl, N,N-di-[(1-4C)alkyl]carbamoyl, and a group of the formula:

$Q^2$-$X^3$— wherein $X^3$ is CO and $Q^2$ is selected from pyrrolidin-1-yl, piperidino and morpholino;

and wherein the ring nitrogen in the pyrrolidinyl or piperidinyl group in $Q^1$ optionally bears a substituent selected from (1-4C)alkyl;

(hh) $Q^1$-$X^2$ is selected from pyrrolidin-3-yl, pyrrolidin-2-ylmethyl and pyrrolidin-3-ylmethyl, and wherein the pyrrolidinyl group carries one substituent in the 5-position selected from N,N-di-[(1-4C)alkyl]carbamoyl and a group of the formula:

Q²-X³— wherein X³ is CO and Q² is morpholino,
and wherein the pyrrolidinyl group optionally bears a substituent at the 1-position selected from (1-4C)alkyl (as will be realised this embodiment covers, for example, a group where Q¹-X² is a pyrrolidin-3-yl group of the formula:

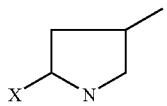

wherein X is the substituent at the 5-position and references in the Examples herein to for example, a 2-(N,N-dimethylcarbamoyl)pyrrolidin-4-yl at the 6-position on the quinazoline ring is an example of such a group);
(ii) Q¹-X² is selected from pyrrolidin-3-yl, piperidin-3-yl, piperidin-4-yl, pyrrolidin-2-ylmethyl, pyrrolidin-3-ylmethyl, piperidin-2-ylmethyl, piperidin-3-ylmethyl and piperidin-4-ylmethyl, and wherein the pyrrolidinyl or piperidinyl group in Q¹-X² is carries one substituent on a ring carbon atom selected from N,N-dimethylcarbamoyl, N,N-diethylcarbamoyl, N-methyl-N-ethylcarbamoyl, and a group of the formula:

Q²-X³— wherein X³ is CO and Q² is morpholino,
and wherein the ring nitrogen in the pyrrolidinyl or piperidinyl group in Q¹ optionally bears a substituent selected from methyl and ethyl;
(jj) Q¹-X² is selected from pyrrolidin-3-yl, pyrrolidin-2-ylmethyl and pyrrolidin-3-ylmethyl, and wherein the pyrrolidinyl group carries a N,N-dimethylcarbamoyl substituent in the 5-position;
(kk) X² is CH₂;
(ll) Q¹ is a non-aromatic saturated or partially saturated 4, 5 or 6 membered monocyclic heterocyclyl ring with 1 or 2 ring nitrogen heteroatom(s), which ring is linked to the group X²—O— by a ring carbon atom, and wherein Q¹ optionally bears 1 or 2 substituents, which may be the same or different, selected from halogeno, cyano, nitro, hydroxy, carbamoyl, acryloyl, (1-6C)alkyl, (1-6C)alkylthio, (2-6C)alkenylthio, (2-6C)alkynylthio, (1-6C)alkylsulfinyl, (2-6C)alkenylsulfinyl, (2-6C)alkynylsulfinyl, (1-6C)alkylsulfonyl, (2-6C)alkenylsulfonyl, (2-6C)alkynylsulfonyl, N-(1-6C)alkylcarbamoyl, N,N-di-[(1-6C)alkyl]carbamoyl, (2-6C)alkanoyl, sulfamoyl, N-(1-6C)alkylsulfamoyl, N,N-di-[(1-6C)alkyl]sulfamoyl, carbamoyl(1-6C)alkyl, N-(1-6C)alkylcarbamoyl(1-6C)alkyl, N,N-di-[(1-6C)alkyl]carbamoyl(1-6C)alkyl, sulfamoyl(1-6C)alkyl, N-(1-6C)alkylsulfamoyl(1-6C)alkyl, N,N-di-[(1-6C)alkyl]sulfamoyl(1-6C)alkyl, (2-6C)alkanoyl(1-6C)alkyl, (2-6C)alkanoyloxy(1-6C)alkyl, (2-6C)alkanoylamino(1-6C)alkyl and N-(1-6C)alkyl-(2-6C)alkanoylamino(1-6C)alkyl, or from a group of the formula:

Q²-X³— wherein X³ is CO and Q² is a heterocyclyl group selected from morpholino, piperidinyl, piperazinyl and pyrrolidinyl (which piperidinyl, piperazinyl or pyrrolidinyl may be linked to X³ by a ring carbon or a ring nitrogen),
and wherein Q² optionally bears 1 or 2 substituents, which may be the same or different, selected from halogeno, hydroxy, (1-4C)alkyl, (2-4C)alkanoyl and (1-4C)alkylsulfonyl,
and wherein any (1-6C)alkyl, or (2-6C)alkanoyl group within Q¹ optionally bears 1 or 2 substituents, which may be the same or different, selected from halogeno, hydroxy and (1-6C)alkyl and/or optionally a substituent selected from cyano, (2-8C)alkenyl, (2-8C)alkynyl, (1-6C)alkoxy, (2-6C)alkanoyl, (2-6C)alkanoyloxy and NR$^a$R$^b$, wherein R$^a$ is hydrogen or (1-4C)alkyl and R$^b$ is hydrogen or (1-4C)alkyl, and wherein any (1-4C)alkyl in R$^a$ or R$^b$ optionally bears one or more substituents (for example 1, 2 or 3) which may be the same or different selected from halogeno and hydroxy and/or optionally a substituent selected from cyano, and (1-4C)alkoxy,
or R$^a$ and R$^b$ together with the nitrogen atom to which they are attached form a 4, 5 or 6 membered ring which does not contain oxygen, which ring optionally bears 1 or 2 substituents, which may be the same or different, on an available ring carbon atom selected from halogeno, hydroxy, (1-4C)alkyl and (1-3C)alkylenedioxy, and may optionally bear on any available ring nitrogen a substituent (provided the ring is not thereby quaternised) selected from (1-4C)alkyl, (2-4C)alkanoyl and (1-4C)alkylsulfonyl,
and wherein any (1-4C)alkyl or (2-4C)alkanoyl group present as a substituent on the ring formed by R$^a$ and R$^b$ together with the nitrogen atom to which they are attached optionally bears one or more substituents (for example 1, 2 or 3), which may be the same or different, selected from halogeno and hydroxy and/or optionally a substituent selected from (1-4C)alkyl and (1-4C)alkoxy;
and wherein any heterocyclyl group within the Q¹-X²— group optionally bears 1 or 2 oxo (═O) or thioxo (═S) substituents;
(mm) Q¹ is selected from pyrrolidinyl and piperidinyl linked to the group X²—O— by a ring carbon atom and wherein the pyrrolidinyl or piperidinyl group is optionally substituted by 1 or 2 groups selected from halogeno, cyano, hydroxy, carbamoyl, (1-6C)alkyl, (1-6C)alkylthio, (1-6C)alkylsulfinyl, (1-6C)alkylsulfonyl, N-(1-6C)alkylcarbamoyl, N,N-di-[(1-6C)alkyl]carbamoyl, (2-6C)alkanoyl, sulfamoyl, N-(1-6C)alkylsulfamoyl, N,N-di-[(1-6C)alkyl]sulfamoyl, carbamoyl(1-6C)alkyl, N-(1-6C)alkylcarbamoyl(1-6C)alkyl, N,N-di-[(1-6C)alkyl]carbamoyl(1-6C)alkyl, sulfamoyl(1-6C)alkyl, N-(1-6C)alkylsulfamoyl(1-6C)alkyl, N,N-di-[(1-6C)alkyl]sulfamoyl(1-6C)alkyl and (2-6C)alkanoyl(1-6C)alkyl, or from a group of the formula:

Q²-X³— wherein X³ is CO and Q² is a heterocyclyl group selected from morpholino, piperidino, pyrrolidin-1-yl and pyrrolidin-2-yl,
and wherein Q² optionally bears 1 or 2 substituents, which may be the same or different, selected from halogeno, hydroxy, (1-4C)alkyl, (2-4C)alkanoyl and (1-4C)alkylsulfonyl,
and wherein any (1-6C)alkyl, or (2-6C)alkanoyl group within Q¹ optionally bears 1 or 2 substituents, which may be the same or different, selected from halogeno, hydroxy and (1-6C)alkyl and/or optionally a substituent selected from cyano, (2-8C)alkenyl, (2-8C)alkynyl, (1-6C)alkoxy, (2-6C)alkanoyl, (2-6C)alkanoyloxy and NR$^a$R$^b$, wherein R$^a$ is hydrogen or (1-4C)alkyl and R$^b$ is hydrogen or (1-4C)alkyl, and wherein any (1-4C)alkyl in R$^a$ or R$^b$ optionally bears one or more substituents (for example 1, 2 or 3) which may be the same or different selected from halogeno and hydroxy and/or optionally a substituent selected from cyano, and (1-4C) alkoxy, or R$^a$ and R$^b$ together with the nitrogen atom to which they are attached form a ring selected from pyrrolidin-1-yl, piperidino and piperazin-1-yl, which ring optionally bears 1 or 2 substituents, which may be the same or different, on an available ring carbon atom selected from halogeno, hydroxy, (1-4C)alkyl and methylenedioxy, and may optionally bear on any available ring nitrogen a substituent (provided the ring is not thereby quaternised) selected from (1-4C)alkyl, (2-4C) alkanoyl and (1-4C)alkylsulfonyl, and wherein any (1-4C)alkyl or (2-4C)alkanoyl group present as a substituent on the ring formed by R$^a$ and R$^b$ together with the nitrogen atom to which they are attached optionally bears one or more substituents (for example 1, 2 or 3), which may be the same or different, selected from halogeno and hydroxy and/or optionally a substituent selected from (1-4C)alkyl and (1-4C)alkoxy, and wherein any (1-4C)alkyl or (2-4C)alkanoyl group present as a substituent on the ring formed by R$^a$ and R$^b$ together with the nitrogen atom to which they are attached optionally bears one or more substituents (for example 1, 2 or 3), which may be the same or different, selected from halogeno and hydroxy and/or optionally a substituent selected from (1-4C)alkyl and (1-4C)alkoxy, and wherein any heterocyclyl group within the Q$^1$-X$^2$— group optionally bears 1 or 2 oxo (=O) substituents;

(nn) Q$^1$ is selected from pyrrolidinyl and piperidinyl linked to the group X$^2$—O— by a ring carbon atom and wherein the pyrrolidinyl or piperidinyl group is substituted by 1 or 2 groups selected from carbamoyl, (1-4C)alkyl, (1-4C)alkylsulfonyl, N-(1-4C)alkylcarbamoyl, N,N-di-[(1-4C)alkyl]carbamoyl, (2-4C)alkanoyl, sulfamoyl, N-(1-4C)alkylsulfamoyl, N,N-di-[(1-4C)alkyl]sulfamoyl, carbamoyl(1-3C)alkyl, N-(1-4C)alkylcarbamoyl(1-3C)alkyl, N,N-di-[(1-4C)alkyl]carbamoyl(1-3C)alkyl, (2-4C)alkanoyl(1-3C)alkyl, amino(2-4C)alkanoyl, (1-4C)alkylamino-(2-4C)alkanoyl, N,N-di-[(1-4C)alkyl]amino-(2-4C)alkanoyl, (2-4C)alkanoyloxy-(2-4C)alkanoyl, amino(1-3C)alkylsulfonyl, N-(1-4C)alkylamino-(1-3C)alkylsulfonyl, N,N-di[(1-4)alkyl]amino(1-3C)alkylsulfonyl, pyrrolidin-1-yl-(2-4C)alkanoyl, 3,4-methylenedioxypyrrolidin-1-yl-(2-4C)alkanoyl, piperidino-(2-4C)alkanoyl, piperazin-1-yl-(2-4C)alkanoyl, morpholino-(2-4C)alkanoyl and a group of the formula:

Q$^2$-X$^3$— wherein X$^3$ is CO and Q$^2$ is selected from pyrrolidin-1-yl, pyrrolidin-2-yl, morpholino and piperidino, and wherein any pyrrolidin-1-yl, pyrrolidin-2-yl, morpholino, piperidino or piperazin-1-yl group within a substituent on Q$^1$ or which is represented by Q$^2$ optionally bears one or two substituents, which may be the same or different, selected from hydroxy, (1-4C)alkyl, (2-4C)alkanoyl and halogeno (particularly chloro and more particularly fluoro), and wherein any (2-4C)alkanoyl group in a substituent on Q$^1$ optionally bears one or two substituents, which may be the same or different, selected from hydroxy and (1-3C)alkyl, and wherein any (1-4C)alkyl group in a substituent on Q$^1$ optionally bears one or two substituents, which may be the same or different, selected from hydroxy, (1-4C)alkoxy and halogeno (particularly chloro and more particularly fluoro), and wherein any heterocyclyl group within the Q$^1$-X$^2$— group optionally bears an oxo (=O) substituent; and X$^2$ is a direct bond;

(oo) Q$^1$ is selected from pyrrolidinyl and piperidinyl linked to the group X$^2$—O— by a ring carbon atom and wherein the pyrrolidinyl or piperidinyl group is substituted by 1 or 2 groups, which may be the same or different, selected from carbamoyl, (1-4C)alkyl, (1-4C)alkylsulfonyl, N-(1-4C)alkylcarbamoyl, N,N-di-[(1-4C)alkyl]carbamoyl, (2-4C)alkanoyl, sulfamoyl, N-(1-4C)alkylsulfamoyl, N,N-di-[(1-4C)alkyl]sulfamoyl, carbamoyl(1-3C)alkyl, N-(1-4C)alkylcarbamoyl(1-3C)alkyl, N,N-di-[(1-4C)alkyl]carbamoyl(1-3C)alkyl, (2-4C)alkanoyl(1-3C)alkyl, amino(2-4C)alkanoyl, (1-4C)alkylamino-(2-4C)alkanoyl, N,N-di-[(1-4C)alkyl]amino-(2-4C)alkanoyl, (2-4C)alkanoyloxy-(2-4C)alkanoyl, amino(1-3C)alkylsulfonyl, N-(1-4C)alkylamino-(1-3C) alkylsulfonyl N, N-di[(1-4C)alkyl]amino(1-3C)alkylsulfonyl, pyrrolidin-1-yl-(2-4C)alkanoyl, 3,4-methylenedioxypyrrolidin-1-yl-(2-4C)alkanoyl, piperidino-(2-4C)alkanoyl, piperazin-1-yl-(2-4C)alkanoyl and a group of the formula:

Q$^2$-X$^3$— wherein X$^3$ is CO and Q$^2$ is selected from pyrrolidin-1-yl, pyrrolidin-2-yl and piperidino, and wherein any pyrrolidin-1-yl, pyrrolidin-2-yl piperidino or piperazin-1-yl group within a substituent on Q$^1$ or which is represented by Q$^2$ optionally bears one or two substituents, which may be the same or different, selected from hydroxy, (1-4C)alkyl, (2-4C)alkanoyl and halogeno (particularly chloro and more particularly fluoro), and wherein any (2-4C)alkanoyl group in a substituent on Q$^1$ optionally bears one or two substituents, which may be the same or different, selected from hydroxy and (1-3C)alkyl, and wherein any (1-4C)alkyl group in a substituent on Q$^1$ optionally bears one or two substituents, which may be the same or different, selected from hydroxy, (1-4C)alkoxy and halogeno (particularly chloro and more particularly fluoro), and wherein any heterocyclyl group within the Q$^1$-X$^2$— group optionally bears an oxo (=O) substituent; and X$^2$ is CH$_2$;

(pp) Q$^1$ is selected from pyrrolidinyl and piperidinyl linked to the group X$^2$—O— by a ring carbon atom and wherein the pyrrolidinyl or piperidinyl group is substituted by 1 or 2 groups, which may be the same or different, selected from carbamoyl, (1-4C)alkyl, (1-4C)alkylsulfonyl, N-(1-4C)alkylcarbamoyl, N,N-di-[(1-4C)alkyl]carbamoyl, (2-4C)alkanoyl, sulfamoyl, N-(1-4C)alkylsulfamoyl, N,N-di-[(1-4C)alkyl]sulfamoyl, carbamoyl(1-3C)alkyl, N-(1-4C)alkylcarbamoyl(1-3C)alkyl, N,N-di-[(1-4C)alkyl]carbamoyl(1-3C)alkyl, (2-4C)alkanoyl(1-3C)alkyl, amino(2-4C)alkanoyl, (1-4C)alkylamino-(2-4C)alkanoyl, N,N-di-[(1-4C) alkyl]amino-(2-4C)alkanoyl, (2-4C)alkanoyloxy-(2-4C)alkanoyl, amino(1-3C) alkylsulfonyl, N-(1-4C)alkylamino-(1-3C)alkylsulfonyl, N,N-di[(1-4)alkyl]amino(1-3C)alkylsulfonyl, and wherein any (2-4C)alkanoyl group in a substituent on Q$^1$ optionally bears one or two substituents, which may be the same or different, selected from hydroxy and (1-3C)alkyl, and wherein any (1-4C)alkyl group in a substituent on Q$^1$ optionally bears one or two substituents, which may be the same or different, selected from hydroxy, (1-4C)alkoxy and halogeno (particularly chloro and more particularly fluoro), X$^2$ is a direct bond or CH$_2$;

(qq) $Q^1$-$X^2$ is selected from pyrrolidin-2-ylmethyl, (2R)-pyrrolidin-2-ylmethyl, (2S)-pyrrolidin-2-ylmethyl, pyrrolidin-3-yl, (3S)-pyrrolidin-3-yl, pyrrolidin-3-ylmethyl, (3R)-pyrrolidin-3-ylmethyl, (3S)-pyrrolidin-3-ylmethyl, piperidin-4-yl, piperidin-4-ylmethyl, piperidin-3-yl, (3R)-piperidin-3-yl and (3S)-piperidin-3-yl, wherein $Q^1$ is substituted by 1 or 2 groups, which may be the same or different, selected from carbamoyl, (1-4C)alkyl, (1-4C)alkylsulfonyl, N-(1-4C)alkylcarbamoyl, N,N-di-[(1-4C)alkyl]carbamoyl, (2-4C)alkanoyl, sulfamoyl, N-(1-4C)alkylsulfamoyl, N,N-di-[(1-4C)alkyl]sulfamoyl, carbamoyl(1-3C)alkyl, N-(1-4C)alkylcarbamoyl(1-3C)alkyl, N,N-di-[(1-4C)alkyl]carbamoyl(1-3C)alkyl, (2-4C)alkanoyl(1-3C)alkyl, amino(2-4C)alkanoyl, (1-4C)alkylamino-(2-4C)alkanoyl, N,N-di-[(1-4C)alkyl]amino-(2-4C)alkanoyl, (2-4C)alkanoyloxy-(2-4C)alkanoyl, amino(1-3C)alkylsulfonyl, N-(1-4C)alkylamino-(1-3C)alkylsulfonyl, N,N-di[(1-4)alkyl]amino(1-3C)alkylsulfonyl, pyrrolidin-1-yl-(2-4C)alkanoyl, 3,4-methylenedioxypyrrolidin-1-yl-(2-4C)alkanoyl, piperidino-(2-4C)alkanoyl, piperazin-1-yl-(2-4C)alkanoyl, morpholino-(2-4C)alkanoyl and a group of the formula:

$Q^2$-$X^3$— wherein $X^3$ is CO and $Q^2$ is selected from pyrrolidin-1-yl, pyrrolidin-2-yl, morpholino and piperidino, and wherein any pyrrolidin-1-yl, pyrrolidin-2-yl, morpholino, piperidino or piperazin-1-yl group within a substituent on $Q^1$ or which is represented by $Q^2$ optionally bears one or two substituents, which may be the same or different, selected from hydroxy, (1-4C)alkyl, (2-4C)alkanoyl and halogeno (particularly chloro and more particularly fluoro), and wherein any (2-4C)alkanoyl group in a substituent on $Q^1$ optionally bears one or two substituents, which may be the same or different, selected from hydroxy and (1-3C)alkyl, and wherein any (1-4C)alkyl group in a substituent on $Q^1$ optionally bears one or two substituents, which may be the same or different, selected from hydroxy, (1-4C)alkoxy and halogeno (particularly chloro and more particularly fluoro), and wherein any heterocyclyl group within the $Q^1$-$X^2$— group optionally bears an oxo (=O) substituent;

(rr) $Q^1$-$X^2$ is selected from pyrrolidin-2-ylmethyl, (2R)-pyrrolidin-2-ylmethyl, (2S)-pyrrolidin-2-ylmethyl, pyrrolidin-3-yl, (3R)-pyrrolidin-3-yl, (3S)-pyrrolidin-3-yl, pyrrolidin-3-ylmethyl, (3R)-pyrrolidin-3-ylmethyl, (3S)-pyrrolidin-3-ylmethyl, piperidin-4-yl, piperidin-3-yl, (3R)-piperidin-3-yl and (3S)-piperidin-3-yl, wherein the pyrrolidinyl or piperidinyl group in $Q^1$ is substituted at the 1-position by a substituent selected from (1-4C)alkyl, (1-4C)alkylsulfonyl, (2-4C)alkanoyl, (2-4C)alkanoyl(1-3C)alkyl, amino(2-4C)alkanoyl, (1-4C)alkylamino-(2-4C)alkanoyl, N,N-di-[(1-4C)alkyl]amino-(2-4C)alkanoyl, (2-4C)alkanoyloxy-(2-4C)alkanoyl, amino(1-3C)alkylsulfonyl, N-(1-4C)alkylamino-(1-3C)alkylsulfonyl, N,N-di[(1-4)alkyl]amino(1-3C)alkylsulfonyl, pyrrolidin-1-yl-(2-4C)alkanoyl, 3,4-methylenedioxypyrrolidin-1-yl-(2-4C)alkanoyl, piperidino-(2-4C)alkanoyl, piperazin-1-yl-(2-4C)alkanoyl, and a group of the formula:

$Q^2$-$X^3$— wherein $X^3$ is CO and $Q^2$ is pyrrolidin-2-yl, and wherein any pyrrolidin-1-yl, piperidino or piperazin-1-yl goup within a substituent on $Q^1$ or which is represented by $Q^2$ optionally bears one or two substituents, which may be the same or different, selected from hydroxy, oxo, (1-4C)alkyl, (2-4C)alkanoyl and halogeno (particularly chloro and more particularly fluoro), and wherein any (2-4C)alkanoyl group in a substituent on $Q^1$ optionally bears one or two substituents, which may be the same or different, selected from hydroxy and (1-3C)alkyl, and wherein any (1-4C)alkyl group in a substituent on $Q^1$ optionally bears one or two substituents, which may be the same or different, selected from hydroxy, (1-4C)alkoxy and halogeno (particularly chloro and more particularly fluoro);

(ss) $Q^1$-$X^2$ is selected from pyrrolidin-3-yl, (3R)-pyrrolidin-3-yl, (3S)-pyrrolidin-3-yl, piperidin-4-yl, piperidin-3-yl, (3R)-piperidine-3-yl and (3S)-piperidin-3-yl, wherein $Q^1$ is substituted at the 1-position by a group selected from (1-4C)alkyl, (1-4C)alkylsulfonyl, (2-4C)alkanoyl, (2-4C)alkanoyl(1-3C)alkyl, amino(2-4C)alkanoyl, (1-4C)alkylamino-(2-4C)alkanoyl, (N,N-di-[(1-4C)alkyl]amino-(2-4C)alkanoyl, (2-4C)alkanoyloxy-(2-4C)alkanoyl, amino(1-3C)alkylsulfonyl, N-(1-4C)alkylamino-(1-3C)alkylsulfonyl, N,N-di[(1-4)alkyl]amino(1-3C)alkylsulfonyl, pyrrolidin-1-yl-(2-4C)alkanoyl, 3,4-methylenedioxypyrrolidin-1-yl-(2-4C)alkanoyl, piperidino-(2-4C)alkanoyl, piperazin-1-yl-(2-4C)alkanoyl, morpholino-(2-4C)alkanoyl and a group of the formula:

$Q^2$-$X^3$— wherein $X^3$ is CO and $Q^2$ is pyrrolidin-2-yl, and wherein any pyrrolidin-1-yl, pyrrolidin-2-yl, morpholino, piperidino or piperazin-1-yl group within a substituent on $Q^1$ or which is represented by $Q^2$ optionally bears one or two substituents, which may be the same or different, selected from hydroxy, (1-4C)alkyl, (2-4C)alkanoyl and halogeno (particularly chloro and more particularly fluoro), and wherein any (2-4C)alkanoyl group in a substituent on $Q^1$ optionally bears one or two substituents, which may be the same or different, selected from hydroxy and (1-3C)alkyl, and wherein any (1-4C)alkyl group in a substituent on $Q^1$ optionally bears one or two substituents, which may be the same or different, selected from hydroxy, (1-4C)alkoxy and halogeno (particularly chloro and more particularly fluoro), and wherein any heterocyclyl group within the $Q^1$-$X^2$— group optionally bears an oxo (=O) substituent;

(tt) $Q^1$-$X^2$ is selected from pyrrolidin-3-yl, (3R)-pyrrolidin-3-yl, (3S)-pyrrolidin-3-yl, piperidin-3-yl, (3R)-piperidin-3-yl, (3S)-piperidin-3-yl, piperidines-yl, pyrrolidin-2-ylmethyl, (2R)-pyrrolidin-2-ylmethyl, (2S)-pyrrolidin-2-ylmethyl, pyrrolidin-3-ylmethyl, (3R)-pyrrolidin-3-ylmethyl, (3S)-pyrrolidin-3-ylmethyl, piperidin-2-ylmethyl, (2R)-piperidin-2-ylmethyl, (2S)-piperidin-2-ylmethyl, piperidin-3-ylmethyl, (3R)-piperidin-3-ylmethyl, (3S)-piperidin-3-ylmethyl and piperidin-4-ylmethyl, and wherein the pyrrolidinyl or piperidinyl group in $Q^1$-$X^2$ is substituted on a ring nitrogen by a substituent selected from methyl, ethyl, isopropyl, isobutyl, cyclopropylmethyl, methylsulfonyl, ethylsulfonyl, N-methylcarbamoyl, N-ethylcarbamoyl, N-isopropylcarbamoyl, N-cyclopropylmethylcarbamoyl, N,N-dimethylcarbamoyl, N,N-diethylcarbamoyl, N-methyl-N-ethylcarbamoyl, acetyl, propionyl, isobutyryl, N-methylsulfamoyl, N-ethylsulfamoyl, N-isopropylsulfamoyl, N-cyclopropylmethylsulfamoyl, N,N-dimethylsulfamoyl, N,N-diethylsulfamoyl, N-methyl-N-ethylsulfamoyl, carbamoylmethyl, N-methylcarbamoylmethyl, 2-(N-methylcarbamoyl)ethyl, N-ethylcarbamoylmethyl, 2-(N-ethylcarbamoyl)ethyl, N,N-dimethylcarbamoylmethyl, 2-(N, N-dimethylcarbamoyl)ethyl, N,N-diethylcarbamoylmethyl, 2-(N,N-diethylcarbamoyl)ethyl, hydroxyacetyl, 2-hydroxypropionyl, N-methylaminoacetyl, N-ethylaminoacetyl, 2-(N-methylamino)propionyl, 2-(N-ethylamino)propionyl, N,N-dimethylaminoacetyl, 2-(N,N-di-methylamino)propionyl, N,N-diethylaminoacetyl, 2-(N,N-diethylamino)propionyl, N-methyl-N-ethylaminoacetyl, 2-(N-methyl-N-ethylamino)propionyl, acetoxyacetyl, 2-(acetoxy)propionyl, 2-(N-methylamino)ethylsulfonyl, 2-(N-ethylamino)ethylsulfonyl, 2-(N,N-di-methylamino)ethylsulfonyl, 2-(N,N-di-ethylamino)ethylsulfonyl, 3-(N-methylamino)propylsulfonyl, 3-(N-ethylamino)propylsulfonyl, 3-(N,N-di-methylamino)propylsulfonyl, 3-(N,N-di-ethylamino)propylsulfonyl, pyrrolidin-1-ylacetyl, 2-(pyrrolidin-1-yl)propionyl, 3,4-methylenedioxypyrrolidin-1-Aacetyl, 2-(3,4-methylenedioxypyrrolidin-1-yl)propionyl, piperidinoacetyl, 2-piperidinopropionyl, piperazin1-ylacetyl, 2-piperazin-1-ylpropionyl and a group of the formula:

$Q^2-X^3—$ wherein $X^3$ is CO and $Q^2$ is selected from morpholino, pyrrolidin-1-yl, pyrrolidin-2-yl, piperidino and piperazin-1-yl, and wherein any pyrrolidin-1-yl, pyrrolidin-2-yl, morpholino, piperidino or piperazin-1-yl group within a substituent on $Q^1$ or which is represented by $Q^2$ optionally bears one or two substituents, which may be the same or different, selected from hydroxy, oxo, methyl, ethyl, acetyl and fluoro, and wherein any acetyl, propionyl or isobutyryl group in a substituent on $Q^1$ optionally bears one or two substituents, which may be the same or different, selected from hydroxy and methyl, and wherein any (1-4C)alkyl group in a substituent on $Q^1$ optionally bears one or two substituents, which may be the same or different, selected from hydroxy, methoxy, fluoro, chloro;

(uu) $Q^1-X^2$ is selected from pyrrolidin-3-yl, (3S)-pyrrolidin-3-yl, (3R)-piperidin-3-yl, (3S)-piperidin-3-yl, piperidin-4-yl, pyrrolidin-2-ylmethyl, (2R)-pyrrolidin-2-ylmethyl, (2S)-pyrrolidin-2-ylmethyl, pyrrolidin-3-ylmethyl, (3R)-pyrrolidin-3-ylmethyl, (3S)-pyrrolidin-3-ylmethyl, piperidin-2-ylmethyl, (2R)-piperidin-2-ylmethyl, (2S)-piperidin-2-ylmethyl, piperidin-3-ylmethyl, (3R)-piperidin-3-ylmethyl, (3S)-piperidin-3-ylmethyl and piperidin-4-ylmethyl, and wherein the pyrrolidinyl or piperidinyl group in $Q^1-X^2$ is substituted on a ring nitrogen by a substituent selected from, acetyl, propionyl, isobutyryl, N-methylaminoacetyl, N-ethylaminoacetyl, 2-(N-methylamino)propionyl, 2-(N-ethylamino)propionyl, N,N-dimethylaminoacetyl, 2-(N,N-di-methylamino)propionyl, N,N-diethylaminoacetyl, 2-(N,N-diethylamino)propionyl, N-methyl-N-ethylaminoacetyl, 2-(N-methyl-N-ethylamino)propionyl, acetoxyacetyl, 2-(acetoxy)propionyl, pyrrolidin-1-ylacetyl, 2-(pyrrolidin-1-yl)propionyl, 3,4-methylenedioxypyrrolidin-1-ylacetyl, 2-(3,4-methylenedioxypyrrolidin-1-yl)propionyl, piperidinoacetyl, 2-piperidinopropionyl, piperazin1-ylacetyl and 2-piperazin-1-ylpropionyl, and wherein any pyrrolidin-1-yl, piperidino or piperazin-1-yl group within a substituent on $Q^1$ or which is represented by $Q^2$ optionally bears one or two substituents, which may be the same or different, selected from hydroxy, oxo, methyl, ethyl, acetyl and fluoro, and wherein any acetyl, propionyl or isobutyryl group in a substituent on $Q^1$ optionally bears one or two substituents, which may be the same or different, selected from hydroxy and methyl, and wherein any (1-4C)alkyl group in a substituent on $Q^1$ optionally bears one or two substituents, which may be the same or different, selected from hydroxy, methoxy, fluoro, chloro;

(vv) $Q^1-X^2$ is selected from pyrrolidin-2-ylmethyl, (2R)-pyrrolidin-2-ylmethyl, (2S)-pyrrolidin-2-ylmethyl, pyrrolidin-3-ylmethyl, (3R)-pyrrolidin-3-ylmethyl, (3S)-pyrrolidin-3-ylmethyl, and wherein the pyrrolidinyl group in $Q^1-X^2$ is substituted on a ring nitrogen by a substituent selected from methyl, ethyl, isopropyl, isobutyl, cyclopropylmethyl, methylsulfonyl, ethylsulfonyl, N-methylcarbamoyl, N-ethylcarbamoyl, N-isopropylcarbamoyl, N-cyclopropylmethylcarbamoyl, N,N-dimethylcarbamoyl, N,N-diethylcarbamoyl, N-methyl-N-ethylcarbamoyl, acetyl, propionyl, isobutyryl, N-methylsulfamoyl, N-ethylsulfamoyl, N-isopropylsulfamoyl, N-cyclopropylmethylsulfamoyl, N,N-dimethylsulfamoyl, N,N-diethylsulfamoyl, N-methyl-N-ethylsulfamoyl, carbamoylmethyl, N-methylcarbamoylmethyl, 2-methylcarbamoyl)ethyl, N-ethylcarbamoylmethyl, 2-ethylcarbamoyl)ethyl, N,N-dimethylcarbamoylmethyl, 2-(N,N-dimethylcarbamoyl)ethyl, N,N-diethylcarbamoylmethyl, 2-(N,N-diethylcarbamoyl)ethyl, N-methylaminoacetyl, N-ethylaminoacetyl, 2-(N-methylamino)propionyl, 2-(N-ethylamino)propionyl, N,N-dimethylaminoacetyl, 2-(N,N-di-methylamino)propionyl, N,N-diethylaminoacetyl, 2-(N,N-diethylamino)propionyl, N-methyl-N-ethylaminoacetyl, 2-(N-methyl-N-ethylamino)propionyl, acetoxyacetyl, 2-(acetoxy)propionyl, 2-(N-methylamino)ethylsulfonyl, 2-(N-ethylamino)ethylsulfonyl, 2-(N,N-di-methylamino)ethylsulfonyl, 2-(N,N-di-ethylamino)ethylsulfonyl, 3-(N-methylamino)propylsulfonyl, 3-(N-ethylamino)propylsulfonyl, 3-(N,N-di-methylamino)propylsulfonyl, 3-(N,N-di-ethylamino)propylsulfonyl, pyrrolidin-1-ylacetyl, 2-(pyrrolidine-1-yl)propionyl, 3,4-methylenedioxypyrrolidin-1-ylacetyl, 2-(3,4-methylenedioxypyrrolidin-1-yl)propionyl, piperidinoacetyl, 2-piperidinopropionyl, piperazin1-ylacetyl, 2-piperazin-1-ylpropionyl and a group of the formula:

$Q^2-X^3—$ wherein $X^3$ is CO and $Q^2$ is selected from morpholino, pyrrolidin-1-yl, pyrrolidin-2-yl, piperidino and piperazin-1-yl, and wherein any pyrrolidin-1-yl, pyrrolidin-2-yl, morpholino, piperidino or piperazin-1-yl group within a substituent on $Q^1$ or which is represented by $Q^2$ optionally bears one or two substituents, which may be the same or different, selected from hydroxy, oxo, methyl, ethyl, acetyl and fluoro, and wherein any acetyl, propionyl or isobutyryl group in a substituent on $Q^1$ optionally bears one or two substituents, which may be the same or different, selected from hydroxy and methyl, and wherein any (1-4C)alkyl group in a substituent on $Q^1$ optionally bears one or two substituents, which may be the same or different, selected from hydroxy, methoxy, fluoro, chloro;

(ww) $Q^1$-$X^2$ is selected from pyrrolidin-2-ylmethyl, (2R)-pyrrolidin-2-ylmethyl, (2S)-pyrrolidin-2-ylmethyl, pyrrolidin-3-ylmethyl, (3R)-pyrrolidin-3-ylmethyl, (3S)-pyrolidin-3-ylmethyl, and wherein the pyrrolidinyl group in $Q^1$-$X^2$ is substituted on the ring nitrogen by a substituent selected from methyl, ethyl, isopropyl, isobutyl, cyclopropylmethyl, methylsulfonyl, ethylsulfonyl, N-methylcarbamoyl, N-ethylcarbamoyl, N-isopropylcarbamoyl, N-cyclopropylmethylcarbamoyl, N,N-dimethylcarbamoyl, N,N-diethylcarbamoyl, N-methyl-N-ethylcarbamoyl, acetyl, propionyl, isobutyryl, N-methylsulfamoyl, N-ethylsulfamoyl, N-isopropylsulfamoyl, N-cyclopropylmethylsulfamoyl, N,N-dimethylsulfamoyl, N,N-diethylsulfamoyl, N-methyl-N-ethylsulfamoyl, carbamoylmethyl, N-methylcarbamoylmethyl, 2-(N-methylcarbamoyl)ethyl, N-ethylcarbamoylmethyl, 2-ethylcarbamoyl)ethyl, N,N-dimethylcarbamoylmethyl, 2-(N,N-dimethylcarbamoyl)ethyl, N,N-diethylcarbamoylmethyl, 2-(N,N-diethylcarbamoyl)ethyl, N-methylaminoacetyl, N-ethylaminoacetyl, 2-(N-methylamino)propionyl, 2-(N-ethylamino)propionyl, N,N-dimethylaminoacetyl, 2-(N,N-di-ethylamino)propionyl, N,N-diethylaminoacetyl, 2-(N,N-diethylamino)propionyl, N-methyl-N-ethylaminoacetyl, 2-(N-methyl-N-ethylamino)propionyl, acetoxyacetyl, 2-(acetoxy)propionyl, 2-(N-methylamino)ethylsulfonyl, 2-(N-ethylamino)ethylsulfonyl, 2-(N,N-di-methylamino)ethylsulfonyl, 2-(N,N-di-ethylamino)ethylsulfonyl, 3-(N-methylamino)propylsulfonyl, 3-(N-ethylamino)propylsulfonyl, 3-(N,N-di-methylamino)propylsulfonyl, 3-(N,N-di-ethylamino)propylsulfonyl, pyrrolidin-1-ylacetyl, 2-(pyrrolidin-1-yl)propionyl, 3,4-methylenedioxypyrrolidin-1-ylacetyl, 2-(3,4-methylenedioxypyrrolidin-1-yl)propionyl, piperidinoacetyl, 2-piperidinopropionyl piperazin1-ylacetyl, 2-piperazin-1-ylpropionyl and a group of the formula:

$Q^2$-$X^3$— wherein $X^3$ is CO and $Q^2$ is selected from pyrrolidin-1-yl, pyrrolidin-2-yl, piperidine and piperazin-1-yl, and wherein any pyrrolidin-1-yl, pyrrolidin-2-yl, piperidino or piperazin-1-yl group within a substituent on $Q^1$ or which is represented by $Q^2$ optionally bears one or two substituents, which may be the same or different, selected from hydroxy, oxo, methyl, ethyl, acetyl and fluoro, and wherein any acetyl, propionyl or isobutyryl group in a substituent on $Q^1$ optionally bears one or two substituents, which may be the same or different, selected from hydroxy and methyl, and wherein any (1-4C)alkyl group in a substituent on $Q^1$ optionally bears one or two substituents, which may be the same or different, selected from hydroxy, methoxy, fluoro, chloro;

(xx) $Q^1$-$X^2$ is selected from pyrrolidin-2-ylmethyl, (2R)-pyrrolidin-2-ylmethyl, (2S)-pyrrolidin-2-ylmethyl, pyrrolidin-3-ylmethyl, (31Z)-pyrrolidin-3-ylmethyl, (3S)-pyrrolidin-3-ylmethyl, and wherein the pyrrolidinyl group in $Q^1$-$X^2$ is substituted on a ring nitrogen by a substituent selected from morpholinoacetyl and 2-morpholinopropionyl which substituent optionally bears one or two substituents, which may be the same or different, selected from hydroxy, oxo, methyl, ethyl and fluoro;

(yy) $Q^1$-$X^2$ is selected from pyrrolidin-3-yl, (3R)-pyrrolidin-3-yl, (3S)-pyrrolidin-3-yl, piperidin-3-yl, (3R)-piperidin-3-yl, (3S)-piperidin-3-yl and piperidin-4-yl, and wherein a pyrrolidinyl or piperidinyl group in $Q^1$-$X^2$ is substituted on a ring nitrogen by a substituent selected from methyl, ethyl, isopropyl, isobutyl, cyclopropylmethyl, methylsulfonyl, ethylsulfonyl, acetyl, propionyl, isobutyryl, carbamoylmethyl, N-methylcarbamoylmethyl, 2-(N-methylcarbamoyl)ethyl, N-ethylcarbamoylmethyl, 2-ethylcarbamoyl)ethyl, N,N-dimethylcarbamoylmethyl, 2-(N,N-dimethylcarbamoyl)ethyl, N,N-diethylcarbamoylmethyl, 2-(N,N-diethylcarbamoyl)ethyl, N-methylaminoacetyl, N-ethylaminoacetyl, 2-(N-methylamino)propionyl, 2-(N-ethylamino)propionyl, N,N-dimethylaminoacetyl, 2-(N,N-di-methylamino)propionyl, N,N-diethylaminoacetyl, 2-(N,N-diethylamino)propionyl, N-methyl-N-ethylamino)acetyl, 2-(N-methyl-N-ethylamino)propionyl, acetoxyacetyl, 2-(acetoxy)propionyl, 2-(N-methylamino)ethylsulfonyl, 2-(N-ethylamino)ethylsulfonyl, 2-(N,N-dimethylamino)ethylsulfonyl, 2-(N,N-di-ethylamino)ethylsulfonyl, 3-(N-methylamino)propylsulfonyl, 3-(N-ethylamino)propylsulfonyl, 3-(N,N-di-methylamino)propylsulfonyl, 3-(N,N-di-ethylamino)propylsulfonyl, pyrrolidin-1-ylacetyl, 2-(pyrrolidin-1-yl)propionyl, 3,4-methylenedioxypyrrolidin-1-ylacetyl, 2-(3,4-methylenedioxypyrrolidin-1-yl)propionyl, piperidinoacetyl, 2-piperidinopropionyl, morpholinoacetyl, 2-morpholinopropionyl, piperazin1-ylacetyl, 2-piperazin-1-ylpropionyl and a group of the formula:

$Q^2$-$X^3$— wherein $X^3$ is CO and $Q^2$ is selected from morpholino, pyrrolidin-1-yl, pyrrolidin-2-yl, piperidino and piperazin-1-yl, and wherein any pyrrolidin-1-yl, pyrrolidin-2-yl, morpholino, piperidino or piperazin-1-yl group within a substituent on $Q^1$ or which is represented by $Q^2$ optionally bears one or two substituents, which may be the same or different, selected from hydroxy, oxo, methyl, ethyl, acetyl and fluoro, and wherein any acetyl, propionyl or isobutyryl group in a substituent on $Q^1$ optionally bears one or two substituents, which may be the same or different, selected from hydroxy and methyl, and wherein any (1-4C)alkyl group in a substituent on $Q^1$ optionally bears one or two substituents, which may be the same or different, selected from hydroxy, methoxy, fluoro, chloro;

(zz) $Q^1$-$X^2$ is selected from pyrrolidin-3-yl, (3R)-pyrrolidin-3-yl, (3S)-pyrrolidin-3-yl, and wherein the pyrrolidinyl group in $Q^1$-$X^2$ is substituted on a ring nitrogen by a substituent selected from methyl, ethyl, isopropyl, isobutyl, cyclopropylmethyl, methylsulfonyl, ethylsulfonyl, acetyl, propionyl, isobutyryl, carbamoylmethyl, N-methylcarbamoylmethyl, 2-(N-methylcarbamoyl)ethyl, N-ethylcarbamoylmethyl, 2-ethylcarbamoyl)ethyl, N,N-dimethylcarbamoylmethyl, 2-(N,N-dimethylcarbamoyl)ethyl, N,N-diethylcarbamoylmethyl, 2-(N,N-diethylcarbamoyl)ethyl, N-methylaminoacetyl, N-ethylaminoacetyl, 2-(N-methylamino)propionyl, 2-(N-ethylamino)propionyl, N,N-dimethylaminoacetyl, 2-(N, N-di-methylamino)propionyl, N,N-diethylaminoacetyl, 2-(N,N-diethylamino)propionyl, N-methyl-N-ethylaminoacetyl, 2-(N-methyl-N-ethylamino)propionyl, acetoxyacetyl, 2-(acetoxy)propionyl, 2-(N-methylamino)ethylsulfonyl, 2-(N-ethylamino)ethylsulfonyl, 2-(N,N-di-methylamino)ethylsulfonyl, 2-(N,N-di-ethylamino)ethylsulfonyl, 3-(N-methylamino)propylsulfonyl, 3-(N-ethylamino)propylsulfonyl, 3-(N,N-di-methylamino)propylsulfonyl, 3-(N,N-di-ethylamino)propylsulfonyl, pyrrolidin-1-ylacetyl, 2-(pyrrolidin-1-yl)propionyl, 3,4-methylenedioxypyrrolidin-1-ylacetyl, 2-(3,4-methylenedioxypyrrolidin-1-yl)propionyl, piperidinoacetyl, 2-piperidinopropionyl, morpholinoacetyl, 2-morpholinopropionyl, piperazin1-ylacetyl, 2-piperazin-1-ylpropionyl and a group of the formula:

$$Q^2\text{-}X^3\text{—}$$

wherein $X^3$ is CO and $Q^2$ is selected from morpholino, pyrrolidin-1-yl, pyrrolidin-2-yl, piperidino and piperazin-1-yl, and wherein any pyrrolidin-1-yl, pyrrolidin-2-yl, morpholino, piperidino or piperazin-1-yl group within a substituent on $Q^1$ or which is represented by $Q^2$ optionally bears one or two substituents, which may be the same or different, selected from hydroxy, oxo, methyl, ethyl, acetyl and fluoro, and wherein any acetyl, propionyl or isobutyryl group in a substituent on $Q^1$ optionally bears one or two substituents, which may be the same or different, selected from hydroxy and methyl, and wherein any (1-4C)alkyl group in a substituent on $Q^1$ optionally bears one or two substituents, which may be the same or different, selected from hydroxy, methoxy, fluoro, chloro;

(aaa) $Q^1\text{-}X^2$ is selected from piperidin-3-yl, (3R)-piperidin-3-yl, (3S)-piperidin-3-yl and piperidin-4-yl, and wherein the piperidinyl group in $Q^1\text{-}X^2$ is substituted on the ring nitrogen by a substituent selected from methyl, ethyl, isopropyl, isobutyl, cyclopropylmethyl, methylsulfonyl, ethylsulfonyl, acetyl, propionyl, isobutyryl, carbamoylmethyl, N-methylcarbamoylmethyl, 2-(N-methylcarbamoyl)ethyl, N-ethylcarbamoylmethyl, 2-(N-ethylcarbamoyl)ethyl, N,N-dimethylcarbamoylmethyl, 2-(N,N-dimethylcarbamoyl)ethyl, N,N-diethylcarbamoylmethyl, 2-(N-diethylcarbamoyl)ethyl, N-methylaminoacetyl, N-ethylaminoacetyl, 2-(N-methylamino)propionyl, 2-(N-ethylamino)propionyl, N,N-dimethylaminoacetyl, 2-(N,N-di-methylamino)propionyl, N,N-diethylaminoacetyl, 2-(N,N-diethylamino)propionyl, N-methyl-N-ethylaminoacetyl, 2-(N-methyl-N-ethylamino)propionyl, acetoxyacetyl, 2-(acetoxy)propionyl, 2-(N-methylamino)ethylsulfonyl, 2-(N-ethylamino)ethylsulfonyl, 2-(N,N-di-methylamino)ethylsulfonyl, 2-(N,N-di-ethylamino)ethylsulfonyl, 3-(N-methylamino)propylsulfonyl, 3-(N-ethylamino)propylsulfonyl, 3-(N,N-di-methylamino)propylsulfonyl, 3-(N,N-di-ethylamino)propylsulfonyl, pyrrolidin-1-ylacetyl, 2-(pyrrolidin-1-yl)propionyl, 3,4-methylenedioxypyrrolidin-1-ylacetyl, 2-(3,4-methylenedioxypyrrolidin-1-yl)propionyl, piperidinoacetyl, 2-piperidinopropionyl, morpholinoacetyl, 2-morpholinopropionyl, piperazin1-ylacetyl, 2-piperazin-1-ylpropionyl and a group of the formula:

$$Q^2\text{-}X^3\text{—}$$

wherein $X^3$ is CO and $Q^2$ is selected from morpholino, pyrrolidin-1-yl, pyrrolidin-2-yl, piperidino and piperazin-1-yl, and wherein any pyrrolidin-1-yl, pyrrolidin-2-yl, morpholino, piperidino or piperazin-1-yl group within a substituent on $Q^1$ or which is represented by $Q^2$ optionally bears one or two substituents, which may be the same or different, selected from hydroxy, oxo, methyl, ethyl, acetyl, fluoro and chloro, and wherein any acetyl, propionyl or isobutyryl group in a substituent on $Q^1$ optionally bears one or two substituents, which may be the same or different, selected from hydroxy and methyl, and wherein any (1-4C)alkyl group in a substituent on $Q^1$ optionally bears one or two substituents, which may be the same or different, selected from hydroxy, methoxy, fluoro, chloro;

(bbb) $Q^1\text{-}X^2$ is selected from pyrrolidin-3-yl, (3R)-pyrrolidin-3-yl, (3S)-pyrrolidin-3-yl, piperidin-3-yl, (3R)-piperidin-3-yl, (3S)-piperidin-3-yl, piperidin-4-yl, pyrrolidin-2-ylmethyl, (2R)-pyrrolidin-2-ylmethyl, (2S)-pyrrolidin-2-ylmethyl, pyrrolidin-3-ylmethyl, (3R)-pyrrolidin-3-ylmethyl, (3S)-pyrrolidin-3-ylmethyl, piperidin-2-ylmethyl, (2R)-piperidin-2-ylmethyl, (2S)-piperidin-2-ylmethyl, piperidin-3-ylmethyl, (3R)-piperidin-3-ylmethyl, (3S)-piperidin-3-ylmethyl and piperidin-4-ylmethyl;

(ccc) $Q^1\text{-}X^2$ is selected from pyrrolidin-3-yl, (3R)-pyrrolidin-3-yl and (3S)-pyrrolidin-3-yl;

(ddd) $Q^1\text{-}X^2$ is selected from piperidin-3-yl, (3R)-piperidin-3-yl, (3S)-piperidin-3-yl and piperidin-4-yl;

(eee) $Q^1\text{-}X^2$ is selected from pyrrolidin-3-yl, (3R)-pyrrolidin-3-yl, (3S)-pyrrolidin-3-yl, piperidin-3-yl, (3R)-piperidin-3-yl, (3S)-piperidin-3-yl, pyrrolidin-2-ylmethyl, (2R)-pyrrolidin-2-ylmethyl, (2S)-pyrrolidin-2-ylmethyl, pyrrolidin-3-ylmethyl, (3R)-pyrrolidin-3-ylmethyl, (3S)-pyrrolidin-3-ylmethyl, piperidin-2-ylmethyl, (2R)-piperidin-2-ylmethyl, (2S)-piperidin-2-ylmethyl, piperidin-3-ylmethyl, (3R)-piperidin-3-ylmethyl, (3S)-piperidin-3-ylmethyl and piperidin-4-ylmethyl, and wherein the pyrrolidinyl or piperidinyl group in $Q^1\text{-}X^2$ is substituted on the ring nitrogen by a substituent selected from N-methylcarbamoyl, N-ethylcarbamoyl, N-isopropylcarbamoyl, N-cyclopropylmethylcarbamoyl, N,N-dimethylcarbamoyl, N,N-diethylcarbamoyl, N-methyl-N-ethylcarbamoyl, N-methylsulfamoyl, N-ethylsulfamoyl, N-isopropylsulfamoyl, N-cyclopropylmethylsulfamoyl, N,N-dimethylsulfamoyl, N,N-diethylsulfamoyl, N-methyl-N-ethylsulfamoyl, carbamoylmethyl, N-methylcarbamoylmethyl, 2-(Nmethylcarbamoyl)ethyl, N-ethylcarbamoylmethyl, 2-(N-ethylcarbamoyl)ethyl, N,N-dimethylcarbamoylmethyl, 2-(N,N-dimethylcarbamoyl)ethyl, N,N-diethylcarbamoylmethyl, 2-(N,N-diethylcarbamoyl)ethyl, N-methylaminoacetyl, N-ethylaminoacetyl, 2-(N-methylamino)propionyl, 2-(N-ethylamino)propionyl, N,N-dimethylaminoacetyl, 2-(N,N-di-methylamino)propionyl, N,N-diethylaminoacetyl, 2-(N,N-diethylamino)propionyl, N-methyl-N-ethylaminoacetyl, 2-(N-methyl-N-ethylamino)propionyl, acetoxyacetyl, 2-(acetoxy)propionyl, 2-(N-methylamino)ethylsulfonyl, 2-(N-ethylamino)ethylsulfonyl, 2-(N,N-di-methylamino)ethylsulfonyl, 2-(N,N-di-ethylamino)ethylsulfonyl, 3-(N-methylamino)propylsulfonyl, 3-(N-ethylamino)propylsulfonyl, 3-(N, N-di-methylamino)propylsulfonyl, 3-(N,N-di-ethylamino)propylsulfonyl, pyrrolidin-1-ylacetyl, 2-(pyrrolidin-1-yl)propionyl, 3,4-methylenedioxypyrrolidin-1-ylacetyl, 2-(3,4-methylenedioxypyrrolidin-1-yl)propionyl, piperidinoacetyl, 2-piperidinopropionyl piperazin1-ylacetyl, 2-piperazin-1-ylpropionyl and a group of the formula:

$$Q^2-X^3—$$

wherein $X^3$ is CO and $Q^2$ is selected from pyrrolidin-1-yl, pyrrolidin-2-yl, piperidino and piperazin-1-yl, and wherein any pyrrolidin-1-yl, piperidino or piperazin-1-yl group within a substituent on $Q^1$ or which is represented by $Q^2$ optionally bears one or two substituents, which may be the same or different, selected from hydroxy, oxo, methyl, ethyl, acetyl, fluoro and chloro, and wherein any (1-4C)alkyl group in a substituent on $Q^1$ optionally bears one or two substituents, which may be the same or different, selected from hydroxy, methoxy, fluoro, chloro;

(fff) $Q^1-X^2$ is selected from pyrrolidin-3-yl, (3R)-pyrrolidin-3-yl, (3S)-pyrrolidin-3-yl, piperidin-3-yl, (3R)-piperidin-3-yl, (3S)-piperidin-3-yl, piperidin-4-yl, pyrrolidin-2-ylmethyl, (2R)-pyrrolidin-2-ylmethyl, (2S)-pyrrolidin-2-ylmethyl, pyrrolidin-3-ylmethyl, (3R)-pyrrolidin-3-ylmethyl, (3S)-pyrrolidin-3-ylmethyl, piperidin-2-ylmethyl, (2R)-piperidin-2-ylmethyl, (2S)-piperidin-2-ylmethyl, piperidin-3-ylmethyl, (3R)-piperidin-3-ylmethyl, (3S)-piperidin-3-ylmethyl and piperidin-4-ylmethyl, and wherein the pyrrolidinyl or piperidinyl group in $Q^1-X^2$ is substituted on the ring nitrogen by a substituent selected from pyrrolidin-1-ylacetyl, 2-(pyrrolidin-1-yl)propionyl, 3,4-methylenedioxypyrrolidin-1-ylacetyl, 2-(3,4-methylenedioxypyrrolidin-1-yl)propionyl, piperidinoacetyl, 2-piperidinopropionyl piperazin1-ylacetyl and 2-piperazin-1-ylpropionyl and wherein any pyrrolidin-1-yl, piperidino or piperazin-1-yl group within a substituent on $Q^1$ optionally bears one or two substituents, which may be the same or different, selected from hydroxy, oxo, methyl, ethyl, acetyl and fluoro, and wherein any acetyl, propionyl or isobutyryl group in a substituent on $Q^1$ optionally bears one or two substituents, which may be the same or different, selected from hydroxy and methyl, and wherein any (1-4C)alkyl group in a substituent on $Q^1$ optionally bears one or two substituents, which may be the same or different, selected from hydroxy, methoxy, fluoro, chloro;

(ggg) $Q^1-X^2$ is selected from pyrrolidin-3-yl, (3R)-pyrrolidin-3-yl, (3S)-pyrrolidin-3-yl, piperidin-3-yl, (3R)-piperidin-3-yl, (3S)-piperidin-3-yl, piperidin-4-yl, pyrrolidin-2-ylmethyl, (2R)-pyrrolidin-2-ylmethyl, (2S)-pyrrolidin-2-ylmethyl, and piperidin-4-ylmethyl, and wherein the pyrrolidinyl or piperidinyl group in $Q^1-X^2$ is optionally substituted on the ring nitrogen by a substituent selected from methyl, acetyl, carbamoylmethyl, N-methylaminoacetyl, N,N-dimethylaminoacetyl, 3-(N,N-di-methylamino)propylsulfonyl and pyrrolidine-1-ylacetyl, and wherein any pyrrolidin-1-yl, group within a substituent on $Q^1$ optionally bears one or two substituents, which may be the same or different, selected from hydroxy, oxo, methyl, ethyl, acetyl and fluoro, and wherein any (1-4C)alkyl group in a substituent on $Q^1$ optionally bears one or two substituents, which may be the same or different, selected from hydroxy, methoxy, fluoro, chloro, and wherein any acetyl group in a substituent on $Q^1$ optionally bears a hydroxy substituent;

(hhh) $Q^1-X^2$ is selected from pyrrolidin-3-yl, (3R)-pyrrolidin-3-yl, (3S)-pyrrolidin-3-yl, piperidin-3-yl, (3R)-piperidin-3-yl, (3S)-piperidin-3-yl, piperidin-4-yl, pyrrolidin-2-ylmethyl, (2R)-pyrrolidin-2-ylmethyl, (2S)-pyrrolidin-2-ylmethyl, and piperidin-4-ylmethyl, and wherein the pyrrolidinyl or piperidinyl group in $Q^1-X^2$ is substituted on the ring nitrogen by a substituent selected from methyl, acetyl, hydroxyacetyl, carbamoylmethyl, N-methylaminoacetyl, N,N-dimethylaminoacetyl and pyrrolidin-1-ylacetyl;

(iii) $Q^1-X^2$ is selected from piperidin-4-yl, pyrrolidin-2-ylmethyl, (2R)-pyrrolidin-2-ylmethyl and (2S)-pyrrolidin-2-ylmethyl, and wherein the pyrrolidinyl or piperidinyl group in $Q^1-X^2$ is substituted on the ring nitrogen by a substituent selected from acetyl, hydroxyacetyl, N,N-dimethylaminoacetyl and pyrrolidin-1-ylacetyl;

(jjj) $Q^1-X^2$ is selected from pyrrolidin-2-ylmethyl, (2R)-pyrrolidin-2-ylmethyl and (2S)-pyrrolidin-2-ylmethyl, and wherein the pyrrolidinyl in $Q^1-X^2$ is substituted on the ring nitrogen by a substituent selected from N-methylaminoacetyl, N,N-dimethylaminoacetyl and pyrrolidin-1-ylacetyl;

(kkk) $Q^1-X^2$ is a group of the formula A:

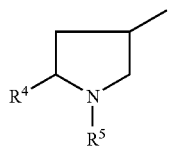

A wherein:
$R^4$ is selected from carbamoyl, N-(1-6C)alkylcarbamoyl, N,N-di-[(1-6C)alkyl]carbamoyl and a group of the formula:

$$Q^2-X^3—$$

wherein $X^3$ is CO and $Q^2$ is a heterocyclyl group selected from a 4, 5 or 6-membered monocyclic heterocyclyl group containing 1 nitrogen heteroatom and optionally 1 or 2 heteroatoms selected from sulfur, oxygen and nitrogen, and wherein $Q^2$ is attached to $X^3$ by a ring nitrogen atom, and wherein $Q^2$ optionally bears one or more substituents (for example 1, 2 or 3), which may be the same or different, selected from halogeno, hydroxy, (1-4C)alkyl and (2-4C)alkanoyl, and wherein any (1-6C)alkyl or (2-6C)alkanoyl group within $R^4$ optionally bears one or more substituents (for example 1, 2 or 3) which may be the same or different selected from halogeno, hydroxy and (1-6C)alkyl anchor optionally a substituent selected from cyano, nitro, (2-8C)alkenyl, (2-8C)alkynyl and (1-6C)alkoxy, $R^5$ is selected from hydrogen, (1-6C)alkyl, (1-6C)alkylthio, (1-6C)alkylsulfinyl, (1-6C)alkylsulfonyl, (2-6C)alkanoyl, carbamoyl(1-6C)alkyl, N-(1-6C)alkylcarbamoyl(1-6C)alkyl, N,N-di-[(1-6C)alkyl]carbamoyl(1-6C)alkyl, sulfamoyl(1-6C)alkyl, N-(1-6C)alkylsulfamoyl(1-6C)alkyl, N,N-di-[(1-6C)alkyl]sulfamoyl(1-6C)alkyl and (2-6C)alkanoyl(1-6C)alkyl, and wherein any (1-6C)alkyl or (2-6C)alkanoyl group within $R^5$ optionally bears one or more substituents (for example 1, 2 or 3), which may be the same or different, selected from halogeno, hydroxy and (1-6C)alkyl and/or optionally a substituent selected from cyano, nitro, (2-8C)alkenyl, (2-8C)alkynyl, (1-6C)alkoxy and NR$^a$R$^b$, wherein R$^a$ is hydrogen or (1-4C)alkyl and R$^b$ is hydrogen or (1-4C)alkyl, and wherein any (1-4C)alkyl in R$^a$ or R$^b$ optionally bears one or more substituents (for example 1, 2 or 3) which may be the same or different selected from halogeno and hydroxy and/or optionally a substituent selected from cyano, nitro and (1-4C)alkoxy, or R$^a$ and R$^b$ together with the nitrogen atom to which they are attached form a 4, 5 or 6 membered ring, which optionally bears 1 or 2 substituents, which may be the same or different, on an available ring carbon atom selected from halogeno, hydroxy, (1-4C)alkyl and (1-3C)alkylenedioxy, and may optionally bear on any available ring nitrogen a substituent (provided the ring is not thereby quaternised) selected from (1-4C)alkyl and (2-4C)alkanoyl, and wherein any (1-4C)alkyl or (2-4C)alkanoyl group present as a substituent on the ring formed by R$^a$ and R$^b$ together with the nitrogen atom to which they are attached optionally bears one or more substituents (for example 1, 2 or 3), which may be the same or different, selected from halogeno and hydroxy and/or optionally a substituent selected from (1-4C)alkyl and (1-4C)alkoxy, and wherein any heterocyclyl group within the Q$^1$-X$^2$— group optionally bears 1 or 2 oxo (=O) or thioxo (=S) substituents;

(lll) Q$^1$-X$^2$ is a group of the formula A as defined in (kkk) above wherein:

R$^4$ is selected from carbamoyl, N-(1-6C)alkylcarbamoyl, N,N-di-[(1-6C)alkyl]carbamoyl and a group of the formula:

Q$^2$-X$^3$— wherein X$^3$ is CO and Q$^2$ is selected from pyrrolidin-1-yl, morpholino, piperidino and piperazin-1-yl and wherein Q$^2$ optionally bears 1 or 2 substituents, which may be the same or different, selected from halogeno, hydroxy, (1-4C)alkyl, oxo and (2-4C)alkanoyl, and wherein any (1-6C)alkyl or (2-6C)alkanoyl group within R$^4$ optionally bears one or more substituents (for example 1, 2 or 3) which may be the same or different selected from halogeno, hydroxy and (1-6C)alkyl and/or optionally a substituent selected from cyano, nitro, (2-8C)alkenyl, (2-8C)alkynyl and (1-6C)alkoxy, R$^5$ is selected from hydrogen, (1-6C)alkyl, (1-6C)alkylthio, (1-6C)alkylsulfinyl, (1-6C)alkylsulfonyl, (2-6C)alkanoyl, carbamoyl(1-6C)alkyl, N-(1-6C)alkylcarbamoyl(1-6C)alkyl, N,N-di-[(1-6C)alkyl]carbamoyl(1-6C)alkyl, sulfamoyl(1-6C)alkyl, N-(1-6C)alkylsulfamoyl(1-6C)alkyl, N,N-di-[(1-6C)alkyl]sulfamoyl(1-6C)alkyl and (2-6C)alkanoyl(1-6C)alkyl, and wherein any (1-6C)alkyl or (2-6C)alkanoyl group within R$^5$ optionally bears one or more substituents (for example 1, 2 or 3) which may be the same or different selected from halogeno, hydroxy and (1-6C)alkyl and/or optionally a substituent selected from cyano, nitro, (2-8C)alkenyl, (2-8C)alkynyl, (1-6C)alkoxy and NR$^a$R$^b$, wherein R$^a$ is hydrogen or (1-4C)alkyl and R$^b$ is hydrogen or (1-4C)alkyl, and wherein any (1-4C)alkyl in R$^a$ or R$^b$ optionally bears one or more substituents (for example 1, 2 or 3) which may be the same or different selected from halogeno and hydroxy and/or optionally a substituent selected from cyano, nitro and (1-4C)alkoxy, or R$^a$ and R$^b$ together with the nitrogen atom to which they are attached form a ring selected from pyrrolidin-1-yl, piperidino, morpholino and piperazin-1-yl, which ring optionally bears 1 or 2 substituents, which may be the same or different, on an available ring carbon atom selected from halogeno, hydroxy, (1-4C)alkyl and oxo, and may optionally bear on any available ring nitrogen a substituent (provided the ring is not thereby quaternised) selected from (1-4C)alkyl and (2-4C)alkanoyl, and wherein any (1-4C)alkyl or (2-4C)alkanoyl group present as a substituent on the ring formed by R$^a$ and R$^b$ together with the nitrogen atom to which they are attached optionally bears one or more substituents (for example 1, 2 or 3), which may be the same or different, selected from halogeno and hydroxy and/or optionally a substituent selected from (1-4C)alkyl and (1-4C)alkoxy;

(mmm) Q$^1$-X$^2$ is a group of the formula A as defined in (kkk) above wherein:

R$^4$ is selected from carbamoyl, N-(1-6C)alkylcarbamoyl, N,N-di-[(1-6C)alkyl]carbamoyl and a group of the formula:

Q$^2$-X$^3$— wherein X$^3$ is CO and Q$^2$ is selected from pyrrolidin-1-yl, morpholino, piperidino and piperazin-1-yl and wherein Q$^2$ optionally bears 1 or 2 substituents, which may be the same or different, selected from fluoro, chloro, hydroxy, methyl, oxo and acetyl, and wherein any (1-6C)alkyl group within R$^4$ optionally bears one or more substituents (for example 1, 2 or 3) which may be the same or different selected from fluoro, chloro and hydroxy and/or optionally a substituent selected from cyano, nitro, vinyl, ethynyl and methoxy, R$^5$ is selected from hydrogen, (1-4C)alkyl, (1-4C)alkylthio, (1-4C)alkylsulfinyl, (1-4C)alkylsulfonyl, (2-4C)alkanoyl, carbamoyl(1-4C)alkyl, N-(1-4C)alkylcarbamoyl(1-4C)alkyl, N,N-di-[(1-4C)alkyl]carbamoyl(1-4C)alkyl, sulfamoyl(1-4C)alkyl, N-(1-4C)alkylsulfamoyl(1-4C)alkyl, N,N-di-[(1-4C)alkyl]sulfamoyl(1-4C)alkyl and (2-4C)alkanoyl(1-4C)alkyl, and wherein any (1-4C)alkyl or (2-4C)alkanoyl group within R$^5$ optionally bears one or more substituents (for example 1, 2 or 3), which may be the same or different, selected from fluoro, chloro, hydroxy, methyl and ethyl and/or optionally a substituent selected from cyano, nitro, vinyl, ethynyl, methoxy and NR$^a$R$^b$, wherein R$^a$ is hydrogen or (1-4C)alkyl and R$^b$ is hydrogen or (1-4C)alkyl, and wherein any (1-4C)alkyl in R$^a$ or R$^b$ optionally bears one or more substituents (for example 1, 2 or 3), which may be the same or different, selected from fluoro, chloro and hydroxy and/or optionally a substituent selected from cyano, nitro and methoxy, or R$^a$ and R$^b$ together with the nitrogen atom to which they are attached form a ring selected from pyrrolidin-1-yl, piperidino, morpholino and piperazin-1-yl, which ring optionally bears 1 or 2 substituents, which may be the same or different, on an available ring carbon atom selected from halogeno, hydroxy, methyl, ethyl and oxo, and may optionally bear on any available ring nitrogen a substituent (provided the ring is not thereby quaternised) selected from methyl, ethyl and acetyl;

(nnn) Q$^1$-X$^2$ is a group of the formula A as defined in (kkk) above wherein:

R$^4$ is selected from carbamoyl, N-(1-4C)alkylcarbamoyl, N,N-di-[(1-4C)alkyl]carbamoyl and a group of the formula:

Q$^2$-X$^3$— wherein X$^3$ is CO and Q$^2$ is selected from pyrrolidin-1-yl, morpholino, piperidino and piperazin-1-yl, and wherein $Q^2$ optionally bears 1 or 2 substituents, which may be the same or different, selected from fluoro, chloro, hydroxy, methyl, oxo and acetyl, and wherein any (1-4C)alkyl group within $R^4$ optionally bears 1 or 2 substituents, which may be the same or different, selected from fluoro, chloro and hydroxy and/or optionally a substituent selected from cyano, nitro, vinyl, ethynyl and methoxy, $R^5$ is selected from hydrogen, methyl, ethyl, isopropyl, isobutyl, cyclopropylmethyl, methylsulfonyl, ethylsulfonyl, acetyl, propionyl, isobutyryl, carbamoylmethyl, N-(1-4C)alkylcarbamoylmethyl, N,N-di-[(1-4C)alkyl]carbamoylmethyl, sulfamoylmethyl, N-(1-4C)alkylsulfamoylmethyl and N,N-di-[(1-4C)alkyl]sulfamoylmethyl and wherein any (1-4C)alkyl, acetyl, propionyl or isobutyryl group within $R^5$ optionally bears 1 or 2 substituents, which may be the same or different, selected from fluoro, chloro and hydroxy, methyl and ethyl and/or optionally a substituent selected from cyano, nitro, vinyl, ethynyl, methoxy and $NR^aR^b$, wherein $R^a$ is hydrogen or (1-4C)alkyl and $R^b$ is hydrogen or (1-4C)alkyl, and wherein any (1-4C)alkyl in $R^a$ or $R^b$ optionally bears 1 or 2 substituents, which may be the same or different, selected from fluoro, chloro and hydroxy and/or optionally a substituent selected from cyano, nitro and methoxy, or $R^a$ and $R^b$ together with the nitrogen atom to which they are attached form a ring selected from pyrrolidin-1-yl, piperidino, morpholino and piperazin-1-yl, which ring optionally bears 1 or 2 substituents, which may be the same or different, on an available ring carbon atom selected from halogeno, hydroxy, methyl, and oxo, and may optionally bear on any available ring nitrogen a substituent (provided the ring is not thereby quaternised) selected from methyl and acetyl;

(ooo) $Q^1$-$X^2$ is a group of the formula A as defined in (kick) above wherein:

$R^4$ is selected from N,N-di-[(1-4C)alkyl]carbamoyl and a group of the formula:

$$Q^2\text{-}X^3\text{—}$$

wherein $X^3$ is CO and $Q^2$ is selected from pyrrolidin-1-yl, morpholino and piperidino, and wherein $Q^2$ optionally bears 1 or 2 substituents, which may be the same or different, selected from fluoro, chloro, hydroxy, methyl and oxo, and wherein any (1-4C)alkyl group within $R^4$ optionally bears 1 or 2 substituents, which may be the same or different, selected from fluoro, chloro and hydroxy and/or optionally a substituent selected from methoxy, $R^5$ is selected from hydrogen, methyl, ethyl, isopropyl, isobutyl and cyclopropylmethyl, and wherein any (1-4C)alkyl group within $R^5$ optionally bears 1 or 2 substituents, which may be the same or different, selected from fluoro, chloro and hydroxy, and/or optionally a substituent selected from methoxy;

(ppp) $Q^1$-$X^2$ is a group of the formula A as defined in (kkk) above wherein:

$R^4$ is selected from N,N-dimethylcarbamoyl, N,N-diethylcarbamoyl, N-methyl-N-ethylcarbamoyl, and a group of the formula:

$$Q^2\text{-}X^3\text{—}$$

wherein $X^3$ is CO and $Q^2$ is morpholino (particularly $R^4$ is N,N-dimethylcarbamoyl), $R^5$ is selected from hydrogen, methyl and ethyl (particularly $R^5$ is hydrogen or methyl, more particularly methyl);

(qqq) $R^1$—$X^1$ is selected from hydrogen, (1-6C)alkoxy and (1-4C)alkoxy(1-6C)alkoxy, and wherein any (1-6C) alkoxy group within $R^1X^1$ optionally bears 1, 2 or 3 substituents, which may be the same or different, selected from hydroxy, fluoro and chloro, for example $R^1$—$X^1$ is selected from methoxy, ethoxy, isopropyloxy, cyclopropylmethoxy, 2-hydroxyethoxy, 2-fluoroethoxy, 2-methoxyethoxy, 2,2-difluoroethoxy, 2,2,2-trifluoroethoxy or 3-hydroxy-3-methylbutoxy.

As will be realised the group represented by formula A in paragraphs (kkk) to (ppp) above contains two chiral centres on the pyrrolidinyl ring. As mentioned hereinbefore the present invention encompasses all stereoisomers of the group of formula A, for example the (2R,4R), (2S,4S), (2R,4S) and (2S,4R) isomers.

A further embodiment of the invention is a quinazoline derivative of the Formula wherein:

$R^1$—$X^1$— is selected from hydrogen, (1-6C)alkoxy and (1-6C)alkoxy(1-6C)alkoxy, wherein any (1-6C)alkoxy group in $R^1$—$X^1$— optionally bears one or more hydroxy substituent (suitably 1 or 2) and/or a substituent selected from amino, (1-4C)alkylamino, di-[(1-4C)alkyl]amino, carbamoyl, N-(1-4C)alkylcarbamoyl and N,N-di-[(1-4C)alkyl]carbamoyl, sulfamoyl, N-(1-4C)alkylsulfamoyl and N,N-di-[(1-4C)alkyl]sulfamoyl;

$X^2$ is a direct bond or $[CR^2R^3]_m$, wherein m is 1, 2 or 3 (particularly 1 or 2, more particularly 1), and $R^2$ and $R^3$ each independently is hydrogen, methyl, ethyl or hydroxy (preferably hydrogen);

$Q^1$ is a non-aromatic saturated or partially saturated 3 to 7 membered monocyclic heterocyclyl ring with 1 nitrogen heteroatom and optionally 1 or 2 heteroatoms selected from oxygen, nitrogen and sulfur, which ring is linked to the group $X^2$—O— by a carbon atom in the ring, and wherein the nitrogen atom of any NH group in $Q^1$ optionally bears a substituent selected from cyano, carbamoyl, trifluoromethyl, (1-6C)alkyl, (2-8C)alkenyl, (2-8C)alkynyl, (1-6C)alkylthio, (1-6C)alkylsulfinyl, (1-6C)alkylsulfonyl, (1-6C)alkoxycarbonyl, N-(1-6C)alkylcarbamoyl, N,N-di-[(1-6C)alkyl]carbamoyl, (2-6C)alkanoyl, sulfamoyl, N-(1-6C)alkylsulfamoyl, N,N-di-[(1-6C)alkyl]sulfamoyl, hydroxy(1-6C)alkyl, cyano(1-6C)alkyl, amino(1-6C)alkyl, (1-6C)alkylamino(1-6C)alkyl, di-[(1-6C)alkyl]amino(1-6C) alkyl, amino(2-6C)alkanoyl, (1-6C)alkylamino-(2-6C)alkanoyl, N,N-di-[(1-6C)alkyl]amino-(2-6C)alkanoyl, (1-6C) alkoxy(1-6C)alkyl, hydroxy(1-6C)alkoxy(1-6C)alkyl, carbamoyl(1-6C)alkyl, N-(1-6C)alkylcarbamoyl(1-6C)alkyl, N,N-di-[(1-6C)alkyl]carbamoyl(1-6C)alkyl, (2-6C)alkanoyl (1-6C)alkyl, (2-6C)alkanoyloxy(1-6C)alkyl, (2-6C)alkanoylamino(1-6C)alkyl, N-(1-6C)alkyl-(2-6C)alkanoylamino(1-6C)alkyl, (1-6C) alkoxycarbonyl(1-6C)alkyl, (1-6C)alkoxy(1-6C)alkylS(O)$_q$ (wherein q is 0, 1 or 2), amino(1-6C)alkylS(O)$_q$ (wherein q is 0, 1 or 2), N-(1-6C)alkylamino(1-6C)alkylS(O)$_q$ (wherein q is 0, 1 or 2) and N,N-di[(1-6C)alkyl]amino(1-6C)alkylS(O)$_q$ (wherein q is 0, 1 or 2), and $Q^1$ optionally bears on any available carbon atom in the ring 1 or 2 substituents selected from (1-4C)alkyl, (2-6C) alkenyl, (2-6C)alkynyl and oxo, and wherein any (1-6C)alkyl, (2-8C)alkenyl, (2-8C)alkynyl or (2-6C)alkanoyl group in $Q^1$ optionally bears 1 or 2 substituents which may be the same or different selected from fluoro and chloro; and $G^1$ and $G^2$ each independently is selected from fluoro, chloro and bromo (particularly $G^1$ is fluoro and $G^2$ chloro);

or a pharmaceutically acceptable salt thereof.

A further embodiment of the invention is a quinazoline derivative of the Formula I wherein:

$R^1$—$X^1$— is selected from hydrogen, methoxy, ethoxy and 2-methoxyethoxy;

$X^2$ is a direct bond or $[CH_2]_m$, wherein m is 1 or 2 (suitably 1);

$Q^1$ is a non-aromatic saturated 5 or 6 membered monocyclic heterocyclyl ring with 1 nitrogen heteroatom and optionally 1 or 2 (suitably 1) heteroatoms selected from oxygen and nitrogen, which ring is linked to the group $X^2$—O— by a carbon atom in the ring, and wherein the nitrogen atom of any NH group in $Q^1$ optionally bears a substituent selected from cyano, carbamoyl, (1-4C)alkyl, (2-6C)alkenyl, (2-6C)alkynyl, (1-4C)alkylsulfonyl, N-(1-4C)alkylcarbamoyl, N,N-di-[(1-4C)alkyl]carbamoyl, (2-4C)alkanoyl, sulfamoyl, N-(1-4C)alkylsulfamoyl, N,N-di-[(1-4C)alkyl]sulfamoyl, cyano(1-4C)alkyl, (1-4C)alkoxy(1-4C)alkyl, amino(2-4C)alkanoyl, (1-4C)alkylamino-(2-4C)alkanoyl, N,N-di-[(1-4C)alkyl]amino-(2-4C)alkanoyl, carbamoyl (1-3C)alkyl, N-(1-4C)alkylcarbamoyl (1-3C)alkyl, N,N-di-[(1-4C)alkyl]carbamoyl(1-3C)alkyl, (1-4C)alkoxy(1-3C)alkylS(O)$_q$ (wherein q is 0, 1 or suitably 2), amino(1-3C)alkylS(O)$_q$ (wherein q is 0, 1 or suitably 2), N-(1-4C)alkylamino(1-3C)alkylS(O)$_q$ (wherein q is 0, 1 or suitably 2) and N,N-di[(1-4)alkyl]amino(1-3C)alkylS(O)$_q$ (wherein q is 0, 1 or suitably 2), and $Q^1$ optionally bears on any available carbon atom in the ring 1 or 2 substituents selected from oxo, (1-4C)alkyl, (2-6C)alkenyl and (2-6C)alkynyl, and wherein any (1-4C)alkyl, (2-6C)alkenyl or (2-6C)alkynyl in $Q^1$ optionally bears 1 or 2 substituents which may be the same or different selected from fluoro and chloro; and $G^1$ and $G^2$ each independently is selected from fluoro, chloro and bromo (particularly $G^1$ is fluoro and $G^2$ chloro);

or a pharmaceutically acceptable salt thereof.

A further embodiment of the invention is a quinazoline derivative of the Formula I wherein:

$R^1$—$X^1$— is selected from hydrogen, methoxy, ethoxy and 2-methoxyethoxy, $X^2$ is a direct bond or $CH_2$;

$Q^1$ is selected from pyrrolidin-2-yl, pyrrolidin-3-yl, 2-pyrrolin-2-yl, 2-pyrrolin-3-yl, 3-pyrrolin-3-yl, morpholin-2-yl, morpholin-3-yl, thiomorpholin-2-yl, piperidin-2-yl, piperidin-3-yl, piperidin-4-yl, 2-3- or 4-homopiperidinyl, 2-oxopiperazin-1-yl, 3-oxopiperazin-1-yl, piperazin-2-yl, 1,2,3,6-tetrahydropyridin-4-yl, 1,2,3,6-tetrahydropyridin-5-yl, 1,2,3,4-tetrahydropyridin-5-yl, 1,2,3,6-tetrahydropyridin-6-yl, 2,3,4,6 or 7-homopiperazinyl and azetidin-3-yl, and wherein the nitrogen atom of any NH group in $Q^1$ optionally bears a substituent selected from cyano, (1-4C)alkyl, cyano(1-4C)alkyl, (1-4C)alkoxy(1-4C)alkyl, (1-4C)alkylsulfonyl, trifluoromethyl, carbamoyl, N-(1-4C)alkylcarbamoyl, N,N-di-[(1-4C)alkyl]carbamoyl, (2-4C)alkanoyl, sulfamoyl, N-(1-4C)alkylsulfamoyl, N,N-di-[(1-4C)alkyl]sulfamoyl, amino(2-4C)alkanoyl, (1-4C)alkylamino-(2-4C)alkanoyl, N,N-di-[(1-4C)alkyl]amino-(2-4C)alkanoyl, carbamoyl(1-3C)alkyl, N-(1-4C)alkylcarbamoyl(1-3C)alkyl, N,N-di-[(1-4C)alkyl]carbamoyl(1-3C)alkyl, (1-4C)alkoxy(1-3C)alkylsulfonyl, amino(1-3C)alkylsulfonyl, N-(1-4C)alkylamino(1-3C)alkylsulfonyl and N,N-di[(1-4)alkyl]amino(1-3C)alkylsulfonyl, and $Q^1$ optionally bears on any available carbon atom in the ring 1 or 2 substituents selected from (1-4C)alkyl and oxo, and wherein any (1-4C)alkyl group in $Q^1$ optionally bears 1 or 2 fluoro substituents (to give for example 2-fluoroethyl or 2,2-difluoroethyl); and $G^1$ and $G^2$ each independently is selected from fluoro and chloro (particularly $G^1$ is fluoro and $G^2$ chloro);

or a pharmaceutically acceptable salt thereof.

Suitable values for $Q^1X^2$ in this embodiment include, for example, 1-methyl pyrrolidin-3-yl, piperidin-4-yl, piperidin-4-ylmethyl, 1-methylpiperidin-4-yl, 1-methylpiperidin-4-ylmethyl, 1-(2-methoxyethyl)piperidin-4-yl, 1-(2-methoxyethyl)piperidin-4-ylmethyl, 1-methylsulfonylpiperidin-4-yl, 1-methylsulfonylpiperidin-4-ylmethyl, 1-cyanopiperidin-4-yl, 1-cyanopiperidin-4-ylmethyl, 1-cyanomethylpiperidin-4-yl, 1-cyanomethylpiperidin-4-ylmethyl, 1-carbamoylmethylpiperidin-4-yl, 1-carbamoylmethylpiperidin-4-ylmethyl.

A further embodiment of the invention is a quinazoline derivative of the Formula I wherein:

$R^1$—$X^1$— is selected from hydrogen and methoxy;

$X^2$ is a direct bond;

$Q^1$ is selected from pyrrolidin-2-yl, pyrrolidin-3-yl, piperidin-2-yl, piperidin-3-yl and piperidin-4-yl, and wherein the nitrogen atom of any NH group in $Q^1$ optionally bears a substituent selected from cyano, cyanomethyl, methyl, ethyl, carbamoyl, carbamoylmethyl, 2-methoxyethyl, methylsulfonyl and ethylsulfonyl (suitably methylsulfonyl and carbamoylmethyl), and $Q^1$ optionally bears on any available carbon atom in the ring 1 or 2 substituents selected from methyl, ethyl and oxo; and $G^1$ and $G^2$ each independently is selected from fluoro, chloro and bromo (particularly $G^1$ is fluoro and $G^2$ chloro);

or a pharmaceutically acceptable salt thereof.

Suitable values for $Q^1X^2$ in this embodiment include, for example, piperidin-4-yl, 1-methylpiperidin-4-yl, 1-(2-methoxyethyl)piperidin-4-yl, 1-methylsulfonylpiperidin-4-yl, 1-cyanopiperidin-4-yl, 1-cyanomethylpiperidin-4-yl and 1-carbamoylmethylpiperidin-4-yl.

A further embodiment of the invention is a quinazoline derivative of the Formula I wherein:

$R^1$—$X^1$— is selected from hydrogen, (1-4C)alkoxy and (1-4C)alkoxy(1-4C)alkoxy (particularly hydrogen and methoxy);

$X^2$ is a direct bond or $CH_2$;

$Q^1$ is a fully saturated 5 or 6 membered monocyclic heterocyclyl ring with 1 nitrogen heteroatom and optionally 1 additional heteroatom selected from oxygen, nitrogen and sulfur, which ring is linked to the group $X^2$—O— by a carbon atom in the ring, and wherein $Q^1$ bears one substituent on a ring carbon atom selected from carbamoyl, N-(1-4C)alkylcarbamoyl, N,N-di-[(1-4C)alkyl]carbamoyl, carbamoyl(1-3C)alkyl, N-(1-4C)alkylcarbamoyl(1-3C)alkyl, N,N-di-[(1-4C)alkyl]carbamoyl(1-3C)alkyl, (2-4C)alkanoyl, amino(2-4C)alkanoyl, (1-4C)alkylamino-(2-4C)alkanoyl, N,N-di-[(1-4C)alkyl]amino-(2-4C)alkanoyl, pyrrolidin-1-yl-(2-4C)alkanoyl, piperidino-(2-4C)alkanoyl, piperazine-1-yl-(2-4C)alkanoyl and morpholino-(24C)alkanoyl, or a group of the formula:

$Q^2$-$X^3$— wherein $X^3$ is CO and $Q^2$ is selected from pyrrolidin-1-yl, morpholino and piperidino, and wherein the nitrogen atom of any NH group in $Q^1$ optionally bears a substituent selected from (1-4C)alkyl, and wherein any heterocyclyl group within the $Q^1$-$X^2$— group optionally bears an oxo (═O) substituent; and G¹ and G² each independently is selected from fluoro and chloro (particularly G¹ is fluoro and G² chloro);

or a pharmaceutically acceptable salt thereof.

A further embodiment of the invention is a quinazoline derivative of the Formula I wherein:

R¹—X¹— is selected from hydrogen and (1-4C)alkoxy (particularly hydrogen and methoxy);

Q¹-X² is selected from pyrrolidin-3-yl, piperidin-3-yl, piperidin-4-yl, pyrrolidin-2-ylmethyl, pyrrolidin-3-ylmethyl, piperidin-2-ylmethyl, piperidin-3-ylmethyl and piperidin-4-ylmethyl, and wherein a pyrrolidinyl or piperidinyl group in Q¹-X² carries one or two substituents selected from (1-4C)alkyl, (1-4C)alkylsulfonyl, N-(1-4C)alkylcarbamoyl, N,N-di-[(1-4C)alkyl]carbamoyl, (2-4C)alkanoyl, N,N-di-[(1-4C)alkyl]sulfamoyl, N-(1-4C)alkylcarbamoyl(1-3C)alkyl, N,N-di-[(1-4C)alkyl]carbamoyl(1-3C)alkyl, hydroxy(2-4C)alkanoyl,
N-(1-4C)alkylamino-(2-4C)alkanoyl, N,N-di-[(1-4C)alkyl]amino-(2-4C)alkanoyl, (2-4C)alkanoyloxy-(2-4C)alkanoyl,
N-(1-4)alkylamino-(1-3C)alkylsulfonyl, N,N-di[(1-4)alkyl]amino(1-3C)alkylsulfonyl, pyrrolidin-1-yl-(2-4C)alkanoyl, piperidino-(2-4C)alkanoyl, morpholino-(2-4C)alkanoyl and a group of the formula:

Q²-X³— wherein X³ is CO and Q² is selected from pyrrolidin-1-yl, morpholino and piperidino; and G¹ and G² each independently is selected from fluoro and chloro (particularly G¹ is fluoro and G² chloro);

or a pharmaceutically acceptable salt thereof.

A further embodiment of the invention is a quinazoline derivative of the Formula I wherein:

R¹—X¹— is selected from hydrogen and (1-4C)alkoxy (particularly methoxy);

Q¹-X² is selected from pyrrolidin-3-yl, pyrrolidin-2-ylmethyl and pyrrolidin-3-ylmethyl, and wherein the pyrrolidinyl group carries one substituent in the 5-position selected from N,N-di-[(1-4C)alkyl]carbamoyl and a group of the formula:

Q²-X³— wherein X³ is CO and Q² is morpholino, and wherein the pyrrolidinyl group optionally bears a substituent at the 1-position selected from (1-4C)alkyl;

G¹ is fluoro; and
G² is chloro;

or a pharmaceutically acceptable salt thereof.

A further embodiment of the invention is a quinazoline derivative of the Formula I wherein:

R¹—X¹— is selected from hydrogen and (1-4C)alkoxy (particularly methoxy);

Q¹-X² is selected from pyrrolidin-3-yl, piperidin-3-yl, pyrrolidin-2-ylmethyl, pyrrolidin-3-ylmethyl, piperidin-2-ylmethyl, piperidin-3-ylmethyl and piperidin-4-ylmethyl, and wherein a pyrrolidinyl or piperidinyl group in Q¹-X² carries a substituent at the 1-position selected from (1-4C)alkyl, (1-4C)alkylsulfonyl, (2-4C)alkanoyl, hydroxy(2-4C)alkanoyl, N-(1-4C)alkylamino-(2-4C)alkanoyl, N,N-di-[(1-4C)alkyl]amino-(2-4C)alkanoyl, (2-4C)alkanoyloxy-(2-4C)alkanoyl, N,N-di[(1-4)alkyl]amino(1-3C)alkylsulfonyl, pyrrolidin-1-yl-(2-4C)alkanoyl, piperidino-(2-4C)alkanoyl and morpholino-(2-4C)alkanoyl or a group of the formula:

Q²-X³— wherein X³ is CO and Q² is morpholino;
G¹ is fluoro; and
G² is chloro;

or a pharmaceutically acceptable salt thereof.

A further embodiment of the invention is a quinazoline derivative of the Formula I wherein:

R¹—X¹ is selected from hydrogen, (1-6C)alkoxy and (1-4C)alkoxy(1-6C)alkoxy, and wherein any (1-6C)alkoxy group within R¹X¹ optionally bears 1, 2 or 3 substituents, which may be the same or different, selected from hydroxy, fluoro, chloro (for example R¹—X¹ is selected from hydrogen, methoxy, ethoxy, isopropyloxy, cyclopropylmethoxy, 2-hydroxyethoxy, 2-fluoroethoxy, 2-methoxyethoxy, 2,2-difluoroethoxy, 2,2,2-trifluoroethoxy or 3-hydroxy-3-methylbutoxy, a particular value for R¹—X¹ being hydrogen or (1-4C)alkoxy, more particularly (1-4C)alkoxy, such as methoxy);

Q¹-X² is selected from pyrrolidin-3-yl, (3R)-pyrrolidin-3-yl, (3S)-pyrrolidin-3-yl, piperidin-3-yl, (3R)-piperidin-3-yl, (3S)-piperidin-3-yl, piperidin-4-yl, pyrrolidin-2-ylmethyl, (2R)-pyrrolidin-2-ylmethyl, (2S)-pyrrolidin-2-ylmethyl, (3R)-pyrrolidin-3-ylmethyl, (3S)-pyrrolidin-3-ylmethyl, (2R)-piperidin-2-ylmethyl, (2S)-piperidin-2-ylmethyl, piperidin-3-ylmethyl, (3R)-piperidin-3-ylmethyl, (3S)-piperidin-3-ylmethyl and piperidin-4-ylmethyl, and wherein the pyrrolidinyl or piperidinyl group in Q¹-X² carries a substituent at the 1 position selected from (1-4C)alkyl, (1-4C)alkylsulfonyl, (2-4C)alkanoyl, carbamoyl(1-3C)alkyl, N-(1-4C)alkylcarbamoyl(1-3C)alkyl, N,N-di-[(1-4C)alkyl]carbamoyl(1-3C)alkyl, hydroxy(2-4C)alkanoyl, N-(1-4C)alkylamino-(2-4C)alkanoyl, N,N-di-[(1-4C)alkyl]amino-(2-4C)alkanoyl, (2-4C)alkanoyloxy-(2-4C)alkanoyl,
N-(1-4)alkylamino-(1-3C)alkylsulfonyl, N,N-di[(1-4)alkyl]amino(1-3C)alkylsulfonyl, pyrrolidin-1-yl-(2-4C)alkanoyl, 3,4-methylenedioxypyrrolidin-1-yl-(2-4C)alkanoyl, piperidino-(2-4C)alkanoyl, piperazin-1-yl-(2-4C)alkanoyl and a group of the formula:

Q²-X³— wherein X³ is CO and Q² is selected from pyrrolidin-2-yl, and wherein any pyrrolidinyl, piperidino or piperazin-1-yl within a substituent on Q¹ optionally bears one or two substituents selected from fluoro, chloro, hydroxy, oxo, methyl and acetyl;

G¹ is fluoro; and
G² is chloro;

or a pharmaceutically acceptable salt thereof.

A further embodiment of the invention is a quinazoline derivative of the Formula I wherein:

R¹—X¹ is selected from hydrogen, (1-6C)alkoxy and (1-4C)alkoxy(1-6C)alkoxy, and wherein any (1-6C)alkoxy group within R¹X¹ optionally bears 1, 2 or 3 substituents, which may be the same or different, selected from hydroxy, fluoro, chloro (for example R¹—X¹ is selected from hydrogen, methoxy, ethoxy, isopropyloxy, cyclopropylmethoxy, 2-hydroxyethoxy, 2-fluoroethoxy, 2-methoxyethoxy, 2,2-difluoroethoxy, 2,2,2-trifluoroethoxy or 3-hydroxy-3-methylbutoxy, a particular value for R¹—X¹ being hydrogen or (1-4C)alkoxy, more particularly (1-4C)alkoxy such as methoxy);

Q¹-X² is selected from pyrrolidin-3-yl, (3R)-pyrrolidin-3-yl, (3S)-pyrrolidin-3-yl, piperidin-3-yl, (3R)-piperidin-3-yl, (3S)piperidin-3-yl, piperidin-4-yl, pyrrolidin-2-ylmethyl, (2R)-pyrrolidin-2-ylmethyl, (2S)-pyrrolidin-2-ylmethyl, pyrrolidin-3-ylmethyl, (3R)-pyrrolidin-3-ylmethyl, (3S)-pyrrolidin-3-ylmethyl, piperidin-2-ylmethyl, (2R)-piperidin-2-ylmethyl, (2S)-piperidin-2-ylmethyl, piperidin-3-ylmethyl, (3R)-piperidin-3-ylmethyl, (3S)-piperidin-3-ylmethyl and piperidin-4-ylmethyl, and wherein the pyrrolidinyl or piperidinyl group in $Q^1$-$X^2$ carries a substituent at the 1 position selected from morpholino(2-4C)alkanoyl;

$G^1$ is fluoro; and $G^2$ is chloro;

or a pharmaceutically acceptable salt thereof.

A further embodiment of the invention is a quinazoline derivative of the Formula I wherein:

$R^1$—$X^1$ is selected from hydrogen, (1-6C)alkoxy and (1-4C)alkoxy(1-6C)alkoxy, and wherein any (1-6C)alkoxy group within $R^1X^1$ optionally bears 1, 2 or 3 substituents, which may be the same or different, selected from hydroxy, fluoro, chloro (for example $R^1$—$X^1$ is selected from hydrogen, methoxy, ethoxy, isopropyloxy, cyclopropylmethoxy, 2-hydroxyethoxy, 2-fluoroethoxy, 2-methoxyethoxy, 2,2-difluoroethoxy, 2,2,2-trifluoroethoxy or 3-hydroxy-3-methylbutoxy, a particular value for $R^1$—$X^1$ being hydrogen or (1-4C)alkoxy, more particularly (1-4C)alkoxy such as methoxy);

$Q^1$-$X^2$ is a group of the formula A:

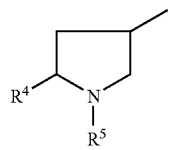

A wherein:

$R^4$ is selected from carbamoyl, N-(1-6C)alkylcarbamoyl, N,N-di-[(1-6C)alkyl]carbamoyl and a group of the formula:

$Q^2$-$X^3$— wherein $X^3$ is CO and $Q^2$ is a heterocyclyl group selected from a 4, 5 or 6-membered monocyclic heterocyclyl group containing 1 nitrogen heteroatom and optionally 1 or 2 heteroatoms selected from sulfur, oxygen and nitrogen, and wherein $Q^2$ is attached to $X^3$ by a ring nitrogen atom, and wherein $Q^2$ optionally bears one or more substituents (for example 1, 2 or 3), which may be the same or different, selected from halogeno, hydroxy, (1-4C)alkyl, oxo and (2-4C)alkanoyl, and wherein any (1-6C)alkyl or (2-6C)alkanoyl group within $R^4$ optionally bears one or more substituents (for example 1, 2 or 3) which may be the same or different selected from halogeno, hydroxy and (1-6C)alkyl and/or optionally a substituent selected from cyano, nitro, (2-8C)alkenyl, (2-8C)alkynyl and (1-6C)alkoxy, $R^5$ is selected from hydrogen, (1-6C)alkyl, (1-6C)alkylthio, (1-6C)alkylsulfinyl, (1-6C)alkylsulfonyl, (2-6C)alkanoyl, carbamoyl(1-6C)alkyl, N-(1-6C)alkylcarbamoyl(1-6C)alkyl, N,N-di-[(1-6C)alkyl]-carbamoyl(1-6C)alkyl, sulfamoyl(1-6C)alkyl, N-(1-6C)alkylsulfamoyl(1-6C)alkyl, N,N-di-[(1-6C)alkyl]sulfamoyl(1-6C)alkyl and (2-6C)alkanoyl(1-6C)alkyl, and wherein any (1-6C)alkyl or (2-6C)alkanoyl group within $R^5$ optionally bears one or more substituents (for example 1, 2 or 3) which may be the same or different selected from halogeno, hydroxy and (1-6C)alkyl and/or optionally a substituent selected from cyano, nitro, (2-8C)alkenyl, (2-8C)alkynyl, (1-6C)alkoxy and $NR^aR^b$, wherein $R^a$ is hydrogen or (1-4C)alkyl and $R^b$ is hydrogen or (1-4C)alkyl, and wherein any (1-4C)alkyl in $R^a$ or $R^b$ optionally bears one or more substituents (for example 1, 2 or 3) which may be the same or different selected from halogeno and hydroxy and/or optionally a substituent selected from cyano, nitro and (1-4C)alkoxy, or $R^a$ and $R^b$ together with the nitrogen atom to which they are attached form a 4, 5 or 6 membered ring, which optionally bears 1 or 2 substituents, which may be the same or different, on an available ring carbon atom selected from halogeno, hydroxy, (1-4C)alkyl, (1-3C)alkylenedioxy and oxo, and may optionally bear on any available ring nitrogen a substituent (provided the ring is not thereby quaternised) selected from (1-4C)alkyl and (2-4C)alkanoyl, and wherein any (1-4C)alkyl or (2-4C)alkanoyl group present as a substituent on the ring formed by $R^a$ and $R^b$ together with the nitrogen atom to which they are attached optionally bears one or more substituents (for example 1, 2 or 3), which may be the same or different, selected from halogeno and hydroxy and/or optionally a substituent selected from (1-4C)alkyl and (1-4C)alkoxy;

$G^1$ is fluoro; and $G^2$ is chloro;

or a pharmaceutically acceptable salt thereof.

A further embodiment of the invention is a quinazoline derivative of the Formula I wherein:

$R^1$—$X^1$ is selected from hydrogen, (1-6C)alkoxy and (1-4C)alkoxy(1-6C)alkoxy, and wherein any (1-6C)alkoxy group within $R^1X^1$ optionally bears 1, 2 or 3 substituents, which may be the same or different, selected from hydroxy, fluoro, chloro (for example $R^1$—$X^1$ is selected from hydrogen, methoxy, ethoxy, isopropyloxy, cyclopropylmethoxy, 2-hydroxyethoxy, 2-fluoroethoxy, 2-methoxyethoxy, 2,2-difluoroethoxy, 2,2,2-trifluoroethoxy or 3-hydroxy-3-methylbutoxy, a particular value for $R^1$—$X^1$ being hydrogen or (1-4C)alkoxy, more particularly (1-4C)alkoxy such as methoxy);

$Q^1$-$X^2$ is a group of the formula A:

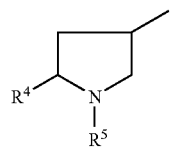

A wherein:

$R^4$ is selected from N,N-di-[(1-4C)alkyl]carbamoyl and a group of the formula:

$Q^2$-$X^3$— wherein $X^3$ is CO and $Q^2$ is selected from pyrrolidin-1-yl, morpholino and piperidino (for example $R^4$ is N,N-dimethylcarbamoyl or morpholinocarbonyl, particularly $R^4$ is N,N-dimethylcarbamoyl), and wherein $Q^2$ optionally bears 1 or 2 substituents, which may be the same or different, selected from fluoro, chloro, hydroxy, methyl and oxo, and wherein any (1-4C)alkyl group within $R^4$ optionally bears 1 or 2 substituents, which may be the same or different, selected from fluoro, chloro and hydroxy and/or optionally a substituent selected from methoxy, $R^5$ is selected from hydrogen, methyl, ethyl, isopropyl, isobutyl and cyclopropylmethyl, and wherein any (1-4C)alkyl group within R⁵ optionally bears 1 or 2 substituents, which may be the same or different, selected from fluoro, chloro and hydroxy, and/or optionally a substituent selected from methoxy;

$G^1$ is fluoro; and
$G^2$ is chloro;

or a pharmaceutically acceptable salt thereof.

A further embodiment of the invention is a quinazoline derivative of the Formula I wherein:

$R^1$—$X^1$ is selected from hydrogen, (1-6C)alkoxy and (1-4C)alkoxy(1-6C)alkoxy, and wherein any (1-6C)alkoxy group within $R^1X^1$ optionally bears 1, 2 or 3 substituents, which may be the same or different, selected from hydroxy, fluoro, chloro (for example $R^1$—$X^1$ is selected from hydrogen, methoxy, ethoxy, isopropyloxy, cyclopropylmethoxy, 2-hydroxyethoxy, 2-fluoroethoxy, 2-methoxyethoxy, 2,2-difluoroethoxy, 2,2,2-trifluoroethoxy or 3-hydroxy-3-methylbutoxy, a particular value for $R^1$—$X^1$ being hydrogen or (1-4C)alkoxy, more particularly (1-4C)alkoxy such as methoxy);

$Q^1$-$X^2$ is selected from (2S,4R)-2-(N,N-dimethylcarbamoyl)-1-methylpyrrolidin-4-yl,
(2R,4S)-2-(N,N-dimethylcarbamoyl)-1-methylpyrrolidin-4-yl,
(2R,4R)-2-(N,N-dimethylcarbamoyl)-1-methylpyrrolidin-4-yl,
(2S,4S)-2-(N,N-dimethylcarbamoyl)-1-methylpyrrolidin-4-yl,
(2S,4R)-2-(N,N-dimethylcarbamoyl)pyrrolidin-4-yl,
(2S,4S)-2-(N,N-dimethylcarbamoyl)pyrrolidin-4-yl,
(2R,4R)-2-(N,N-dimethylcarbamoyl)pyrrolidin-4-yl and
(2S,4S)-2-(N,N-dimethylcarbamoyl)pyrrolidin-4-yl;

$G^1$ is fluoro; and
$G^2$ is chloro;

or a pharmaceutically acceptable salt thereof.

A preferred compound of the invention is, for example, a quinazoline derivative of the Formula I selected from:

4-(3-Chloro-2-fluoroanilino)-6-{[1-(methylsulfonyl)piperidin-4-yl]oxy}-7-methoxyquinazoline; and
6-{[1-(carbamoylmethyl)piperidin-4-yl]oxy}-4-(3-chloro-2-fluoroanilino)-7-methoxyquinazoline;

or a pharmaceutically acceptable acid addition salt thereof.

Another preferred compound of the invention is, for example, a quinazoline derivative of the Formula I selected from:

4-(3-Chloro-2-fluoroanilino)-7-methoxy-6-[(1-methylpyrrolidin-3-yl)oxy]quinazoline;
4-(3-Chloro-2-fluoroanilino)-7-methoxy-6-[(piperidin-4-yl)oxy]quinazoline;
4-(3-Chloro-2-fluoroanilino)-7-methoxy-6-[(piperidin-4-yl)methoxy]quinazoline;
4-(3-Chloro-2-fluoroanilino)-7-methoxy-6-[(1-methylpiperidin-4-yl)oxy]quinazoline;
4-(3-Chloro-2-fluoroanilino)-7-methoxy-6-[(1-methylpiperidin-4-yl)methoxy]quinazoline;
4-(3-Chloro-2-fluoroanilino)-7-methoxy-6-[2-(1-methylpiperidin-4-yl)ethoxy]quinazoline;
4-(3-Chloro-2-fluoroanilino)-7-methoxy-6-{[1-(2-methoxyethyl)piperidin-4-yl]oxy}quinazoline:
4-(3-Chloro-2-fluoroanilino)-7-methoxy-6-{[1-(2-methoxyethyl)piperidin-4-yl]methoxy}quinazoline;
4-(3-Chloro-2-fluoroanilino)-6-{[1-(methylsulfonyl)piperidin-4-yl]methoxy}-7-methoxyquinazoline;
6-{[1-(carbamoylmethyl)piperidin-4-yl]methoxy}-4-(3-fluoroanilino)-7-methoxyquinazoline;
4-(3-Chloro-2-fluoroanilino)-6-{[1-(cyanomethyl)piperidin-4-yl]oxy}-7-methoxyquinazoline;
4-(3-Chloro-2-fluoroanilino)-6-{[1-(cyanomethyl)piperidin-4-yl]methoxy}-7-methoxyquinazoline; and
4-(3-Chloro-2-fluoroanilino)-6-[(1-cyanopiperidin-4-yl)methoxy]-7-methoxyquinazoline;

or a pharmaceutically acceptable acid addition salt thereof.

Another preferred compound of the invention is, for example, a quinazoline derivative of the Formula I selected from:

6-(1-acetylpiperidin-4-yloxy)-4-(3-chloro-2-fluoroanilino)-7-methoxyquinazoline;
4-(3-chloro-2-fluoroanilino)-6-[1-(N,N-dimethylaminoacetyl)piperidin-4-yloxy]-7-methoxyquinazoline;
6-[1-(N,N-dimethylsulfamoyl)piperidin-4-yloxy]-4-(3-chloro-2-fluoroanilino)-7-methoxyquinazoline;
4-(3-chloro-2-fluoroanilino)-7-methoxy-6-[1-(morpholinoacetyl)piperidin-4-yloxy]quinazoline;
4-(3-chloro-2-fluoroanilino)-7-methoxy-6-[1-(pyrrolidin-1-ylacetyl)piperidin-4-yloxy]quinazoline;
4-(3-chloro-2-fluoroanilino)-6-{1-[3-(dimethylamino)propylsulfonyl]piperidin-4-yloxy}-7-methoxyquinazoline;
4-(3-chloro-2-fluoroanilino)-6-[1-(methylsulfonyl)piperidin-3-yl)oxy)-7-methoxyquinazoline;
4-(3-chloro-2-fluoroanilino)-6-[(3R)-1-(methylsulfonyl)piperidin-3-yloxy]-7-methoxyquinazoline;
4-(3-chloro-2-fluoroanilino)-6-[(3S)-1-(methylsulfonyl)piperidin-3-yloxy]-7-methoxyquinazoline;
6-(1-acetylpiperidin-3-yloxy)-4-(3-chloro-2-fluoroanilino)-7-methoxyquinazoline;
4-(3-chloro-2-fluoroanilino)-6-[(2S,4S)-2-(N,N-dimethylcarbamoyl)pyrrolidin-4-yloxy]-7-methoxyquinazoline;
4-(3-chloro-2-fluoroanilino)-6-[(2S,4S)-2-(N,N-dimethylcarbamoyl)-1-methylpyrrolidin-4-yloxy]-7-methoxyquinazoline;
4-(3-chloro-2-fluoroanilino)-6-[1-(N,N-dimethylaminoacetyl)piperidin-3-yloxy]-7-methoxyquinazoline;
4-(3-chloro-2-fluoroanilino)-6-[(3R)-1-(N,N-dimethylaminoacetyl)piperidin-3-yloxy]-7-methoxyquinazoline;
4-(3-chloro-2-fluoroanilino)-6-[(3S)-1-(N,N-dimethylaminoacetyl)piperidin-3-yloxy]-7-methoxyquinazoline;
4-(3-chloro-2-fluoroanilino)-6-[1-(hydroxyacetyl)piperidin-3-yloxy]-7-methoxyquinazoline;
6-[1-(acetoxyacetyl)piperidin-3-yloxy]-4-(3-chloro-2-fluoroanilino)-7-methoxyquinazoline;
4-(3-chloro-2-fluoroanilino)-6-[(3R)-1-methylsulfonyl)pyrrolidin-3-yloxy]-7-methoxyquinazoline;
4-(3-chloro-2-fluoroanilino)-6-[(3S)-1-methylsulfonyl)pyrrolidin-3-yloxy]-7-methoxyquinazoline;
4-(3-chloro-2-fluoroanilino)-7-methoxy-6-{[(2S)-1-methylpyrrolidin-2-yl]methoxy}quinazoline;
4-(3-chloro-2-fluoroanilino)-7-methoxy-6-{[(2R)-1-methylsulfonylpyrrolidin-2-yl]methoxy}quinazoline;
4-(3-chloro-2-fluoroanilino)-7-methoxy-6-{[1-(methylsulfonyl)pyrrolidin-3-yl]methoxy}quinazoline;
4-(3-chloro-2-fluoroanilino)-6-[(3R)-1-methylpyrrolidin-3-yloxy]-7-methoxyquinazoline;
4-(3-chloro-2-fluoroanilino)-6-[(3S)-1-methylpyrrolidin-3-yloxy]-7-methoxyquinazoline;
4-(3-chloro-2-fluoroanilino)-7-methoxy-6-{[(2S)-1-methylpyrrolidin-2-yl]methoxy}quinazoline;
4-(3-chloro-2-fluoroanilino)-7-methoxy-6-[(1-methylpyrrolidin-3-yl)methoxy]quinazoline;
6-[(3R)-1-acetylpyrrolidin-3-yloxy]-4-(3-chloro-2-fluoroanilino)-7-methoxyquinazoline;
6-{[(2S)-1-acetylpyrrolidin-2-yl]methoxy}-4-(3-chloro-2-fluoroanilino)-7-methoxyquinazoline;
6-{[(2R)-1-acetylpyrrolidin-2-yl]methoxy}-4-(3-chloro-2-fluoroanilino)-7-methoxyquinazoline;

6-[(1-acetylpyrrolidin-3-yl)methoxy]-4-(3-chloro-2-fluoroanilino)-7-methoxyquinazoline;
4-(3-chloro-2-fluoroanilino)-7-methoxy-6-[(3S)-1-(N,N-dimethylsulfamoyl)pyrrolidin-3-yloxy]quinazoline;
4-(3-chloro-2-fluoroanilino)-7-methoxy-6-{[(2S)-1-(morpholinoacetyl)pyrrolidin-2-yl]methoxy}quinazoline;
4-(3-chloro-2-fluoroanilino)-7-methoxy-6-{[(2S)-1-(hydroxyacetyl)pyrrolidin-2-yl]methoxy}quinazoline;
4-(3-chloro-2-fluoroanilino)-7-methoxy-6-(piperidin-3-yloxy)quinazoline;
4-(3-chloro-2-fluoroanilino)-6-[(2S,4R)-2-(N,N-dimethylcarbamoyl)-1-methylpyrrolidin-4-yloxy]-7-methoxyquinazoline;
4-(3-chloro-2-fluoroanilino)-6-[(2R,4R)-2-(N,N-dimethylcarbamoyl)-1-methylpyrrolidin-2-yloxy]-7-methoxyquinazoline:
4-(3-chloro-2-fluoroanilino)-7-methoxy-6-{[(2S)-1-(N-methylaminoacetyl)pyrrolidin-2-yl]methoxy}quinazoline;
4-(3-chloro-2-fluoroanilino)-7-methoxy-6-{[(2S)-1-(N,N-dimethylaminoacetyl)pyrrolidin-2-yl]methoxy}quinazoline;
4-(3-chloro-2-fluoroanilino)-7-methoxy-6-{[(2S)-1-(pyrrolidin-1-ylacetyl)pyrrolidin-2-yl]methoxy}quinazoline;
4-(3-chloro-2-fluoroanilino)-7-methoxy-6-{[(2RS,4R)-1-methyl-2-(morpholinocarbonyl)-pyrrolidin-4-yloxy]quinazoline;
4-(3-chloro-2-fluoroanilino)-7-methoxy-6-[(3S)-piperidin-3-yloxy]quinazoline;
6-[(3S)-1-acetylpiperidin-3-yloxy]-4-(3-chloro-2-fluoroanilino)-7-methoxyquinazoline;
4-(3-chloro-2-fluoroanilino)-7-methoxy-6-[(3S)-1-(methylsulfonyl)piperidin-3-yloxy]quinazoline;
4-(3-chloro-2-fluoroanilino)-6-{(3S)-1-[(dimethylamino)acetyl]piperidin-3-yloxy}-7-methoxyquinazoline; 4-(3-chloro-2-fluoroanilino)-7-methoxy-6-[1-(pyrrolidin-1-ylacetyl)piperidin-3-yloxy]quinazoline;
4-(3-chloro-2-fluoroanilino)-7-methoxy-6-[(3S)-1-(pyrrolidin-1-ylacetyl)piperidin-3-yloxy]quinazoline;
4-(3-chloro-2-fluoroanilino)-6-{[(2S)-1-(3,4-methylenedioxypyrrolidin-1-ylacetyl)pyrrolidin-2-yl]methoxy}-7-methoxyquinazoline;
4-(3-chloro-2-fluoroanilino)-7-methoxy-6-{[(2S)-1-(1-methylpiperazin-4-yl acetyl)pyrrolidin-2-yl]methoxy}quinazoline;
4-(3-chloro-2-fluoroanilino)-7-methoxy-6-{[(2S)-1-(1-methylpiperazin-4-ylacetyl)pyrrolidin-2-yl]methoxy}quinazoline;
4-(3-chloro-2-fluoroanilino)-6-[(3R)-1-(hydroxyacetyl)pyrrolidin-3-yloxy]-7-methoxyquinazoline;
4-(3-chloro-2-fluoroanilino)-7-methoxy-6-{[(2S)-1-(2-hydroxyisobutyryl)pyrrolidin-2-yl]methoxy}quinazoline;
4-(3-Chloro-fluoroanilino)-7-methoxy-6-{1-[(2S)-1-methylpyrrolidin-2-ylcarbonyl]piperidin-3-yloxy}quinazoline;
4-(3-Chloro-2-fluoroanilino)-7-methoxy-6-[1-(N,N-dimethylcarbamoylmethyl)piperidin-3-yloxy]quinazoline;
4-(3-Chloro-2-fluoroanilino)-7-methoxy-6-{[1-(3,3-difluoropyrrolidin-1-yl)acetyl]piperidin-3-yloxy}quinazoline;
4-(3-Chloro-2-fluoroanilino)-7-methoxy-6-{1-[[(3R)-3-hydroxypyrrolidin-1-yl]acetyl]piperidin-3-yloxy}quinazoline;
4-(3-Chloro-2-fluoroanilino)-7-methoxy-6-{[1-(4-methyl-3-oxopiperazin-1-yl)acetyl]piperidin-3-yloxy}quinazoline;
4-(3-Chloro-2-fluoroanilino)-7-methoxy-6-{1-[(4-acetylpiperazin-1-yl)acetyl]piperidin-3-yloxy}quinazoline; and
4-(3-chloro-2-fluoroanilino)-7-methoxy-6-{[(2R)-1-methylpyrrolidin-2-yl]methoxy}quinazoline;
or a pharmaceutically acceptable salt thereof.

Synthesis of Quinazoline Derivatives of the Formula I

A further aspect the present invention provides a process for preparing a quinazoline derivative of Formula I or a pharmaceutically-acceptable salt thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher. John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an amyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art.

A quinazoline derivative of the Formula I, or a pharmaceutically-acceptable salt thereof, may be prepared by any process known to be applicable to the preparation of chemically-related compounds. Such processes, when used to prepare a quinazoline derivative of the Formula I, or a pharmaceutically-acceptable salt thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples. Alternatively, necessary starting materials are obtainable by analogous procedures to those illustrated which are within the ordinary skill of an organic chemist. Information on the preparation of necessary starting materials or related compounds (which may be adapted to form necessary starting materials) may also be found in the following patent and application publications, the contents of the relevant process sections of which are hereby incorporated herein by reference: WO94/27965, WO 95/03283, WO 96/33977, WO 96/33978, WO 96/33979, WO 96/33980, WO 96/33981, WO 97/30034, WO 97/38994, WO01/66099, U.S. Pat. No. 5,252, 586, EP 520 722, EP 566 226, FP 602 851 and FP 635 507.

The present invention also provides that quinazoline derivatives of the Formula I, or pharmaceutically acceptable salts thereof, can be prepared by a process (a) to (h) as follows (wherein the variables are as defined above unless otherwise stated):

Process (a) By reacting a compound of the Formula II:

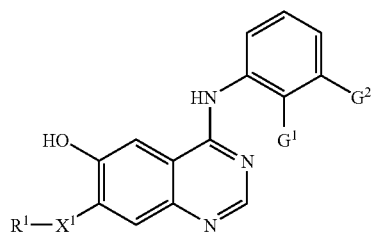

Formula II wherein $R^1$, $X^1$, $G^1$ and $G^2$ have any of the meanings defined hereinbefore except that any functional group is protected if necessary,
with a compound of the Formula III:

 

Formula III wherein $Q^1$, $X^2$ have any of the meanings defined hereinbefore except that any functional group is protected if necessary and Lg is a displaceable group, wherein the reaction is conveniently performed in the presence of a suitable base,
and whereafter any protecting group that is present is removed by conventional means.

A convenient displaceable group Lg is, for example, a halogeno, alkanesulfonyloxy or arylsulfonyloxy group, for example a chloro, bromo, methanesulfonyloxy, 4-nitroben-zenesulfonyloxy or toluene 1-sulfonyloxy group (suitably a methanesulfonyloxy, 4-nitrobenzenesulfonyloxy or toluene-4-sulfonyloxy group).

The reaction is advantageously carried out in the presence of base. A suitable base is, for example, an organic amine base such as, for example, pyridine, 2,6-lutidine, collidine, 4-dimethylaminopyridine, triethylamine, N-methylmorpholine or diazabicyclo[5.4.0]undec-7-ene, or for example, an alkali metal or alkaline earth metal carbonate or hydroxide, for example sodium carbonate, potassium carbonate, cesium carbonate, calcium carbonate, sodium hydroxide or potassium hydroxide. Alternatively such a base is, for example, an alkali metal hydride, for example sodium hydride, an alkali metal or alkaline earth metal amide, for example sodium amide or sodium bis(trimethylsilyl)amide, or a sufficiently basic alkali metal halide, for example cesium fluoride or sodium iodide. The reaction is suitably effected in the presence of an inert solvent or diluent, for example an alkanol or ester such as methanol, ethanol, 2-propanol or ethyl acetate, a halogenated solvent such as methylene chloride, trichloromethane or carbon tetrachloride, an ether such as tetrahydrofuran or 1,4-dioxan, an aromatic hydrocarbon solvent such as toluene, or (suitably) a dipolar aprotic solvent such as N, N-dimethylformamide, N,N-dimethylacetamide, N-methylpyrrolidin-2-one or dimethylsulfoxide. The reaction is conveniently effected at a temperature in the range, for example, 10 to 150° C. (or the boiling point of the solvent), suitably in the range 20 to 90° C.

When $X^2$ is a direct bond a particularly suitable base is cesium fluoride. This reaction is suitably performed in an inert dipolar aprotic solvent such as N,N-dimethylacetamide or N,N-dimethylformamide. The reaction is suitably carried out at a temperature of from 25 to 85° C.

Process (b) By modifying a substituent in or introducing a substituent into another quinazoline derivative of Formula I or a pharmaceutically acceptable salt thereof, as hereinbefore defined except that any functional group is protected if necessary, and whereafter any protecting group that is present is removed by conventional means.

Methods for converting substituents into other substituents are known in the art. For example an alkylthio group may be oxidised to an alkylsulfinyl or alkylsulfonyl group, a cyano group reduced to an amino group, a nitro group reduced to an amino group, a hydroxy group alkylated to a methoxy group, a carbonyl group converted to a thiocarbonyl group (eg. using Lawsson's reagent), a bromo group converted to an alkylthio group, an amino group may be acylated to give an alkanoylamino group (for example by reaction with a suitable acid chloride or acid anhydride) or an alkanoyloxy group may be hydrolysed to a hydroxy group (for example an acetyloxyacetyl group may be converted to a hydroxyacetyl group) Conveniently, one $R^1$ group may be converted into another $R^1$ group as a final step in the preparation of a compound of the Formula I. It is also possible to introduce a substituent onto the group $Q^1$ as a final step in the preparation of a compound of the Formula I. For example when the compound of Formula I contains primary or secondary amino group, for example an NH group in the ring $Q^1$, a substituent may be added to the nitrogen atom of the primary or secondary amino group by reacting the compound of the Formula I containing a primary or secondary amino group with a compound of the formula R-Lg, wherein Lg is a displaceable group (for example halogeno such as chloro or bromo) and R is the required substituent (for example (1-6C)alkyl, (2-6C)alkanoyl, cyano, cyano(1-6C)alkyl, (1-6C)alkylsulfonyl, carbamoyl, N-(1-6C)alkylcarbamoyl, N, N-di-[(1-6C)alkyl]carbamoyl, carbamoyl(1-6C)alkyl, N-(1-6C)alkylcarbamoyl(1-6C)alkyl, N,N-di-[(1-6C)alkyl]carbamoyl(1-6C)alkyl sulfamoyl, N-(1-6C)alkylsulfamoyl, N,N-di[(1-6C)alkyl]sulfamoyl or a group $Q^2-X^3$—, wherein $Q^2-X^3$— are as hereinbefore defined, which groups may be optionally substituted as hereinbefore defined). The reactions described above are conveniently performed in the presence of a suitable base (such as those described above in process (a), for example potassium carbonate, sodium iodide or di-isopropylethylamine) and conveniently in the presence of an inert solvent or diluent (for example the inert solvents and diluents described in process (a) such as N,N-dimethylacetamide, methanol, ethanol or methylene chloride). Conveniently, when $Q^1$ carries, for example an (2-6C)alkanoyl or (1-6C)alkylsulfonyl group, which is substituted by a group $NR^aR^b$, as hereinbefore defined, the $NR^aR^b$ group may be introduced by reaction of a compound of the Formula I wherein $Q^1$ carries a group of the formula Lg-(2-6C)alkanoyl or Lg-(1-6C)alkylsulfonyl, wherein Lg is a suitable displaceable group such as chloro, with a compound of the formula $NHR^aR^b$; wherein the reaction is conveniently performed in the presence of a suitable base and optionally in a suitable inert solvent or diluent. For example a pyrrolidin-1-ylacetyl group on $Q^1$ may be prepared by reacting a compound of the Formula I wherein $Q^1$ is substituted by a chloroacetyl group with pyrrolidine, analogous procedures may be used to prepare substituents on $Q^1$ such as morpholinoacetyl, N-methylaminoacetyl, N,N-dimethylaminoacetyl. Similarly, for example a 3-(N,N-dimethylamino)propylsulfonyl substituent on $Q^1$ may be prepared by reacting a compound of the Formula I wherein $Q^1$ carries a 3-chloropropylsulfonyl substituent with di-methylamine. Further examples of to modifying or converting substituents into other substituents are well known to those skilled in the art and further methods are contained in the accompanying non-limiting Examples.

Process (c) By removal of a protecting group from a quinazoline derivative of Formula I, or a pharmaceutically acceptable salt thereof.

Suitable methods for removal of protecting groups are well known and are discussed herein. For example for the production of those compounds of the Formula I wherein $Q^1$ or $R^1$ contains a primary or secondary amino group, the cleavage of the corresponding compound of Formula I wherein $Q^1$ or $R^1$ contains a protected primary or secondary amino group.

Suitable protecting groups for an amino group are, for example, any of the protecting groups disclosed hereinbefore for an amino group. Suitable methods for the cleavage of such amino protecting groups are also disclosed hereinbefore. In particular, a suitable protecting group is a lower alkoxycarbonyl group such as a tort-butoxycarbonyl group which may be cleaved under conventional reaction conditions such as under acid-catalysed hydrolysis, for example in the presence of trifluoroacetic acid.

Process (d) By reacting a compound of the Formula II as hereinbefore defined with a compound of the Formula III as defined hereinbefore except Lg is OH under Mitsunobu conditions, and whereafter any protecting group that is present is removed by conventional means.

Suitable Mitsunobu conditions include, for example, reaction in the presence of a suitable tertiary phosphine and a di-alkylazodicarboxylate in an organic solvent such as THF, or suitably dichloromethane and in the temperature range 0° C.-60° C., but suitably at ambient temperature. A suitable tertiary phosphine includes for example tri-n-butylphosphine or suitably tri-phenylphosphine. A suitable di-alkylazodicarboxylate includes for example diethyl azodicarboxylate (DEAD) or suitably di-tert-butyl azodicarboxylate. Details of Mitsunobu reactions are contained in Tet. Letts., 31, 699, (1990); The Mitsunobu Reaction, D. L. Hughes, Organic Reactions, 1992, Vol. 42, 335-656 and Progress in the Mitsunobu Reaction, D. L. Hughes, Organic Preparations and Procedures International, 1996, Vol. 28, 127-164.

Process (e) For the preparation of those compounds of the Formula I wherein $R^1$—$X^1$ is a hydroxy group by the cleavage of a quinazoline derivative of the Formula I wherein $R^1$—$X^1$ is a (1-6C)alkoxy group.

The cleavage reaction may conveniently be carried out by any of the many procedures known for such a transformation. The cleavage reaction of a compound of the Formula I wherein $R^1$ is a (1-6C)alkoxy group may be carried out, for example, by treatment of the quinazoline derivative with an alkali metal (1-6C)alkylsulfide such as sodium ethanethiolate or, for example, by treatment with an alkali metal diarylphosphide such as lithium diphenylphosphide. Alternatively the cleavage reaction may conveniently be carried out, for example, by treatment of the quinazoline derivative with a boron or aluminium trihalide such as boron tribromide, or by reaction with an organic or inorganic acid, for example trifluoroacetic acid. Such reactions are suitably carried out in the presence of a suitable inert solvent or diluent as defined hereinbefore. A preferred cleavage reaction is the treatment of a quinazoline derivative of the Formula I with pyridine hydrochloride. The cleavage reactions are suitably carried out at a temperature in the range, for example, of from 10 to 150° C., for example from 25 to 80° C.

Process (f) For the preparation of those compounds of the Formula I wherein $X^1$ is O, by the reaction of a compound of the Formula IV (a compound of Formula I wherein $R^1$—$X^1$ is OH):

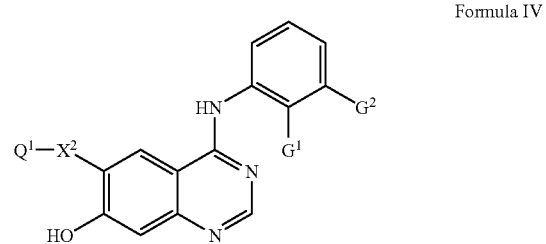

Formula IV wherein $Q^1$, $X^2$, $G^1$ and $G^2$ have any of the meanings defined hereinbefore except that any functional group is protected if necessary, with a compound of the formula $R^1$-Lg wherein $R^1$ has any of the meanings defined hereinbefore, except that any functional group is protected if necessary and Lg is a displaceable group, wherein the reaction is conveniently performed in the presence of a suitable base;

and whereafter any protecting group that is present is removed by conventional means. Suitable displaceable groups, Lg, are as hereinbefore defined for process a, for example chloro or bromo. The reaction is suitably performed in the presence of a suitable base. Suitable solvents, diluents and bases include, for example those hereinbefore described in relation to process (a).

Process (g)

For the preparation of those compounds of the Formula I wherein $Q^1$ or $R^1$ contains a (1-6C)alkoxy or substituted (1-6C)alkoxy group or a (1-6C)alkylamino or substituted (1-6C)alkylamino group, the alkylation, conveniently in the presence of a suitable base as defined hereinbefore for process a, of a quinazoline derivative of the Formula I wherein $Q^1$ or $R^1$ contains a hydroxy group or a primary or secondary amino group as appropriate.

A suitable alkylating agent is, for example, any agent known in the art for the alkylation of hydroxy to alkoxy or substituted alkoxy, or for the alkylation of amino to alkylamino or substituted alkylamino, for example an alkyl or substituted alkyl halide, for example a (1-6C)alkyl chloride, bromide or iodide or a substituted (1-6C)alkyl chloride, bromide or iodide, conveniently in the presence of a suitable base as defined hereinbefore, in a suitable inert solvent or diluent as defined hereinbefore and at a temperature in the range; for example, 10 to 140° C., conveniently at or near ambient temperature. An analogous procedure may be used to introduce optionally substituted (2-6C)alkanoyloxy, (2-6C)alkanoylamino and (1-6C)alkanesulfonylamino groups into $Q^1$ or $R^1$.

Conveniently for the production of those compounds of the Formula I wherein $Q^1$ or $R^1$ contains a (1-6C)alkylamino or substituted (1-6C)alkylamino group, a reductive amination reaction may be employed using formaldehyde or a (2-6C) alkanolaldehyde (for example acetaldehyde or propionaldehyde). For example, for the production of those compounds of the Formula I wherein $Q^1$ or $R^1$ contains an N-methyl group, the corresponding compound containing a N—H group may be reacted with formaldehyde in the presence of a suitable reducing agent. A suitable reducing agent is, for example, a hydride reducing agent, for example formic acid, an alkali metal aluminium hydride such as lithium aluminium hydride, or, suitably, an alkali metal borohydride such as sodium borohydride, sodium cyanoborohydride, sodium triethylborohydride, sodium trimethoxyborohydride and sodium triacetoxyborohydride. The reaction is conveniently performed in a suitable inert solvent or diluent, for example tetrahydrofuran and diethyl ether for the more powerful reducing agents such as lithium aluminium hydride, and, for example, methylene chloride or a protic solvent such as methanol and ethanol for the less powerful reducing agents such as sodium triacetoxyborohydride and sodium cyanoborohydride. When the reducing agent is formic acid the reaction is conveniently carried out using an aqueous solution of the formic acid. The reaction is performed at a temperature in the range, for example, 10 to 100° C., such as 70 to 90° C. or, conveniently, at or near ambient temperature. Conveniently, when the reducing agent is formic acid, protecting groups such as tert-butoxycarbonyl on the NH group to be alkylated (for example present from the synthesis of the starting material) may be removed in-situ during the reaction.

Process (h)

For the preparation of those compounds of the Formula I wherein $R^1$ is substituted by a group T, wherein T is selected from (1-6C)alkylamino, di-[(1-6C)alkyl]amino, (2-6C)alkanoylamino, (1-6C)alkylthio, (1-6C)alkylsulfinyl and (1-6C)alkylsulfonyl, the reaction of a compound of the formula V:

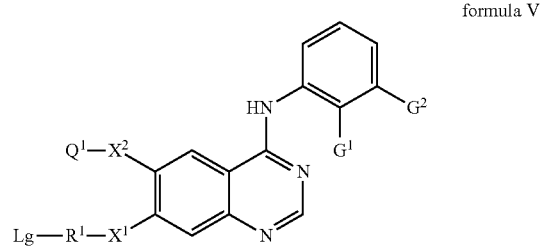

formula V wherein $Q^1$, $X^1$, $X^2$, $R^1$, $G^1$ and $G^2$ have any of the meanings defined hereinbefore except that any functional group is protected if necessary and Lg is a displaceable group (for example chloro or bromo) with a compound of the formula TH, wherein T is as defined above except that any functional group is protected if necessary;

and whereafter any protecting group that is present is removed by conventional means. The reaction is conveniently carried out in the presence of a suitable base. The reaction may conveniently be performed in a suitable inert solvent of diluent. Suitable bases, solvents and diluents are for example those described under process (a). The reaction is suitable performed at a temperature of for example, from 10 to 150° C., for example 30 to 60° C.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group.

Process (i)

By reacting a compound of the formula VI:

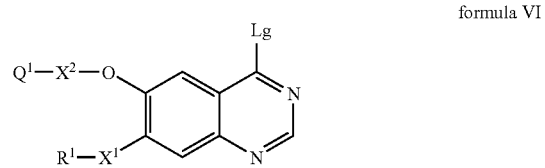

formula VI wherein $R^1$, $X^1$, $X^2$, $Q^1$ have any of the meanings defined hereinbefore except that any functional group is protected if necessary and Lg is a displaceable group as hereinbefore defined, with an aniline of the formula VII:

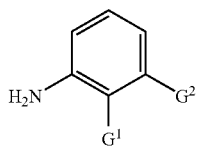

formula VII wherein $G^1$ and $G^2$ have any of the meanings defined hereinbefore except that any functional group is protected if necessary, and wherein the reaction is conveniently performed in the presence of a suitable acid, and whereafter any protecting group that is present is removed by conventional means.

Suitable displaceable groups represented by Lg are as hereinbefore defined, in particular halogeno such as chloro.

The reaction is conveniently carried out in the presence of a suitable inert solvent or diluent, for example an alcohol or ester such as methanol, ethanol, isopropanol or ethyl acetate, a halogenated solvent such as methylene chloride, chloroform or carbon tetrachloride, an ether such as tetrahydrofuran or 1,4-dioxane, an aromatic solvent such as toluene, or a dipolar aprotic solvent such as N,N-dimethylformamide, N,N-dimethylacetamide, N-methylpyrrolidin-2-one acetonitrile or dimethylsulfoxide. The reaction is conveniently carried out at a temperature in the range, for example, 10 to 250° C., conveniently in the range 40 to 120° C. or where a solvent or diluent is used at the reflux temperature. Conveniently, the compound of formula VI may is reacted with a compound of the formula VII in the presence of a protic solvent such as isopropanol, conveniently in the presence of an acid, for example hydrogen chloride gas in diethyl ether or dioxane, or hydrochloric acid, for example a 4M solution of hydrogen chloride in dioxane, under the conditions described above. Alternatively, this reaction may be conveniently carried out in an aprotic solvent, such as dioxane or a dipolar aprotic solvent such as N,N-dimethylacetamide or acetonitrile in the presence of an acid, for example hydrogen chloride gas in diethyl ether or dioxane, or hydrochloric acid. The compound of the formula VI, wherein Lg is halogeno, may be reacted with a compound of the formula VII in the absence of an acid. In this reaction displacement of the halogeno leaving group Lg results in the formation of the acid HLg in-situ and autocatalysis of the reaction. Conveniently the reaction is carried out in a suitable inert organic solvent, for example isopropanol, dioxane or N,N-dimethylacetamide. Suitable conditions for this reaction are as described above.

Alternatively, the compound of formula VI may is reacted with a compound of the formula VII in the presence of a suitable base. Suitable bases for this reaction are as hereinbefore defined under Process (a). This reaction is conveniently performed in an inert solvent or diluent, for example those mentioned above in relation to this process (i);

Process (j)

For the preparation of those compounds of the Formula I wherein $Q^1$ carries a substituted carbamoyl group (such as N,N-di-[(1-6C)alkyl]carbamoyl) or a group $Q^2$-$X^3$—, wherein $Q^2$ is a nitrogen containing heterocyclyl group linked to $X^3$ by a ring nitrogen and $X^3$ is as CO; the coupling of a compound of the Formula I, as hereinbefore defined, except any functional group is protected if necessary, and wherein $Q^1$ carries a carboxy group, with a primary or secondary amine or a group of the formula $Q^2H$, wherein $Q^2H$ is a heterocyclic group containing an NH group; and whereafter any protecting group that is present is removed by conventional means.

The coupling reaction is conveniently carried out in the presence of a suitable coupling agent, such as a carbodiimide (for example 1-[3-(Dimethylamino)propyl]-3-ethylcarbodiimide), or a suitable peptide coupling agent, for example O-(7-azabenzotriazol-1-yl)-N,N,N',N'-tetramethyluronium hexafluoro-phosphate (HATU). The coupling reaction is conveniently carried out in an inert solvent such as, for example, a halogenated solvent such as methylene chloride, or a dipolar aprotic solvent such as N,N-dimethylfoiruamide, N,N-dimethylacetamide, 1-methyl-2-pyrrolidinone. Suitably the coupling reaction is carried out in the presence of a suitable base, such as an organic amine, for example di-isopropylethylamine or 4-dimethylaminopyridine. The coupling reaction is suitable performed at −25° C. to 150° C., conveniently at ambient temperature.

Persons skilled in the art will appreciate that, in order to obtain compounds of the invention in an alternative and in some occasions, more convenient manner, the individual process steps mentioned hereinbefore may be performed in different order, and/or the individual reactions may be performed at different stage in the overall route (i.e. chemical transformations may be performed upon different intermediates to those associated hereinbefore with a particular reaction).

When a pharmaceutically-acceptable salt of a quinazoline derivative of the Formula I is required, for example an acid-addition salt, it may be obtained by, for example, reaction of said quinazoline derivative with a suitable acid using a conventional procedure. To facilitate isolation of the compound during preparation, the compound may be prepared in the form of a salt that is not a pharmaceutically acceptable salt. The resulting salt can then be modified by conventional techniques to give a pharmaceutically acceptable salt of the compound. Such techniques include, for example ion exchange techniques or re-precipitation of the compound in the presence of a pharmaceutically acceptable counter ion. For example re-precipitation in the presence of a suitable acid such as HCl to give a hydrochloride acid addition salt.

As mentioned hereinbefore some of the compounds according to the present invention may contain one of more chiral centers and may therefore exist as stereoisomers (for example when $Q^1$ contains a pyrrolidin-3-yl group). Stereoisomers may be separated using conventional techniques, e.g. chromatography or fractional crystallisation. The enantiomers may be isolated by separation of a racemate for example by fractional crystallisation, resolution or HPLC. The diastereomers may be isolated by separation by virtue of the different to physical properties of the diastereoisomers, for example, by fractional crystallisation, HPLC or flash chromatography. Alternatively particular stereoisomers may be made by chiral synthesis from chiral starting materials under conditions which will not cause racemisation or epimerisation, or by derivatisation, with a chiral reagent. Examples of suitable chiral synthesis and separation of isomers are described in the Examples. When a specific stereoisomer is isolated it is suitably isolated substantially free for other stereoisomers, for example containing less than 20%, particularly less than 10% and more particularly less than 5% by weight of other stereoisomers.

In the section above the expression "inert solvent" refers to a solvent which does not react with the starting materials, reagents, intermediates or products in a manner which adversely affects the yield of the desired product.

Preparation of Starting Materials

Compounds of Formula II are commercially available or may be prepared using conventional techniques or analogous processes to those described in the prior art. In particular those patents and applications listed hereinbefore, such as WO96/15118, WO 01/66099 and EP 566 226. For example, the compounds of Formula II may be prepared in accordance with Reaction Scheme 1:

Reaction Scheme 1

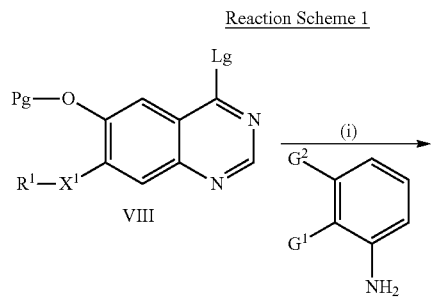

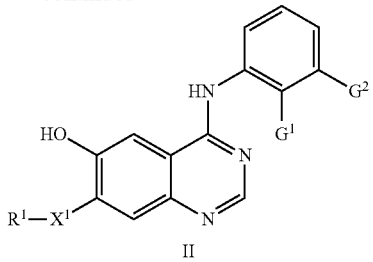

wherein $R^1$, $X^1$, Lg, $G^1$ and $G^2$ are as hereinbefore defined and Pg is a hydroxy protecting group.

(i) Reaction suitably in an inert protic solvent (such as an alkanol for example iso-propanol), an aprotic solvent (such as dioxane) or a dipolar aprotic solvent (such as N,N-dimethylacetamide) in the presence of an acid, for example hydrogen chloride gas in diethyl ether or dioxane, or hydrochloric acid, under analogous conditions to those described above under process (i).

Alternatively the reaction may be carried out in one of the above inert solvents conveniently in the presence of a base, for example potassium carbonate. The above reactions are conveniently carried out at a temperature in the range, for example, 0 to 150° C., suitably at or near the reflux temperature of the reaction solvent.

(ii) Cleavage of Pg may be performed under standard conditions for such reactions. For example when Pg is an alkanoyl group such as acetyl, it may be cleaved by heating in the presence of a methanolic ammonia solution.

Compounds of formula VIII are known or can be prepared using known processes for the preparation of analogous compounds. If not commercially available, compounds of the formula (VIII) may be prepared by procedures which are selected from standard chemical techniques, techniques which are analogous to the synthesis of known, structurally similar compounds, or techniques which are analogous to the procedures described in the Examples. For example, standard chemical techniques are as described in Houben Weyl. By way of example the compound of the formula VIII in which $R^1$—$X^1$— is methoxy, Lg is chloro and Pg is acetyl may be prepared using the process illustrated in Reaction Scheme 2:

Reaction scheme 2

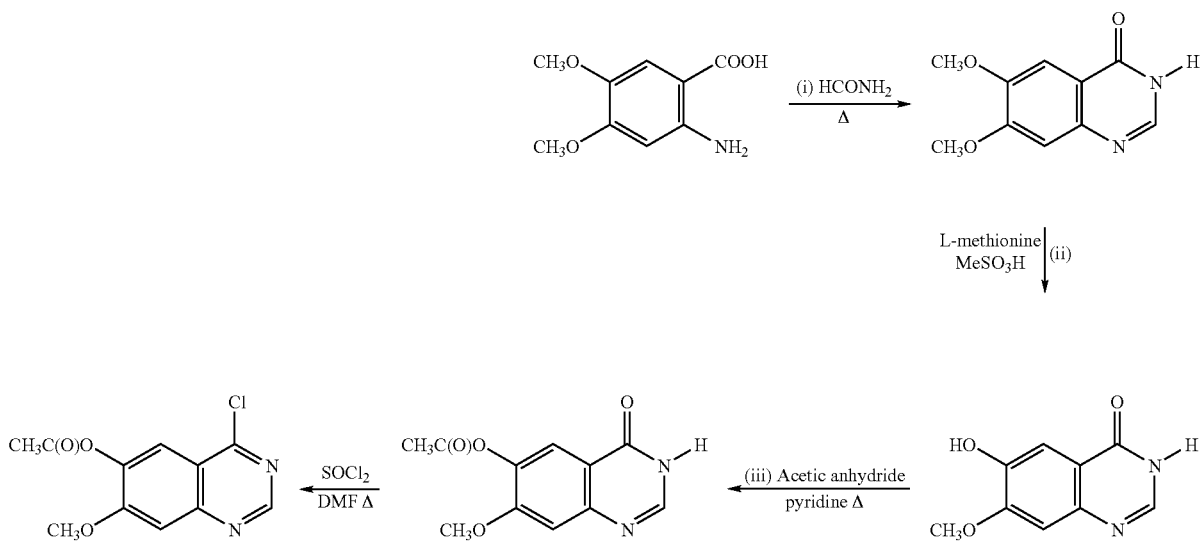

Reaction Scheme 2 may be generalised by the skilled man to apply to compounds within the present specification which are not specifically illustrated (for example to introduce a substituent other than methoxy at the 7-position in the quinazoline ring).

Compounds of the Formula III are commercially available or may be prepared using standard techniques, for example as illustrated in U.S. Pat. No. 5,252,586 and WO 94/27965.

Compounds of the Formula IV may be prepared using process (e) above, starting with a compound prepared, for example using Process (a).

Compounds of the formula V may be prepared using, for example process (a) or process (d) in which the group represented by $R^1$ is appropriately functionalised with a suitable displaceable group Lg such as chloro or bromo.

Compounds of the formula VI may be prepared using conventional methods well known in the art. For example the hydroxy protecting group, Pg, in a compound of the formula VIII as hereinbefore described in Reaction Scheme 1 is removed to give the compound of the formula X:

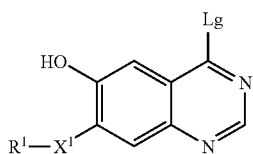

X

The protecting group Pg may be removed from the compound of formula X using conventional techniques.

The compound of the formula X may then be coupled with a compound of the Formula III as hereinbefore defined using analogous conditions to those described in Process (a) or Process (d).

Certain novel intermediates utilised in the above processes are provided as a further feature of the present invention together with the process for their preparation.

According to a further feature of the present invention there is provided the compounds of the formulae II and IX or a salt thereof, (including pharmaceutically acceptable salts thereof), as hereinbefore defined. Particularly compounds of the formula II and IX wherein $R^1$—$X^1$ is hydrogen or (1-4C) alkoxy. More particularly compounds of the formula II and IX wherein $R^1$—$X^1$ is hydrogen or (1-4C)alkoxy, and $G^1$ and $G^2$ are selected from fluoro and chloro.

Biological Assays

The following assays may be used to measure the effects of the compounds of the present invention as inhibitors of the erb-tyrosine kinases, as inhibitors in-vitro of the proliferation of KB cells (human naso-pharangeal carcinoma cells) and as inhibitors in vivo on the growth in nude mice of xenografts of LoVo tumour cells (colorectal adenocarcinoma).

a) Protein Tyrosine Kinase phosphorylation Assays

This test measures the ability of a test compound to inhibit the phosphorylation of a tyrosine containing polypeptide substrate by EGFR tyrosine kinase enzyme.

Recombinant intracellular fragments of EGFR, erbB2 and erbB4 (accession numbers X00588, X03363 and L07868 respectively) were cloned and expressed in the baculovirus/Sf21 system. Lysates were prepared from these cells by treatment with ice-cold lysis buffer (20 mM N-2-hydroxyethylpiperizine-N'-2-ethanesulfonic acid (HEPES) pH7.5, 150 mM NaCl, 10% glycerol, 1% Triton X-100, 1.5 mM $MgCl_2$, 1 mM ethylene glycol-bis(β-aminoethyl ether) N',N',N',N'-tetraacetic acid (EGTA), plus protease inhibitors and then cleared by centrifugation.

Constitutive kinase activity of the recombinant protein was determined by its ability to phosphorylate a synthetic peptide (made up of a random co-polymer of Glutamic Acid, Alanine and Tyrosine in the ratio of 6:3:1). Specifically, Maxisorb™ 96-well immunoplates were coated with synthetic peptide (0.2 μg of peptide in a 100 μl phosphate buffered saline (PBS) solution and incubated at 4° C. overnight). Plates were washed in PBS-T (phosphate buffered saline with 0.5% Tween 20) then in 50 mM HEPES pH 7.4 at room temperature to remove any excess unbound synthetic peptide. EGFR, ErbB2 or ErbB4 tyrosine kinase activity was assessed by incubation in peptide coated plates for 20 minutes at 22° C. in 100 mM HEPES pH 7.4, adenosine trisphosphate (ATP) at Km concentration for the respective enzyme, 10 mM $MnCl_2$, 0.1 mM $Na_3VO_4$, 0.2 mM DL-dithiothreitol (DTT), 0.1% Triton X-100 with test compound in DMSO (final concentration of 2.5%). Reactions were terminated by the removal of the liquid components of the assay followed by washing of the plates with PBS-T.

The immobilised phospho-peptide product of the reaction was detected by immunological methods. Firstly, plates were incubated for 90 minutes at room temperature with anti-phosphotyrosine primary antibodies that were raised in the mouse (4G10 from Upstate Biotechnology). Following extensive washing, plates were treated with Horseradish Peroxidase (HRP) conjugated sheep anti-mouse secondary antibody (NXA931 from Amersham) for 60 minutes at room temperature. After further washing, HRP activity in each well of the plate was measured calorimetrically using 22'-Azino-di-[3-ethylbenzthiazoline sulfonate (6)] diammonium salt crystals (ABTS™ from Roche) as a substrate.

Quantification of colour development and thus enzyme activity was achieved by the measurement of absorbance at 405 nm on a Molecular Devices ThermoMax microplate reader. Kinase inhibition for a given compound was expressed as an $IC_{50}$ value. This was determined by calculation of the concentration of compound that was required to give 50% inhibition of phosphorylation in this assay. The range of phosphorylation was calculated from the positive (vehicle plus ATP) and negative (vehicle minus ATP) control values.

b) EGFR Driven KB Cell Proliferation Assay

This assay measures the ability of a test compound to inhibit the proliferation of KB cells (human naso-pharangeal carcinoma obtained from the American Type Culture Collection (ATCC).

KB cells (human naso-pharangeal carcinoma obtained from the ATCC were cultured in Dulbecco's modified Eagle's medium (DMEM) containing 10% foetal calf serum, 2 mM glutamine and non-essential amino acids at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $1.25 \times 10^3$ cells per well of a 96 well plate in DMEM containing 2.5% charcoal stripped serum, 1 mM glutamine and non-essential amino acids at 37° C. in 7.5% $CO_2$ and allowed to settle for 4 hours, Following adhesion to the plate, the cells are treated with or without EGF (final concentration of 1 ng/ml) and with or without compound at a range of concentrations in dimethyl-sulfoxide (DMSO) (0.1% final) before incubation for 4 days. Following the incubation period, cell numbers were determined by addition of 50 μl of 3-(4,5-Dimethylthiazol-2-yl)-

2,5-diphenyltetrazolium bromide (MIT) (stock 5 mg/ml) for 2 hours. MIT solution was then tipped off, the plate gently tapped dry and the cells dissolved upon the addition of 100 µl of DMSO.

Absorbance of the solubilised cells was read at 540 nm using a Molecular Devices ThermoMax microplate reader. Inhibition of proliferation was expressed as an $IC_{50}$ value. This was determined by calculation of the concentration of compound that was required to give 50% inhibition of proliferation. The range of proliferation was calculated from the positive (vehicle plus EGF) and negative (vehicle minus EGF) control values.

c) H16N-2 Cell Proliferation Assay

This assay measures the ability of a test compound to inhibit heregulin β or EGF driven proliferation of H16N-2 cells. These non-neoplastic eptihelial cells respond in a proliferative manner to stimulation with either EGF or heregulin β (Ram, G. R. and Ethier, S. P. (1996) *Cell Growth and Differentiation*, 7, 551-561) were isolated human mammary tissue (Band, V. and Sager, R. Tumour progression in breast cancer. In: J. S. Rhim and A. Dritschilo (eds.), *Neoplastic Transformation in human Cell Culture*, pp 169-178. Clifton, N.J.: Humana Press, 1991) and were obtained from the Dana-Farber Cancer Institute, 44 Binney Street, Boston, Mass. 02115.

H16N-2 cells were routinely cultured in culture medium (a 1:1 mix of Gibco F12 and Ham's αMEM media containing 1% foetal calf serum, 10 mM HEPES, 1 µg/ml Insulin, 12.5 ng/ml EGF, 2.8 µM Hydrocortisone, 2 nM Estradiol 5 µM Ascorbic Acid, 10 µg/ml Transferrin, 0.1 mM Phosphoethanolamine, 15 nM Sodium Selenite, 2mM Glutamine, 10 nM Tri-iodo-thrynoine, 35 µg/ml Bovine pituitary Extract and 0.1 mM Ethanolamine) at 37° C. in a 7.5% $CO_2$ air incubator. Cells were harvested from the stock flasks using Trypsin/ethylaminediaminetetraacetic acid (EDTA). Cell density was measured using a haemocytometer and viability was calculated using trypan blue solution before being seeded at a density of $1.0 \times 10^3$ cells per well of a 96 well plate in the above media at 37° C. in 7.5% $CO_2$ and allowed to settle for 72 hours.

Following this, the cells were starved of serum for 24 hours upon the addition of starvation medium (a 1:1 mix of Gibco F1.2 and Ham's αMEM media containing, 10 mM HEPES, 2 nM Estradiol, 5 µM Ascorbic Acid, 10 µg/ml Transferrin, 0.1 mM Phosphoethanolamine, 15nM Sodium Selenite, 2 mM Glutamine, and 0.1 mM Ethanolamine) and incubated at 37° C. in 7,5% $CO_2$. The cells were then treated with or without compound at a range of concentrations in dimethylsulphoxide (DMSO) (1% final) for two hours before the addition of exogenous ligand (at a final concentration of 100 ng/ml of heregulin β or 5 ng/ml of EGF) and incubation with both ligand and compound for 4 days at 37° C. in 7.5% $CO_2$. Following the incubation period, cell numbers were determined by removal of the media by aspiration and incubating with 50 µl of 3-(4,5-Dimethylthiazol-2-yl)-2,5-diphenyltetrazolium bromide (MTT) (stock 5 mg/ml) for 2 hours. MTT solution was then removed by aspiration, allowed to air dry and the cells dissolved upon the addition of 100 µl of DMSO.

Absorbance of this solubilised cells was read at 540 nm to quantify cell biomass. Inhibition of proliferation was expressed as an $IC_{50}$ value. This was determined by calculation of the concentration of compound that was required to give 50% inhibition of proliferation. The range of proliferation was calculated from the positive (vehicle plus ligand) and negative (vehicle minus ligand) control values.

d) In Vivo Xenograft Assay

This assay measures the ability of a test compound to inhibit the growth of a LoVo tumour (colorectal adenocarcinoma obtained from the ATCC) in Female Swiss athymic mice (Alderley Park, nu/nu genotype).

Female Swiss athymic (nu/nu genotype) mice were bred and maintained in Alderley Park in negative pressure Isolators (PFI Systems Ltd.). Mice were housed in a barrier facility with 12 hr light/dark cycles and provided with sterilised food and water ad libitum. All procedures were performed on mice of at least 8 weeks of age. LoVo tumour cell (colorectal adenocarcinoma obtained from the ATCC) xenografts were established in the hind flank of donor mice by sub cutaneous injections of $1 \times 10^7$ freshly cultured cells in 100 µl of serum free media per animal. On day 5 post-implant, mice were randomised into groups of 7 prior to the treatment with compound or vehicle control that was administered once daily at 0.1 ml/10 g body weight. Tumour volume was assessed twice weekly by bilateral Vernier calliper measurement, using the formula (length×width)×√(length×width)×(π/6), where length was the longest diameter across the tumour, and width was the corresponding perpendicular. Growth inhibition from start of study was calculated by comparison of the mean changes in tumour volume for the control and treated groups, and statistical significance between the two groups was evaluated using a Students t test.

e) hERG-Encoded Potassium Channel Inhibition Assay

This assay determines the ability of a test compound to inhibit the tail current flowing through the human ether-a-go-go-related-gene (hERG)-encoded potassium channel.

Human embryonic kidney (HEK) cells expressing the hERG-encoded channel were grown in Minimum Essential Medium Eagle (EMEM; Sigma-Aldrich catalogue number M2279), supplemented with 10% Foetal Calf Serum (Labtech International; product number 4-101-500), 10% M1 serum-free supplement (Egg Technologies; product number 70916) and 0.4 mg/ml Geneticin G418 (Sigma-Aldrich; catalogue number G7034). One or two days before each experiment, the cells were detached from the tissue culture flasks with Accutase (TCS Biologicals) using standard tissue culture methods. They were then put onto glass coverslips resting in wells of a 12 well plate and covered with 2 ml of the growing media.

For each cell recorded, a glass coverslip containing the cells was placed at the bottom of a Perspex chamber containing bath solution (see below) at room temperature (~20° C.). This chamber was fixed to the stage of an inverted, phase-contrast microscope. Immediately after placing the coverslip in the chamber, bath solution was perfused into the chamber from a gravity-fed reservoir for 2 minutes at a rate of ~2 ml/min. After this time, perfusion was stopped.

A patch pipette made from borosilicate glass tubing (GC120F, Harvard Apparatus) using a P-97 micropipette puller (Sutter Instrument Co.) was filled with pipette solution (see hereinafter). The pipette was connected to the headstage of the patch clamp amplifier (Axopatch 200B, Axon Instruments) via a silver/silver chloride wire. The headstage ground was connected to the earth electrode. This consisted of a silver/silver chloride wire embedded in 3% agar made up with 0.85% sodium chloride.

The cell was recorded in the whole cell configuration of the patch clamp technique. Following "break-in", which was done at a holding potential of −80 mV (set by the amplifier), and appropriate adjustment of series resistance and capacitance controls, electrophysiology software (Clampex, Axon Instruments) was used to set a holding potential (−80 mV) and to deliver a voltage protocol. This protocol was applied every 15 seconds and consisted of a 1 s step to +40 mV followed by a 1 s step to −50 mV. The current response to each imposed voltage protocol was low pass filtered by the amplifier at 1 kHz. The filtered signal was then acquired, on line, by digitising this analogue signal from the amplifier with an analogue to digital converter. The digitised signal was then captured on a computer running Clampex software (Axon Instruments). During the holding potential and the step to +40 mV the current was sampled at 1 kHz. The sampling rate was then set to 5 kHz for the remainder of the voltage protocol.

The compositions, pH and osmolarity of the bath and pipette solution are tabulated below.

| Salt | Pipette (mM) | Bath (mM) |
|---|---|---|
| NaCl | — | 137 |
| KCl | 130 | 4 |
| MgCl$_2$ | 1 | 1 |
| CaCl$_2$ | — | 1.8 |
| HEPES | 10 | 10 |
| glucose | — | 10 |
| Na$_2$ATP | 5 | — |
| EGTA | 5 | — |

| Parameter | Pipette | Bath |
|---|---|---|
| pH | 7.18-7.22 | 7.40 |
| pH adjustment with | 1M KOH | 1M NaOH |
| Osmolarity (mOsm) | 275-285 | 285-295 |

The amplitude of the hERG-encoded potassium channel tail current following the step from +40 mV to −50 mV was recorded on-line by Clampex software (Axon Instruments). Following stabilisation of the tail current amplitude, bath solution containing the vehicle for the test substance was applied to the cell. Providing the vehicle application had no significant effect on tail current amplitude, a cumulative concentration effect curve to the compound was then constructed.

The effect of each concentration of test compound was quantified by expressing the tail current amplitude in the presence of a given concentration of test compound as a to percentage of that in the presence of vehicle.

Test compound potency (IC$_{50}$) was determined by fitting the percentage inhibition values making up the concentration-effect to a four parameter Hill equation using a standard data-fitting package. If the level of inhibition seen at the highest test concentration did not exceed 50%, no potency value was produced and a percentage inhibition value at that concentration was quoted.

Although the pharmacological properties of the compounds of the Formula I vary with structural change as expected, in general activity possessed by compounds of the Formula I, may be demonstrated at the following concentrations or doses in one or more of the above tests (a), (b) and (c):—

Test (a):—IC$_{50}$ in the range, for example, 0.001-10 μM;
Test (b):—IC$_{50}$ in the range, for example, 0.001-10 μM;
Test (c):—IC$_{50}$ in the range, for example, 0.001-10 μM;
Test (d):—activity in the range, for example, 1-200 mg/kg/day;

No physiologically unacceptable toxicity was observed in Test (c) at the effective dose for compounds tested of the present invention. Accordingly no untoward toxicological effects are expected when a compound of Formula I, or a pharmaceutically-acceptable salt thereof, as defined hereinbefore is administered at the dosage ranges defined hereinafter.

According to a further aspect of the invention there is provided a pharmaceutical composition which comprises a quinazoline derivative of the Formula I, or a pharmaceutically-acceptable thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing to or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage fowl will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet fog n. Typically, unit dosage forms will contain about 0.5 mg to 0.5 g of a compound of this invention.

We have found that the compounds of the present invention possess anti-proliferative properties such as anti-cancer properties that are believed to arise from their erbB family receptor tyrosine kinase inhibitory activity, particularly inhibition of the EGF receptor (erbB1) tyrosine kinase. Furthermore, certain of the compounds according to the present invention possess substantially better potency against the EGF receptor tyrosine kinase, than against other tyrosine kinase enzymes, for example erbB2. Such compounds possess sufficient potency against the EGF receptor tyrosine kinase that they may be used in an amount sufficient to inhibit EGF receptor tyrosine kinase whilst demonstrating little, or significantly lower, activity against other tyrosine kinase enzymes such as erbB2. Such compounds are likely to be useful for the selective inhibition of EGF receptor tyrosine kinase and are likely to be useful for the effective treatment of, for example EGF driven tumours.

Accordingly, the compounds of the present invention are expected to be useful in the treatment of diseases or medical conditions mediated alone or in part by erbB receptor tyrosine kinases (especially EGF receptor tyrosine kinase), i.e. the compounds may be used to produce an erbB receptor tyrosine kinase inhibitory effect in a warm-blooded animal in need of such treatment. Thus the compounds of the present invention provide a method for the treatment of malignant cells characterised by inhibition of one or more of the erbB family of receptor tyrosine kinases. Particularly the compounds of the invention may be used to produce an anti-proliferative and/or pro-apoptotic and/or anti-invasive effect mediated alone or in part by the inhibition of erbB receptor tyrosine kinases. Particularly, the compounds of the present invention are expected to be useful in the prevention or treatment of those tumours that are sensitive to inhibition of one or more of the erbB receptor tyrosine kinases, such as EGF and/or erbB2 and/or erbB4 receptor tyrosine kinases (especially EGF receptor tyrosine kinase) that are involved in the signal transduction steps which drive proliferation and survival of these tumour cells. Accordingly the compounds of the present invention are expected to be useful in the treatment of psoriasis, benign prostatic hyperplasia (BPH), atherosclerosis and restenosis and/or cancer by providing an anti-proliferative effect, particularly in the treatment of erbB receptor tyrosine kinase sensitive cancers. Such benign or malignant tumours may affect any tissue and include non-solid tumours such as leukaemia, multiple myeloma or lymphoma, and also solid tumours, for example bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancers.

According to this aspect of the invention there is provided a compound of the Formula I, or a pharmaceutically acceptable salt thereof, for use as a medicament.

According to a further aspect of the invention there is provided a compound of the Formula I, or a pharmaceutically acceptable salt thereof, for use in the production of an anti-proliferative effect in a warm-blooded animal such as man.

Thus according to this aspect of the invention there is provided the use of a quinazoline derivative of the Formula I, or a pharmaceutically-acceptable salt thereof, as defined hereinbefore in the manufacture of a medicament for use in the production of an anti-proliferative effect in a warm-blooded animal such as man.

According to a further feature of this aspect of the invention there is provided a method for producing an anti-proliferative effect in a warm-blooded animal, such as man, in need of such treatment which comprises administering to said animal an effective amount of a quinazoline derivative of the Formula I, or a pharmaceutically acceptable salt thereof, as hereinbefore defined.

According to a further aspect of the invention there is provided the use of a quinazoline derivative of the Formula I, or a pharmaceutically-acceptable salt thereof, as defined hereinbefore in the manufacture of a medicament for use in the prevention or treatment of those turnouts which are sensitive to inhibition of erbB receptor tyrosine kinases, such as EGFR and/or erbB2 and/or erbB4 (especially EGFR), that are involved in the signal transduction steps which lead to the proliferation of tumour cells.

According to a further feature of this aspect of the invention there is provided a method for the prevention or treatment of those turnouts which are sensitive to inhibition of one or more of the erbB family of receptor tyrosine kinases, such as EGFR and/or erbB2 and/or erbB4 (especially EGFR), that are involved in the signal transduction steps which lead to the proliferation and/or survival of tumour cells which comprises administering to said animal an effective amount of a quinazoline derivative of the Formula I, or a pharmaceutically-acceptable salt thereof, as defined hereinbefore.

According to a further feature of this aspect of the invention there is provided a compound of the Formula I, or a pharmaceutically acceptable salt thereof, for use in the prevention or treatment of those turnouts which are sensitive to inhibition of erbB receptor tyrosine kinases, such as EGFR and/or erbB2 and/or erbB4 (especially EGFR), that are involved in the signal transduction steps which lead to the proliferation of tumour cells.

According to a further aspect of the invention there is provided the use of a quinazoline derivative of the Formula I, or a pharmaceutically-acceptable salt thereof, as defined hereinbefore in the manufacture of a medicament for use in providing a EGFR and/or erbB2 and/or erbB4 (especially a EGFR) tyrosine kinase inhibitory effect.

According to a further feature of this aspect of the invention there is provided a method for providing a EGFR and/or an erbB2 and or an erbB4 (especially a EGFR) tyrosine kinase inhibitory effect which comprises administering to said animal an effective amount of a quinazoline derivative of the Formula I, or a pharmaceutically-acceptable salt thereof, as defined hereinbefore.

According to a further feature of this aspect of the invention there is provided a compound of the Formula I, or a pharmaceutically acceptable salt thereof, for use in providing a EGFR and/or erbB2 and/or erbB4 (especially a EGFR) tyrosine kinase inhibitory effect.

According to a further feature of the present invention there is provided the use of a quinazoline derivative of the Formula I, or a pharmaceutically-acceptable salt thereof, as defined hereinbefore in the manufacture of a medicament for use in providing a selective EGFR tyrosine kinase inhibitory effect.

According to a further feature of this aspect of the invention there is provided a method for providing a selective EGFR tyrosine kinase inhibitory effect which comprises administering to said animal an effective amount of a quinazoline derivative of the Formula I, or a pharmaceutically-acceptable salt thereof, as defined hereinbefore.

According to a further feature of this aspect of the invention there is provided a compound of the Formula I, or a pharmaceutically acceptable salt thereof, for use in providing a selective EGFR tyrosine kinase inhibitory effect.

By "a selective EGFR kinase inhibitory effect" is meant that the quinazoline derivative of Formula I is more potent against EGF receptor tyrosine kinase than it is against other kinases. In particular some of the compounds according to the invention are more potent against EGF receptor kinase than it is against other tyrosine kinases such as other erbB receptor tyrosine kinases such erbB2. For example a selective EGFR kinase inhibitor according to the invention is at least 5 times, preferably at least 10 times more potent against erbB2 receptor tyrosine kinase driven proliferation than it is against EGFR tyrosine kinase driven proliferation, as determined from the relative $IC_{50}$ values in a suitable assay (for example the H116N-2 assay described above).

According to a further aspect of the present invention there is provided the use of a quinazoline derivative of the Formula I, or a pharmaceutically-acceptable salt thereof, as defined hereinbefore in the manufacture of a medicament for use in the treatment of a cancer (for example a cancer selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer).

According to a further feature of this aspect of the invention there is provided a method for treating a cancer (for example a cancer selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer) in a warm-blooded animal, such as man, in need of such treatment, which comprises administering to said animal an effective amount of a quinazoline derivative of the Formula I, or a pharmaceutically-acceptable salt thereof, as defined hereinbefore.

According to a further aspect of the invention there is provided a compound of the Formula I, or a pharmaceutically acceptable salt thereof, for use in the treatment of a cancer (for example selected from leukaemia, multiple myeloma, lymphoma, bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancer).

As mentioned above the size of the dose required for the therapeutic or prophlyactic treatment of a particular disease will necessarily be varied depending upon, amongst other things, the host treated, the route of administration and the severity of the illness being treated.

The anti-proliferative treatment defined hereinbefore may be applied as a sole therapy or may involve, in addition to the quinazoline derivative of the invention, conventional surgery or radiotherapy or chemotherapy. Such chemotherapy may include one or more of the following categories of anti-tumour agents:—

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example other inhibitors of the epidermal growth factor family (for example EGFR family tyrosine kinase inhibitors such as N-(3-chloro-4-fluorophenyl)-7-methoxy-6- (3-morpholinopropoxy)quinazolin-4-amine (gefitinib, AZD1839), N-(3-ethynylphenyl)-6,7-bis(2-methoxyethoxy) quinazolin-4-amine (erlotinib, OSI-774) and 6-acrylamido-N-(3-chloro-4-fluorophenyl)-7-(3- morpholinopropoxy) quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multidrug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a pharmaceutical product comprising a quinazoline derivative of the Formula I as defined hereinbefore and an additional anti-tumour agent as defined hereinbefore for the conjoint treatment of cancer.

Although the compounds of the Formula I are primarily of value as therapeutic agents for use in warm-blooded animals (including man), they are also useful whenever it is required to inhibit the effects of the erbB receptor tyrosine protein kinases. Thus, they are useful as pharmacological standards for use in the development of new biological tests and in the search for new pharmacological agents.

The invention will now be illustrated by the following non limiting examples in which, unless stated otherwise:

(i) temperatures are given in degrees Celsius (° C.); operations were carried out at room or ambient temperature, that is at a temperature in the range of 18-25° C.;

(ii) organic solutions were dried over anhydrous magnesium sulfate; evaporation of solvent was carried out using a rotary evaporator under reduced pressure (600-4000 Pascals; 4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC and/or analytical LCMS, and reaction times are given for illustration only;

(v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; b, broad;

(viii) chemical symbols have their usual meanings; SI units and symbols are used;

(ix) solvent ratios are given in volume:volume (v/v) terms; and (x) mass spectra (MS) were run with an electron energy of 70 electron volts in the chemical ionization (CI) mode using a direct exposure probe and ionization was effected by electrospray; values for m/z are given; generally, only ions which indicate the parent mass are reported; and unless otherwise stated, the mass ion quoted is (MH)$^+$;

(xi) unless stated otherwise compounds containing an asymmetrically substituted carbon and/or sulfur atom have not been resolved;

(xii) where a synthesis is described as being analogous to that described in a previous example the amounts used are the millimolar ratio equivalents to those used in the previous example;

| DCM | dichloromethane; |
|---|---|
| DMF | N,N-dimethylformamide; |
| DMA | N,N-dimethylacetamide; |
| THF | Tetrahydrofuran; |

HATU O-(7-azabenzotriazol-1-yl)-N,N,N',N'-tetramethyluronium hexafluorophosphate xvii) where a synthesis is described as leading to an acid addition salt (e.g. HCl salt), the specific stoichiometry of the salt was not confirmed.

xviii) In Examples 1 to 15 and the Reference Examples unless otherwise stated, all NMR data is reported on free-base material, with isolated salts converted to the free-base form prior to characterisation.

EXAMPLE 1

4-(3-Chloro-2-fluoroanilino)-7-methoxy-6-[(1-methylpyrrolidin-3-yl)oxy]quinazoline

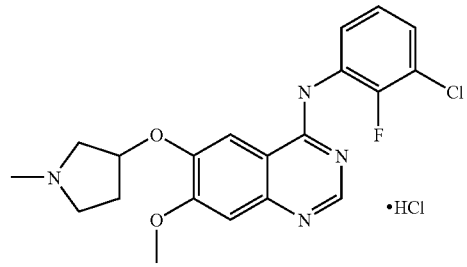 [SMILES: COc1cc2ncnc(Nc3cccc(Cl)c3F)c2cc1OC1CCN(C)C1 ; Cl]

To a suspension of 4-(3-chloro-2-fluoroanilino)-6-hydroxy-7-methoxyquinazoline (Reference Example 2, 639 mg, 2.0 mmol) in DCM (30 ml) was added 1-methyl-3-pyrrolidinol (658 µl, 6.0 mmol) and triphenyl phosphine (1572 mg, 6.0 mmol). The suspension was cooled to 0° C. under a nitrogen atmosphere. Di-tent-butyl azodicarboxylate (1380 mg, 6 mmol) was added as a solution in DCM (20 ml), dropwise over the course of 15 minutes. The resulting light brown solution was allowed to warm to room temperature and was stirred overnight. The solution was evaporated, and the residue purified by chromatography, eluting with 0 to 5% methanol in DCM. The appropriate fractions were combined and evaporated, and the crude product (230 mg) re-dissolved in 1:1 methanol/DCM (5 ml). Ethereal HO (1M, 1.14 ml) was added, and the mixture evaporated. Crystallisation from ethanol diethyl ether gave the title product as a hydrochloride salt in the form of a white crystalline solid (154 mg, 16%); $^1$H NMR (hydrochloride salt): 2.30 (m, 1H), 2.65-2.75 (m, 1H), 2.88 (s, 3H), 3.30-3.80 (m, 3H), 3.85-4.05 (m, 1H), 4.00 (s, 3H), 5.46 (m, 1H), 7.35 (dd, 1H), 7.45 (s, 1H), 7.51 (dd, 1H), 7.62 (dd, 1H), 8.53 (s, 1H), 8.72 (s, 1H), 8.81 (s, 1H); Mass Spectrum: 403.3, 405.3.

EXAMPLE 2

4-(3-Chloro-2-fluoroanilino)-7-methoxy-6-[(piperidin-4-yl)oxy]quinazoline

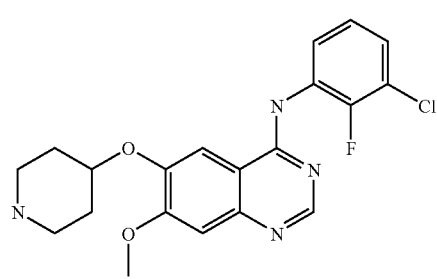 [SMILES: COc1cc2ncnc(Nc3cccc(Cl)c3F)c2cc1OC1CCNCC1]

6-{[(1-tert-Butoxycarbonyl)piperidin-4-yl]oxy}-4-(3-chloro-2-fluoroanilino)-7-methoxyquinazoline (Reference Example 3; 350 mg, 0.70 mmol) was dissolved in trifluoroacetic acid (5 ml), and the solution stood for 2 hours. The excess trifluoroacetic acid was evaporated, and the residue was azeotroped twice with DCM. The residue was purified by chromatography, eluting with 0 to 4% (7:1 MeOH/concentrated aqueous NH$_4$OH) in DCM. Evaporation of the appropriate fractions gave the product as an off-white solid (270 mg, 96%); $^1$H NMR: 1.53-1.64 (m, 2H), 2.00-2.05 (m, 2H), 2.64-2.72 (m, 2H), 3.00-3.07 (m, 2H), 3.92 (s, 3H), 4.60 (m, 1H), 7.20 (s, 1H), 7.26 (ddd, 1H), 7.47 (dd, 1H), 7.50 (dd, 1H), 7.82 (s, 1H), 8.34 (s, 1H), 9.56 (s, 1H); Mass Spectrum: 403.2, 405.2

EXAMPLE 3

4-(3-Chloro-2-fluoroanilino)-7-methoxy-6-[(piperidin-4-yl)methoxy]quinazoline

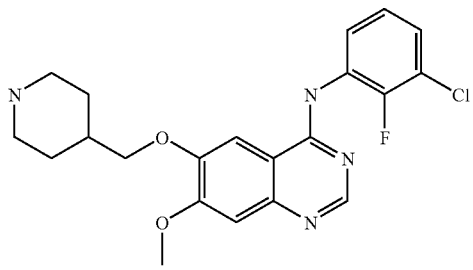 [SMILES: COc1cc2ncnc(Nc3cccc(Cl)c3F)c2cc1OCC1CCNCC1]

The procedure described in Example 2 was repeated but using 6-{[(1-tert-butoxycarbonyl)piperidin-4-yl]methoxy}(3-chloro-2-fluoroanilino)-7-methoxyquinazoline 2.0 (Reference Example 4). The title compound was obtained in 91% yield; $^1$H NMR: 1.45-1.61 (m, 2H), 1.95-2.00 (m, 2H), 2.18 (m, 1H), 2.92 (m, 2H), 3.25-3.35 (m, 2H), 3.93 (s, 3H), 4.03 (d, 2H), 7.20 (s, 1H), 7.26 (dd, 1H), 7.46 (dd, 1H), 7.50 (dd, 1H), 7.89 (s, 1H), 8.36 (s, 1H), 8.72 (br. s, 1H), 9.74 (s, 1H); Mass Spectrum: 417.4, 419.

EXAMPLE 4

4-(3-Chloro-2-fluoroanilino)-7-methoxy-6-[(1-methylpiperidin-4-yl)oxy]quinazoline

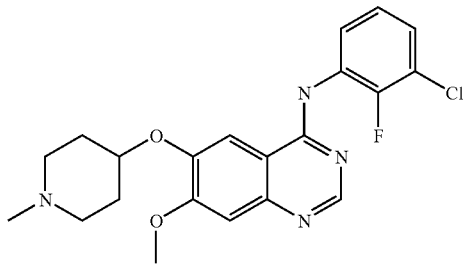 [SMILES: COc1cc2ncnc(Nc3cccc(Cl)c3F)c2cc1OC1CCN(C)CC1]

6-{[(1-tert-Butoxycarbonyl)piperidin-4-yl]oxy}-4-(3-chloro-2-fluoroanilino)-7-methoxyquinazoline (Reference Example 3; 300 mg, 0.66 mmol) was dissolved in formic acid (10 ml). Aqueous formaldehyde solution (40%, 1 ml) was added, and the mixture heated to 90° C. for 3 hours. The mixture was evaporated, and the residue dissolved in water (30 ml). The solution was adjusted to pH 8-9 by the addition of sodium hydroxide solution (1M), causing precipitation of a white solid; this was collected by filtration and washed with water (20 ml). The crude product was purified by chromatography, eluting with 0 to 2.5% (7:1 MeOH/concentrated aqueous NH$_4$OH) in DCM. Evaporation of the appropriate fractions followed by crystallisation of the residue from acetonitrile gave the product as a white crystalline solid (55 mg, 20%); $^1$H NMR: 1.66-1.76 (m, 2H), 1.95-2.05 (m, 2H), 2.14-2.22 (m, 2H), 2.18 (s, 3H), 2.65-2.70 (m, 2H), 3.92 (s, 3H), 4.51 (m, 1H), 7.19 (s, 1H), 7.26 (dd, 1H), 7.47 (dd, 1H), 7.51 (dd, 1H), 7.78 (s, 1H), 8.34 (s, 1H), 9.53 (s, 1H); Mass Spectrum: 417.2, 419.3

EXAMPLE 5

4-(3-Chloro-2-fluoroanilino)-7-methoxy-6-[(1-methylpiperidin-4-yl)methoxy]quinazoline

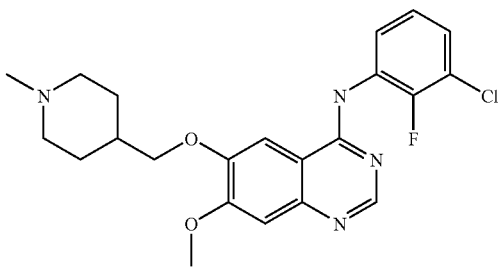 [SMILES: COc1cc2ncnc(Nc3cccc(Cl)c3F)c2cc1OCC1CCN(C)CC1]

The procedure described in Example 4 was repeated using 6-{[(1-tert-Butoxycarbonyl)piperidin-4-yl]methoxy}-4-(3-chloro-2-fluoroanilino)-7-methoxyquinazoline (reference example 4) to give the title compound in 42% yield after crystallisation from methyl tert-butyl ether; $^1$H NMR: 1.28-1.42 (m, 2H), 1.79-1.95 (m, 5H), 2.17 (s, 3H), 2.80 (m, 2H), 195 (s, 3H), 3.98 (d, 2H), 7.20 (s, 1H), 7.28 (dd, 1H), 7.48 (dd, 1H), 7.52 (dd, 1H), 7.77 (s, 1H), 8.37 (s, 1H), 9.59 (s, 1H); Mass Spectrum: 431.1, 430.0

EXAMPLE 6

4-(3-Chloro-2-fluoroanilino)-7-methoxy-6-[2-(1-methylpiperidin-4-yl)ethoxy]quinazoline

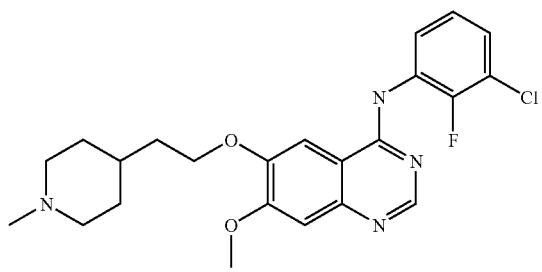 [SMILES: COc1cc2ncnc(Nc3cccc(Cl)c3F)c2cc1OCCC1CCN(C)CC1]

The procedure described in Example 4 was repeated using 6-{2-(1-tert-Butoxycarbonyl)piperidin-4-yl]ethoxy}-4-(3-chloro-2-fluoroanilino)-7-methoxyquinazoline (reference example 5) to give the title compound in 60% yield after crystallisation from methyl tert butyl ether; $^1$H NMR: 1.17-1.30 (m; 2H), 1.43 (m, 1H), 1.65-1.85 (m, 6H), 2.11 (s, 3H), 2.73 (m, 2H), 3.92 (s, 3H), 4.14 (t, 2H), 7.18 (s, 1H), 7.26 (ddd, 1H), 7.46 (dd, 1H), 7.51 (dd, 1H), 7.76 (s, 1H), 8.35 (s, 1H), 9.53 (s, 1H); Mass Spectrum: 445.5, 447.

EXAMPLE 7

4-(3-Chloro-2-fluoroanilino)-7-methoxy-6-{[1-(2-methoxyethyl)piperidin-4-yl]oxy}quinazoline

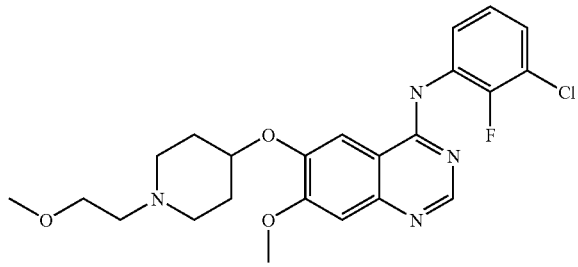 [SMILES: COCCN1CCC(Oc2cc3c(Nc4cccc(Cl)c4F)ncnc3cc2OC)CC1]

6-{[(1-tert-Butoxycarbonyl)piperidin-4-yl]oxy}-4-(3-chloro-2-fluoroanilino)-7-methoxyquinazoline (Reference Example 3; 485 mg, 1.07 mmol) was dissolved in trifluoroacetic acid (10 ml), and the solution stirred at ambient temperature for 2 hours. The excess trifluoroacetic acid was evaporated, and the residue was azeotroped twice with DCM. The residue was dissolved in DMA (25 ml); potassium carbonate (887 mg, 6.42 mmol) and 1-bromo-2-methoxyethane (100 μl, 1.07 mmol) were added. The mixture was stirred at ambient temperature for 16 hours. Further potassium carbonate (444 mg, 3.21 mmol) and 1-bromo-2-methoxyethane (100 μl, 1.07 mmol) were added, and the mixture heated at 60° C. for a further 4 hours. The solvent was evaporated; the residue was partitioned between DCM (50 ml) and water (50 ml). The aqueous layer was extracted with DCM (2×30 ml) and the extractions combined with the DCM layer. The combined DCM fractions were filtered through a silicone-treated filter paper and evaporated. The residue was purified by chromatography, eluting with 0 to 2% (7:1 MeOH/concentrated aqueous NH$_4$OH) in DCM. Evaporation of the appropriate fractions followed by crystallisation of the residue from acetonitrile gave the product as a white crystalline solid (153 mg, 38%); $^1$H NMR: 1.60-1.75 (m, 2H), 1.95-2.05 (m, 2H), 2.30 (m, 2H), 2.49 (t, 2H), 2.75-2.82 (m, 2H), 3.22 (s, 3H), 3.43 (t, 2H), 3.92 (s, 3H), 4.51 (m, 1H), 7.19 (s, 1H), 7.26 (ddd, 1H), 7.47 (dd, 1H), 7.51 (dd, 1H), 7.78 (s, 1H), 8.34 (s, 1H), 9.53 (s, 1H); Mass Spectrum: 461.2, 463.2

EXAMPLE 8

4-(3-Chloro-2-fluoroanilino)-7-methoxy-6-{[1-(2-methoxyethyl)piperidin-4-yl]methoxy}quinazoline

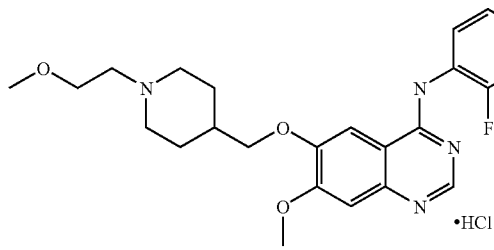

4-(3-Chloro-2-fluoroanilino)-7-methoxy-6-[(piperidin-4-yl)methoxy]quinazoline (Example 3, 104 mg, 0.25 mmol) was dissolved in DMA (5 ml). Potassium carbonate (138 mg, 1.00 mmol) and 1-bromo-2-methoxyethane (24 μl, 0.25 mmol) were added. The mixture was stirred at 60° C. for 4 hours. Further potassium carbonate (138 mg, 1.00 mmol) and 1-bromo-2-methoxyethane (24 μl, 0.25 mmol) were added; heating was continued at 60° C. for a further 4 hours. The solvent was evaporated and the residue was partitioned between DCM (20 ml) and water (20 ml). The aqueous layer was extracted with DCM (2×10 ml) and the extractions combined with the DCM layer. The combined DCM fractions were filtered through a silicone-treated filter paper and evaporated. The residue was purified by chromatography, eluting with 0 to 2.5% (7:1 MeOH/concentrated aqueous NH$_4$OH) in DCM. The appropriate fractions were combined and evaporated, and the crude product (40 mg) re-dissolved in 1:1 methanol/DCM (5 ml). Ethereal HCl (1M, 0.5 ml) was added, and the mixture evaporated. Crystallisation from iso-propanol/diethyl ether gave the title product as a hydrochloride salt, a yellow solid (28 mg, 20%); $^1$H NMR (hydrochloride salt): 1.60-1.75 (m, 2H), 2.00-2.05 (m, 2H), 2.16 (m, 1H), 2.95-3.10 (m, 2H), 3.22 (t, 2H), 3.29 (s, 3H), 3.50-3.57 (m, 2H), 3.70 (t, 2H), 3.99 (s, 3H), 4.12 (d, 2H), 7.34 (dd, 1H), 7.39 (s, 1H), 7.51 (dd, 1H), 7.61 (dd, 1H), 8.46 (s, 1H), 8.78 (s, 1H), 10.08 (br. s, 1H); Mass Spectrum: 475.5, 477

EXAMPLE 9

4-(3-Chloro-2-fluoroanilino)-6-{[(methylsulfonyl)piperidin-4-yl]oxy}-7-methoxyquinazoline

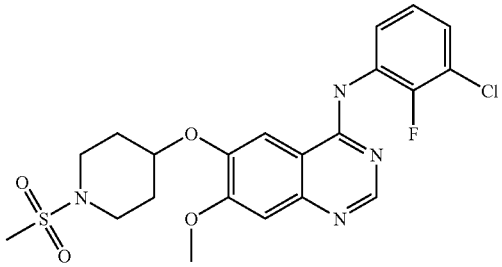 [SMILES: COc1cc2ncnc(Nc3cccc(Cl)c3F)c2cc1OC1CCN(S(C)(=O)=O)CC1]

4-(3-Chloro-2-fluoroanilino)-7-methoxy-6-[(piperidin-4-yl)oxy]quinazoline (Example 2, 1360 mg, 3.38 mmol) was dissolved in DCM (40 ml), and diisopropylethylamine (882 μl, 5.07 mmol) was added. Methanesulfonyl chloride (392 μl, 5.07 mmol) was added dropwise, and the solution stirred for 16 hours at ambient temperature. The solvent was evaporated, and the residue purified by chromatography, eluting with 0 to 2% (7:1 MeOH concentrated aqueous NH$_4$OH) in DCM. The appropriate fractions were combined and evaporated, and the residue crystallised from ethyl acetate/hexane to give the product as a white crystalline solid (650 mg, 40%); $^1$H NMR: 1.80-1.90 (m, 2H), 2.04-2.13 (m, 2H), 2.91 (s, 3H), 3.10-3.20 (m, 2H), 3.34-3.44 (m, 2H), 3.93 (s, 3H), 4.67 (m, 1H), 7.22 (s, 1H), 7.27 (dd, 1H), 7.47 (dd, 1H), 7.51 (dd, 1H), 7.86 (s, 1H), 8.37 (s, 1H), 9.55 (s, 1H); Mass Spectrum: 481.2, 483.1

EXAMPLE 10

4-(3-Chloro-2-fluoroanilino)-6-{[(1-(methylsulfonyl)piperidin-4-yl]methoxy}-7-methoxyquinazoline

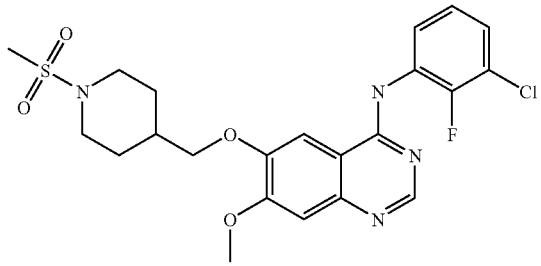 [SMILES: COc1cc2ncnc(Nc3cccc(Cl)c3F)c2cc1OCC1CCN(S(C)(=O)=O)CC1]

The procedure described in Example 9 was repeated using 4-(3-chloro-2-fluoroanilino)-7-methoxy-6-[(piperidin-4-yl)methoxy]quinazoline (Example 3). Thus was obtained the compound below in 71% yield after trituration with diethyl ether; $^1$H NMR: 1.31-1.47 (m, 2H), 1.90-2.07 (m, 3H), 2.76 (m, 2H), 2.85 (s, 3H), 3.56-3.67 (m, 2H), 3.93 (s, 3H), 4.01 (d, 2H), 7.19 (s, 1H), 7.26 (dd, 1H), 7.46 (dd, 1H), 7.50 (dd, 1H), 7.78 (s, 1H), 8.36 (s, 1H), 9.61, (s, 1H); Mass Spectrum: 495.4, 497.4

EXAMPLE 11

6-{[1-(carbamoylmethyl)piperidin-4-yl]oxy}-4-(3-chloro-2-fluoroanilino)-7-methoxyquinazoline

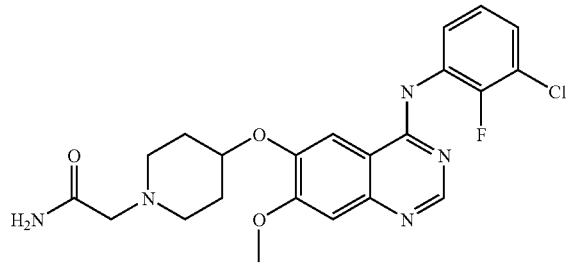 [SMILES: COc1cc2ncnc(Nc3cccc(Cl)c3F)c2cc1OC1CCN(CC(N)=O)CC1]

4-(3-Chloro-2-fluoroanilino)-7-methoxy-6-[(piperidin-4-yl)oxy]quinazoline (Example 2, 70 mg, 0.17 mmol) was dissolved in DCM (10 ml), and diisopropylethylamine (45 µl, 0.26 mmol) was added. 2-Bromoacetamide (36 mg, 0.26 mmol) was added, and the solution stirred for 16 hours at ambient temperature. The solvent was evaporated, and the residue purified by chromatography, eluting with 0 to 3% (7:1 MeOH/concentrated aqueous NH$_4$OH) in DCM. The appropriate fractions were combined and evaporated, and the residue crystallised from acetonitrile to give the product as a white crystalline solid (48 mg, 60%); $^1$H NMR: 1.70-1.84 (m, 2H), 1.98-2.09 (m, 2H), 2.38 (m, 2H), 2.70-2.80 (m, 2H), 2.89 (s, 2H), 3.92 (s, 3H), 4.54 (m, 1H), 7.08 (br. s, 2H), 7.20 (s, 1H), 7.26 (ddd, 1H), 7.47 (ddd, 1H), 7.51 (ddd, 1H), 7.80 (s, 1H), 8.35 (s, 1H), 9.53 (s, 1H); Mass Spectrum: 460.5, 462.4.

EXAMPLE 12

6-{[1-(Carbamoylmethyl)piperidin-4-yl]methoxy}-4-(3-chloro-2-fluoroanilino)-7-methoxyquinazoline

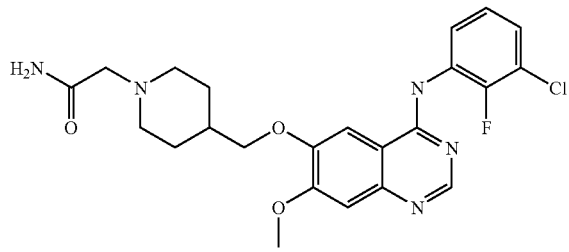 [SMILES: COc1cc2ncnc(Nc3cccc(Cl)c3F)c2cc1OCC1CCN(CC(N)=O)CC1]

The procedure of Example 11 was repeated but using 4-(3-chloro-2-fluoroanilino)-7-methoxy-6-[(piperidin-4-yl)methoxy]quinazoline (Example 3). The title compound was obtained in 44% yield after crystallisation from acetonitrile; $^1$H NMR: 1.34-1.50 (m, 2H), 1.77-1.90 (m, 3H), 2.05-2.20 (m, 2H), 2.80-2.95 (m, 4H), 3.93 (s, 3H), 3.97 (d, 2H), 7.04-7.16 (m, 2H), 7.19 (s, 1H), 7.26 (ddd, 1H), 7.46 (ddd, 1H), 7.50 (ddd, 1H), 7.76 (s, 1H), 8.35 (s, 1H), 9.58 (s, 1H); Mass Spectrum: 474.4, 476.4

EXAMPLE 13

4-(3-Chloro-2-fluoroanilino)-6-{[1-(cyanomethyl)piperidin-4-yl]oxy}-7-methoxyquinazoline

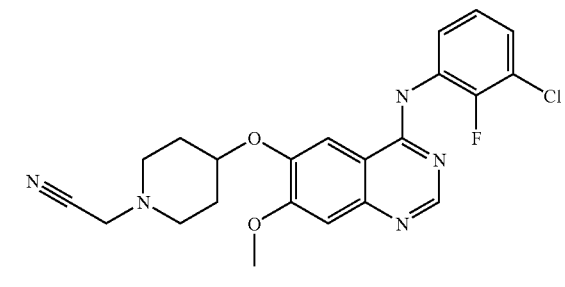 [SMILES: COc1cc2ncnc(Nc3cccc(Cl)c3F)c2cc1OC1CCN(CC#N)CC1]

4-(3-Chloro-2-fluoroanilino)-7-methoxy-6-[(piperidin-4-yl)oxy]quinazoline (Example 2, 70 mg, 0.17 mmol) was dissolved in DMA (5 ml). Potassium carbonate (96 mg, 0.70 mmol) and chloroacetonitrile (17 µl, 0.25 mmol) were added. The mixture was stirred at 60° C. for 4 hours. The solvent was evaporated and the residue was partitioned between DCM (20 ml) and water (20 ml). The aqueous layer was extracted with DCM (2×10 ml) and the extractions combined with the DCM layer. The combined DCM fractions were filtered through a silicone-treated filter paper and evaporated. The residue was purified by chromatography, eluting with 0 to 2% (7:1 MeOH/concentrated aqueous NH$_4$OH) in DCM. The appropriate fractions were combined and evaporated, and the residue triturated with diethyl ether, giving the product as a white solid (28 mg, 36%); $^1$H NMR: 1.67-1.80 (m, 2H), 2.03-2.13 (m, 2H), 2.46 (m, 2H), 2.77-2.85 (m, 2H), 3.76 (s, 2H), 3.92 (s, 3H), 4.55 (m, 1H), 7.20 (s, 1H), 7.27 (dd, 1H), 7.47 (dd, 1H), 7.52 (dd, 1H), 7.80 (s, 1H), 8.35 (s, 1H), 9.54 (s, 1H); Mass Spectrum: 412.4, 444.4.

EXAMPLE 14

4-(3-Chloro-2-fluoroanilino)-6-{[1-(cyanomethyl)piperidin-4-yl]methoxy}-7-methoxyquinazoline

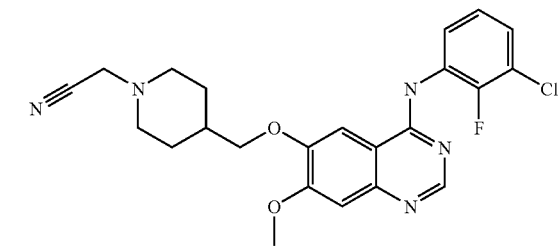 [SMILES: COc1cc2ncnc(Nc3cccc(Cl)c3F)c2cc1OCC1CCN(CC#N)CC1]

4-(3-Chloro-2-fluoroanilino)-7-methoxy-6-[(piperidin-4-yl)methoxy]quinazoline (Example 3, 104 mg, 0.25 mmol)

was dissolved in DMA (5 ml). Potassium carbonate (138 mg, 1.00 mmol) and chloroacetonitrile (17 μl, 0.25 mmol) were added. The mixture was stirred at 60° C. for 4 hours. Further potassium carbonate (138 mg, 1.00 mmol) and chloroacetortitrile (17 μl, 0.25 mmol) were added, and heating was continued at 60° C. for a further 4 hours. The solvent was evaporated and the residue was partitioned between DCM (20 ml) and water (20 ml). The aqueous layer was extracted with DCM (2×10 ml) and the extractions combined with the DCM layer. The combined DCM fractions were filtered through a silicone-treated filter paper and evaporated. The residue was purified by chromatography, eluting with 0 to 2% (7:1 MeOH/concentrated aqueous NH$_4$OH) in DCM. The appropriate fractions were combined and evaporated. The residue was further purified using reverse phase HPLC, eluting with 5 to 95% acetonitrile in water containing 0.2% trifluoroacetic acid. The appropriate fractions were combined; the acetonitrile was evaporated from the solution, and the resulting aqueous solution was adjusted to pH 8 using concentrated aqueous ammonia. The resulting suspension was extracted twice with DCM, and the extractions combined, filtered through a silicone-treated filter paper, and evaporated. The residue was triturated with diethyl ether to give the product as a white solid (10 mg, 9%); $^1$H NMR: 132-1.46 (m, 2H), 1.75-1.92 (m, 3H), 220 (m, 2H), 2.84 (m, 2H), 3.72 (s, 2H), 3.93 (s, 3H), 3.98 (d, 2H), 7.20 (s, 1H), 7.26 (dd, 1H), 7.47 (dd, 1H), 7.50 (dd, 1H), 7.76 (s, 1H), 8.36 (s, 1H), 9.59 (s, 1H); Mass Spectrum; 456.4, 458.4

EXAMPLE 15

4-(3-Chloro-2-fluoroanilino)-6-[(1-cyanopiperidin-4-yl)methoxy]-7-methoxyquinazoline

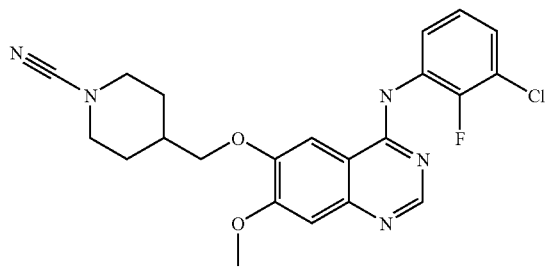 [SMILES: COc1cc2ncnc(Nc3cccc(Cl)c3F)c2cc1OCC1CCN(C#N)CC1]

4-(3-Chloro-2-fluoroanilino)-7-methoxy-6-[(piperidin-4-yl)methoxy]quinazoline (Example 3, 104 mg, 0.25 mmol) was dissolved in DCM (10 ml), and diisopropylethylamine (4 μl, 0.28 mmol) was added. Cyanogen bromide solution (3M in DCM, 92 μl, 0.28 mmol) was added, and the solution stirred for 16 hours at ambient temperature. The solvent was evaporated, and the residue purified by chromatography, eluting with 0 to 2% (7:1 MeOH/concentrated aqueous NH$_4$OH) in DCM. The appropriate fractions were combined and evaporated, and the residue triturated with diethyl ether to give the product as a white solid (75 mg, 68%); $^1$H NMR: 1.34-1.50 (m, 2H), 1.80-1.90 (m, 2H), 2.02 (m, 1H), 3.10 (m, 2H), 3.37-3.46 (m, 2H), 3.93 (s, 3H), 3.99 (d, 2H), 7.19 (s, 1H), 7.26 (dd, 1H), 7.46 (dd, 1H), 7.46 (dd, 1H), 7.50 (dd, 1H), 7.77 (s, 1H), 8.36 (s, 1H), 9.57 (s, 1H); Mass Spectrum: 442.4, 444.4.

EXAMPLE 16

6-(1-Acetylpiperidin-4-yloxy)-4-(3-chloro-2-fluoroanilino)-7-methoxyquinazoline

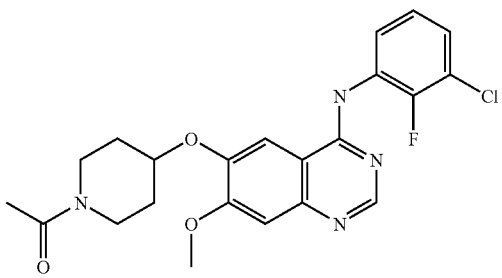 [SMILES: COc1cc2ncnc(Nc3cccc(Cl)c3F)c2cc1OC1CCN(C(C)=O)CC1]

Acetyl chloride (179 mg) was added to a solution of 6-(piperidin-4-yloxy)-4-(3-chloro-2-fluoroanilino)-7-methoxyquinazoline dihydrochloride (1 g) and diisopropylethylamine (735 mg) in methylene chloride that was cooled at 0° C. and the mixture was stirred for 2 hours and allowed to warm to room temperature. The reaction mixture was adsorbed onto silica and the residue was purified by column chromatography eluting with increasingly polar mixtures of methylene chloride/methanol (100/0 to 90/10). The fractions containing the desired product were combined and evaporated under vacuum to give the title product as a colourless foam (0.655 g); $^1$H NMR Spectrum: (DMSO d$_6$) 1.54-1.78 (m, 2H), 1.91-2.10 (m, 5H), 3.29-3.41 (m, 2H), 3.66-3.76 (m, 1H), 3.78-3.88 (m, 1H), 3.93 (s, 3H), 4.74 (m, 1H), 7.20 (s, 1H), 7.27 (t, 1H), 7.44-7.55 (m, 2H), 7.87 (s, 1H), 836 (s, 1H), 9.54 (s, 1H); Mass Spectrum: (M+H)$^+$ 445.

The 6-(piperidin-4-yloxy)-4-(3-chloro-2-fluoroanilino)-7-methoxyquinazoline dihydrochloride starting material was prepared as follows:

6-Acetoxy-4-chloro-7-methoxyquinazoline, (Example 25-5 of in WO01/66099; 10.0 g, 39.6 mmole) was added in portions to a stirred 7N methanolic ammonia solution (220 ml) cooled to 10° C. in an ice/water bath. After stirring for one hour the precipitate was filtered, washed with diethylether and dried thoroughly under high vacuum to give 4-chloro-6-hydroxy-7-methoxyquinazoline (5.65 g, 67.8%); $^1$H NMR Spectrum: (DMSO d$_6$) 3.96 (s, 3H); 7.25 (s, 1H); 7.31 (s, 1H); 8.68 (s, 1H); Mass Spectrum: (M+H)$^+$ 211

Di-tert-butylazodicarboxylate (9.22 g) in methylene chloride (20 ml) was added slowly to a stirred suspension of 4-chloro-6-hydroxy-7-methoxyquinazoline (5.63 g), 4-hydroxy-1-tert-butoxycarbonylpiperidine (8.06 g) and triphenylphosphine (10.5 g) in methylene chloride (100 ml) at 5° C. under an atmosphere of nitrogen. The reaction mixture was allowed to warm to room temperature for 16 hours. The reaction mixture was then evaporated under vacuum and adsorbed onto silica and the product was eluted with isohexane/ethyl acetate/triethylamine (75/24/1 followed by 70/29/1). The fractions containing the desired product were combined and evaporated under vacuum to give tent-butyl 4-[(4-chloro-7-methoxyquinazolin-6-yl)oxy]piperidine-1-carboxylate as a white solid (10.3 g); $^1$H NMR Spectrum: (DMSO d$_6$) 1.40 (s, 9H), 1.56-1.69 (m, 2H), 1.93-2.04 (m, 2H), 3.20-331 (m, 2H), 3.60-3.70 (m, 2H), 4.00 (s, 3H), 4.89 (m, 1H), 7.45 (s, 1H), 7.50 (s, 1H), 8.86 (s, 1H); Mass Spectrum: (M+H)+ 394.

4.0M HCl in Dioxane (4.0 ml) was added to a suspension of tert-butyl 4-[(4-chloro-7-methoxyquinazolin-6-yl)oxy]piperidine-1-carboxylate (2.62 g) and 3-chloro-2-fluoroaniline (1.08 g) in iso-propanol (50 ml). The reaction mixture was stirred and heated at 100° C. for 2 hours. The yellow precipitate was filtered hot and washed with iso-propanol followed by diethylether and dried under vacuum to give 6-(piperidin-4-yloxy)-4-(3-chloro-2-fluoroanilino)-7-methoxyquinazoline as a di-hydrochloride salt (2.38 g); $^1$H NMR Spectrum: (DMSO d$_6$) 1.84-1.99 (m, 2H), 2.22-2.33 (m, 2H), 3.12-3.33 (m, 4H), 4.00 (s, 3H), 5.08 (m, 1H), 7.34 (t, 1H), 7.40 (s, 1H), 7.50 (t, 1H), 7.62 (t, 1H), 8.80 (s, 1H), 8.84-8.94 (m, 2H), 8.99-9.11 (m, 1H); Mass Spectrum: (M+H)+ 403.

EXAMPLE 17

4-(3-Chloro-2-fluoroanilino)-6-[1-(N,N-dimethylaminoacetyl)piperidin-4-yloxy]-7-methoxyquinazoline

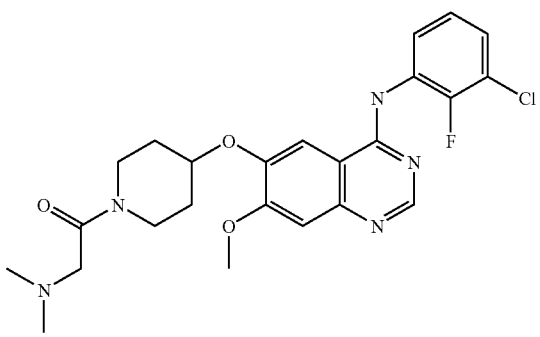 [SMILES: COc1cc2ncnc(Nc3cccc(Cl)c3F)c2cc1OC1CCN(C(=O)CN(C)C)CC1]

A suspension of 4-(3-chloro-2-fluoroanilino)-6-[1-(chloroacetyl)piperidin-4-yloxy]-7-methoxyquinazoline (0.14 g) and sodium iodide (0.1 g) in an ethanolic solution of dimethylamine (33%) (10 ml) was stirred at ambient temperature for 2 hours. The mixture was evaporated under vacuum and the residue dissolved in methylene chloride and purified by column chromatography on silica eluting with increasingly polar mixtures of methylene chloride/methanol (saturated with ammonia) (100/0 to 85/15). The fractions containing the title product were combined and evaporated under vacuum and the residue triturated with diethyl ether and filtered to give the title product as a crystalline solid (0.085 g); $^1$H NMR Spectrum: (DMSO d$_6$) 1.56-1.78 (m, 2H), 1.92-2.08 (m, 2H), 2.20 (s, 6H), 3.05-3.18 (m, 2H), 3.30-3.48 (m, 2H), 3.79-3.90 (m, 2H), 3.94 (s, 3H), 4.75 (m, 1H), 7.21 (s, 1H), 7.28 (t, 1H), 7.44-7.56 (m, 2H), 7.86 (s, 1H), 8.37 (s, 1H), 9.53 (s, 1H); Mass Spectrum: (M+H)+ 488.

The 4-(3-chloro-2-fluoroanilino)-6-[1-(chloroacetyl)piperidin-4-yloxy]-7-methoxyquinazoline starting material was prepared as follows:

Chloroacetyl chloride (135 mg) was added to a solution of 4-(3-chloro-2-fluoroanilino)-6-(piperidin-4-yloxy)-7-methoxyquinazoline di-hydrochloride (500 mg) (Starting material for Example 16) and diisopropylethylamine (368 mg) in methylene chloride (15 ml) that was cooled at 0° C. and the mixture was stirred for 2 hours and allowed to warm to room temperature. The reaction mixture was adsorbed onto silica and the residue purified by column chromatography on silica eluting with increasingly polar mixtures of methylene chloride/methanol (100/0 to 94/6). The fractions containing the expected product were combined and were re-purified by column chromatography on silica eluting with increasingly polar mixtures of methylene chloride/methanol (100/0 to 96/4). The fractions containing the expected product were combined and evaporated under vacuum to give 4-(3-chloro-2-fluoroanilino)-6-[1-(chloroacetyl)piperidin-4-yloxy]-7-methoxyquinazoline as a crystalline solid (0.33 g); $^1$H NMR Spectrum: (DMSO d$_6$) 1.60-1.83 (m, 2H), 1.94-2.10 (m, 2H), 3.36-3.46 (m, 2H), 3.67-3.86 (m, 2H), 3.94 (s, 3H), 4.40 (s, 2H), 4.77 (m, 1H), 7.22 (s, 1H), 7.27 (t, 1H), 7.46-7.55 (m, 2H), 7.89 (s, 1H), 8.38 (s, 1H), 9.60 (s, 1H); Mass Spectrum: (M+H)+ 479.

EXAMPLE 18

6-[1-(N,N-Dimethylsulfamoyl)piperidin-4-yloxy]-4-(3-chloro-2-fluoroanilino)-7-methoxyquinazoline

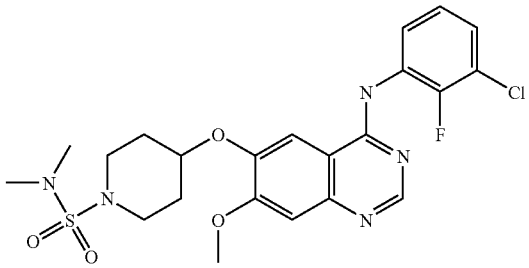 [SMILES: COc1cc2ncnc(Nc3cccc(Cl)c3F)c2cc1OC1CCN(S(=O)(=O)N(C)C)CC1]

Dimethylsulfamoyl chloride (90 mg) was added to a solution of 6-(piperidin-4-yloxy)-4-(3-chloro-2-fluoroanilino)-7-methoxyquinazoline dihydrochloride (250 mg) (starting material Example 16) and diisopropylethylamine (184 mg) in methylene chloride (10 ml). The reaction mixture was stirred for 16 hours at ambient temperature. The reaction mixture was adsorbed onto silica and the residue was purified by column chromatography on silica eluting with increasingly polar mixtures of methylene chloride/methanol (100/0 to 95/5). The fractions containing the expected product were combined and evaporated under vacuum and the residue triturated with diethylether to give the title product as a white solid (0.23 g); $^1$H NMR. Spectrum: (DMSO d$_6$) 1.72-1.86 (m, 2H), 2.00-2.12 (m, 2H), 2.76 (s, 6H); 3.12-3.23 (m, 2H), 3.40-3.51 (m, 2H), 3.94 (s, 3H), 4.68 (m, 1H), 7.19-7.30 (m, 2H), 7.43-7.54 (m, 2H), 7.85 (s, 1H), 8.37 (s, 1H), 9.52 (s, 1H); Mass Spectrum: (M+H)+ 510.

EXAMPLE 19

4-(3-Chloro-2-fluoroanilino)-7-methoxy-6-[1-(morpholinoacetyl)piperidin-4-yloxy]quinazoline

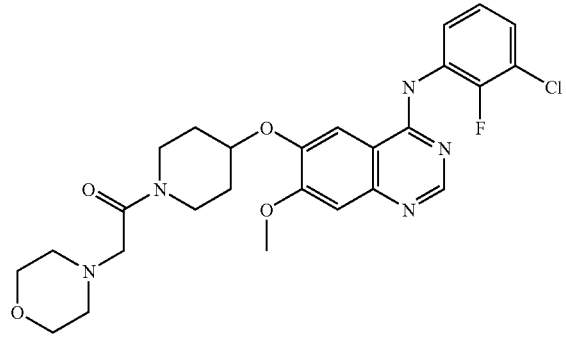 [SMILES: COc1cc2ncnc(Nc3cccc(Cl)c3F)c2cc1OC1CCN(C(=O)CN2CCOCC2)CC1]

A suspension of 4-(3-chloro-2-fluoroanilino)-6-[1-(chloroacetyl)piperidin-4-yloxy]-7-methoxyquinazoline (0.15 g) (starting material for Example 17) and sodium iodide (0.02 g) in morpholine (5 ml) was stirred at ambient temperature for 16 hours. The mixture was evaporated under vacuum and the residue dissolved in methylene chloride/methanol. This was adsorbed onto silica and purified by column chromatography on silica eluting with increasingly polar mixtures of methylene chloride/methanol (100/0 to 90/10). The fractions containing the title product were combined and evaporated under vacuum. The residue was triturated with diethylether, filtered and dried under vacuum to give the title product as a beige crystalline solid (0.105 g); $^1$H NMR Spectrum: (DMSO $d_6$ and $CD_3COOD$) 1.57-1.80 (m, 2H), 1.91-2.12 (m, 2H), 2.40-2.51 (m, 4H), 3.14-3.48 (m, 4H), 3.52-3.61 (m, 4H), 3.81-3.90 (m, 2H), 3.94 (s, 3H), 4.76 (m, 1H), 7.20-7.30 (m, 2H), 7.42-7.54 (m, 2H), 7.85 (s, 1H), 8.36 (s, 1H); Mass Spectrum: $(M+H)^+$ 530.

EXAMPLE 20

4-(3-Chloro-2-fluoroanilino)-7-methoxy-6-[1-(pyrrolidin-1-ylacetyl)piperidin-4-yloxy]quinazoline

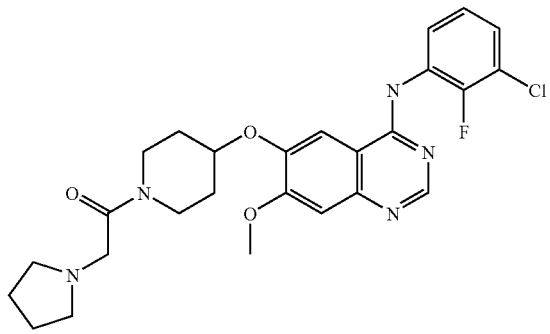 [SMILES: COc1cc2ncnc(Nc3cccc(Cl)c3F)c2cc1OC1CCN(C(=O)CN2CCCC2)CC1]

A suspension of 4-(3-chloro-2-fluoroanilino)-6-[1-(chloroacetyl)piperidin-4-yloxy]-7-methoxyquinazoline (0.15 g) (starting material used in Example 17) and sodium iodide (0.02 g) in pyrrolidine (5 ml) was stirred at ambient temperature for 16 hours. The mixture was evaporated under vacuum and the residue dissolved in methylene chloride/methanol. This was adsorbed onto silica and purified by column chromatography eluting with increasingly polar mixtures of methylene chloride/methanol (100/0 to 92/8). The fractions containing the title product were combined and evaporated under vacuum and the residue triturated with diethyl ether, filtered and dried under vacuum to give the title product as a white crystalline solid. (0.085 g); $^1$H NMR Spectrum: (DMSO $d_6$) 1.57-1.77 (m, 6H), 1.92-2.09 (m, 2H), 3.20-3.48 (m, 8H), 3.80-3.90 (m, 2H), 3.94 (s, 3H), 4.75 (m, 1H), 7.2-7.31 (m, 2H), 7.45-7.55 (m, 2H), 7.86 (s, 1H), 8.37 (s, 1H), 9.53 (s, 1H); Mass Spectrum: $(M-H)^+$ 514.

EXAMPLE 21

4-(3-Chloro-2-fluoroanilino)-6-{1-[3-(dimethylamino)propylsulfonyl]piperidin-4-yloxy}-7-methoxyquinazoline

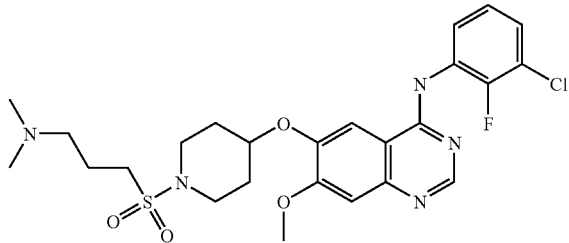 [SMILES: COc1cc2ncnc(Nc3cccc(Cl)c3F)c2cc1OC1CCN(S(=O)(=O)CCCN(C)C)CC1]

A suspension of 4-(3-chloro-2-fluoroanilino)-6-{1-[3-chloropropylsulfonyl]piperidin-4-yloxy}-7-methoxyquinazoline (0.15 g) and sodium iodide (0.03 g) in an ethanolic solution of dimethylamine (33%) (15 ml) was stirred at ambient temperature for 16 hours. The reaction mixture was adsorbed onto silica and purified by column chromatography on silica eluting with increasingly polar mixtures of methylene chloride/methanol (saturated with ammonia) (100/0 to 88/12). The fractions containing the title product were combined and evaporated under vacuum to give the title product (0.105 g); $^1$H NMR Spectrum: (DMSO $d_6$) 1.75-1.87 (m, 4H), 2.0-2.11 (m, 2H), 2.12 (s, 6H), 2.30 (t, 2H), 3.05-3.14 (m, 2H), 3.17-3.29 (m, 2H), 3.40-3.50 (m, 2H), 3.93 (s, 3H), 4.69 (m, 1H), 7.22 (s, 1H), 7.28 (t, 1H), 7.44-7.55 (m, 2H), 7.86 (s, 1H), 8.37 (s, 1H), 9.53 (s, 1H); Mass Spectrum: $(M+H)^+$ 552

The 4-(3-chloro-2-fluoroanilino)-6-{1-[3-chloropropylsulfonyl]piperidin-4-yloxy}-7-methoxyquinazoline starting material was prepared as follows:

3-chloropropanesulfonylchloride (174 mg) was added to a solution of 6-(piperidin-4-yloxy)-4-(3-chloro-2-fluoroanilino)-7-methoxyquinazoline dihydrochloride (190 mg; starting material for Example 16) and diisopropylethylamine (140 mg) in methylene chloride (5 ml) at ambient temperature and the reaction mixture was stirred for 16 hours. The reaction mixture was adsorbed onto silica and the residue was purified by column chromatography on silica eluting with increasingly polar mixtures of methylene chloride/methanol (100/0 to 94/6). The fractions containing the expected product were combined and evaporated under vacuum to give 4-(3-chloro-2-fluoroanilino)-6-{1-[3-chloropropylsulfonyl]piperidin-4-yloxy}-7-methoxyquinazoline as a brown gum (0.15 g); Mass Spectrum: $(M+H)^+$ 543.

EXAMPLE 22

4-(3-Chloro-2-fluoroanilino)-6-[1-(methylsulfonyl)piperidin-3-yloxy]-7-methoxyquinazoline

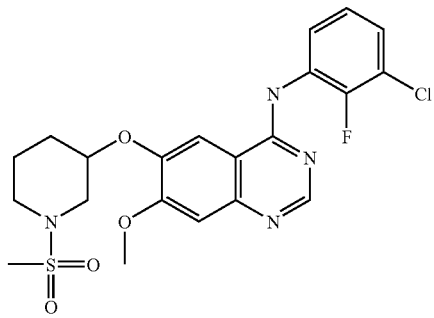

Methanesulfonyl chloride (42 mg) was added to a solution of 4-(3-chloro-2-fluoroanilino)-7-methoxy-6-(piperidin-3-yloxy)quinazoline (134 mg) and diisopropylethylamine (65 mg) in methylene chloride (5 ml) at ambient temperature. The reaction mixture was stirred for 16 hours at ambient temperature. The reaction mixture was adsorbed onto silica and the residue was purified by column chromatography eluting with increasingly polar mixtures of methylene chloride/methanol (100/0 to 95/5). The fractions containing the title product were combined and evaporated under vacuum and the residue triturated with diethyl ether, filtered and dried under vacuum to give the title product as a mixture of the 3R and 3S isomers (0.10 g); $^1$H NMR Spectrum: (DMSO $d_6$ and $CD_3COOD$) 1.54-2.07 (m, 4H), 2.95 (s, 3H), 3.10-120 (m, 1H), 3.21-3.37 (m, 2H), 3.50-3.59 (m, 1H), 3.93 (s, 3H), 4.70 (m, 1H), 7.20-7.29 (m, 2H), 7.40-7.55 (m, 2H), 7.89 (s, 1H), 8.37 (s, 1H); Mass Spectrum: $(M+H)^+$ 481.

The 4-(3-chloro-2-fluoroanilino)-7-methoxy-6-(piperidin-3-yloxy)quinazoline starting material was prepared as follows:

4-Nitrobenzenesulfonyl chloride (4.4 g) was added to a stirred solution of tert-butyl 3-hydroxypiperidine-1-carboxylate (4.0 g) and pyridine (2.25 ml) in methylene chloride (80 ml) and stirred at ambient temperature for 16 hours. The reaction mixture was poured into saturated sodium bicarbonate solution. The organic layer was separated, washed with brine and dried over sodium sulfate. The solution was evaporated under vacuum and triturated with diethylether and filtered to remove undesired solids. The diethylether liquors were evaporated under vacuum and dissolved in methylene chloride before purification by column chromatography on silica eluting with ethyl acetate/isohexane (20/80). The fractions containing the expected product were combined and evaporated under vacuum to give tert-butyl 3-[(4-nitrophenyl)sulfonyloxy]piperidine-1-carboxylate as a yellow crystalline solid (6.77 g); $^1$H NMR Spectrum: (CDCl$_3$) 1.43 (s, 9H), 1.40-1.54 (m, 1H), 1.70-1.94 (m, 3H), 3.22-3.60 (m, 4H), 4.67 (m, 1H), 8.11 (s, 2H), 8.40 (s, 2H).

Dimethylformamide (23 ml) was added to 4-(3-chloro-2-fluoroanilino)-6-hydroxy-7-methoxyquinazoline, tert-butyl 3-[(4-nitrophenyl)sulfonyloxy]piperidine-1-carboxylate (1.93 g) and cesium fluoride (2.28 g). The reaction mixture was then stirred at room temperature for 4 days. The reaction mixture was evaporated under vacuum and partitioned between methylene chloride and water. The solutions were filtered to remove insoluble solids and the methylene chloride was washed with water and saturated brine and adsorbed onto silica. The product was then purified by column chromatography on silica eluting with increasingly polar mixtures of methylene chloride/methanol (100/0 to 94/6). The fractions containing the required product were combined and evaporated under vacuum to give 4-(3-chloro-2-fluoroanilino)-6-(1-tert-butoxycarbonylpiperidin-3-yloxy)-7-methoxyquinazoline as a yellow gum (0.67 g); Mass Spectrum: (M+H)$^+$ 503.

Trifluoroacetic acid (5 ml) was added to a solution of 4-(3-chloro-2-fluoroanilino)-6-(1-tert-butoxycarbonylpiperidin-3-yloxy)-7-methoxyquinazoline (0.67 g) in methylene chloride (15 ml) and the reaction mixture was stirred at ambient temperature for 1 hour. The reaction mixture was evaporated under vacuum and the residue dissolved in methylene chloride. The methylene chloride solution was washed with a saturated solution of sodium bicarbonate, water, brine, dried over MgSO$_4$ and evaporated to give 4-(3-chloro-2-fluoroanilino)-7-methoxy-6-(piperidin-3-yloxy)quinazoline (0.28 g); Mass Spectrum: (M+H)$^+$ 403.

The 4-(3-chloro-2-fluoroanilino)-6-hydroxy-7-methoxyquinazoline starting material to used above was prepared as follows:

6-Acetoxy-4-chloro-7-methoxyquinazoline (Example 25-5 in WO01/66099; 10.0 g, 39.6 mmole) was suspended in acetonitrile (400 ml) and 3-chloro-2-fluoroaniline (6.05 g, 41.6 mmole) and hydrogen chloride (4.0M solution in 1,4-dioxane) (10.4 ml, 41.6 mmole) were added. The reaction mixture was refluxed for one hour and then allowed to cool to ambient temperature. The resulting precipitate was filtered off, washed with acetonitrile and diethylether to give a white solid. This solid was added in portions to a stirred 1N methanolic ammonia solution (400 ml). The mixture was stirred for two hours and the precipitate filtered, washed with acetonitrile followed by diethylether and dried under vacuum to give 4-(3-chloro-2-fluoroanilino)-6-hydroxy-7-methoxyquinazoline as a white solid (12.1 g, 95%); $^1$H NMR Spectrum: (DMSOd$_6$) 3.95 (s, 3H); 7.18 (s, 1H); 7.20-7.25 (m, 1H); 7.39-7.44 (m, 1H); 7.47-7.52 (m, 1H); 7.65 (s, 1H); 8.31 (s, 1H); 9.45 (br.s, 1H); Mass Spectrum: (M+H)$^+$ 320.

EXAMPLE 22.1

Resolution to 4-(3-Chloro-2-fluoroanilino)-6-[(3R)-1-(methylsulfonyl)piperidin-3-yloxy]-7-methoxyquinazoline and 4-(3-Chloro-2-fluoroanilino)-6-[(3S)-1-(methylsulfonyl)piperidin-3-yloxy]-7-methoxyquinazoline

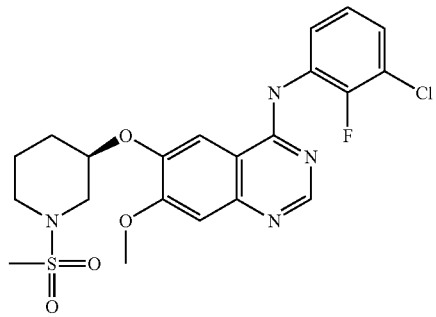

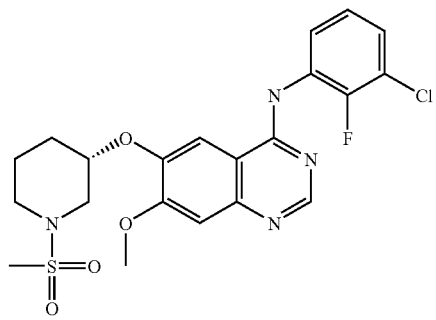 [SMILES: COc1cc2ncnc(Nc3cccc(Cl)c3F)c2cc1OC1CCCN(S(C)(=O)=O)C1]

The racemic mixture obtained in Example 22 (36 mg) was resolved into the 3R and 3S enantiomers by chiral HPLC using the following conditions:

| | |
|---|---|
| Column | 10 μm Chiralpak AS (20 mm × 250 mm) No. AS00CJ-IB004 |
| Eluent | Iso-hexane/ethanol (80/20) |
| Oven Temperature | Ambient |
| Flow | 10 ml/min |
| Wavelength | 254 nm |
| Sample Concentration | 0.9 mg/ml in ethanol |
| Run Time | 110 mins |

First eluted enantiomer (10.1 mg); $^1$H NMR Spectrum: (DMSO d$_6$) 1.60-1.80 (m, 1H), 1.80-1.95 (m, 1H), 1.95-2.08 (m, 1H), 2.08-2.22 (m, 1H), 3.08 (s, 3H), 3.20-3.45 (m, 1H), 3.45-3.50 (m, 2H), 3.70 (dd, 1H), 4.05 (s, 3H), 4.70-4.90 (m, 1H), 7.30-7.50 (m, 2H), 7.50-7.70 (m, 2H), 8.02 (s, 1H), 8.50 (s, 1H), 9.50 (s, 1H); Mass Spectrum: (M+H)$^+$ 481.

Second eluted enantiomer (18.7 mg); $^1$H NMR Spectrum: (DMSO d$_6$) 1.60-1.80 (m, 1H), 1.80-1.95 (m, 1H), 1.95-2.08 (m, 1H), 2.08-2.22 (m, 1H), 3.08 (s, 3H), 3.20-3.45 (m, 1H), 3.45-3.50 (m, 2H), 3.70 (dd, 1H), 4.05 (s, 3H), 4.70-4.90 (m, 1H), 7.30-7.50 (m, 2H), 7.50-7.70 (m, 2H), 8.02 (s, 1H), 8.50 (s, 1H), 9.50 (s, 1H); Mass Spectrum: (M+H)+ 481.

EXAMPLE 23

6-(1-Acetylpiperidin-3-yloxy)-4-(3-chloro-2-fluoroanilino)-7-methoxyquinazoline

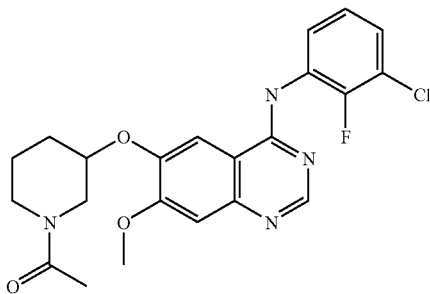 [SMILES: COc1cc2ncnc(Nc3cccc(Cl)c3F)c2cc1OC1CCCN(C(C)=O)C1]

Acetyl chloride (27 mg) was added to a solution of 4-(3-chloro-2-fluoroanilino)-6-(piperidin-3-yloxy)-7-methoxyquinazoline (starting material described in Example 22; 134 mg) and diisopropylethylamine (65 mg) in methylene chloride (5 ml) and the reaction mixture was stirred at ambient temperature for 16 hours. The reaction mixture was adsorbed onto silica and purified by column chromatography eluting with increasingly polar mixtures of methylene chloride/methanol (100/0 to 95/5). The fractions containing the required product were combined and evaporated to give the title product (0.07 g); $^1$H NMR Spectrum: (DMSO $d_6$ at 373K) 1.52-1.62 (m, 1H), 1.80-1.94 (m, 2H), 2.00 (s, 3H), 2.06-2.15 (m, 1H), 3.43-3.64 (m, 3H), 3.82-4.04 (m, 4H), 4.58 (m, 1H), 7.20-7.29 (m, 2H), 7.42 (t, 1H), 7.59 (t, 1H), 7.93 (s, 1H), 8.40 (s, 1H), 9.30 (s, 1H); Mass Spectrum: (M+H)+ 445.

EXAMPLE 24

4-(3-Chloro-2-fluoroanilino)-6-[(2S,4S)-2-(N,N-dimethylcarbamoyl)pyrrolidin-4-yloxy]-7-methoxyquinazoline

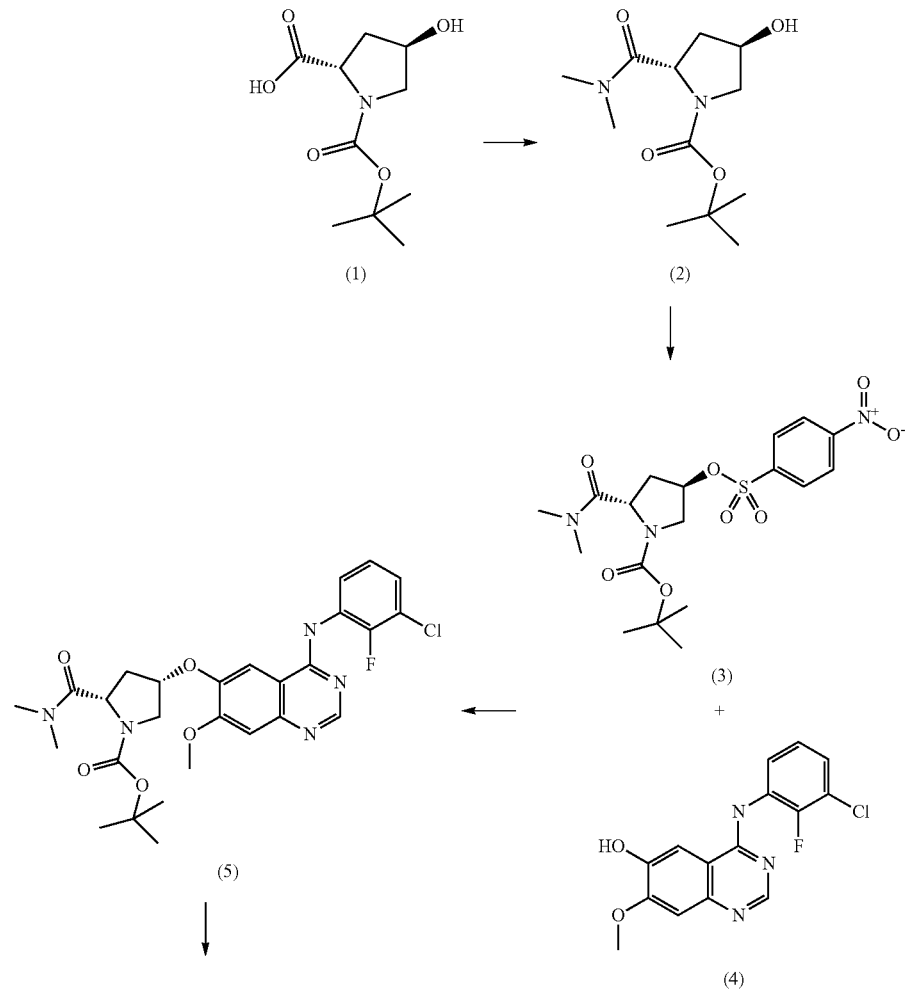

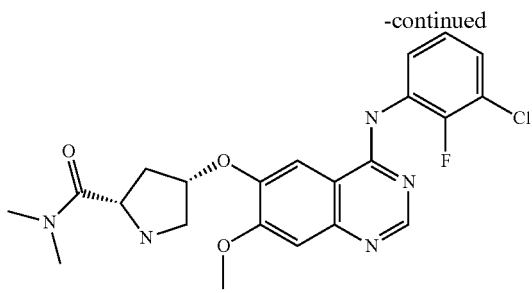

Trifluoroacetic acid (5 ml) was added to a solution of 4-(3-chloro-2-fluoroanilino)-6-[(2S,4S)-1-(tert-butoxycarbonyl)-2-(N,N-dimethylcarbamoyl)pyrrolidin-4-yloxy]-7-methoxyquinazoline (0.17 g) in methylene chloride (10 ml) and the reaction mixture was stirred at ambient temperature for 2 hours. The reaction mixture was evaporated under vacuum and the residue dissolved in methanol (saturated with ammonia)/methylene chloride, adsorbed onto silica and purified by column chromatography eluting with increasingly polar mixtures of methylene chloride/methanol (saturated with ammonia) (100/0 to 85/15). The fractions containing the required product were combined and evaporated under vacuum to give the title product as a colourless gum which crystallised on standing (0.13 g); $^1$H NMR Spectrum: (DMSO d$_6$ and CD$_3$COOD) 1.85-1.96 (m, 1H), 2.84-2.95 (m, 4H), 3.00 (s, 3H), 3.24-332 (m, 1H), 3.40-3.48 (m, 1H), 3.95 (s, 3H), 4.31 (m, 1H), 5.21 (m, 1H), 7.20-7.30 (m, 2H), 7.47-7.55 (m, 2H), 7.76 (s, 1H), 8.37 (s, 1H); Mass Spectrum: (M+H)$^+$ 460.

The 4-(3-chloro-2-fluoroanilino)-6-[(2S,4S)-1-(tert-butoxycarbonyl)-2-(N,N-dimethylcarbamoyl)pyrrolidin-4-yloxy]-7-methoxyquinazoline starting material was prepared as follows:

1-[3-(Dimethylamino)propyl]-3-ethylcarbodiimide hydrochloride (2.48 g) was added to a stirred suspension of N-tert-butoxycarbonyl-L-hydroxyproline (2.0 g), 4-(dimethylamino)pyridine (5.28 g) and dimethylamine hydrochloride (1.4 g) in methylene chloride (100 ml) and the reaction mixture was stirred at room temperature for 16 hours. The reaction mixture was washed with citric acid (1.0 M), saturated sodium bicarbonate and saturated brine before drying over magnesium sulfate. The product was then purified by column chromatography on silica eluting with increasingly polar mixtures of methylene chloride/methanol (100/0 to 90/10). The fractions containing the expected product were combined and evaporated under vacuum to give (2S,4R)-1-(tert-butoxycarbonyl)-4-hydroxy-2-(N,N-dimethylcarbamoyl)pyrrolidine as a colourless gum (1.01 g); $^1$H NMR Spectrum: (DMSO d$_6$) 1.29-1.40 (m, 9H), 1.74-1.83 (m, 1H), 2.04-2.15 (m, 1H), 2.80-2.87 (m, 3H), 3.03 (s, 3H), 3.26 (m, 1H), 3.40 (m, 1H), 4.28 (m, 1H), 4.64 (m, 1H), 4.95 (d, 1H).

4-Nitrobenzenesulfonyl chloride (0.895 g) was added to a stirred solution of (2S,4R)-1-(tert-butoxycarbonyl)-4-hydroxy-2-(N,N-dimethylcarbamoyl)pyrrolidine (0.993 g) and pyridine (0.6 g) in methylene chloride (10 ml) and stirred at 4° C. for 16 hours under an atmosphere of nitrogen. The reaction mixture was washed with aqueous citric acid (1.0 M), saturated sodium bicarbonate and dried over magnesium sulfate. The product was then purified by column chromatography on silica eluting with increasingly polar mixtures of methylene chloride/methanol (100/0 to 95/5). The fractions containing the required product were combined and evaporated under vacuum to give (2S,4R)-1-(tert-butoxycarbonyl)-2-(N,N-dimethylcarbamoyl)-4-[(4-nitrophenyl)sulfonyloxy]pyrrolidine as a yellow gum (0.685 g); $^1$H NMR Spectrum: (DMSO d$_6$) 1.30-1.36 (s, 9H), 1.98-2.07 (m, 1H); 2.37-2.48 (m, 1H); 2.83 (s, 3H), 3.00 (s, 3H), 3.45-3.55 (m, 2H), 4.70 (m, 1H), 5.23 (m, 1H), 8.21 (d, 2H), 8.47 (d, 2H).

Dimethylformamide (8 ml) was added to 4-(3-chloro-2-fluoroanilino)-6-hydroxy-7-methoxyquinazoline (0.489 g; prepared as described in the starting materials for Example 22), (2S,4R)-1-(tert-butoxycarbonyl)-2-(N,N-dimethylcarbamoyl)-4-[(4-nitrophenyl)sulfonyloxy]pyrrolidine (0.678 g) and cesium fluoride (0.697 g). The reaction mixture was then stirred at room temperature for 16 hours. The reaction mixture was evaporated under vacuum and the residue dissolved in methylene chloride/methanol and adsorbed onto silica. The product was then purified by column chromatography eluting with increasingly polar mixtures of methylene chloride/methanol (100/0 to 90/10). The fractions containing the expected product were combined and evaporated. The residue was re-purified by column chromatography eluting with increasingly polar mixtures of ethyl acetate/methanol (100/0 to 92/8). The fractions containing the required product were combined and evaporated under vacuum to give 4-(3-chloro-2-fluoroanilino)-6-[(2S,4S)-1-(tert-butoxycarbonyl)-2-(N,N-dimethylcarbamoyl)pyrrolidin-4-yloxy]-7-methoxyquinazoline as a colourless gum which crystallised on standing (0.36 g); $^1$H NMR Spectrum: (DMSO d$_6$ @ 373K) 1.41 (s, 9H), 1.99 (m, 1H), 2.92-3.03 (m, 7H); 3.44 (m, 1H), 3.96 (s 3H), 4.14 (m, 1H), 4.70 (t, 1H), 5.10 (m, 1H), 7.22-7.30 (m, 2H), 7.44 (t, 1H), 7.62 (t, 1H), 7.84 (s, 1H), 8.40 (s, 1H), 9.30 (s, 1H); Mass Spectrum: (M+H)$^+$ 560.

EXAMPLE 25

4-(3-Chloro-2-fluoroanilino)-6-[(2S4S)-2-(N,N-dimethylcarbamoyl)-1-methylpyrrolidin-4-yloxy]-7-methoxyquinazoline

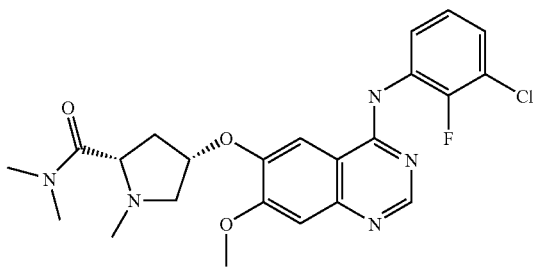 [SMILES: COc1cc2ncnc(Nc3cccc(Cl)c3F)c2cc1O[C@H]1C[C@@H](C(=O)N(C)C)N(C)C1]

4-(3-chloro-2-fluoroanilino)-6-[(2S,4S)-1-(tert-butoxycarbonyl)-2-(N,N-dimethylcarbamoyl)pyrrolidin-4-yloxy]-7-methoxyquinazoline (prepared as described in Example 24;

0.18 g), formic acid (0.31 ml) and formaldehyde (0.51 ml) were heated at 85° C. for 6 hours. The reaction mixture was cooled and evaporated under vacuum. The resulting residue was partitioned between methylene chloride/n-propanol and saturated sodium bicarbonate. The organic layer was dried over magnesium sulfate, adsorbed onto silica and purified by column chromatography eluting with increasingly polar mixtures of methylene chloride/methanol (100/0 to 90/10). The fractions containing the desired product were combined and evaporated under vacuum to yield a white crystalline solid. The solid was washed with water, dissolved in methylene chloride and dried over magnesium sulfate. The solvent was removed under vacuum to give the title product (0.11 g); $^1$H NMR Spectrum: (DMSO d$_6$) 1.87 (t, 1H), 2.24 (s, 3H), 2.61-2.68 (m, 1H), 2.83 (s, 3H), 2.85-2.94 (m, 1H), 3.10 (s, 3H), 3.22-3.31 (m, 2H), 3.92 (s, 3H), 5.04 (m, 1H), 7.22 (s, 1H), 7.29 (t, 1H), 7.45-7.56 (m, 2H), 7.64 (s, 1H), 8.35 (s, 1H), 9.56 (s, 1H); Mass Spectrum: (M+H)$^+$ 474.

EXAMPLE 26

4-(3-Chloro-2-fluoroanilino)-6-[−1-(N,N-dimethylaminoacetyl)piperidin-3-yloxy]-7-methoxyquinazoline

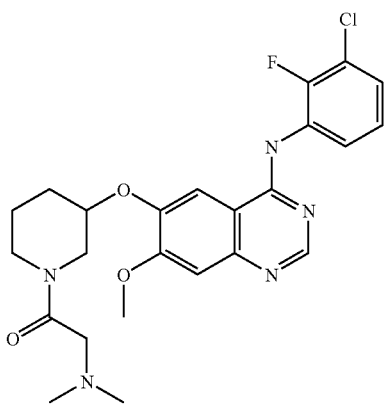 [SMILES: COc1cc2ncnc(Nc3cccc(Cl)c3F)c2cc1OC1CCCN(C(=O)CN(C)C)C1]

6-[1-(chloroacetyl)piperidin-3-yloxy]-4-(3-chloro-2-fluoroanilino)-7-methoxyquinazoline (470 mg, 0.98 mmol) was treated with a 33% solution of dimethylamine in ethanol (20 ml) and stirred at room temperature for 3 hours. The solvent was evaporated under vacuum and the residue purified by column chromatography eluting with methylene chloride/methanol (9/1). The fractions containing the expected product were combined and evaporated under vacuum. The residue was re-columned eluting with methylene chloride/methanol (saturated with ammonia) (92/8). The fractions containing the expected product were combined and evaporated to give the title product (185 mg, 39%); $^1$H NMR Spectrum: (DMSO d$_6$ at 100° C.) 1.40-1.65 (m, 1H); 1.75-1.95 (m, 2H); 2.00-2.30 (m, 7H); 3.05 (dd, 2H); 3.40-3.62 (m, 2H); 3.62-3.75 (m, 1H); 3.88 (dd, 1H); 3.95 (s, 3H); 4.45-4.65 (m, 1H); 7.15-7.30 (m, 2H); 7.30-7.47 (m, 1H); 7.50-7.7 (m, 1H); 7.88 (s, 1H); 8.40 (s, 1H); 9.25 (s, 1H); Mass Spectrum: (M+H)$^+$ 488.

The 6-[1-(chloroacetyl)piperidin-3-yloxy]-4-(3-chloro-2-fluoroanilino)-7-methoxyquinazoline material was prepared as follows: —4-(3-chloro-2-fluoroanilino)-7-methoxy-6-(piperidin-3-yloxy)quinazoline (430 mg, 1.07 mmol) (Prepared as described in Example 22 under preparation of starting material), chloroacetyl chloride (126 mg, 1.12 mmol) and N,N-diisopropylethylamine (519 mg, 4.02 mmol) in methylene chloride (15 ml) was stirred at room temperature for 2 hours. The solvent was evaporated under vacuum and the residue purified by column chromatography eluting with methylene chloride/methanol (saturated with ammonia) (92/8) solvent, Removal of the solvent under vacuum gave 6-[1-(chloroacetyl)piperidin-3-yloxy]-4-(3-chloro-2-fluoroanilino)-7-methoxyquinazoline as a yellow gum (470 mg). This material was used without any further purification); Mass Spectrum: (M+H)$^+$ 479.

EXAMPLE 26.1

Resolution to 4-(3-Chloro-2-fluoroanilino)-6-[(3R)-1-(N,N-dimethylaminoacetyl) piperidin-3-yloxy]-7-methoxyquinazoline and 4-(3-Chloro-2-fluoroanilino)-6-[(3S)-1-(N,N-dimethylaminoacetyl)piperidin-3-yloxy]-7-methoxyquinazoline

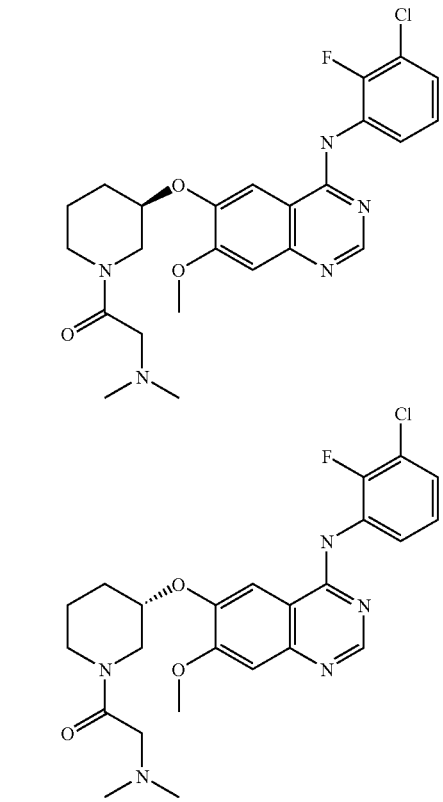

The racemic mixture obtained in Example 26 (320 mg) was resolved into the 3R and 3S enantiomers by chiral HPLC using the following conditions:

| Column | Merck 50 mm 20 μm Chiralpak AS VCSP No. AS00SC-JG001 |

-continued

| | |
|---|---|
| Eluent | Iso-Hexane/EtOH 80/20 |
| Oven Temperature | Ambient |
| Flow | 40 ml/min |
| Wavelength | 254 nm |
| Sample Concentration | 10 mg/ml in EtOH/Acetonitrile 80/20 |
| Run Time | 110 mins |

First eluted enantiomer (103 mg); Mass Spectrum: (M+H)+ 488.

Second eluted enantiomer (97 mg); Mass Spectrum: (M+H)+ 488.

EXAMPLE 27

6-[1-(Acetoxyacetyl)piperidin-3-yloxy]-4-(3-chloro-2-fluoroanilino)-7-methoxyquinazoline

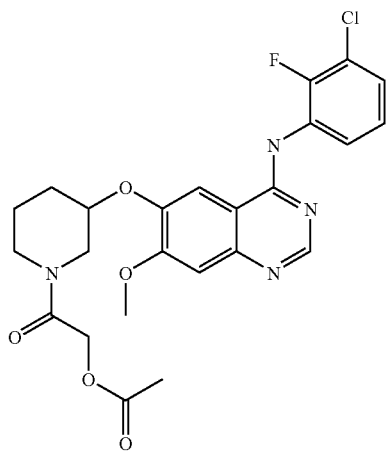 [SMILES: COc1cc2ncnc(Nc3cccc(Cl)c3F)c2cc1OC1CCCN(C(=O)COC(C)=O)C1]

A suspension of 4-(3-chloro-2-fluoroanilino)-7-methoxy-6-(piperidin-3-yloxy)quinazoline dihydrochloride (1.0 g, 2.28 mmol; prepared as described in Example 45) in methylene chloride (30 ml) was treated with N,N-diisopropylethylamine (1.21 g, 9.33 mmol) and stirred at room temperature for 30 minutes. The resulting solution was cooled to 0° C. in a nitrogen atmosphere, acetoxyacetyl, chloride (354 mg, 2.60 mmol) added and the mixture allowed to slowly warm to room temperature with stirring. The solvent was evaporated under vacuum and the residue purified by column chromatography eluting with methylene chloride/methanol (saturated with ammonia) (98/2) solvent. The fractions containing the expected product were combined and evaporated under vacuum to give the title product (1.0 g, 87%); $^1$H NMR Spectrum: (DMSO $d_6$ at 100° C.) 1.50-1.60 (m, 1H), 1.80-1.93 (m, 2H), 2.03 (s, 3H); 2.04-2.10 (m, 1H); 3.40-3.60 (m, 3H); 3.78-3.86 (m, 1H); 3.97 (s, 3H); 4.52-4.60 (m, 1H); 4.75 (d, 2H); 7.20-7.28 (m, 2H); 7.38-7.44 (m, 1H); 7.54-7.64 (m, 1H); 7.88 (s, 1H); 8.40 (s, 1H); 9.22 (bs, 1H); Mass Spectrum: (M+H)+ 503

EXAMPLE 28

4-(3-Chloro-2-fluoroanilino)-6-[1-(hydroxyacetyl)piperidin-3-yloxy]-7-methoxyquinazoline

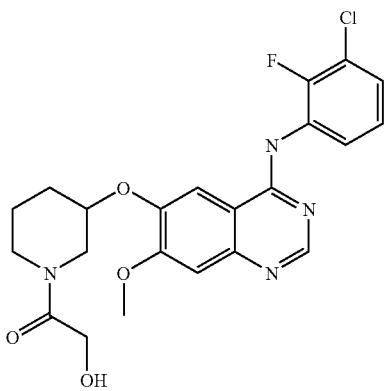 [SMILES: COc1cc2ncnc(Nc3cccc(Cl)c3F)c2cc1OC1CCCN(C(=O)CO)C1]

6-[1-(acetoxyacetyl)piperidin-3-yloxy]-4-(3-chloro-2-fluoroanilino)-7-methoxyquinazoline (930 mg, 1.85 mmol) (prepared as described in Example 27) and potassium carbonate (385 mg, 2.79 mmol) in methanol (50 ml) was stirred at room temperature for 3 hours. The solvent was evaporated under vacuum and the residue purified by column chromatography eluting with methylene chloride/methanol (saturated with ammonia) (92/8). The fractions containing the expected product were combined and evaporated. The residue was triturated with acetone, filtered and dried to give the title product (574 mg, 67%);
$^1$H NMR Spectrum: (DMSO $d_6$ at 100° C.) 1.50-1.60 (m, 1H); 1.80-1.92 (m, 2H); 2.04-2.13 (m, 1H); 3.44-3.56 (m, 3H); 3.77-3.88 (m, 1H); 3.97 (s, 3H); 4.10 (d, 2H); 4.50-4.60 (m, 1H); 7.20-7.27 (m, 2H); 7.38-7.42 (m, 1H); 7.55-7.60 (m, 1H); 7.88 (s, 1H); 8.38 (s, 1H); 9.25 (bs, 1H); Mass Spectrum (M+H)+ 461.

EXAMPLE 29

4-(3-Chloro-2-fluoroanilino)-6-[(3R)-1-(methylsulfonyl)pyrrolidin-3-yloxy]-7-methoxyquinazoline

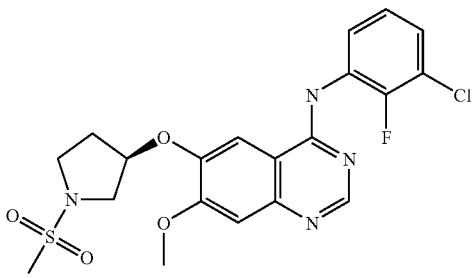 [SMILES: COc1cc2ncnc(Nc3cccc(Cl)c3F)c2cc1O[C@@H]1CCN(S(C)(=O)=O)C1]

4-(3-chloro-2-fluoroanilino)-6-[(3R)-pyrrolidin-3-yloxy]-7-methoxyquinazoline hydrochloride (0.21 g, 0.49 mmole) was dissolved in a mixture of dichloromethane (4 ml), pyridine (1 ml) and diisopropylethylamine (0.17 ml) under a nitrogen atmosphere. Methanesulfonyl chloride (0.06 ml, 0.07 mmol) was added to the stirred solution. After stirring 2 hours at room temperature, the reaction mixture was partitioned between ethyl acetate and saturated aqueous sodium bicarbonate. The organic layer was washed with brine, dried over anhydrous sodium sulfate, filtered and evaporated. The residue was purified by column chromatography eluting with methylene chloride/methanol (saturated with ammonia) (96/4). The fractions containing the expected product were combined and evaporated under vacuum and the residual gum was triturated with diethylether, filtered and dried under vacuum to give the title product as a white solid (0.17 g, 74%); $^1$H NMR Spectrum: (DMSO $d_6$) 2.18-2.37 (m, 2H); 2.93 (s, 3H); 3.33-3.45 (m, 2H); 3.5 (d, 1H); 3.69 (dd, 1H); 3.92 (s, 3H); 5.17 (m, 1H); 7.15-7.35 (m, 2H); 7.40-7.60 (m, 2H); 7.5 (m, 2H); 7.80 (s, 1H); 8.37 (s, 1H); 9.6 (s, 1H); Mass Spectrum: (M+H)$^+$ 467.

The 4-(3-chloro-2-fluoroanilino)-6-[(3R)-pyrrolidin-3-yloxy]-7-methoxyquinazoline hydrochloride starting material was prepared as follows:

(3S)-1-tent-butoxycarbonyl-3-hydroxypyrrolidine (3.75 g, 20 mmole) was reacted with 4-nitrobenzenesulfonyl chloride using the same methodology as described in the preparation of tent-butyl 3-[(4-nitrophenyl)sulfonyloxy]piperidine-1-carboxylate in Example 22 to give tert-butyl (3S)-3-[(4-nitrophenyl)sulfonyloxy]pyrrolidine-1-carboxylate as a crystalline pale-brown solid (5.0 g, 67%); $^1$H NMR Spectrum: (CDCl$_3$) 1.44 (s, 9H); 2.05-2.2 (m, 2H); 3.37-3.59 (m, 4H); 5.16-5.23 (m, 1H); 8.12 (d, 2H); 8.41 (d, 2H).

4-(3-chloro-2-fluoroanilino)-6-hydroxy-7-methoxyquinazoline (prepared as described in the starting materials used in Example 22; 4.0 g, 12.5 mmol) was mixed with tert-butyl (3S)-3-[(4-nitrophenyl)sulfonyloxy]pyrrolidine-1-carboxylate (4.7 g, 12.6 mmol) and cesium fluoride (5.7 g, 7.5 mmol). Dry N,N-dimethylformamide (60 ml) was then added and the mixture stirred at ambient temperature overnight. The mixture was diluted with ethyl acetate and filtered. The filtrate was washed with water, 50% aqueous brine then brine, dried over Na$_2$SO$_4$, filtered and evaporated. The residue was purified by column chromatography eluting with methylene chloride/methanol (saturated with ammonia) (98/2). The fractions containing the expected product were combined and evaporated to give 4-(3-chloro-2-fluoroanilino)-6-[(3R)-1-(tert-butoxycarbonyl)pyrrolidin-3-yloxy]-7-methoxyquinazoline as a dry foam (2.35 g, 38%); $^1$H NMR Spectrum: (DMSO $d_6$) 1.39 (s, 9H); 2.10-2.30 (m, 2H); 3.35-3.50 (m, 3H); 3.64-3.71 (m, 1H); 3.92 (s, 3H); 5.12 (m, 1H); 7.21 (s, 1H); 7.23-7.27 (m, 1H); 7.44-7.55 (m, 2H); 7.80 (s, 1H); 8.37 (s, 1H); 9.61 (s, 1H); Mass Spectrum: (M+H)$^+$ 489.

4-(3-chloro-2-fluoroanilino)-6-[(3R)-1-(tert-butoxycarbonyl)pyrrolidin-3-yloxy]-7-methoxyquinazoline (2.3 g, 4.7 mmole) was dissolved in acetonitrile (35 ml) and hydrogen chloride (4.0M in 1,4-dioxane) (4.7 ml, 18.8 mmole) was added. The mixture was heated to reflux for one hour. After cooling to room temperature, the solid was filtered, washed with acetonitrile and diethylether, and dried under vacuum to give 4-(3-chloro-2-fluoroanilino)-6-[(3R)-pyrrolidin-3-yloxy]-7-methoxyquinazoline hydrochloride as a white solid (1.9 g, 95%); $^1$H NMR Spectrum (DMSO $d_6$) 2.17-2.29 (m, 1H); 2.34-2.44 (m, 1H); (m, 3H); 3.72-3.84 (m, 1H); 4.00 (s, 3H); 5.44 (m, 1H); 7.31-7.38 (m, 1H); 7.45 (s, 1H); 7.49-7.55 (m, 1H); 7.59-7.65 (m, 1H); 8.67 (s, 1H); 8.80 (s, 1H); 9.43 (br.s 1H); 9.62 (br.s, 1H); 12.25 (br.s, 1H); Mass Spectrum: (M−H)$^-$ 387.

EXAMPLE 30

4-(3-Chloro-2-fluoroanilino)-6-[(3S)-1-(methylsulfonyl)pyrrolidin-3-yloxy]-7-methoxyquinazoline Using a similar procedure to that described in Example 29, 4-(3-chloro-2-fluoroanilino)-6-[(3S)-pyrrolidin-3-yloxy]-7-methoxyquinazoline hydrochloride (210 mg) was reacted with methane sulfonyl chloride to give the title product (100 mg, 43%); $^1$H NMR Spectrum: (DMSO $d_6$) 2.18-2.37 (m, 2H); 2.93 (s, 3H); 3.38-3.52 (m, 3H); 3.69 (dd, 1H); 3.92 (s, 3H); 5.17 (m, 1H); 7.15-7.35 (m, 2H); 7.40-7.60 (m, 2H); 7.80 (s, 1H); 8.38 (s, 1H); 9.58 (s, 1H); Mass Spectrum: (M+H)$^+$ 467.

The 4-(3-chloro-2-fluoroanilino)-6-[(3S)-pyrrolidin-3-yloxy]-7-methoxyquinazoline hydrochloride starting material was prepared using a similar process to that described for the preparation of the starting materials in Example 29 as described below:

(R)-1-tert-butoxycarbonyl-3-hydroxypyrrolidine (3.75 g, 20 mmole) was converted to tert-butyl (3R)-3-[(4-nitrophenyesulfonyloxy]pyrrolidine-1-carboxylate (2.21 g, 59%); $^1$H NMR Spectrum: (DMSO $d_6$) 1.44 (s, 9H); 2.05-2.25 (m, 2H); 3.37-3.59 (m, 4H); 5.20 (s, 1H); 8.11 (d, 2H); 8.41 (d, 2H).

4-(3-chloro-2-fluoroanilino)-6-hydroxy-7-methoxyquinazoline was reacted with tert-butyl (3R)-3-[(4-nitrophenyl)sulfonyloxy]pyrrolidine-1-carboxylate to give 4-(3-chloro-2-fluoroanilino)-6-[(3S)-1-(tert-butoxycarbonyl)pyrrolidin-3-yloxy]-7-methoxyquinazoline as a dry foam (2.9 g, 95%); $^1$H NMR Spectrum: (DMSO $d_6$) 1.40 (s, 9H); 2.07-2.29 (m, 21-1); 3.32-3.50 (m, 3H); 3.64-3.70 (dd, 1H); 3.92 (s, 3H); 5.08-5.18 (m, 1H); 7.21 (s, 1H); 7.23-7.30 (m, 1H); 7.43-7.55 (m, 2H); 7.79 (s, 1H); 8.36 (s, 1H); 9.6 (s, 1H); Mass Spectrum: (M+H)$^+$ 489.

4-(3-chloro-2-fluoroanilino)-6-[(3S)-1-(tert-butoxycarbonyl)pyrrolidin-3-yloxy]-7-methoxyquinazoline was reacted with hydrogen chloride (4.0M in 1,4-dioxane) to give 4-(3-chloro-2-fluoroanilino)-6-[(3S)-pyrrolidin-3-yloxy]-7-methoxyquinazoline hydrochloride (1.94 g, 93%); $^1$H NMR Spectrum: (DMSO d) 2.18-2.28 (m, 1H); 135-145 (m, 1H); 3.27-3.46 (m, 3H); 3.73-3.82 (m, 1H); 3.99 (s, 3H); 5.41-5.47 (m, 1H); 7.31-7.37 (m, 1H); 7.44 (s, 1H); 7.47-7.54 (m, 1H); 7.58-7.64 (m, 1H); 8.66 (s, 1H); 8.80 (s, 1H); 9.42 (bs, 1H); 9.61 (bs, 1H); 12.24 (bs, 1H); Mass Spectrum: (M−H)$^+$389.

EXAMPLE 31

4-(3-Chloro-2-fluoroanilino)-7-methoxy-6-{[(2S)-1-methylsulfonylpyrrolidin-2-yl]methoxy}quinazoline

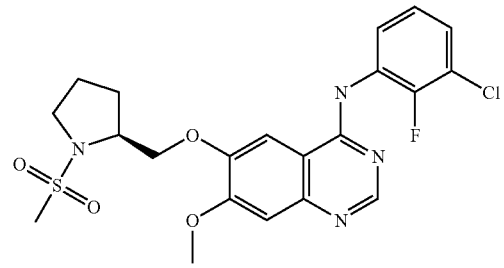 [SMILES: COc1cc2ncnc(Nc3cccc(Cl)c3F)c2cc1OC[C@@H]1CCCN1S(C)(=O)=O]

Using a similar procedure to that described in Example 29, 4-(3-chloro-2-fluoroanilino)-7-methoxy-6-{[(2S)-pyrrolidin-2-yl]methoxy}quinazoline hydrochloride (300 mg) was reacted with methane sulfonyl chloride to give the title product (200 mg, 61%); $^1$H NMR Spectrum: (DMSO d$_6$) 1.88-2.17 (m, 4H); 2.98 (s, 3H); 3.38 (m, 2H); 3.93 (s, 3H); 4.02 (m, 1H); 4.15 (m, 2H); 7.20 (s, 1H); 7.20-7.30 (m, 1H); 7.42-7.53 (m, 2H); 7.81 (s, 1H); 8.37 (s. 1H); 9.62 (s, 1H); Mass Spectrum: (M+H)$^+$ 481.

The 4-(3-chloro-2-fluoroanilino)-7-methoxy-6-{[(2S)-pyrrolidin-2-yl]methoxy}quinazoline hydrochloride starting material was prepared as described below:

4-Chloro-6-hydroxy-7-methoxyquinazoline (prepared as described in the preparation of starting materials for Example 16; 2.75 g, 13 mmol) was mixed with triphenylphosphine (5.13 g, 19.6 mmole) and (2S)-1-(tent-butoxycarbonyl)-2-(hydroxymethyl)pyrrolidine (3.94 g, 19.6 mmole). Methylene chloride (85 ml) was added and the mixture cooled under nitrogen in an ice/water bath. Di-tert-butyl azodicarboxylate (4.51 g, 19.6 mmole) was dissolved in methylene chloride (35 ml) and added dropwise such that the internal temperature remained less than 10° C. Once the addition was complete the cooling bath was removed and the reaction mixture stirred for 3 hours. The solvent was removed under vacuum and the residue purified by column chromatography eluting with methylene chloride/ethyl acetate (saturated with ammonia) (70/30) to give 4-chloro-7-methoxy-6-{[(2S)-1-tert-butoxycarbonylpyrrolidin-2-yl]methoxy}quinazoline as a guru (6.15 g); Mass Spectrum: (M+H)$^+$394.

To a solution of 4-chloro-7-methoxy-6-{[(2S)-1-tert-butoxycarbonylpyrrolidin-2-yl]methoxy}quinazoline in acetonitrile (120 ml), 3-chloro-2-fluoroaniline (1.4 ml, 12.7 mmole) and hydrogen chloride (4.0M in 1,4-dioxane) (13 ml, 52 mmole) were added. This mixture was heated to reflux for one hour. After cooling to ambient temperature the precipitate was filtered off, washed with acetonitrile followed by diethylether and dried under vacuum to give 4-(3-chloro-2-fluoroanilino)-7-methoxy-6-{[(2S)-pyrrolidin-2-yl]methoxy}quinazoline hydrochloride as a yellow solid (5.73 g, 100%); $^1$H NMR Spectrum: (DMSO d$_6$) 1.70-2.10 (m, 3H); 2.10-2.30 (m, 1H); 3.00-3.80 (m, 2H); 3.97-4.10 (m, 4H); 4.45-4.57 (m, 2H); 7.32-7.38 (m, 1H); 7.46 (s, 1H); 7.49-7.55 (m, 1H); 7.59-7.65 (m, 1H); 8.65 (s, 1H); 8.81 (s, 1H); 9.31 (bs, 1H); 9.67 (bs, 1H); 12.09 (bs, 1H); Mass Spectrum: (M+H)$^+$ 403.

EXAMPLE 32

4-(3-Chloro-2-fluoroanilino)-7-methoxy-6-{[(2R)-1-methylsulfonylpyrrolidin-2-yl]methoxy}quinazoline

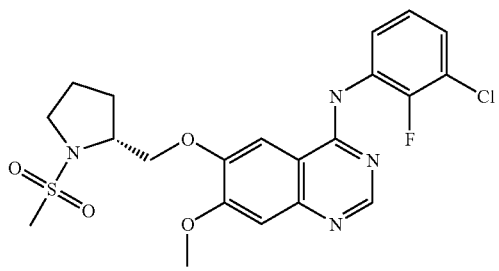 [SMILES: COc1cc2ncnc(Nc3cccc(Cl)c3F)c2cc1OC[C@H]1CCCN1S(C)(=O)=O]

Using a similar process to that described in Example 29, 4-(3-chloro-2-fluoroanilino)-7-methoxy-6-[(2R)-pyrrolidin-2-ylmethoxy]quinazoline hydrochloride (300 mg) was reacted with methane sulfonyl chloride to give the title product (250 mg, 76%); $^1$H NMR Spectrum: (DMSO d$_6$) 1.88-2.12 (m, 4H); 2.99 (s, 3H); 3.30-3.34 (m, 2H); 3.94 (s, 3H); 4.02 (m, 1H); 4.15 (m, 2H); 7.15-7.30 (m, 2H); 7.40-7.55 (m, 2H); 7.81 (s, 1H); 8.36 (s, 1H); 9.62 (s, 1H); Mass Spectrum: (M+H)$^+$ 481.

The 4-(3-chloro-2-fluoroanilino)-7-methoxy-6-[(2R)-pyrrolidin-2-ylmethoxy]quinazoline hydrochloride starting material was prepared using an analogous process to that described for the preparation of the starting material used in Example 31: 4-Chloro-7-methoxy-6-hydroxyquinazoline (2.78 g) was reacted with (2R)-1-(tert-butoxycarbonyl)-2-(hydroxymethyl)pyrrolidine (3.98 g) to give 4-chloro-7-methoxy-6-{[(2R)-1-(tert-butoxycarbonyl)pyrrolidin-2-yl]methoxy}quinazoline (5.0 g, 100%); $^1$H NMR Spectrum: (DMSO d$_6$) 1.37 (s, 9H); 1.66-1.88 (m, 2H); 1.90-2.07 (m, 2H); 3.15-3.24 (m, 1H); 3.41-3.49 (m, 1H); 4.00 (s, 3H); 4.10-4.25 (m, 3H); 7.44 (d, 2H); 8.85 (s, 1H); Mass Spectrum: (M+H)$^+$ 394.

4-chloro-7-methoxy-6-{[(2R)-1-(tert-butoxycarbonyl)pyrrolidin-2-yl]methoxy}quinazoline was reacted with 3-chloro-2-fluoroaniline to give 4-(3-chloro-2-fluoroanilino)-7-methoxy-6-{[(2R)-pyrrolidin-2-yl]methoxy}quinazoline hydrochloride (5.3 g 100%); $^1$H NMR Spectrum: (DMSO d$_6$) 1.70-1.84 (m, 1H); 1.87-1.97 (m, 1H); 1.99-2.08 (m, 1H); 2.17-2.28 (m, 1H); 3.18-3.27 (m, 2H); 3.98-4.10 (m, 4H); 4.45-4.57 (m, 2H); 7.32-7.38 (m, 1H); 7.47 (s, 1H); 7.49-7.55 (m, 1H); 7.59-7.65 (m, 1H); 8.66 (s, 1H); 8.81 (s, 1H); 9.30 (bs, 1H); 9.67 (bs, 1H); 12.09 (bs, 1H); Mass Spectrum: (M–H)$^-$ 401.

EXAMPLE 33

4-(3-Chloro-2-fluoroanilino)-7-methoxy-6-{[1-(methylsulfonyl)pyrrolidin-3-yl]methoxy}quinazoline

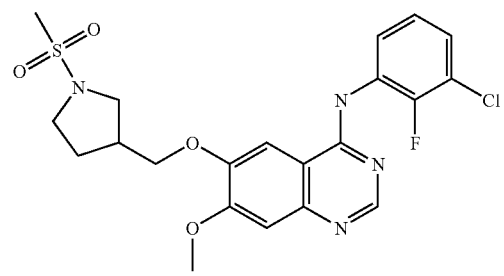 [SMILES: COc1cc2ncnc(Nc3cccc(Cl)c3F)c2cc1OCC1CCN(S(C)(=O)=O)C1]

Using a similar procedure to that described in Example 29, 4-(3-chloro-2-fluoroanilino)-7-methoxy-6-(pyrrolidin-3-ylmethoxy)quinazoline hydrochloride (300 mg) was reacted with methane sulfonyl chloride to give the title product (200 mg, 67%); $^1$H-NMR Spectrum: (DMSO d$_6$+CD3COOD) 1.75-1.89 (m, 1H); 2.08-2.18 (m, 1H); 2.77-2.86 (m, 1H); 2.91 (s, 3H); 3.12-3.18 (m, 1H); 3.25-3.43 (m, 2H); 3.47-3.52 (m, 1H); 3.94 (s, 3H; 4.06-4.09 (m, 2H); 7.15-7.30 (m, 2H); 7.43-7.53 (m, 2H); 7.81 (s, 1H); 8.38 (s, 1H); Mass Spectrum: (M+H)$^+$ 481.

The 4-(3-chloro-2-fluoroanilino)-7-methoxy-6-(pyrrolidin-3-ylmethoxy)quinazoline hydrochloride starting material was prepared using an analogous process to that described for the preparation of the starting materials in Example 31 as follows:

4-Chloro-7-methoxy-6-hydroxyquinazoline (2.5 g) was reacted with 1-(tert-butoxycarbonyl)-3-(hydroxymethyl)pyrrolidine (3.58 g) to give 4-chloro-7-methoxy-6-{[1-(tert-butoxycarbonyl)pyrrolidin-3-yl]methoxy}quinazoline (5.36 g, 100%); $^1$H NMR Spectrum: (DMSO $d_6$) 1.39 (s, 9H); 1.45-1.79 (m, 2H); 1.97-2.08 (m, 1H); 2.65-2.74 (m, 1H); 2.91-3.17 (m, 2H); 3.40-3.52 (m, 1H); 4.01 (s, 3H); 4.15-4.22 (m, 2H); 7.42 (s, 1H); 7.45 (s, 1H); 8.86 (s, 1H); Mass Spectrum: (M+H)$^+$ 394.

4-chloro-7-methoxy-6-{[1-(tert-butoxycarbonyl)pyrrolidin-3-yl]methoxy}quinazoline (4.5 g) was reacted with 3-chloro-2 fluoroaniline to give 4-(3-chloro-2-fluoroanilino)-7-methoxy-6-(pyrrolidin-3-ylmethoxy)quinazoline hydrochloride (5.45 g, 100%); $^1$H NMR Spectrum: (DMSO $d_6$) 1.71-1.85 (m, 1H); 2.10-2.22 (m, 1H); 2.81-2.91 (m, 1H); 2.97-3.07 (m, 1H); 3.11-3.22 (m, 1H); 3.24-3.33 (m, 1H); 3.35-3.46 (m, 1H); 4.00 (s, 3H); 4.28-4.34 (m, 2H); 7.31-7.37 (m, 1H); 7.43 (s, 1H); 7.49-7.54 (m, 1H); 7.59-7.64 (m, 1H); 8.60 (s, 1H); 8.80 (s, 1H); 9.32 (bs, 2H); 12.05 (bs, 1H); Mass Spectrum: (M−H)$^−$ 401.

EXAMPLE 34

4-(3-Chloro-2-fluoroanilino)-6-[(3R)-1-methylpyrrolidin-3-yloxy]-7-methoxyquinazoline

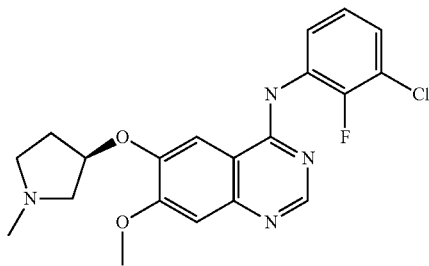 [SMILES: COc1cc2ncnc(Nc3cccc(Cl)c3F)c2cc1O[C@@H]1CCN(C)C1]

4-(3-chloro-2-fluoroanilino)-6-[(3R)-pyrrolidin-3-yloxy]-7-methoxyquinazoline hydrochloride (0.24 g, 0.56 mmole; prepared as described in Example 29-preparation of starting materials) was dissolved in formic acid (4 ml) and formaldehyde (37% w/v in water) (2 ml) was added. The mixture was heated to 85° C. for one hour and then evaporated under vacuum and azeotroped with toluene. The residue was partitioned between ethyl acetate and saturated aqueous NaFfCO$_3$. The organic layer was separated, washed with brine, dried over Na$_2$SO$_4$, filtered and evaporated. The residue was purified by column chromatography eluting with methylene chloride/methanol (saturated with ammonia) (94/6). The fractions containing the expected product were combined, evaporated and the residue triturated with isohexane/diethylether, filtered and dried under vacuum to give the title product as a white solid (0.13 g; 59%); $^1$H NMR Spectrum: (DMSO d$_6$) 1.70-1.9 (m, 1H); 2.27 (s, 3H); 2.30-2.50 (m, 2H); 2.55-2.75 (na, 2H); 2.91-3.00 (m, 1H); 3.91 (s, 3H); 4.90-5.10 (m, 1H); 7.18 (s, 1H); 7.20-7.35 (m, 1H); 7.40-7.58 (m, 2H); 7.64 (s, 1H); 8.35 (s, 1H); 9.57 (s, 1H); Mass Spectrum: (M−H)$^−$ 401.

EXAMPLE 35

4-(3-Chloro-2-fluoroanilino)-6-[(3S)-1-methylpyrrolidin-3-yloxy]-7-methoxyquinazoline

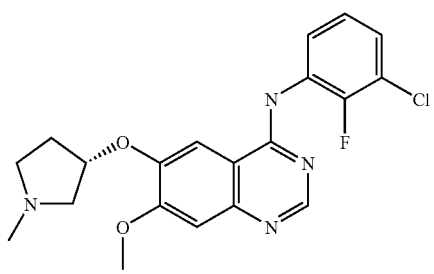 [SMILES: COc1cc2ncnc(Nc3cccc(Cl)c3F)c2cc1O[C@H]1CCN(C)C1]

4-(3-chloro-2-fluoroanilino)-6-[(3S)-1-tert-butoxycarbonylpyrrolidin-3-yloxy]-7-methoxyquinazoline (0.30 g) was dissolved in formic acid (5 ml) and formaldehyde (37% w/v in water) (2.5 ml) was added. The mixture was heated to 85° C. for one hour and then evaporated under vacuum and azeotroped with toluene. The residue was partitioned between ethyl acetate and saturated aqueous NaHCO$_3$. The organic layer was separated, washed with brine, dried over Na$_2$SO$_4$, filtered and evaporated. The residue was purified by column chromatography eluting with increasingly polar mixtures of methylene chloride/methanol (saturated with ammonia) (100/0 to 94l6). The fractions containing the expected product were combined, evaporated and the residue triturated with diethylether, filtered and dried under vacuum to give the title product as a white solid (0.133 g; 35%);
$^1$H NMR Spectrum: (DMSO-d$_6$) 1.70-1.90 (m, 1H), 2.28 (s, 3H), 2.32-2.50 (m, 2H), 2.55-2.75 (m, 2H), 2.80-3.00 (m, 1H), 3.91 (s, 3H), 4.93-5.10 (m, 1H), 7.18 (s, 1H), 7.20-7.35 (m, 1H), 7.40-7.55 (m, 2H), 7.65 (s, 8.35 (s, 1H), 9.55 (s, 1H); Mass Spectrum: (M+H)$^+$ 403.

The 4-(3-chloro-2-fluoroanilino)-6-[(3S)-1-tert-butoxycarbonylpyrrolidin-3-yloxy]-7-methoxyquinazoline starting material was prepared as follows:
A solution of 4-nitrobenzenesulfonyl chloride (4.44 g) in methylene chloride (50 ml) was added to a stirred solution of tert-butyl 3-(R)-hydroxypyrrolidine-1-carboxylate (3.75 g) and pyridine (2.5 ml) in methylene chloride (30 ml) at 10° C. and the mixture allowed to warm to ambient temperature with stirring. The reaction mixture was poured into saturated sodium bicarbonate solution. The organic layer was separated, washed with brine and dried over sodium sulfate. The solution was evaporated under vacuum to give tert-butyl3-(R)-[(4-nitrophenyl)sulfonyloxy]pyrrolidine-1-carboxylate as a yellow crystalline solid. (4.37 g, 59%); $^1$H NMR Spectrum: (CDCl$_3$) 1.43 (s, 9H), 1.80-2.40 (m, 2H), 3.30-3.65 (m, 4H), 5.20 (hs, 1H), 8.10 (d, 2H), 8.42 (d, 2H).

A mixture of 4-(3-chloro-2-fluoroanilino)-6-hydroxy-7-methoxyquinazoline (2.0 g; prepared as described in Example 22-preparation of starting materials), tert-butyl-3-(R)-[(4-nitrophenyl)sulfonyloxy]pyrrolidine-1-carboxylate (2.4 g) and cesium fluoride (2.9 g) in dimethylformamide (30 ml) was stirred at room temperature for 18 hours. The reaction mixture was evaporated under vacuum and partitioned between methylene chloride and water. The solutions were filtered to remove insoluble solids and the methylene chloride was washed with water, saturated brine and adsorbed onto silica. The product was then purified by column chromatography on silica eluting with increasingly polar mixtures of methylene chloride/methanol (saturated with ammonia) (100/0 to 96/4). The fractions containing the required product were combined and evaporated under vacuum to give 4-(3-chloro-2-fluoroanilino)-6-[(3S)-1-tert-butoxycarbonylpyrrolidin-3-yloxy]-7-methoxyquinazoline as a yellow foam (2.9 g, 95%); $^1$H NMR Spectrum: (DMSO-$d_6$) 1.40 (s, 9H), 2.00-2.32 (m, 2H), 3.20-3.55 (m, 3H), 3.69 (dd, 1H), 3.92 (s, 3H), 5.00-5.20 (m, 1H), 7.20 (s, 1H), 7.20-7.32 (m, 1H), 7.40-7.57 (m, 2H), 7.80 (s, 1H), 8.37 (s, 1H), 9.60 (s, 1H); Mass Spectrum: $(M+H)^+$ 489.

EXAMPLE 36

4-(3-Chloro-2-fluoroanilino)-7-methoxy-6-{[(2S)-1-methylpyrrolidin-2-yl]methoxy}quinazoline

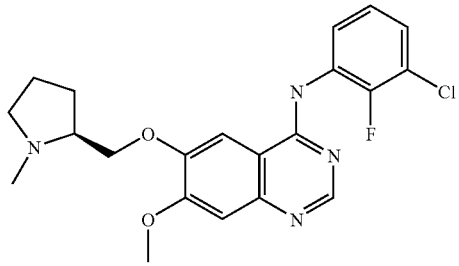 [SMILES: COc1cc2ncnc(Nc3cccc(Cl)c3F)c2cc1OC[C@@H]1CCCN1C]

Using a similar procedure to that described in Example 34, 4-(3-chloro-2-fluoroanilino)-7-methoxy-6-{[(2S)-1-pyrrolidin-2-yl]methoxy}quinazoline hydrochloride (300 mg; prepared as described in Example 31-preparation of starting materials) was reacted with formaldehyde (2.5 ml) to give the title product (220 mg, 77%); $^1$H NMR Spectrum: (DMSO $d_6$) 1.57-1.76 (m, 3H); 1.96-2.08 (m, 1H); 2.24 (q, 1H); 2.42 (s, 3H); 2.71 (m, 1H); 2.97 (m, 1H); 3.92 (s, 3H); 3.95-4.09 (m, 2H); 7.19 (s, 1H); 7.20-7.30 (m, 1H); 7.42-7.54 (m, 2H); 7.81 (s, 1H); 8.36 (s, 1H); 9.56 (s, 1H); Mass Spectrum: $(M+H)^+$ 417.

EXAMPLE 37

4-(3-Chloro-2-fluoroanilino)-7-methoxy-6-{[1-(methylpyrrolidin)-3-yl]methoxy}quinazoline

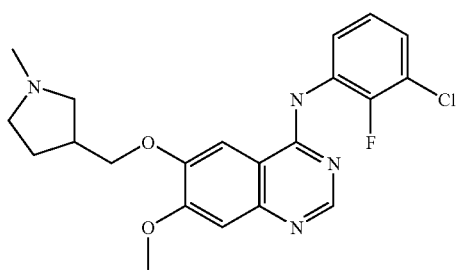 [SMILES: COc1cc2ncnc(Nc3cccc(Cl)c3F)c2cc1OCC1CCN(C)C1]

Using a procedure identical to that described for the synthesis of Example 34, 4-(3-chloro-2-fluoroanilino)-7-methoxy-6-(pyrrolidin-3-ylmethoxy)quinazoline hydrochloride (250 mg; prepared as described in Example 33-starting material) was reacted with formaldehyde (2.5 ml) to give the title product (125 mg, 52%); $^1$H NMR Spectrum: (CDCl$_3$) 1.61-1.72 (m, 1H); 2.08-2.20 (m, 1H); 2.38 (s, 3H); 2.47 (q, 1H); 2.65 (m, 2H); 2.69-2.77 (m, 1H); 2.81-2.88 (m, 1H); 4.01 (s, 3H); 4.06-4.13 (ran, 2H); 7.05-7.23 (m, 3H); 7.26 (s, 1H); 7.45 (s, 1H); 8.41-8.47 (m, 1H); 8.68 (s, 1H); Mass Spectrum: $(M+H)^-$ 415.

EXAMPLE 38

4-(3-Chloro-2-fluoroanilino)-6-[(3R)-1-acetylpyrrolidin-3-yloxy]-7-methoxyquinazoline

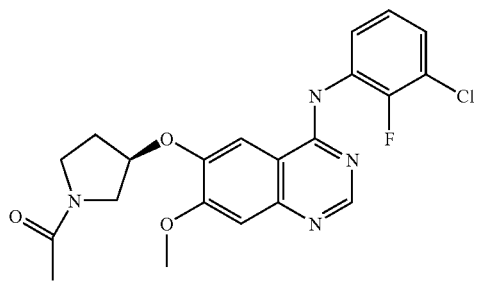 [SMILES: COc1cc2ncnc(Nc3cccc(Cl)c3F)c2cc1O[C@@H]1CCN(C(C)=O)C1]

4-(3-chloro-2-fluoroanilino)-6-[(3R)-pyrrolidin-3-yloxy]-7-methoxyquinazoline (0.22 g, 0.51 mmole) (prepared as described in Example 29-preparation of starting materials) was dissolved in a mixture of methylene chloride (4 ml), pyridine (1 ml) and diisopropylethylamine (0.17 ml) under a nitrogen atmosphere. Acetic anhydride (0.1 ml, 1.0 mmole) was added and the mixture stirred at ambient temperature for 3 hours. The mixture was then partitioned between saturated aqueous NaHCO$_3$ and ethyl acetate. The organic layer was separated, washed with brine, dried over Na$_2$SO$_4$, filtered and evaporated. The residue was purified by column chromatography eluting with methylene chloride/methanol (saturated with ammonia) (96/4). The fractions containing the expected product were evaporated and triturated with diethylether. The solid was filtered and dried under vacuum to give the title product as a white solid (0.12 g: 55%); $^1$H NMR Spectrum: (DMSO $d_6$) 1.95-1.98 (m, 3H); 2.14-2.40 (m, 2H); 3.53-3.70 (m, 3H); 3.91 (m, 4H); 5.12-5.21 (m, 1H); 7.15-7.30 (m, 2H); 7.4-7.60 (m, 2H); 7.70-7.90 (m, 1H); 8.36-8.37 (d, 1H); 9.60-9.62 (m, 1H); Mass Spectrum: $(M+H)^+$ 431.

EXAMPLE 39

6-{[(2S)-1-Acetylpyrrolidin-2-yl]methoxy}-4-(3-chloro-2-fluoroanilino)-7-methoxyquinazoline

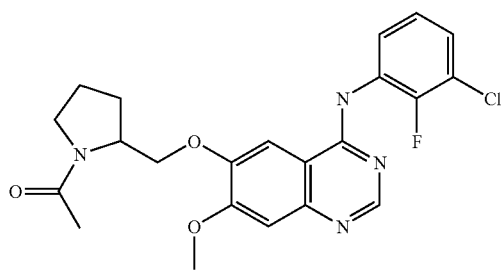 [SMILES: COc1cc2ncnc(Nc3cccc(Cl)c3F)c2cc1OCC1CCCN1C(C)=O]

Using a similar procedure to that described in Example 38, 4-(3-chloro-2-fluoroanilino)-7-methoxy-6-[(2S)-pyrrolidin-2-ylmethoxy]quinazoline hydrochloride (300 mg; prepared as described in Example 31) was reacted with acetic anhydride to give the title product (280 mg, 92%); $^1$H NMR Spectrum: (DMSO d$_6$) 1.89-2.05 (m, 6H); 2.15 (m, 1H); 3.43-3.56 (m, 2H); 3.93 (s, 3H); 4.00-4.11 (m, 1H); 4.17-4.21 (m, 1H); 4.32-4.42 (m, 1H); 7.19-7.29 (m, 2H); 7.41-7.54 (m, 2H); 7.79-7.82 (m, 1H); 8.36-8.37 (m, 1H); 9.52-9.55 (m, 1H); Mass Spectrum: (M+H)$^+$ 445.

EXAMPLE 40

6-{[(2R)-1-Acetylpyrrolidin-2-yl]methoxy}-4-(3-chloro-2-fluoroanilino)-7-methoxyquinazoline Using a procedure similar to that described in Example 38, 4-(3-chloro-2-fluoroanilino)-7-methoxy-6-[(2R)-pyrrolidin-2-ylmethoxy]quinazoline hydrochloride (300 mg; prepared as described in Example 32-preparation of starting materials) was reacted with acetic anhydride to give the title product (203 mg, 66%); $^1$H NMR Spectrum (DMSO d$_6$) 1.89-2.05 (m, 6H); 2.11-2.21 (m, 1H); 3.43-3.56 (m, 2H); 3.94 (s, 3H); 4.00-4.11 (m, 1H); 4.17-4.21 (m, 1H); 4.30-4.37 (m, 1H); 7.19-7.29 (m, 2H); 7.42-7.53 (m, 2H); 7.79-7.82 (m, 1H); 8.37 (s, 1H); 9.54-9.57 (m, 1H); Mass Spectrum (M+H)$^#$ 445.

EXAMPLE 41

6-[(1-Acetylpyrrolidin-3-yl)methoxy]-4-(3-chloro-2-fluoroanilino)-7-methoxyquinazoline

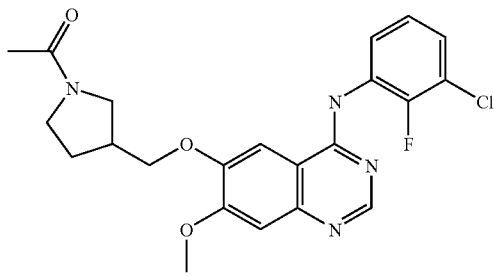 [SMILES: COc1cc2ncnc(Nc3cccc(Cl)c3F)c2cc1OCC1CCN(C(C)=O)C1]

Using a procedure similar to that described in Example 38, 4-(3-chloro-2-fluoroanilino)-7-methoxy-6-(pyrrolidin-3-ylmethoxy)quinazoline hydrochloride (300 mg; prepared as described in Example 33-starting material) was reacted with acetic anhydride to give the title product (194 mg, 63%); $^1$H NMR Spectrum (DMSO d$_6$+CD3COOD) 1.71-1.90 (m, 1H); 1.93-1.94 (m, 3H); 2.00-2.20 (m, 1H); 2.66-2.86 (m, 1H); 3.18-3.31 (m, 1H); 3.43-3.72 (m, 3H); 3.93 (m, 3H); 4.04-4.18 (m, 2H); 7.15-7.32 (m, 2H); 7.42-7.53 (m, 2H); 7.78-7.80 (m, 1H); 8.35-8.37 (m, 1H); Mass Spectrum: (M+H)$^+$ 445.

EXAMPLE 42

4-(3-Chloro-2-fluoroanilino)-7-methoxy-6-[(3S)-1-(N,N-dimethylsulfamoyl)pyrrolidin-3-yloxy]quinazoline

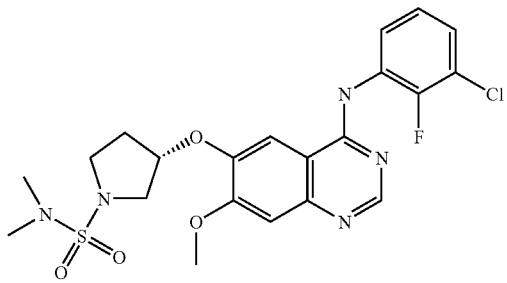 [SMILES: COc1cc2ncnc(Nc3cccc(Cl)c3F)c2cc1O[C@H]1CCN(S(=O)(=O)N(C)C)C1]

4-(3-chloro-2-fluoroanilino)-7-methoxy-6-[(3S)-pyrrolidin-3-yloxy]quinazoline hydrochloride (0.21 g, 0.49 mmole; prepared as described in Example 30-preparation of starting materials) was dissolved in a mixture of methylene chloride (4 ml), pyridine (1 ml) and di-isopropylethyl amine (0.17 ml) under a nitrogen atmosphere. Dimethylsulfamoyl chloride (0.08 ml, 0.75 mmole) was added to the stirred solution. After stirring overnight at ambient temperature, the reaction mixture was partitioned between ethyl acetate and saturated aqueous NaHCO$_3$. The organic layer was washed with brine, dried over Na$_2$SO$_4$, filtered and evaporated. The residue was purified by column chromatography eluting with methylene chloride/methanol (saturated with ammonia)(98/2). The fractions containing the expected product were evaporated under vacuum and the residual gum was triturated with diethylether and evaporated to give the title product as a dry foam (0.13 g; 53%); $^1$H NMR Spectrum: (DMSO d$_6$) 2.16-2.21 (m, 1H); 2.25-2.38 (m, 1H); 2.76 (s, 6H); 3.41-3.50 (m, 3H); 3.71 (dd, 1H); 3.93 (m, 3H); 5.18 (m, 1H); 7.15-7.35 (m, 2H); 7.44-7.55 (m, 2H); 7.78 (s, 1H); 8.37 (s, 1H); 9.59 (s, 1H); Mass Spectrum: (M+H) 496.

EXAMPLE 43

4-(3-Chloro-2-fluoroanilino)-7-methoxy-6-{[(2S)-1-(morpholinoacetyl)pyrrolidin-2-yl]methoxy}quinazoline

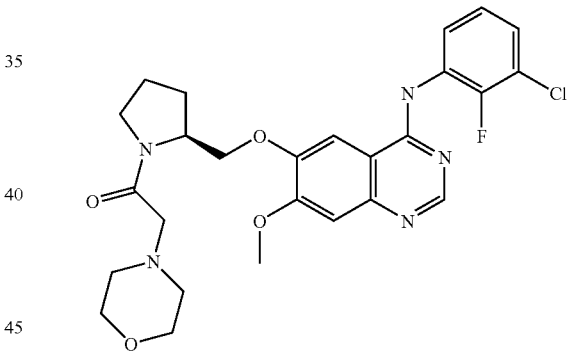

4-(3-chloro-2-fluoroanilino)-7-methoxy-6-{[(2S)-1-(chloroacetyl)pyrrolidin-2-yl]methoxy}quinazoline (0.45 g, 0.94 mmole) was dissolved in morpholine (7.5 ml) and stirred at ambient temperature overnight in the presence of potassium iodide (10 mg). The solvent was evaporated and the residue purified by column chromatography eluting with methylene chloride/methanol (saturated with ammonia) (98/2). The fractions containing the expected product were combined and evaporated under vacuum to give the title product as a foam (0.22 g, 44%); $^1$H NMR Spectrum: (CDCl3) 1.91-2.01 (m, 1H); 2.06-2.14 (m, 2H); 2.19-2.27 (m, 1H); 2.48-2.53 (m, 2H); 2.62-2.68 (m, 2H); 3.18 (q, 2H); 3.41-3.52 (m, 1H); 3.56-3.72 (m, 5H); 4.01-4.08 (m, 4H); 4.53 (d, 1H); 4.72 (t, 1H); 7.11-7.28 (m, 3H); 7.96 (m, 1H); 8.36 (s, 1H); 8.60 (s, 1H); 8.63 (s, 1H); Mass Spectrum: (M−H)$^−$ 528.

The 4-(3-chloro-2-fluoroanilino)-7-methoxy-6-{[(2S)-1-(chloroacetyl)pyrrolidin-2-yl]methoxy}quinazoline starting material was prepared as follows:

4-(3-chloro-2-fluoroanilino)-7-methoxy-6-[(2S)-pyrrolidin-2-ylmethoxy]quinazoline hydrochloride (1.1 g, 2.5 mmol; prepared as described in Example 31-starting materials) was dissolved in a mixture methylene chloride (20 ml) and diisopropylethylamine (1.0 ml) under a nitrogen atmosphere. The solution was cooled in an ice/water bath to 4° C. and chloroacetyl chloride (0.2 ml, 2.63 mmole) was added. The reaction mixture was stirred cold for two 25 hours and then partitioned between methylene chloride and saturated aqueous NaHCO₃. The organic layer was separated, washed with brine, dried over Na₂SO₄, filtered and evaporated to give 4-(3-chloro-2-fluoroanilino)-7-methoxy-6-{[(2S)-1-(chloroacetyl)pyrrolidin-2-yl]methoxy}quinazoline (1.14 g, 94.9%); Mass Spectrum: (M+H)⁺ 479.

EXAMPLE 44

4-(3-Chloro-2-fluoroanilino)-7-methoxy-6-{[(2S)-1-(hydroxyacetyl)pyrrolidin-2-yl]methoxy}quinazoline

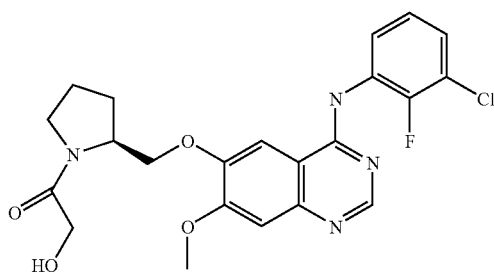 [SMILES: COc1cc2ncnc(Nc3cccc(Cl)c3F)c2cc1OC[C@@H]1CCCN1C(=O)CO]

4-(3-chloro-2-fluoroanilino)-7-methoxy-6-[(2S)-pyrrolidin-2-ylmethoxy]quinazoline hydrochloride (0.25 g, 0.57 mmole; prepared as described in Example 31-starting materials) was dissolved in a mixture of methylene chloride (5 ml) and diisopropylethylamine (0.3 ml). The solution was cooled in an ice/water bath to 4° C. and acetoxyacetyl chloride (0.064 ml, 0.6 mmol) added. The reaction mixture was stirred cold for two hours and then partitioned between methylene chloride and saturated aqueous NaHCO₃. The organic layer was separated, washed with brine, dried over Na₂SO₄, filtered and evaporated. The residue was dissolved in methanol (5 ml) containing anhydrous powdered potassium carbonate (0.2 g). After stirring overnight the solvent was evaporated and the residue purified by column chromatography eluting with methylene chloride/isopropanol (96/4)(containing 0.5% triethylamine). The fractions containing the expected product were evaporated and the residue was triturated with diethyl-ether to give the title product as a white solid (0.1 g, 38%); ¹H NMR Spectrum: (CDCl₃) 1.95-2.29 (m, 4H); 3.29 (m, 1H); 3.46 (m, 2H); 4.03 (s, 3H); 4.07-4.18 (m, 3H); 4.55 (d, 1H); 4.69 (t, 1H); 7.13-7.16 (m, 2H); 7.26 (s, 1H); 8.26 (m, 1H); 8.35 (s, 1H); 8.48 (s, 1H); 8.66 (s, 1H); Mass Spectrum: (M+H)⁺ 461.

EXAMPLE 45

4-(3-Chloro-2-fluoroanilino)-7-methoxy-6-(piperidin-3-yloxy)quinazoline

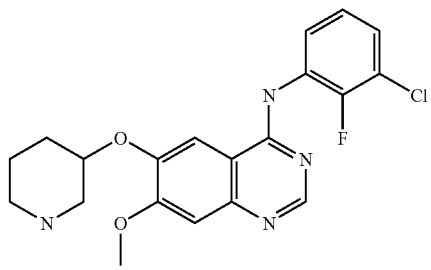 [SMILES: COc1cc2ncnc(Nc3cccc(Cl)c3F)c2cc1OC1CCCNC1]

HCl (4.63 ml, 4M solution in dioxane) was added to a mixture of 4-chloro-7-methoxy-6-[1-(tert-butoxycarbonyl)piperidin-3-yloxy)]quinazoline (2.47 g) and 3-chloro-2-fluoroaniline (1.01 g) in acetonitrile (40 ml). The mixture was heated to reflux for 1 hour, cooled and the precipitate collected to give the title product as a dihydrochloride salt, a white solid (2.51 g, 91%); ¹H NMR Spectrum: (DMSOd₆) 1.9 (m, 2H); 2.0 (m, 1H); 2.2 (m, 1H); 3.0 (m, 1H); 3.2 (m, 2H); 3.5 (m, 1H); 4.0 (s, 3H); 5.0 (m, 1H); 7.4 (m, 1H); 7.5 (m, 1H); 7.6 (s, 1H); 7.6 (m, 1H); 8.8 (s, 1H); 8.9 (s, 1H); 9.2 (br s, 2H); 12.3 (br s, 1H); Mass Spectrum: (M+H): 403.

The 4-chloro-7-methoxy-6-[1-4A-butoxycarbonyl)piperidin-3-yloxy)]quinazoline starting material was prepared as follows:

Diethyl azodicarboxylate (9.41 ml, 40% solution in toluene) was added to a mixture of 4-chloro-6-hydroxy-7-methoxyquinazoline (2.90 g; prepared as described in Example 16-preparation of starting materials), triphenylphosphine (5.43 g) and tert-butoxycarbonyl-3-hydroxypiperidine (4.15 g) in dichloromethane (75 ml). The resulting solution was heated to 40° C. for 6 hours, and then allowed to stand overnight at room temperature. This was purified by flash column chromatography eluting with isohexane (79%), acetone (20%), and triethylamine (1%) to give 4-chloro-7-methoxy-6-[1-(tert-butoxycarbonyl)piperidin-3-yloxy]quinazoline as a white solid (2.47 g, 53%); ¹H NMR Spectrum: (CDCl₃) 1.5 (m, 9H); 1.6 (m, 1H); 1.9 (m, 2H); 2.1 (m, 1H); 3.5 (m, 1H); 3.6 (m, 1H); 4.0 (s, 3H); 4.2-3.9 (m, 2H); 4.5 (m, 1H); 7.3 (s, 1H); 7.4 (s, 1H); 8.9 (s, 1H); Mass Spectrum: (M+H): 394.

EXAMPLE 46
4-(3-Chloro-2-fluoroanilino)-6-[(2S,4R)-2-(N,N-dimethylcarbamoyl)-1-methylpyrrolidin-4-yloxy]-7-methoxyquinazoline and
4-(3-Chloro-2-fluoroanilino)-6-[(2R,4R)-2-(N,N-dimethylcarbamoyl)-1-methylpyrrolidin-4-yloxy]-7-methoxyquinazoline
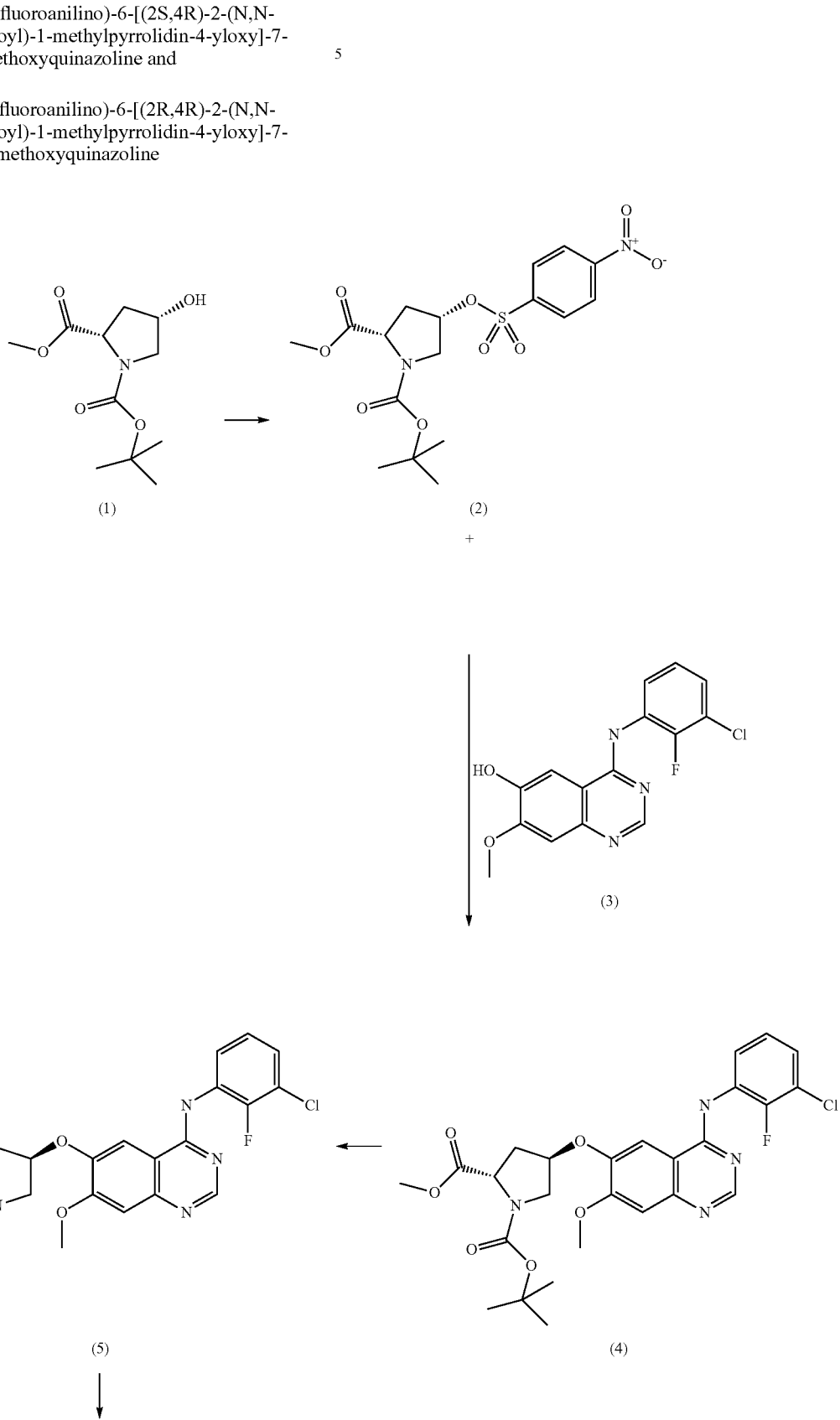

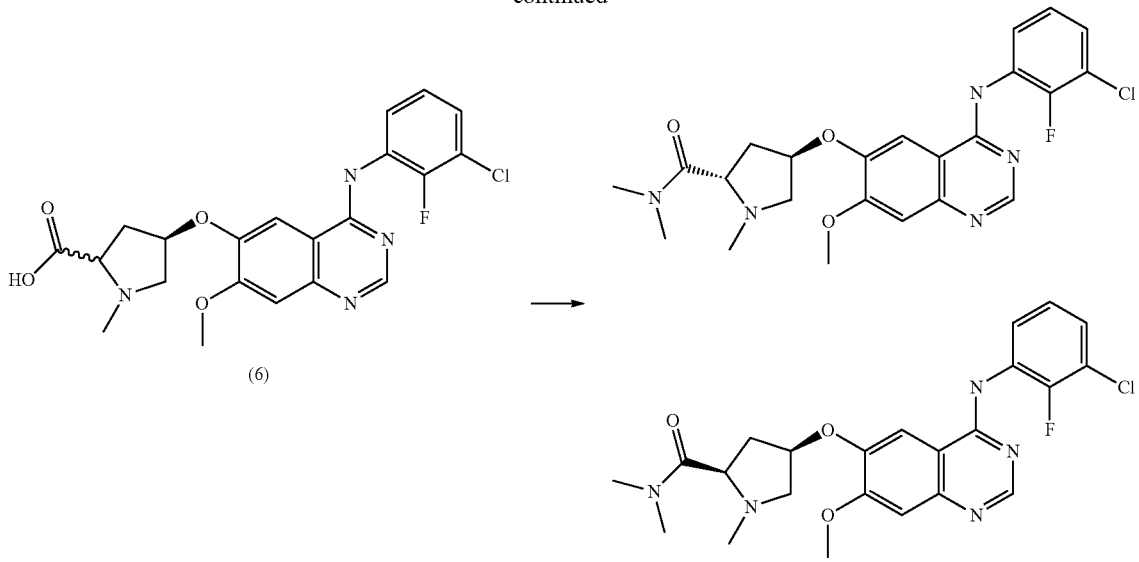

O-(7-azabenzotriazol-1-yl)-N,N,N',N'-tetramethyluronium hexafluorophosphate (HATU) (192 mg, 0.5 mmol) was added to a stirred solution of 4-(3-chloro-2-fluoroanilino)-6-[(2RS,4R)-1-methyl-2-carboxypyrrolidin-4-yloxy]-7-methoxyquinazoline (150 mg, 0.336 mmol), dimethylamine hydrochloride (41 mg, 0.5 mmol) and diisopropyl ethylamine (175 μl, 1.0 mmol) in DMF (5 ml). After 18 hrs the reaction mixture was evaporated to dryness. The residues were dissolved in methylene chloride (50 ml) and washed with water (50 ml), dried (MgSO$_4$), filtered and concentrated to an orange gum. This was then purified by flash chromatography on silica eluting with increasingly polar mixtures of methylene chloride/methanol (100/0 to 90/10) to give the following diastereoisomers.

The first eluted product fractions were combined and evaporated to give a colourless gum that was triturated with diethylether to yield 4-(3-chloro-2-fluoroanilino)-6-[(2S,4R)-2-(N,N-dimethylcarbamoyl)-1-methylpyrrolidin-4-yloxy]-7-methoxyquinazoline as a white powder (56.1 mg); $^1$H NMR Spectrum: (Benzene-4) 2.10 (s, 3H), 2.1-2.28 (m, 1H), 2.28-2.45 (m, 6H), 2.65-2.80 (m, 1H), 2.80-2.90 (m, 1H), 3.20 (t, 1H), 3.45 (s, 3H), 3.60-3.75 (m, 1H), 5.70-5.80 (m, 1H), 6.65-6.75 (m, 1H), 6.85-7.00 (m, 1H), 7.55 (s, 1H), 7.93 (t, 1H), 8.05 (s, 1H), 8.93 (s, 1H), 9.08 (s, 1H); Mass Spectrum: (M+H)$^+$ 474.

The second eluted product fractions were combined and evaporated to give 4-(3-chloro-2-fluoroanilino)-6-[(2R,4R)-2-(N,N-dimethylcarbamoyl)-1-methylpyrrolidin-4-yloxy]-7-methoxyquinazoline as a white foam (37.8 mg); $^1$H NMR Spectrum: (Benzene-d$_6$+DMSO-d$_6$+Acetic Acid-d$_4$) 2.10-2.25 (m, 1H), 2.60 (s, 3H), 2.68 (s, 3H), 2.83 (s, 3H), 3.40-3.60 (m, 1H), 3.83 (s, 3H), 3.90 (dd, 1H), 4.03 (d, 1H), 4.90-5.05 (m, 1H), 5.40-5.55 (m, 1H), 6.89 (t, 1H), 7.10 (t, 1H), 7.65 (t, 1H), 7.92 (s, 1H), 7.95 (s, 1H), 8.80 (s, 1H); Mass Spectrum: (M+H)$^+$ 474.

The 4-(3-chloro-2-fluoroanilino)-6-[(2RS,4R)-1-methyl-2-carboxypyrrolidin-4-yloxy]7-methoxyquinazoline starting material was prepared as follows:

4-Nitrobenzenesulfonyl chloride (1.89 g) was added to a stirred solution of 1-tent-butyl 2-methyl (2S,4S)-4-hydroxy-pyrrolidine-1,2-dicarboxylate (2.0 g) and pyridine (1.29 g) in methylene chloride (30 ml) and stirred at 4° C. for 16 hours under an atmosphere of nitrogen. The reaction mixture was washed with citric acid (1.0 M), saturated sodium bicarbonate and dried over magnesium sulfate. The product was then purified by column chromatography on silica eluting with increasingly polar mixtures of methylene chloride/methanol (100/0 to 92/8). The fractions containing the expected product were combined and evaporated under vacuum to give 1-tert-butyl 2-methyl (2S,4S)-4-[(4-nitrophenyl)sulfonyloxy]pyrrolidine-1,2-dicarboxylate as a yellow gum (0.89 g); NMR Spectrum: (DMSO d$_6$) 1.31-1.42 (m, 9H), 2.12-2.21 (m, 1H), 2.53-2.67 (m, 1H), 3.40-3.50 (m, 1H), 3.58-3.69 (m, 4H), 4.36 (m, 1H), 5.25 (m, 1H), 8.14 (d, 2H), 8.46 (d, 2H).

Dimethylformamide (15 ml) was added to 4-(3-chloro-2-fluoroanilino)-7-methoxy-6-hydroxyquinazoline (0.66 g; prepared as described in Example 22-preparation of starting materials), 1-tert-butyl 2-methyl (2S,4S)-4-[(4-nitrophenyl)sulfonyloxy]pyrrolidine-1,2-dicarboxylate (0.889 g) and cesium fluoride (0.941 g). The reaction mixture was then stirred at room temperature for 16 hours. The reaction mixture was evaporated under vacuum and the residue partitioned between ethyl acetate and water. The organics were washed with water and saturated brine and dried over magnesium sulfate. The product was then purified by column chromatography eluting with increasingly polar mixtures of methylene chloride/methanol (100/0 to 95/5). The fractions containing the expected product were combined and evaporated under vacuum to give 4-(3-chloro-2-fluoroanilino)-6-[(2S,4R)-1-(tert-butoxycarbonyl)-2-(methoxycarbonyl)pyrrolidin-4-yloxy]-7-methoxyquinazoline as a colourless gum (0.36 g); Mass Spectrum: (M+H)$^+$ 547.

A solution of 4-(3-chloro-2-fluoroanilino)-6-[(2S,4R)-1-(tert-butoxycarbonyl)-2-(methoxycarbonyl)pyrrolidin-4-yloxy]-7-methoxyquinazoline (480 mg, 0.88 mmol) in formic acid (50 ml) was reacted with paraformaldehyde (29 mg, 0.97 mmol) and the resulting mixture heated at 85° C. for 6 hours. The reaction mixture was evaporated and the residues partitioned between saturated aqueous NaHCO$_3$ (50 ml) and ethyl acetate (100 ml). The organic layer was dried over MgSO$_4$, filtered and evaporated. The residue was purified by flash chromatography on silica eluting with increasingly polar mixtures of methylene chloride/methanol (100/0 to 90/10). The fractions containing the expected product were combined and evaporated to give 4-(3-chloro-2-fluoroanilino)-6-[(2RS,4R)-1-methyl-2-(methoxycarbonyl)pyrrolidin-4-yloxy]-7-methoxyquinazoline as a white foam (265 mg); Mass Spectrum: (M+H)+ 461.

2M NaOH (1 ml, 2 mmol) was added to a stirred solution of 4-(3-chloro-2-fluoroanilino)-6-[(2RS,4R)-1-methyl-2-(methoxycarbonyl)pyrrolidin-4-yloxy]-7-methoxyquinazoline (250 mg, 0.54 mmol) in methanol (5 ml) and the mixture stirred at room temperature for 18 hours. The reaction mixture was evaporated and the residues re-dissolved in water (50 ml). This was then washed with ethyl acetate (25 ml) and the aqueous phase evaporated to dryness and azeotroped with toluene. The residues were triturated with methylene chloride/methanol (9/1) (25 ml), filtered and the liquors evaporated to give 4-(3-chloro-2-fluoroanilino)-6-[(2RS,4R)-1-methyl-2-carboxypyrrolidin-4-yloxy]-7-methoxyquinazoline as a white foam (155 mg); Mass Spectrum: (M+H)+ 447,

EXAMPLE 47

4-(3-Chloro-2-fluoroanilino)-7-methoxy-6-[(2RS, 4R)-1-methyl-2-(morpholinocarbonyl)pyrrolidin-4-yloxy]quinazoline

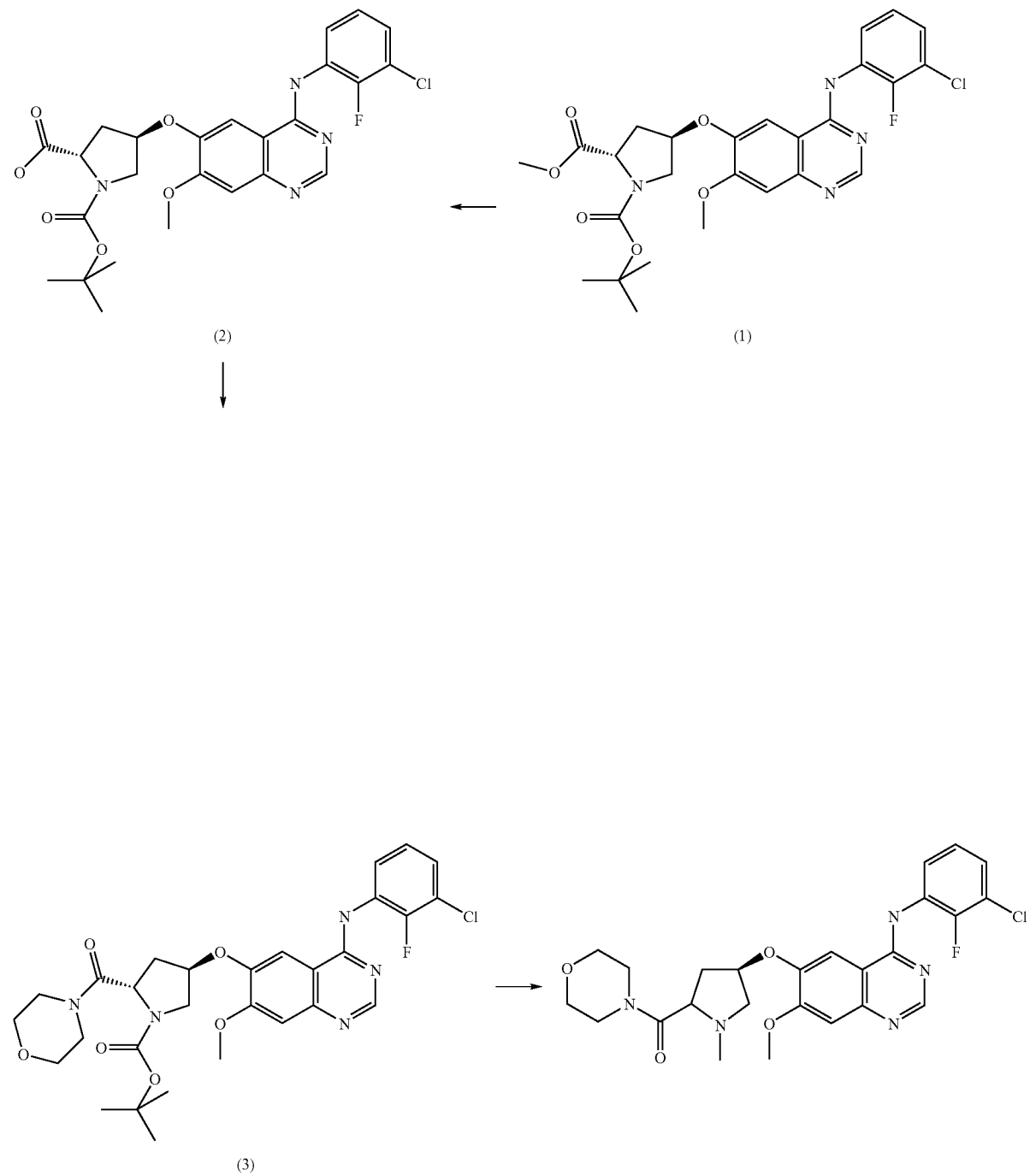

A solution of 4-(3-chloro-2-fluoroanilino)-7-methoxy-6-[(2S,4R)-1-(tert-butoxycarbonyl)-2-(morpholinocarbonyl) pyrrolidin-4-yloxy]quinazoline (0.3 g), formic acid (3.0 ml) and paraformaldehyde (0.047 mg) was stirred at 80° C. for 8 hours. The reaction was cooled, reduced under vacuum and adsorbed onto silica. The product was eluted with increasingly polar mixtures of methylene chloride/methanol (100/0 to 90/10). The fractions containing the desired product were combined and evaporated under vacuum. The product was then re-purified by preparative HPLC on a reverse phase Hi-Chrom HIRPB column. The product was eluted with decreasingly polar mixtures of acetonitrile/water (0.1% trifluoroacetic acid) (20/80 to 50150). The fractions containing the desired product were combined and evaporated under vacuum and the residue dissolved in methylene chloride/methanol (saturated with ammonia) and adsorbed onto silica. The product was eluted with increasingly polar mixtures of methylene chloride/methanol (saturated with ammonia) (100/0 to 90/10). The fractions containing the desired product were combined and evaporated under vacuum to give the title product as a colourless foam (0.058 g); $^1$H NMR Spectrum: (DMSO d$_6$) 2.10-2.18 (m, 1H), 2.31 (s, 3H), 2.53-2.60 (m, 1H), 3.44-3.67 (m, 10H), 3.72 (t, 1H), 3.92 (s, 3H), 5.10 (m, 1H), 7.21 (s, 1H), 7.28 (t, 1H), 7467.56 (m, 2H), 7.71 (s, 1H), 8.36 (s, 1H), 9.64 (s, 1H); Mass Spectrum: (M+H)$^+$ 516.

The 4-(3-chloro-2-fluoroanilino)-7-methoxy-6-[(2S,4R)-1-(tert-butoxycarbonyl)-2-(morpholinocarbonyl)pyrrolidin-4-yloxy]quinazoline starting material was prepared as follows:

Aqueous sodium hydroxide solution (2M, 1.0 ml) was added to a stirred solution of 4-(3-chloro-2-fluoroanilino)-6-[(2S,4R)-1-(tert-butoxycarbonyl)-2-(methoxycarbonyl)pyrrolidin-4-yloxy]-7-methoxyquinazoline (prepared as described in Example 46; preparation of starting materials) in methanol (8 ml) and THF (3 ml) and the reaction mixture was stirred at room temperature for 16 hours. The reaction mixture was then reduced under vacuum and the residue dissolved in water and adjusted to pH 6 by the addition of hydrochloric acid (2N). The product was extracted with ethylacetate/n-propanol and the organic layer was washed with brine, dried over MgSO$_4$ and the solvent removed under vacuum to give 4-(3-chloro-2-fluoroanilino)-6-[(2S,4R)-1-(tert-butoxycarbonyl)-2-carboxypyrrolidin-4-yloxy]-7-methoxyquinazoline as a white powder solid (0.42 g); Mass Spectrum: (M+H)$^+$ 532.98

HATU (214 mg) was added to a stirred solution of 4-(3-chloro-2-fluoroanilino)-6-[(2S,4R)-1-(text-butoxycarbonyl)-2-carboxypyrrolidin-4-yloxy]-7-methoxyquinazoline (215 mg), morpholine (50 mg) and diisopropylethylamine (200 µl) in DMA (5 ml). After stirring for 18 hours at ambient temperature, the reaction mixture was evaporated to dryness. The residues were dissolved in methylene chloride (50 ml) and washed with water (50 ml), brine (50 ml), dried (MgSO$_4$), filtered and the solvent removed under vacuum to yield 4-(3-chloro-2-fluoroanilino)-7-methoxy-6-[(2S,4R)-1-(tert-butoxycarbonyl)-2-(morpholinocarbonyl)pyrrolidin-4-yloxy]quinazoline as a pale yellow gum (300 mg). The residue was used without further purification; Mass Spectrum: (M–H)$^+$ 602.08.

EXAMPLE 48

4-(3-Chloro-2-fluoroanilino)-7-methoxy-6-[1-(pyrrolidin-1-ylacetyl)piperidin-3-yloxy]quinazoline

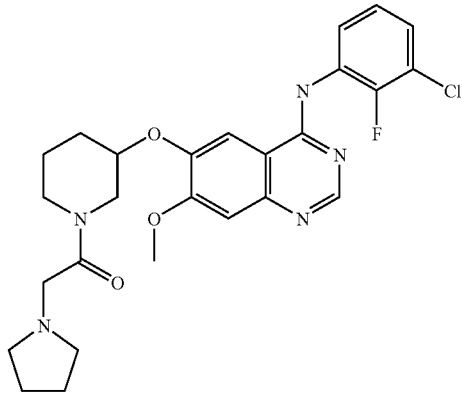 [SMILES: COc1cc2ncnc(Nc3cccc(Cl)c3F)c2cc1OC1CCCN(C(=O)CN2CCCC2)C1]

Chloroacetyl chloride (89 µl) was added to a solution of 4-(3-chloro-2-fluoroanilino)-7-methoxy-6-(piperidin-3-yloxy)quinazoline dihydrochloride (469 mg; prepared as described in Example 45) and diisopropylethylamine (700 µl) in methylene chloride (15 ml) that was cooled to 0° C. The mixture was stirred at room temperature for 2 hours to give 6-[1-(chloroacetyl)piperidin-3-yloxy]-4-(3-chloro-2-fluoroanilino)-7-methoxyquinazoline; Mass Spectrum: (M+H)$^+$ 479.

Pyrrolidine (0.5 ml) was then added, and the solution was further stirred for 1 hour and purified by flash chromatography eluting with methylene chloride/methanol (containing ammonia 7N) (97/3). The fractions containing the expected product were combined and evaporated under vacuum to give the title product as a colourless foam (0.327 g); $^1$H NMR Spectrum: (DMSO d$_6$, 100° C.) 1.50-1.72 (m, 5H), 1.83-1.95 (m, 2H), 2.08-2.18 (m, 1H), 2.40-2.58 (m, 4H), 3.18 (d, 1H), 3.37 (d, 1H), 3.48-3.56 (m, 1H), 3.58-3.64 (m, 1H), 3.68-3.77 (m, 1H), 3.89-3.93 (m, 1H), 3.95 (s, 3H), 4.51-4.59 (m, 1H), 7.23-7.31 (m, 2H), 7.40-7.48 (m, 1H), 7.57-7.64 (m, 1H), 7.90 (s, 1H), 8.41 (s, 1H), 9.25 (br s, 1H); Mass Spectrum: (M+H)$^+$ 514.

EXAMPLE 49

4-(3-Chloro-2-fluoroanilino)-7-methoxy-6-[(3S)-piperidin-3-yloxy]quinazoline

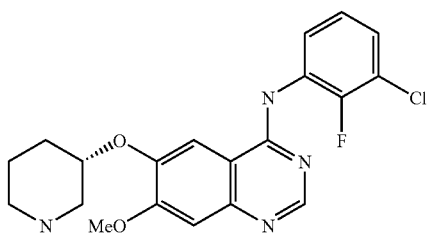 [SMILES: COc1cc2ncnc(Nc3cccc(Cl)c3F)c2cc1O[C@H]1CCCNC1]

HCl (1.0 ml, 4M solution in dioxane) was added to 4-chloro-7-methoxy-6-[(3S)-1-(tert-butoxycarbonyl)piperidin-3-yloxy]quinazoline (0.786 g) and 3-chloro-2-fluoroaniline (0.304 g) dissolved in acetonitrile (25 ml). The mixture was heated to 60° C. for 2 hours, cooled and the precipitate collected to give 4-(3-chloro-2-fluoroanilino)-7-methoxy-6-[(3S)-piperidin-3-yloxy]quinazoline hydrochloride as a white solid (0.577 g, 66%); $^1$H NMR Spectrum: (DMSOd$_6$); 1.70-1.95 (m, 2H), 1.95-2.10 (m, 1H); 2.10-2.25 (m, 1H), 2.95-3.10 (m, 1H), 3.10-3.30 (m, 2H), 3.45-3.65 (m, 1H); 4.03 (s, 3H); 4.95-5.10 (m, 1H); 7.30-7.45 (m, 1H); 7.45-7.60 (m, 2H); 7.60-7.73 (m, 1H), 8.85 (s, 1H); 8.90 (s, 1H); 9.15 (bs, 2H); 12.3 (bs, 1H); Mass Spectrum: (M+H): 403.

The 4-chloro-7-methoxy-6-[(3S)-1-(tert-butoxycarbonyl)piperidin-3-yloxy]quinazoline starting material was prepared as follows:

Diethyl azodicarboxylate (2.76 ml, 40% solution in toluene) was added to 4-chloro-6-hydroxy-7-methoxyquinazoline (0.89 g; prepared as described in Example 16), triphenylphosphine (1.66 g) and (3R)-1-(tert-butoxycarbonyl)-3-hydroxypiperidine (CAS Registry No 143900-43-0) (1.28 g) in dichloromethane (25 ml). The resulting solution was allowed to stir overnight at room temperature. This was purified by flash column chromatography eluting with an increasingly polar mixture of acetone/isohexane/triethylamine (79/20/1 to 64/35/1) to give 4-chloro-7-methoxy-6-[(3S)-1-(tert-butoxycarbonyl)piperidin-3-yloxy)]quinazoline as a white solid (0.794 g, 48%); Mass Spectrum: (M+H)+ 394.

EXAMPLE 50

4-(3-Chloro-2-fluoroanilino)-7-methoxy-6-[(3S)-1-(pyrrolidin-1-ylacetyl)piperidin-3-yloxy]quinazoline

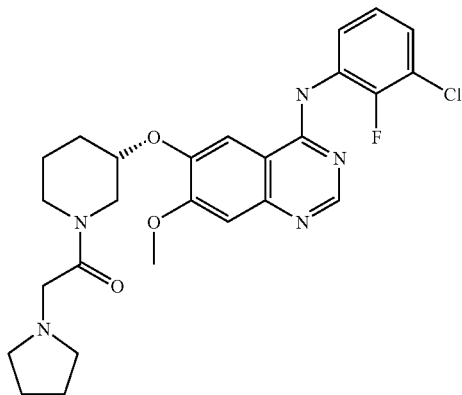

Chloroacetyl chloride (66 µl) was added to a solution of 4-(3-chloro-2-fluoroanilino)-7-methoxy-6-[(3S)-piperidin-3-yloxy]quinazoline hydrochloride (350 mg; prepared according to Example 49) and diisopropylethylamine (522 µl) in methylene chloride (10 ml) that was cooled to 0° C. and the mixture was stirred at room temperature for 30 mins. Pyrrolidine (0.37 ml) was added, and the solution stirred for 1 hour before being purified by flash column chromatography eluting with methylene chloride/methanol (containing ammonia 7N) (97/3). The fractions containing the expected product were combined and evaporated to give a foam. This foam was dissolved in methylene chloride (5 ml) and crystallised by the addition of isohexane (50 ml) to give the title product (0.206 g); $^1$H NMR Spectrum: (DMSO d$_6$, 100° C.) 1.50-1.72 (m, 5H), 1.83-1.95 (m, 2H), 2.08-2.18 (m, 1H), 2.40-2.58 (m, 4H), 3.18 (d, 1H), 3.37 (d, 1H), 3.48-3.56 (m, 1H), 3.58-3.64 (m, 1H), 3.68-3.77 (m, 1H), 3.89-3.93 (m, 1H), 3.95 (s, 3H), 4.51-4.59 (m, 1H), 7.23-7.31 (m, 2H), 7.40-7.48 (m, 1H), 7.57-7.64 (m, 1H), 7.90 (s, 1H), 8.41 (br s, 1H), 9.25 (br s, 1H); Mass Spectrum: (M+H)$^+$ 514.

EXAMPLE 51

4-(3-Chloro-2-fluoroanilino)-7-methoxy-6-{[(2S)-1-(N-methylaminoacetyl)pyrrolidin-2-yl]methoxy}quinazoline

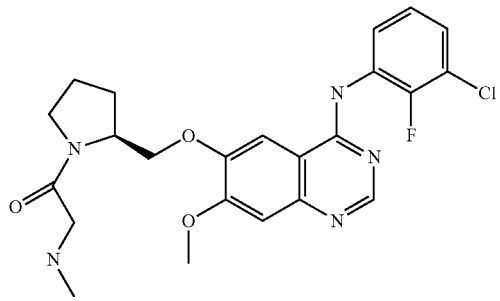 [SMILES: CNCC(=O)N1CCC[C@H]1COc1cc2c(Nc3cccc(Cl)c3F)ncnc2cc1OC]

Using a procedure similar to that described for the synthesis Example 43, 4-(3-chloro-2-fluoroanilino)-7-methoxy-6-{[(2S)-1-(chloracetyl)pyrrolidin-2-yl]methoxy}quinazoline (0.28 g; prepared as described in Example 43, preparation of starting materials) was reacted with 33% methylamine in ethanol (5 ml) to give the title product as a foam (0.131 g, 47%); $^1$H NMR Spectrum: (CDCl$_3$) 1.91-2.22 (m, 4H), 2.22 (s, 3H), 2.70-2.90 (m, 1H), 3.28-3.40 (m, 2H), 3.44-3.54 (m, 2H), 3.97-4.09 (m, 4H), 4.47-4.51 (d, 1H), 4.60-4.66 (t, 1H), 7.06-7.20 (m, 2H), 7.24 (s, 1H), 8.07-8.13 (m, 1H), 8.57-8.70 (m, 3H); Mass Spectrum: (M−H)$^-$ 472.

EXAMPLE 52

4-(3-Chloro-2-fluoroanilino)-7-methoxy-6-{[(2S)-1-(N,N-dimethylaminoacetyl)pyrrolidin-2-yl]methoxy}quinazoline

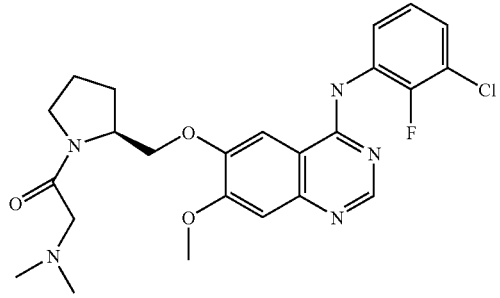

Using a procedure similar to that described for the preparation of Example 43, 4-(3-chloro-2-fluoroanilino)-7-methoxy-6-{[(2S)-1-(chloroacetyl)pyrrolidin-2-yl]methoxy}quinazoline (0.28 g) was reacted with 33% dimethylamine in ethanol (5 ml) to give the title product as a foam (0.165 g, 58%); $^1$H NMR Spectrum: (CDCl$_3$) 1.91-2.01 (m, 1H), 2.04-2.11 (m, 2H), 2.14-2.22 (m, 1H), 2.33 (s, 6H), 3.02-3.22 (dd, 2H), 3.40-3.50 (m, 1H), 3.59-3.66 (m, 1H), 4.02 (s, 3H), 4.05-4.09 (m, 1H), 4.51-4.55 (d, 1H), 4.66-4.72

(m, 1H), 7.09-7.21 (m, 2H), 7.23 (s, 1H), 8.00-8.06 (m, 1H), 8.47 (bs, 1H), 8.62 (s, 1H), 8.68 (s, 1H); Mass Spectrum: (M−H)⁻ 486.

EXAMPLE 53

4-(3-Chloro-2-fluoroanilino)-7-methoxy-6-{[(2S)-1-(pyrrolidin-1-ylacetyl)pyrrolidin-2-yl]methoxy}quinazoline

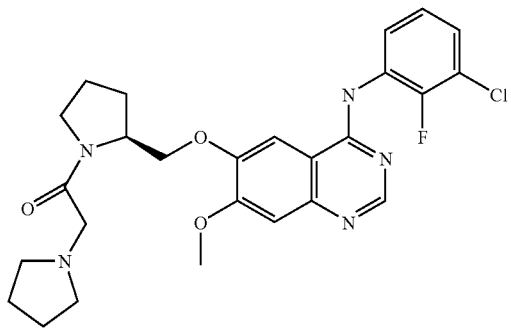 [SMILES: COc1cc2ncnc(Nc3cccc(Cl)c3F)c2cc1OC[C@@H]1CCCN1C(=O)CN1CCCC1]

Using a procedure similar to that described in Example 43, 4-(3-chloro-2-fluoroanilino)-7-methoxy-6-{[(2S)-1-(chloroacetyl)pyrrolidin-2-yl]methoxy}quinazoline (0.28 g) was reacted with pyrrolidine (2.5 ml) to give the title product as a foam (0.151 g, 50%); ¹H NMR Spectrum: (CDCl₃) 1.68-1.75 (m, 4H), 1.90-2.01 (m, 1H), 2.04-2.14 (m, 2H), 2.15-2.23 (m, 1H), 2.51-2.61 (m, 2H), 2.66-2.74 (m, 2H), 3.15-3.21 (d, 1H), 3.38-3.48 (m, 2H), 3.55-3.62 (m, 1H), 4.00-4.08 (m, 4H), 4.52-4.55 (d, 1H), 4.68-4.74 (t, 1H), 7.06-7.27 (m, 3H), 7.90-7.96 (m, 1H), 8.43 (s, 1H), 8.60 (s, 1H), 8.69 (s, 1H); Mass Spectrum: (M−H)⁻ 512.

EXAMPLE 54

4-(3-Chloro-2-fluoroanilino)-6-{[(2S)-1-(3,4-methylenedioxypyrrolidin-1-ylacetyl)pyrrolidin-2-yl]methoxy}-7-methoxyquinazoline

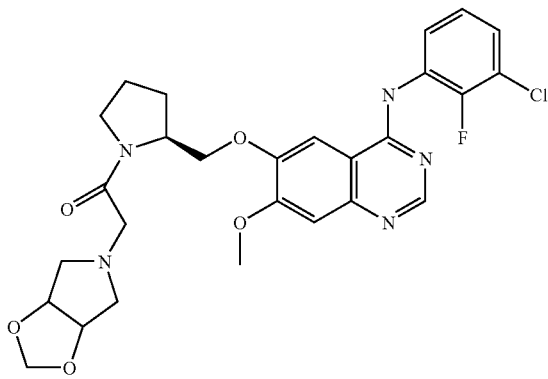 [SMILES: COc1cc2ncnc(Nc3cccc(Cl)c3F)c2cc1OC[C@@H]1CCCN1C(=O)CN1CC2OCOC2C1]

3,4-methylenedioxypyrrolidine hydrochloride (87 mg) was added to a stirred solution of 4-(3-chloro-2-fluoroanilino)-7-methoxy-6-{[(2S)-1-(chloroacetyl)pyrrolidin-2-yl]methoxy}quinazoline (0.25 g; prepared as described in Example 43) and diisopropylethylamine (0.2 ml) in acetonitrile (10 ml) and the mixture heated at reflux for 2 hours. The reaction mixture was partitioned between ethyl acetate and saturated aqueous NaHCO₃. The organic layer was washed with brine, dried over Na₂SO₄, filtered and evaporated. The residue was purified by column chromatography eluting with increasingly polar mixtures of methylene chloride/isopropanol/triethylamine (97/2/1) to (95/4/1). The fractions containing the expected product were evaporated under vacuum to give the title product as a yellow solid (0.203 g; 70%); ¹H NMR Spectrum: (CDCl₃) 1.92-222 (m, 4H), 2.54-2.61 (m, 2H), 3.05-3.15 (m, 2H), 3.26-3.38 (q, 2H), 3.42-3.47 (m, 1H), 3.58-3.65 (m, 1H), 4.00-4.10 (m, 4H), 4.47-4.55 (m, 3H), 4.65-4.72 (m, 1H), 4.84 (s, 1H), 5.02 (s, 1H), 7.11-7.22 (m, 2H), 7.24 (s, 1H), 7.96-8.02 (m, 1H), 8.38 (s, 1H), 8.61 (s, 1H), 8.63 (s, 1H); Mass Spectrum: (M+H)⁺ 558.

The 3,4-methylenedioxypyrrolidine hydrochloride used as a starting material was prepared as follows:—

A solution of di-tent-butyl dicarbonate (Boc₂O, 78.95 g) in ethyl acetate (125 ml) was added dropwise to a stirred mixture of 3-pyrroline (25 g; 65% pure containing pyrrolidine) and ethyl acetate (125 ml) which had been cooled to 0° C. The reaction temperature was maintained at 5-10° C. during the addition. The resultant reaction mixture was allowed to warm to ambient temperature overnight. The reaction mixture was washed successively with water, 0.1N aqueous hydrochloric acid solution, water, a saturated aqueous sodium bicarbonate solution and brine, dried over magnesium sulphate and evaporated. There was thus obtained, as a colorless oil (62 g), a 2:1 mixture of tert-butyl 3-pyrroline-1-carboxylate, NMR: (CDCl₃) 1.45 (s, 9H), 4.1 (d, 4H), 6.75 (m, 2H), and tert-butyl pyrrolidine-1-carboxylase, NMR: (CDCl₃) 1.5 (s, 9H), 1.8 (br s, 4H), 3.3 (br s, 4H).

A solution of the mixture of materials so obtained in acetone (500 ml) was added dropwise to a mixture of N-methylmorpholine-N-oxide (28.45 g), osmium tetroxide (1 g) and water (500 ml) whilst keeping the reaction temperature below 25° C. The reaction mixture was then stirred at ambient temperature for 5 hours. The solvent was evaporated and the residue was partitioned between ethyl acetate and water. The organic phase was washed with brine, dried over magnesium sulphate and evaporated. The residue was purified by column chromatography on silica using increasingly polar mixtures of petroleum ether (b.p. 40-60° C.) and ethyl acetate as eluent and by further column chromatography on silica using increasingly polar mixtures of methylene chloride and methanol. There was thus obtained tert-butyl 3,4-dihydroxypyrrolidine-1-carboxylate as an oil (34.6 g); NMR Spectrum: (CDCl₃) 1.45 (s, 9H), 2.65 (m, 2H), 3.35 (m, 2H), 3.6 (m, 2H), 4.25 (m, 2H).

A solution of sere-butyl 3,4-dihydroxypyrrolidine-1-carboxylate (34.6 g) in DMF (400 ml) was cooled to 0-5° C. and sodium hydride (60% dispersion in mineral oil, 0.375 mol) was added portionwise. The reaction mixture was stirred at 5° C. for 1 hour. Dibromomethane (15.6 ml) was added and the reaction mixture was stirred at 5° C. for 30 minutes. The reaction mixture was allowed to warm to ambient temperature and was stirred for 16 hours. The DMF was evaporated and the residue was partitioned between ethyl acetate and water. The organic phase was washed with water and with brine, dried over magnesium sulphate and evaporated. The residue was purified by column chromatography on silica using increasingly polar mixtures of petroleum ether (b.p. 40-60° C.) and ethyl acetate as eluent. There was thus obtained tert-butyl 3,4-methylenedioxypyrrolidine-1-carboxylate as a colourless oil (19.77 g); NMR Spectrum: (CDCl₃) 1.45 (s, 9H), 3.35 (m, 2H), 3.75 (br s, 2H), 4.65 (m, 2H), 4.9 (s, m), 5.1 (s, 1H).

A cooled 5M solution of hydrogen chloride in isopropanol (150 ml) was added to a solution of tert-butyl 3,4-methylenedioxypyrrolidine-1-carboxylase (19.7 g) in methylene chloride (500 ml) that was cooled in an ice bath. The reaction mixture was allowed to warns to ambient temperature and was stirred for 4 hours. The solvent was evaporated and the residue was triturated under diethyl ether. The precipitate was collected by filtration, washed with diethyl ether and dried. There was thus obtained 3,4-methylenedioxypyrrolidine hydrochloride as a beige solid (13.18 g); NMR Spectrum: (DMSOd$_6$) 3.15 (m, 2H), 3.35 (m, 2H), 4.65 (s, 1H), 4.8 (m, 2H), 5.1 (s, 1H).

EXAMPLE 55

4-(3-Chloro-2-fluoroanilino)-7-methoxy-6-{[(2S)-1-(1-methylpiperazin-4-ylacetyl)pyrrolidin-2-yl]methoxy}quinazoline

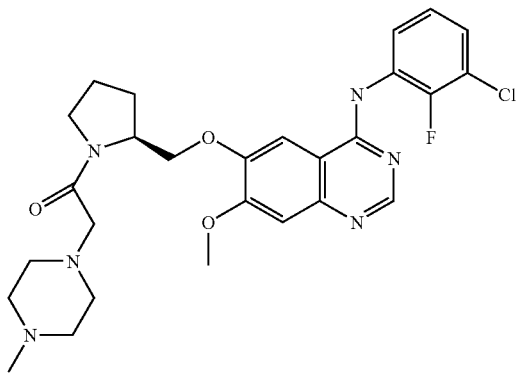 [SMILES: COc1cc2ncnc(Nc3cccc(Cl)c3F)c2cc1OC[C@@H]1CCCN1C(=O)CN1CCN(C)CC1]

Using a procedure similar to that described in Example 43, 4-(3-chloro-2-fluoroanilino)-7-methoxy-6-{[(2.5)-1-(chloroacetyl)pyrrolidin-2-yl]methoxy}quinazoline (0.14 g) was reacted with 1-methylpiperazine (5 ml) to give the title product as a white foam (0.122 g); $^1$H NMR Spectrum: (CDCl$_3$) 1.91-2.01 (m, 1H), 2.04-2.12 (m, 2H), 2.17-2.23 (m, 1H), 2.25 (s, 3H), 2.34-2.45 (m, 3H), 2.49-2.59 (m, 2H), 2.62-2.72 (m, 2H), 3.08-3.26 (q, 2H), 3.40-3.51 (m, 2H), 3.54-3.61 (m, 1H), 4.00-4.08 (m, 4H), 4.50-4.56 (m, 1H), 4.67-4.74 (m, 1H), 7.10-7.24 (m, 2H), 7.23 (s, 1H), 7.91-7.97 (m, 1H), 8.38 (s, 1H), 8.60 (s, 1H), 8.66 (s, 1H); Mass Spectrum: (M−H)$^-$ 541.

EXAMPLE 56

4-(3-Chloro-2-fluoroanilino)-6-[(3R)-1-(hydroxyacetyl)pyrrolidin-3-yloxy]-7-methoxyquinazoline

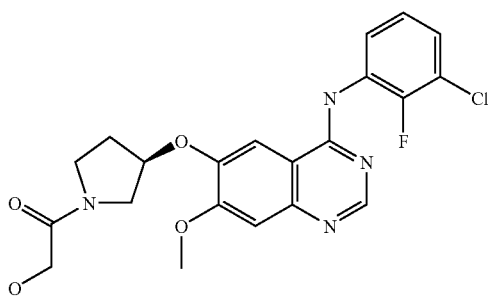 [SMILES: COc1cc2ncnc(Nc3cccc(Cl)c3F)c2cc1O[C@@H]1CCN(C(=O)CO)C1]

4-(3-chloro-2-fluoroanilino)-6-[(3R)-pyrrolidin-3-yloxy]-7-methoxyquinazoline hydrochloride (0.25 g; prepared as described in Example 29) was dissolved in a mixture of methylene chloride (10 ml) and diisopropylethylamine (0.3 ml). The solution was cooled in an ice/water bath to 4° C. and acetoxyacetyl chloride (0.069 ml) added. The reaction mixture was stirred cold for two hours and then partitioned between methylene chloride and saturated aqueous NaHCO$_3$. The organic layer was separated, washed with brine, dried over Na$_2$SO$_4$, filtered and evaporated. The residue was dissolved in 7M methanolic ammonia (10 ml) and the resulting solution stirred overnight. The solvent was evaporated and the residue purified by column chromatography eluting with increasingly polar mixtures of methylene chloride/methanol (saturated with ammonia) 98/2 to 92/8 The fractions containing the expected product were evaporated and the residue was triturated with diethylether to give the title product as a pale yellow solid (0.161 g, 61%); $^3$H NMR Spectrum: (DMSO-d$_6$ @ 393K, 500 MHz) 2.10-2.40 (m, 2H), 3.50-3.70 (m, 3H), 3.70-3.85 (m, 1H), 3.95 (s, 3H), 4.05 (s, 2H), 5.15 (s, 1H), 7.15-730 (m, 2H), 7.30-7.45 (m, 1H), 7.50-7.70 (m, 1H), 7.85 (s, 1H), 8.40 (s, 1H), 9.20 (bs, 1H); Mass Spectrum: (M+H)$^+$ 447.

EXAMPLE 57

6-[(3S)-1-Acetylpiperidin-3-yloxy]-4-(3-chloro-2-fluoroanilino)-7-methoxyquinazoline

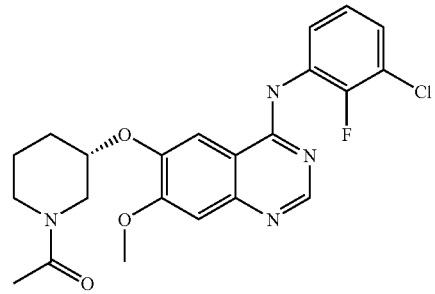 [SMILES: COc1cc2ncnc(Nc3cccc(Cl)c3F)c2cc1O[C@H]1CCCN(C(C)=O)C1]

A solution of acetic anhydride (42 µl) in methylene chloride (5 ml) was added dropwise to a stirred solution of 4-(3-chloro-2-fluoroanilino)-7-methoxy-6-[(3S)-piperidin-3-yloxy]quinazoline hydrochloride (0.175 g, 0.4 mmol; prepared as described in Example 49) and diisopropylethylamine (208 µl) in methylene chloride (20 ml) at 0° C. and the mixture was stirred for 2 hours and allowed to warm to room temperature. The reaction mixture was washed with saturated sodium bicarbonate solution, dried (MgSO$_4$), filtered and evaporated to give a white foam. This was purified by column chromatography eluting with increasingly polar mixtures of methylene chloride/methanol (100/0 to 95/5). The fractions containing the desired product were combined and evaporated under vacuum to give the title product as a colourless foam (0.117 g, 66%); $^1$H NMR Spectrum: (DMSO d$_6$ at 373K) 1.40-1.65 (m, 1H), 1.70-1.94 (m, 2H), 2.00 (s, 3H), 1.95-2.20 (m, 1H), 3.20-3.70 (m, 3H), 3.70-4.10 (m, 1H), 3.95 (s, 3H), 4.40-4.70 (m, 1H), 7.15-7.33 (m, 2H), 7.33-7.50 (m, 1H), 7.50-7.70 (m, 7.90 (s, 1H), 8.40 (s, 1H), 9.25 (s, 1H); Mass Spectrum: (M₊H)⁺ 445.

EXAMPLE 58

4-(3-chloro-2-fluoroanilino-6-[(3S)-1-(methylsulfonyl)piperidin-3-yloxy]-7-methoxyquinazoline

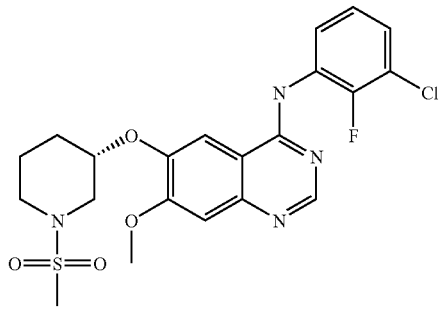 [SMILES: COc1cc2ncnc(Nc3cccc(Cl)c3F)c2cc1O[C@H]1CCCN(S(C)(=O)=O)C1]

A solution of methanesulfonyl chloride (34 μl) in methylene chloride (5 ml) was added to dropwise to a stirred solution of 4-(3-chloro-2-fluoroanilino)-7-methoxy-6-[(3S)-piperidin-3-yloxy]quinazoline hydrochloride (175 mg; prepared as described in Example 49) and diisopropylethylamine (208 μl) in methylene chloride (20 ml) at 0° C. The reaction mixture was allowed to stir for 2 hours to room temperature. The reaction mixture was washed with saturated sodium bicarbonate solution, dried (MgSO₄), filtered and evaporated to a foam. This was purified by column chromatography eluting with increasingly polar mixtures of methylene chloride/methanol (100/0 to 97/3). The fractions containing the desired product were combined and evaporated under vacuum to give the title product as a white foam (0.164 g, 85%); ¹H NMR Spectrum: (DMSO d₆) 1.5-1.67 (m, 1H), 1.67-1.83 (m, 1H), 1.83-1.95 (m, 1H), 1.95-2.12 (m, 1H), 2.95 (s, 3H), 3.1-3.23 (m, 1H), 3.23-3.45 (m, 2H+H₂O), 3.5-3.65 (m, 1H), 3.95 (s, 3H), 4.70 (m, 1H), 7.18-7.35 (m, 2H), 7.40-7.60 (m, 2H), 7.90 (s, 1H), 8.38 (s, 1H), 9.58 (s, 1H); Mass Spectrum: (M+H)⁺ 481.

EXAMPLE 59

4-(3-chloro-2-fluoroanilino)-6-[(1S)-1-(N,N-dimethylaminoacetyl)piperidin-3-yloxy]-7-methoxyquinazoline

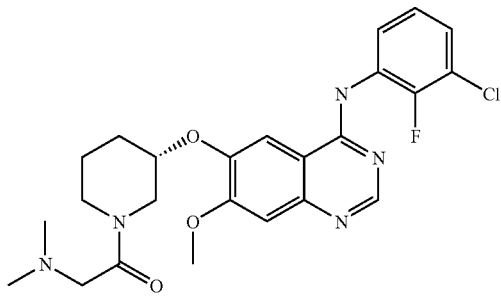 [SMILES: COc1cc2ncnc(Nc3cccc(Cl)c3F)c2cc1O[C@H]1CCCN(C(=O)CN(C)C)C1]

N,N-Dimethylaminoacetyl chloride hydrochloride (69 mg) was added portionwise to a stirred solution of 4-(3-chloro-2-fluoroanilino)-7-methoxy-6-[(3S)-piperidin-3-yloxy]quinazoline hydrochloride (175 mg; prepared as described in Example 49) and diisopropylethylamine (210 μl) in methylene chloride (25 ml) at 0° C. The reaction mixture was allowed to stir for 2 hours to room temperature. The reaction mixture was washed with saturated sodium bicarbonate solution, dried (MgSO₄), filtered and evaporated to a foam. This was purified by column chromatography eluting with increasingly polar mixtures of methylene chloride/methanol (saturated with ammonia) (100/0 to 90/10). The fractions containing the desired product were combined and evaporated under vacuum to give the title product as a white foam (0.152 g, 78%); ¹H NMR Spectrum: (DMSO d₆ at 100° C.) 1.40-1.65 (m, 1H); 1.75-1.95 (m, 2H); 2.00-230 (m, 7H); 3.05 (dd, 2H); 3.40-3.62 (m, 2H); 3.62-3.75 (m, 1H); 3.88 (dd, 1H); 3.95 (s, 3H); 4.45-4.65 (m, 1H); 7.15-7.30 (m, 2H); 7.30-7.47 (m, 1H); 7.50-7.7 (m, 1H); 7.88 (s, 1H); 8.40 (s, 1H); 9.25 (s, 1H); Mass Spectrum: (M+H)⁺ 488.

EXAMPLE 60

4-(3-chloro-2-fluoroanilino)-7-methoxy-6-{[(2E)-1-(2-hydroxyisobutyryl)pyrrolidin-2-yl]methoxy}quinazoline

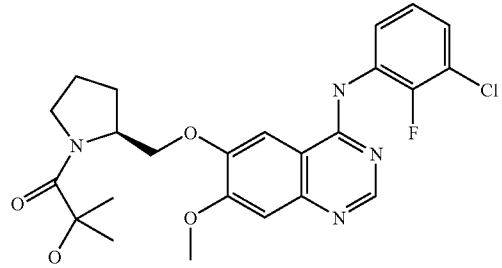 [SMILES: COc1cc2ncnc(Nc3cccc(Cl)c3F)c2cc1OC[C@@H]1CCCN1C(=O)C(C)(C)O]

4-(3-chloro-2-fluoroanilino)-7-methoxy-6-[(2S)-pyrrolidin-2-ylmethoxy]quinazoline hydrochloride (0.25 g; prepared as described in Example 31) was dissolved in a mixture of methylene chloride (5 ml) and diisopropylethylamine (0.3 ml). The solution was cooled in an ice/water bath to 4° C. and 2-acetoxyisobutryl chloride (0.085 ml) added. The reaction mixture was stirred cold for one hour and then partitioned between methylene chloride and saturated aqueous NaHCO₃. The organic layer was separated, washed with brine, dried over Na₂SO₄, filtered and evaporated. The residue was dissolved in 7M Methanolic ammonia (10 ml) and the resulting solution stirred overnight. The solvent was evaporated and the residue purified by column chromatography eluting with increasingly polar mixtures of methylene chloride/iso-propanol/triethylamine (97/2/1)-(95/4/1). The fractions containing the expected product were evaporated and the residue was triturated with diethylether to give the title compound as a white solid (0.210 g); ¹H NMR Spectrum: (CDCl₃) 1.57 (s, 6H), 1.85-230 (m, 4H), 3.55-3.75 (m, 1H), 3.75-3.90 (m, 1H), 3.90-4.20 (m, 5H), 4.53 (d, 1H), 4.7-4.85 (m, 1H), 7.05-7.20

EXAMPLE 61

4-(3-Chloro-2-fluoroanilino)-7-methoxy-6-{1-[(2S)-1-methylpyrrolidin-2-ylcarbonyl]piperidin-3-yloxy}quinazoline

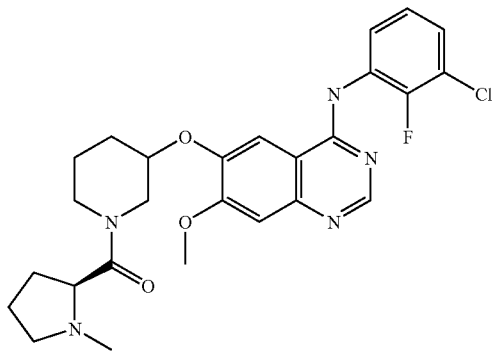 [SMILES: COc1cc2ncnc(Nc3cccc(Cl)c3F)c2cc1OC1CCCN(C(=O)[C@@H]2CCCN2C)C1]

HATU (0.26 g) was added to a solution of 4-(3-Chloro-2-fluoroanilino)-7-methoxy-6-(piperidin-3-yloxy)quinazoline dihydrochloride (250 mg; prepared as described in Example 45), diisopropylethylamine (210 µl) and N-methyl-L-proline (0.120 g) in DMF (7.5 ml) and the mixture was stirred at room temperature for 2.5 hours. The DMF was removed under reduced pressure and the residue dissolved in methylene chloride (50 ml) and washed with sodium bicarbonate (50 ml) then water (50 ml). Purification by flash column chromatography eluting with methylene chloride/methanol (saturated with ammonia) (9614). The fractions containing the expected product were evaporated to give a foam. This foam was dissolved in methylene chloride (5 ml) and crystallised by the addition of isohexane (50 ml) to give the title product as a mixture of two diastereoisomers (0.130 g). $^1$H NMR Spectrum: (DMSO $d_6$) 1.43-1.62 (m, 2H), 1.66-1.95 (m, 4H), 1.96-2.18 (m, 4H), 2.20-2.29 (m, 2H), 2.67-2.80 (m, 1H), 2.96 (m, 1H), 3.03-3.20 (m, 1H), 3.51-3.80 (m, 2H), 3.80-4.05 (m, 4H), 4.51-4.68 (m, 1H), 7.22-7.31 (2H), 7.47-7.59 (m, 2H), 7.89 (m, 1H), 8.39 (s, 1H), 9.55 (m, 1H); Mass Spectrum: (M+H)$^+$ 514.

EXAMPLE 62

4-(3-Chloro-2-fluoroanilino)-7-methoxy-6-[1-(N,N-dimethylcarbamoylmethyl)piperidin-3-yloxy]quinazoline

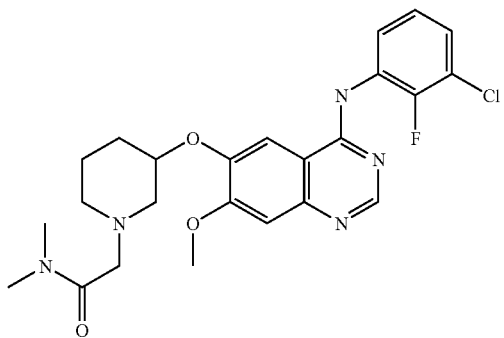 [SMILES: COc1cc2ncnc(Nc3cccc(Cl)c3F)c2cc1OC1CCCN(CC(=O)N(C)C)C1]

2-Chloro-N,N-dimethylacetamide (105 mg) was added to a mixture of 4-(3-Chloro-2-fluoroanilino)-7-methoxy-6-(piperidin-3-yloxy)quinazoline dihydrochloride (250 mg) and potassium carbonate (1.19 g) in DMF (5 ml). The mixture was stirred at room temperature for 30 mins, filtered and the solvent evaporated. Purification by flash column chromatography eluting with methylene chloride/methanol (96/4) gave a foam. This was triturated with diethyl ether and isohexane to give the title product as a white solid (105 mg); $^1$H NMR. Spectrum: (DMSO $d_6$) 1.45 (m, 1H), 1.61 (m, 1H), 1.78 (m, 1H), 2.10 (m, 1H), 2.26 (m, 1H), 2.38 (m, 1H), 2.65-2.77 (m, 1H), 2.75 (s, 3H), 2.99 (s, 3H), 3.04 (m, 1H), 3.22 (s, 2H), 3.94 (s, 3H), 4.62 (m, 1H), 7.21 (s, 1H), 7.29 (m, 1H), 7.47-7.55 (m, 2H), 7.88 (s, 1H), 8.38 (s, 1H), 9.59 (s, 1H); Mass Spectrum: (M+H)$^+$ 488.

EXAMPLE 63

4-(3-Chloro-2-fluoroanilino)-7-methoxy-6-[1-(3,3-difluoropyrrolidin-1-ylacetyl)piperidin-3-yloxy]quinazoline

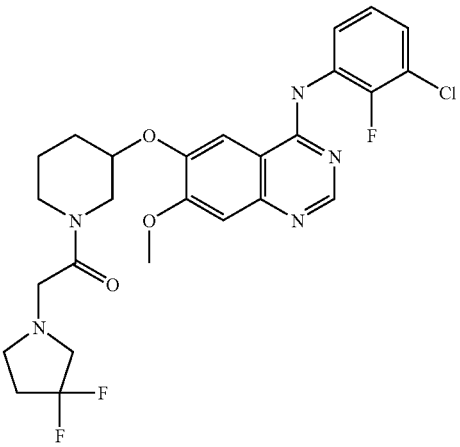 [SMILES: COc1cc2ncnc(Nc3cccc(Cl)c3F)c2cc1OC1CCCN(C(=O)CN2CCC(F)(F)C2)C1]

Chloroacetyl chloride (47 µl) was added to a solution of 4-(3-Chloro-2-fluoroanilino)-7-methoxy-6-(piperidin-3-yloxy)quinazoline dihydrochloride (250 mg) and diisopropylethylamine (373 µl) in methylene chloride (10 ml) and the mixture was stirred at room temperature for 1 hour. 3,3-Difluoropyrrolidine hydrochloride (*Synthetic Letters,* 1995, 1, 55-57; 328 mg) was added, and the solution stirred for 1 hour before being washed with saturated aqueous sodium bicarbonate (10 ml) and purified by flash column chromatography eluting with increasingly polar mixtures of methylene chloride methanol (100/0 to 9515) to give a foam. This was dissolved in methylene chloride (5 ml) and crystallised by the addition of isohexane (50 ml) to give the title product (102 mg). NMR Spectrum (DMSO $d_6$) 1.45-1.57 (m, 1H), 1.73-1.95 (m, 2H), 1.98-2.18 (m, 2H), 2.18-2.33 (m, 1H), 2.63-2.75 (m, 1H), 2.77-2.85 (m, 1H), 2.85-2.99 (m, 1H), 3.04-3.19 (m, 1H), 3.21-3.29 (m, 1H), 3.37-3.50 (m, 2H), 3.52-3.70 (m, 2H), 3.77-3.99 (m, 4H), 4.63 (m, 1H), 7.21-7.29 (m, 2H), 7.47-7.57 (m, 2H), 7.87 (d, 1H), 8.39 (s, 1H), 9.55 (d, 1H); Mass Spectrum: (M+H)$^+$ 550.

EXAMPLE 64

4-(3-Chloro-2-fluoroanilino)-7-methoxy-6-{1-[[(3R)-3-hydroxypyrrolidin-1-yl]acetyl]piperidin-3-yloxy}quinazoline

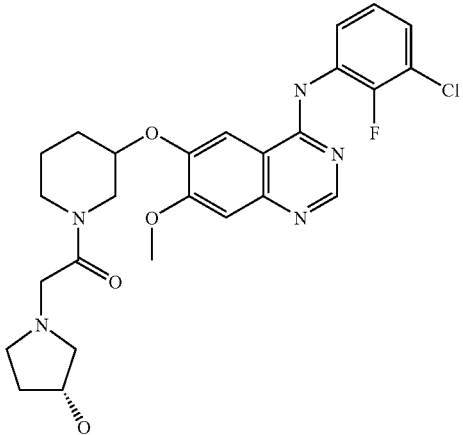 [SMILES: COc1cc2ncnc(Nc3cccc(Cl)c3F)c2cc1OC1CCCN(C(=O)CN2CC[C@@H](O)C2)C1]

Chloroacetyl chloride (47 μl) was added to a solution of 4-(3-Chloro-2-fluoroanilino)-7-methoxy-6-(piperidin-3-yloxy)quinazoline dihydrochloride (250 mg) and diisopropylethylamine (373 μl) in methylene chloride (10 ml) and the mixture was stirred at room temperature for 1 hour. (R)-(+)-3-pyrrolidinol (202 mg) was added, and the solution stirred for 1 hour before being washed with saturated aqueous sodium bicarbonate (10 ml) and purified by flash column chromatography eluting with increasingly polar mixtures of methylene chloride/methanol (saturated with ammonia) (100/0 to 95/5) to give a foam. This foam was dissolved in methylene chloride (5 ml) and crystallised by the addition of isohexane (50 ml) to give the title product as a mixture of two diastereoisomers (68 mg); $^1$H NMR Spectrum: (DMSO d$_6$, 100° C.) 1.52 (m, 2H), 1.87 (m, 3H), 2.09 (m, 1H), 2.38 (m, 1H), 2.61 (m, 1H), 2.77 (m, 1H), 3.18 (m, 1H), 3.36 (d, 1H), 3.53 (m, 2H), 3.68 (m, 1H), 3.89 (m, 1H), 3.94 (s, 3H), 4.15 (m, 1H), 4.23 (m, 1H), 4.53 (m, 1H), 7.27 (m, 2H), 7.41 (m, 1H), 7.59 (m, 1H), 7.89 (s, 1H), 8.38 (s, 1H), 9.24 (br s, 1H); Mass Spectrum: (M+H)$^+$ 530.

EXAMPLE 65

4-(3-Chloro-2-fluoroanilino)-7-methoxy-6-{[1-(4-methyl-3-oxopiperazin-1-yl)acetyl]piperidin-3-yloxy}quinazoline

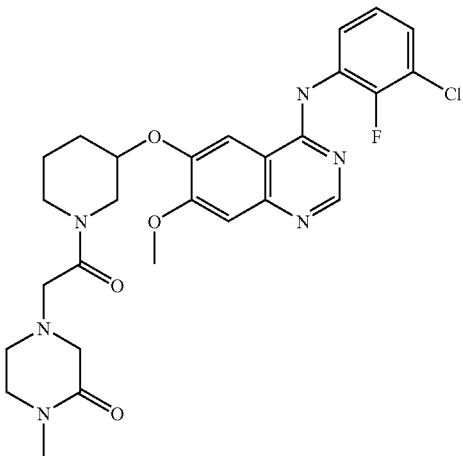 [SMILES: COc1cc2ncnc(Nc3cccc(Cl)c3F)c2cc1OC1CCCN(C(=O)CN2CCN(C)C(=O)C2)C1]

Chloroacetyl chloride (47 μl) was added to a solution of 4-(3-Chloro-2-fluoroanilino)-7-methoxy-6-(piperidin-3-yloxy)quinazoline dihydrochloride (250 mg) and diisopropylethylamine (373 μl) in methylene chloride (10 ml) and the mixture was stirred at room temperature for 1 hour. 1-Methylpiperazin-2-one (195 mg) was added, and the solution stirred for 1 hour before being washed with saturated aqueous sodium bicarbonate (10 ml) and purified by flash column chromatography eluting with increasingly polar mixtures of methylene chloride/methanol (100/0 to 95/5) to give a foam. This foam was dissolved in methylene chloride (5 ml) and crystallised by the addition of isohexane (50 ml) to give the title compound (177 mg); $^1$H NMR. Spectrum: (DMSO d$_6$, 100° C.) 1.57 (m, 1H), 1.91 (m, 2H), 2.08 (m, 1H), 2.67-2.85 (m, 5H), 3.08 (s, 2H), 3.18 (m, 3H), 3.32 (d, J=15 Hz, 1H), 3.47-3.60 (m, 2H), 3.71-3.83 (m, 2H), 3.95 (s, 3H), 4.57 (m, 1H), 7.27 (m, 2H), 7.42 (m, 1H), 7.60 (m, 1H), 7.89 (s, 1H), 8.40 (s, 1H), 9.23 (br s, 1H); Mass Spectrum: (M+H)$^+$ 557.

EXAMPLE 66

4-(3-Chloro-2-fluoroanilino)-7-methoxy-6-{1-[(4-acetylpiperazin-1-yl)acetyl]piperidin-3-yloxy}quinazoline

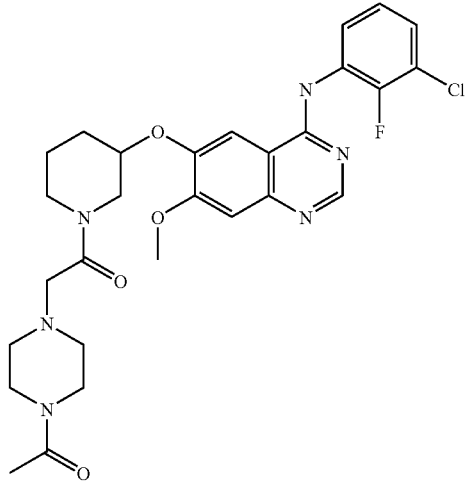 [SMILES: COc1cc2ncnc(Nc3cccc(Cl)c3F)c2cc1OC1CCCN(C(=O)CN2CCN(C(C)=O)CC2)C1]

Chloroacetyl chloride (47 μl) was added to a solution of 4-(3-Chloro-2-fluoroanilino-7-methoxy-6-(piperidin-3-yloxy)quinazoline dihydrochloride (250 mg) and diisopropylethylamine (373 μl) in methylene chloride (10 ml) and the mixture was stilled at room temperature for 1 hour. 1-Acetylpiperazine (292 mg) was added, and the solution stirred for 1 hour before being washed with saturated aqueous sodium bicarbonate (10 ml) and purified by flash column chromatography eluting with increasingly polar mixtures of methylene chloride/methanol (100/0 to 95/5) to give a foam. This foam was dissolved in methylene chloride (5 ml) and crystallised by the addition of isohexane (50 ml) to give the title compound (73 mg); $^1$H NMR. Spectrum: (DMSO d$_6$, 100° C.) 1.55 (m, 1H), 1.88 (m, 2H), 1.92 (s, 3H), 2.11 (m, 1H), 2.30-2.48 (m, 4H), 3.10 (d, 1H), 3.28 (d, 1H), 3.34 (m, 4H), 3.56 (m, 2H), 3.73 (m, 1H), 3.88 (m, 1H), 3.94 (s, 3H), 4.56 (m, 1H), 7.27 (m, 2H), 7.41 (m, 1H), 7.60 (m, 1H), 7.90 (s, 1H), 8.38 (s, 1H), 9.27 (m, 1H); Mass Spectrum: (M+H)$^+$ 571.

EXAMPLE 67

4-(3-chloro-2-fluoroanilino)-7-methoxy-6-{[(2R)-1-methylpyrrolidin-2-yl]methoxy}quinazoline

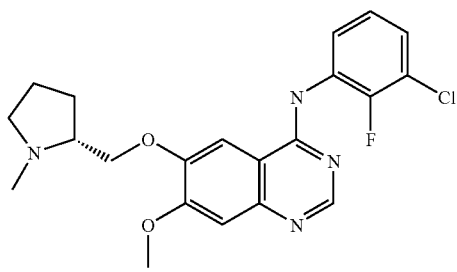 [SMILES: COc1cc2ncnc(Nc3cccc(Cl)c3F)c2cc1OC[C@H]1CCCN1C]

A mixture of 4-(3-chloro-2-fluoroanilino)-7-methoxy-6-[(2R)-pyrrolidin-2-ylmethoxy]quinazoline hydrochloride (250 mg) (Prepared as described in Example 32), formic acid (5 ml) and formaldehyde (37% w/v in water) (2.5 ml) was heated to 85° C. for one hour. The reaction mixture was then evaporated under vacuum, azeotroped with toluene and partitioned between ethyl acetate and saturated aqueous NaHCO$_3$. The organic layer was washed with brine, dried over Na$_2$SO$_4$, filtered and evaporated. The residues were then purified by flash chromatography eluting with increasingly polar mixtures of methylene chloride/methanol (saturated with ammonia) (98/2-94/6). The fractions containing the desired product were combined and evaporated to give a colourless gum, which was triturated with diethylether, filtered and dried under vacuum to give the title product as a white solid (0.15 g); $^1$H NMR Spectrum: (DMSO d$_6$) 1.55-1.83 (m, 3H); 1.95-2.10 (m, 1H); 2.20-2.35 (m, 1H); 2.45 (s, 3H); 2.68-2.85 (m, 1H); 2.93-3.10 (m, 1H); 3.92 (s, 3H); 1924.15 (m, 2H); 7.19 (s, 1H); 7.20-7.30 (m, 1H); 7.40-7.55 (m, 2H); 7.81 (s, 1H); 8.36 (s, 1H); 9.57 (s, 1H); Mass Spectrum: (M+H)$^+$ 417.

EXAMPLE 68

Pharmaceutical Compositions

The following illustrates a representative pharmaceutical dosage forms of the invention as defined herein (the active ingredient being termed "Compound X"), for therapeutic or prophylactic use in humans:

| (a) Tablet I | mg/tablet |
| --- | --- |
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Injection I | (50 mg/ml) |
| --- | --- |
| Compound X | 5.0% w/v |
| 1M Sodium hydroxide solution | 15.0% v/v |
| 0.1M Hydrochloric acid (to adjust pH to 7.6) | |

| (b) Injection I | (50 mg/ml) |
| --- | --- |
| Polyethylene glycol 400 | 4.5% w/v |
| Water for injection to 100%. | |

The above formulations may be obtained by conventional procedures well known in the pharmaceutical art. For example the tablet may be prepared by blending the components together and compressing the mixture into a tablet.

REFERENCE EXAMPLE 1

6-Acetoxy-4-(3-chloro-2-fluoroanilino)-7-methoxyquinazoline hydrochloride

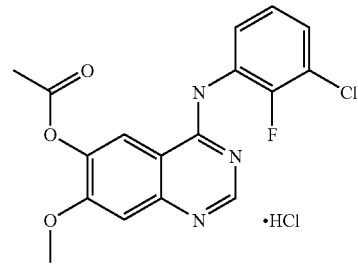 [SMILES: COc1cc2ncnc(Nc3cccc(Cl)c3F)c2cc1OC(C)=O ; Cl]

6-Acetoxy-4-chloro-7-methoxyquinazoline (prepared as described in Example 25-5 of in WO01/66099, 6.00 g, 23.8 mmol) and 3-chloro-2-fluoroaniline (3.46 g, 23.8 mmol) were suspended in iso-propanol (200 ml). The mixture was heated to 80° C. under reflux for 3 hours. The solvent was evaporated; the residue was crystallised from acetonitrile, giving the product hydrochloride as a pale pink crystalline solid (8.16 g, 92%); $^1$H NMR: 2.37 (s, 3H), 4.00 (s, 3H), 7.34 (ddd, 1H), 7.48 (s, 1H), 7.52 (ddd, 1H), 7.61 (ddd, 1H), 8.62 (s, 1H), 8.86 (s, 1H); Mass Spectrum: 362.4, 364.4

REFERENCE EXAMPLE 2

4-(3-Chloro-2-fluoroanilino)-6-hydroxy-7-methoxyquinazoline

6-Acetoxy-4-(3-chloro-2-fluoroanilino)-7-methoxyquinazoline hydrochloride (Reference Example 1, 8.72 g, 21.9 mmol) was dissolved in methanol (200 ml). Concentrated aqueous ammonia (15 ml) was added, and the solution heated to 50° C. with stiffing for 2 hours, causing precipitation of a cream coloured solid. The solid was collected by filtration, washed with diethyl ether (3×200 ml), and dried in vacuo at 60° C. over diphosphorous pentoxide, giving the product as an off white solid (5.40 g, 77%); $^1$H NMR: 3.95 (s, 3H), 7.19 (s, 1H), 7.23 (dd, 1H), 7.42 (dd, 1H), 7.50 (dd, 1H), 7.64 (s, 1H), 8.32 (s, 1H), 9.43 (s, 1H), 9.67 (br.s, 1H); Mass Spectrum: 320.4, 322.4.

REFERENCE EXAMPLE 3

6-{[(1-tert-Butoxycarbonyl)piperidin-4-yl]oxy}-4-(3-chloro-2-fluoroanilino)-7-methoxyquinazoline

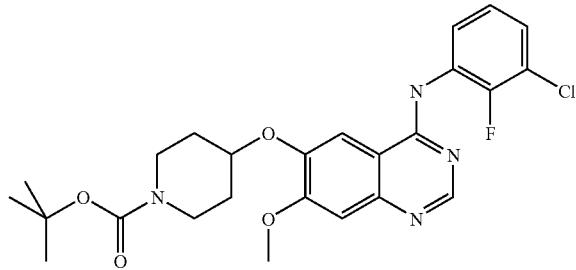 [SMILES: COc1cc2ncnc(Nc3cccc(Cl)c3F)c2cc1OC1CCN(C(=O)OC(C)(C)C)CC1]

4-(3-Chloro-2-fluoroanilino)-6-hydroxy-7-methoxyquinazoline (Reference Example 2, 1870 mg, 5.85 mmol) was dissolved in DMA (50 ml). tert-Butyl (4-methanesulfonyloxy)piperidine-1-carboxylate (prepared as in Chemical & Pharmaceutical Bulletin 2001, 49(7), 822-829; 490 mg, 1.76 mmol) and cesium fluoride (890 mg, 5.85 mmol) were added, and the mixture was heated to 85° C. with stirring. At intervals of 2 hours, 4 hours and 6 hours, tert-butyl 4-methanesulfonyloxypiperidine-1-carboxylate and cesium fluoride were added in the above quantities to the reaction mixture. Heating was continued at 85° C. for a further 6 hours after the final addition. The solvent was evaporated, and the residue was partitioned between DCM (150 ml) and H$_2$O (150 ml). The aqueous layer was extracted with DCM (4×100 ml), and the extractions combined with the DCM layer. The combined DCM fractions were dried over MgSO$_4$ and evaporated. The residue was purified by chromatography, eluting with 0 to 2.5% (7:1 MeOH/concentrated aqueous NH$_4$OH) in DCM. The appropriate fractions were combined and evaporated, giving the product as a light brown foam (2.40 g, 58%, allowing for 2.3 equivalents of residual DMA); $^1$H NMR: 1.40 (s, 9H), 1.60-1.65 (m, 2H), 1.95-2.00 (m, 2H), 3.20-3.25 (m, 2H), 3.65-3.70 (m, 2H), 3.92 (s, 3H), 4.68 (m, 1H), 7.21 (s, 1H), 7.27 (dd, 1H), 7.47 (ddd, 1H), 7.51 (dd, 1H), 7.85 (s, 1H), 836 (s, 1H), 9.53 (s, 1H); Mass Spectrum: 503.5, 505.5

REFERENCE EXAMPLE 4

6-{[(1-tert-Butoxycarbonyl)piperidin-4-yl]methoxy}-4-(3-chloro-2-fluoroanilino)-7-methoxyquinazoline

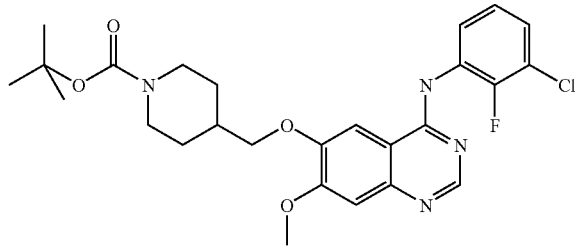 [SMILES: COc1cc2ncnc(Nc3cccc(Cl)c3F)c2cc1OCC1CCN(C(=O)OC(C)(C)C)CC1]

4-(3-Chloro-2-fluoroanilino)-6-hydroxy-7-methoxyquinazoline (Reference Example 2, 700 mg, 2.19 mmol) was dissolved in DMA (35 ml). Potassium carbonate (1209 mg, 8.76 mmol) and ter t-butyl 4-(toluene-4-sulfonyloxymethyl)piperidine-1-carboxylate (prepared as described in Example 1 in WO 9427965; 808 mg, 2.19 mmol) were added, and the mixture was stirred at 80° C. for 4 hours. The solvent was evaporated, and the residue was partitioned between water (100 ml) and DCM (100 ml). The aqueous layer was extracted with DCM (3×100 ml) and the extractions combined with the DCM layer. The combined DCM fractions were filtered through a silicone-treated filter paper, and evaporated, giving the product as a brown solid (1290 mg, 98%): $^1$H NMR: 1.20 (m, 2H), 1.39 (s, 9H), 1.82 (m, 2H), 2.03 (br. m, 1H), 2.70-2.85 (br. m, 2H), 3.93 (s, 3H), 3.95-4.05 (br. m, 2H), 3.98 (d, 2H), 7.19 (s, 1H), 7.26 (dd, 1H), 7.46 (dd, 1H), 7.50 (dd, 1H), 7.76 (s, 1H), 8.35 (s, 1H), 9.57 (s, 1H); Mass Spectrum: 517.3, 519.3

REFERENCE EXAMPLE 5

6-{[(2-(1-tert-Butoxycarbonyl)piperidin-4-yl]ethoxy}-4-(3-chloro-2-fluoroanilino)-7-methoxyquinazoline

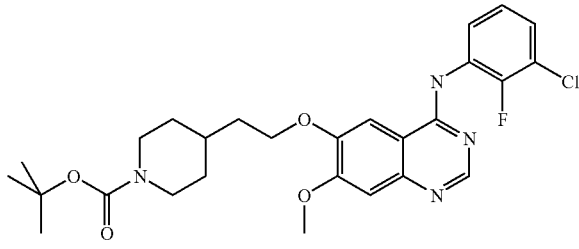 [SMILES: COc1cc2ncnc(Nc3cccc(Cl)c3F)c2cc1OCCC1CCN(C(=O)OC(C)(C)C)CC1]

4-(3-Chloro-2-fluoroanilino)-6-hydroxy-7-methoxyquinazoline (Reference Example 2, 500 mg, 1.56 mmol) was dissolved in DMA (25 ml). Potassium carbonate (864 mg, 6.26 mmol) and tent-butyl 4-[2-(methanesulfonyloxy)ethyl]piperidine-1-carboxylate (prepared as described in Example 20 in U.S. Pat. No. 5,252,586; 504 mg, 1.64 mmol) were added, and the mixture was stirred at 60° C. for 16 hours. The solvent was evaporated, and the residue was partitioned between water (100 ml) and DCM (100 ml). The aqueous layer was extracted with DCM (3×100 ml) and the extractions combined with the DCM layer. The combined DCM fractions were filtered through a silicone-treated filter paper, and evaporated, giving the product as a brown foam (830 mg, 100%); $^1$H NMR: 1.00-1.18 (m, 2H), 1.38 (s, 9H), 1.65-1.80 (m, 5H), 2.65-2.75 (m, 2H), 3.92 (s, 3H), 3.93 (m, 2H), 4.15 (t, 2H), 7.18 (s, 1H), 7.26 (dd, 1H), 7.46 (dd, 1H), 7.51 (dd, 1H), 7.77 (s, 1H), 8.36 (s, 1H), 9.54 (s, 1H); Mass Spectrum: 531.6, 533.6.

The invention claimed is:

1. A quinazoline of Formula I:

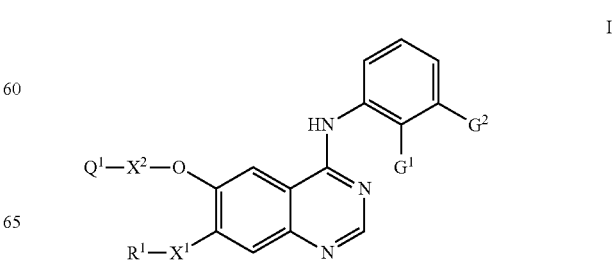

wherein:
G¹ and G² each independently is halogeno;
X¹ is O;
R¹ is (1-4C)alkyl;
X² is a direct bond;
Q¹ is heterocyclyl, wherein Q¹ optionally bears 1 or 2 substituents, which may be the same or different, selected from
carbamoyl,
(1-6C)alkyl,
(1-6C)alkylsulphonyl,
N-(1-6C)alkylcarbamoyl,
N,N-di-[(1-6C)alkyl]carbamoyl,
(2-6C)alkanoyl,
carbamoyl(1-6C)alkyl,
N-(1-6C)alkylcarbamoyl(1-6C)alkyl, and
N,N-di-[(1-6C)alkyl]carbamoyl(1-6C)alkyl, and
wherein any (1-6C)alkyl and (2-6C)alkanoyl group within Q¹ optionally bears a substituent selected from (1-6C)alkoxy and NR$^a$R$^b$, wherein R$^a$ is hydrogen or (1-4C)alkyl and R$^b$ is hydrogen or (1-4C)alkyl, or R$^a$ and R$^b$ together with the nitrogen atom to which they are attached form a 5 or 6 membered ring, which optionally bears 1 or 2 substituents on an available ring carbon atom selected from (1-4C)alkyl;
or a pharmaceutically acceptable salt thereof.

2. A quinazoline according to claim 1, wherein Q¹ is heterocyclyl, optionally bearing 1 or 2 substituents, which may be the same or different, selected from
carbamoyl,
N-(1-6C)alkylcarbamoyl,
N,N-di-[(1-6C)alkyl]carbamoyl,
carbamoyl(1-6C)alkyl,
N-(1-6C)alkylcarbamoyl(1-6C)alkyl, and
N,N-di-[(1-6C)alkyl]carbamoyl(1-6C)alkyl, and
wherein any (1-6C)alkyl and (2-6C)alkanoyl group within Q¹ optionally bears one or more substituents, which may be the same or different, selected from NR$^a$R$^b$, wherein R$^a$ is hydrogen and R$^b$ is hydrogen;
or a pharmaceutically acceptable salt thereof.

3. A quinazoline according to claim 1, wherein Q¹ is heterocyclyl, optionally bearing 1 or 2 substituents, which may be the same or different, selected from
carbamoyl,
(1-6C)alkyl,
N-(1-6C)alkylcarbamoyl,
N,N-di-[(1-6C)alkyl]-carbamoyl,
carbamoyl(1-6C)alkyl,
N-(1-6C)alkylcarbamoyl(1-6C)alkyl, and
N,N-di-[(1-6C)alkyl]carbamoyl(1-6C)alkyl,
and wherein any (1-6C)alkyl and (2-6C)alkanoyl group within Q¹ optionally bears one or more substituents, which may be the same or different, selected from NR$^a$R$^b$, wherein R$^a$ is hydrogen and R$^b$ is hydrogen; or
a pharmaceutically acceptable salts thereof.

4. A quinazoline of Formula I:

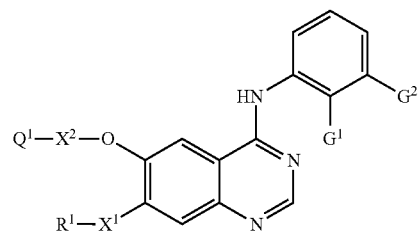

wherein:
G¹ and G² each independently is halogeno;
X¹ is O;
R¹ is (1-4C)alkyl;
X² is a direct bond;
Q¹ is a non-aromatic saturated 4, 5 or 6 membered monocyclic heterocyclyl ring with 1 or 2 ring nitrogen heteroatom(s), which ring is linked to the group X²—O— by a ring carbon atom, wherein Q¹ optionally bears 1 or 2 substituents, which may be the same or different, selected from
carbamoyl,
(1-6C)alkyl,
(1-6C)alkylsulphonyl,
N-(1-6C)alkylcarbamoyl,
N,N-di-[(1-6C)alkyl]carbamoyl,
(2-6C)alkanoyl,
carbamoyl(1-6C)alkyl,
N-(1-6C)alkylcarbamoyl(1-6C)alkyl, and
N,N-di-[(1-6C)alkyl]carbamoyl(1-6C)alkyl, and
wherein any (1-6C)alkyl and (2-6C)alkanoyl group within Q¹ optionally bears a substituent selected from (1-6C)alkoxy and NR$^a$R$^b$, wherein R$^a$ is hydrogen or (1-4C)alkyl and R$^b$ is hydrogen or (1-4C)alkyl, or R$^a$ and R$^b$ together with the nitrogen atom to which they are attached form a 5 or 6 membered ring, which optionally bears 1 or 2 substituents on an available ring carbon atom selected from (1-4C)alkyl;
or a pharmaceutically acceptable salt thereof.

5. A quinazoline according to claim 4, wherein
Q¹ is selected from
pyrrolidin-3-yl,
pyrrolidin-2-yl,
piperidin-4-yl,
piperidin-3-yl,
piperidin-2-yl,
piperazin-2-yl, and
piperazin-3-yl.

6. A quinazoline of Formula I:

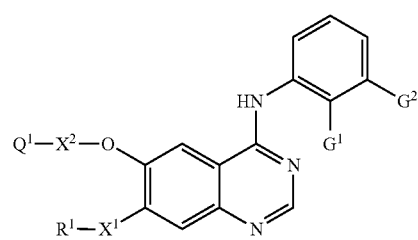

wherein:
G$^1$ and G$^2$ each independently is chosen from fluoro and chloro;
X$^1$ is O;
R$^1$ is (1-4C)alkyl;
X$^2$ is a direct bond;
Q$^1$ is linked to X$^2$—O by a ring carbon atom and is a heterocyclyl chosen from
  pyrrolidin-3-yl,
  pyrrolidin-2-yl,
  3-pyrrolin-3-yl,
  piperidin-4-yl,
  piperidin-3-yl,
  piperidin-2-yl,
  homopiperidin-3-yl,
  homopiperidin-4-yl,
  piperazin-2-yl,
  piperazin-3-yl, and
  1,2,3,6-tetrahydropyridin-4-yl,
  wherein Q$^1$ bears 1 or 2 substituents selected from N-(1-6C)alkylcarbamoyl and N-(1-6C)alkylcarbamoyl(1-6C)alkyl,
or a pharmaceutically acceptable salt thereof.

7. A quinazoline of Formula I:

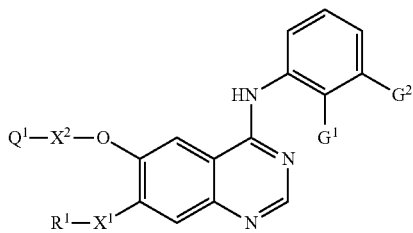

wherein:
G$^1$ and G$^2$ each independently is chosen from fluoro and chloro;
X$^1$ is O;
R$^1$ is (1-4C)alkyl;
X$^2$ is a direct bond;
Q$^1$ is linked to X$^2$—O by a ring carbon atom and is a heterocyclyl chosen from:
  pyrrolidin-3-yl,
  pyrrolidin-2-yl,
  3-pyrrolin-3-yl,
  piperidin-4-yl,
  piperidin-3-yl,
  piperidin-2-yl,
  homopiperidin-3-yl,
  homopiperidin-4-yl,
  piperazin-2-yl,
  piperazin-3-yl, and
  1,2,3,6-tetrahydropyridin-4-yl,
  wherein Q$^1$ bears 1 or 2 substituents selected from:
  N-(1-6C)alkyl-carbamoyl,
  (1-6C)alkyl, and
  N-(1-6C)alkylcarbamoyl(1-6C)alkyl, or
a pharmaceutically acceptable salts thereof.

8. A quinazoline of Formula I:

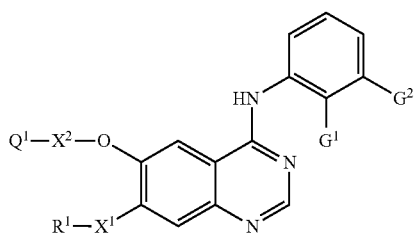

wherein:
G$^1$ and G$^2$ each independently is halogeno;
X$^1$ is O;
R$^1$ is (1-4C)alkyl;
X$^2$ is a direct bond;
Q$^1$ is a non-aromatic saturated 5 or 6 membered monocyclic heterocyclyl ring with at least one nitrogen atom, which ring is linked to the group X$^2$—O— by a carbon atom in the ring, wherein Q$^1$ optionally bears 1 or 2 substituents, which may be the same or different, selected from
  carbamoyl,
  (1-6C)alkyl,
  (1-6C)alkylsulphonyl,
  N-(1-6C)alkylcarbamoyl,
  N,N-di-[(1-6C)alkyl]carbamoyl,
  (2-6C)alkanoyl,
  carbamoyl(1-6C)alkyl,
  N-(1-6C)alkylcarbamoyl(1-6C)alkyl, and
  N,N-di-[(1-6C)alkyl]carbamoyl(1-6C)alkyl, and
wherein any (1-6C)alkyl and (2-6C)alkanoyl group within Q$^1$ optionally bears a substituent selected from (1-6C)alkoxy and NR$^a$R$^b$, wherein R$^a$ is hydrogen or (1-4C)alkyl and R$^b$ is hydrogen or (1-4C)alkyl, or R$^a$ and R$^b$ together with the nitrogen atom to which they are attached form a 5 or 6 membered ring, which optionally bears 1 or 2 substituents on an available ring carbon atom selected from (1-4C)alkyl;
or a pharmaceutically acceptable salt thereof.

9. A quinazoline of Formula I:

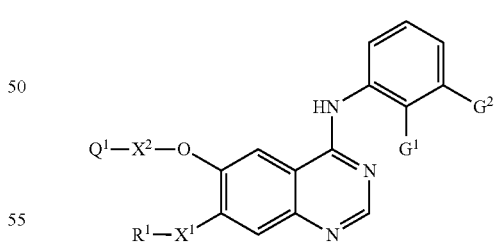

wherein:
G1 is fluoro and G2 is chloro;
X$^1$ is O;
R$^1$ is (1-4C)alkyl;
X$^2$ is a direct bond;
Q$^1$ is linked to X$^2$—O by a ring carbon atom and is a heterocyclyl chosen from
  pyrrolidin-3-yl,
  pyrrolidin-2-yl,
  3-pyrrolin-3-yl, piperidin-4-yl,
piperidin-3-yl,
piperidin-2-yl,
homopiperidin-3-yl,
homopiperidin-4-yl,
piperazin-2-yl,
piperazin-3-yl, and
1,2,3,6-tetrahydropyridin-4-yl, and
wherein $Q^1$ bears 1 or 2 substituents selected from N-(1-6C)alkylcarbamoyl and N-(1-6C)alkylcarbamoyl(1-6C)alkyl,
or a pharmaceutically acceptable salt thereof.

10. A quinazoline of Formula I:

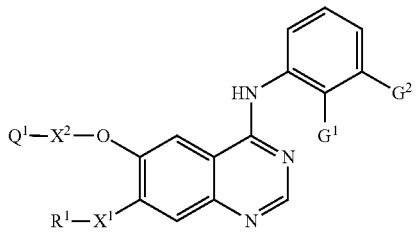

I wherein:
$G^1$ and $G^2$ each independently is chosen from fluoro and chloro;
$X^1$—$R^1$ is methoxy;
$X^2$ is a direct bond;
$Q^1$ is linked to $X^2$ —O by a ring carbon atom and is a heterocyclyl chosen from
pyrrolidin-3-yl,
pyrrolidin-2-yl,
3-pyrrolin-3-yl,
piperidin-4-yl,
piperidin-3-yl,
piperidin-2-yl,
homopiperidin-3-yl,
homopiperidin-4-yl,
piperazin-2-yl,
piperazin-3-yl, and
1,2,3,6-tetrahydropyridin-4-yl, and
wherein $Q^1$ bears 1 or 2 substituents selected from N-(1-6C)alkylcarbamoyl and N-(1-6C)alkylcarbamoyl(1-6C)alkyl,
or a pharmaceutically acceptable salt thereof.

11. A quinazoline of Formula I:

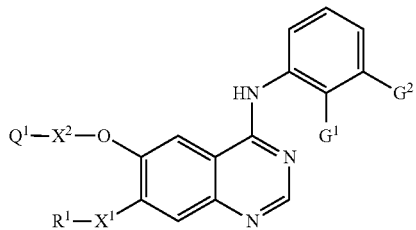

I wherein:
$G^1$ and $G^2$ each independently is chosen from fluoro and chloro;
$X^1$ is O;
$R^1$ is (1-4C)alkyl;
$X^2$ is a direct bond;
$Q^1$ is linked to $X^2$ —O by a ring carbon atom and is a heterocyclyl chosen from
pyrrolidin-3-yl,
pyrrolidin-2-yl,
3-pyrrolin-3-yl,
piperidin-4-yl,
piperidin-3-yl,
piperidin-2-yl,
homopiperidin-3-yl,
homopiperidin-4-yl,
piperazin-2-yl,
piperazin-3-yl, and
1,2,3,6-tetrahydropyridin-4-yl, and
wherein $Q^1$ bears 1 or 2 substituents selected from N-(1-6C)alkylcarbamoyl and N-(1-6C)alkylcarbamoyl(1-6C)alkyl,
or a pharmaceutically acceptable salt thereof.

* * * * *